(12) United States Patent
Abel et al.

(10) Patent No.: US 11,918,650 B2
(45) Date of Patent: Mar. 5, 2024

(54) PHARMACEUTICAL COMPOSITION COMPRISING BISPECIFIC ANTIBODY CONSTRUCTS FOR IMPROVED STORAGE AND ADMINISTRATION

(71) Applicant: AMGEN INC., Thousand Oaks, CA (US)

(72) Inventors: Jeff Abel, Simi Valley, CA (US); Lingwen Cui, Thousand Oaks, CA (US); Devrishi Goswami, Thousand Oaks, CA (US); Joon Huh, Culver City, CA (US); Bharadwaj Jagannathan, Thousand Oaks, CA (US); Sekhar Kanapuram, Thousand Oaks, CA (US); Arnold McAuley, Moorpark, CA (US); Michael Schneider, Thousand Oaks, CA (US); Ananthakrishnan G. Sethuraman, Newbury Park, CA (US); Michael Treuheit, Newbury Park, CA (US); Jun Zhang, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 501 days.

(21) Appl. No.: 15/972,489

(22) Filed: May 7, 2018

(65) Prior Publication Data
US 2019/0151448 A1 May 23, 2019

Related U.S. Application Data

(60) Provisional application No. 62/502,578, filed on May 5, 2017.

(51) Int. Cl.
| | | |
|---|---|---|
| *A61K 39/395* | (2006.01) | |
| *A61K 9/00* | (2006.01) | |
| *A61K 9/08* | (2006.01) | |
| *A61K 9/19* | (2006.01) | |
| *A61K 47/10* | (2017.01) | |
| *A61K 47/12* | (2006.01) | |
| *A61K 47/14* | (2017.01) | |
| *A61K 47/18* | (2017.01) | |
| *A61K 47/24* | (2006.01) | |
| *A61K 47/26* | (2006.01) | |
| *C07K 16/28* | (2006.01) | |
| *C07K 16/46* | (2006.01) | |
| *A61J 1/05* | (2006.01) | |
| *A61J 1/10* | (2006.01) | |
| *A61K 39/00* | (2006.01) | |

(52) U.S. Cl.
CPC ...... *A61K 39/39591* (2013.01); *A61K 9/0019* (2013.01); *A61K 9/08* (2013.01); *A61K 9/19* (2013.01); *A61K 39/3955* (2013.01); *A61K 47/10* (2013.01); *A61K 47/12* (2013.01); *A61K 47/14* (2013.01); *A61K 47/183* (2013.01); *A61K 47/24* (2013.01); *A61K 47/26* (2013.01); *C07K 16/2803* (2013.01); *C07K 16/2809* (2013.01); *C07K 16/2863* (2013.01); *C07K 16/468* (2013.01); *A61J 1/05* (2013.01); *A61J 1/10* (2013.01); *A61K 2039/54* (2013.01); *A61K 2039/545* (2013.01); *A61K 2039/627* (2013.01); *C07K 2317/24* (2013.01); *C07K 2317/31* (2013.01); *C07K 2317/41* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 3,691,016 A | | 9/1972 | Patel et al. |
| 3,773,919 A | | 11/1973 | Boswell et al. |
| 3,969,287 A | | 7/1976 | Jaworek et al. |
| 4,179,337 A | | 12/1979 | Davis et al. |
| 4,195,128 A | | 3/1980 | Hildebrand et al. |
| 4,229,537 A | | 10/1980 | Hodgins et al. |
| 4,247,642 A | | 1/1981 | Hirohara et al. |
| 4,301,144 A | | 11/1981 | Iwashita et al. |
| 4,330,440 A | | 5/1982 | Ayers et al. |
| 4,439,196 A | | 3/1984 | Higuchi |
| 4,447,224 A | | 5/1984 | DeCant, Jr. et al. |

(Continued)

FOREIGN PATENT DOCUMENTS

| | | | |
|---|---|---|---|
| EP | 0036676 A1 | 9/1981 | |
| EP | 0058481 A1 | 8/1982 | |

(Continued)

OTHER PUBLICATIONS

Thirumangalathu et al. Journal of Pharmaceutical Sciences, vol. 95, No. 7, Jul. 2006 (Year: 2006).*

(Continued)

*Primary Examiner* — Meera Natarajan
(74) *Attorney, Agent, or Firm* — MARSHALL, GERSTEIN & BORUN LLP

(57) ABSTRACT

The present invention provides an improved pharmaceutical composition for storage and administration comprising (a) a bispecific antibody construct comprising a first domain binding to a target cell surface antigen and a second domain binding to a second antigen, wherein the bispecific antibody construct is present at a concentration in the range from about 0.5 µg/ml to 20 mg/ml, (b) a preservative at a concentration effective to inhibit the growth of microbes, and (c) a diluent wherein bispecific antibody construct is stable and recoverable.

18 Claims, 17 Drawing Sheets

Specification includes a Sequence Listing.

(56) References Cited

U.S. PATENT DOCUMENTS

| | | |
|---|---|---|
| 4,447,233 A | 5/1984 | Mayfield |
| 4,475,196 A | 10/1984 | La Zor |
| 4,485,045 A | 11/1984 | Regen |
| 4,486,194 A | 12/1984 | Ferrara |
| 4,487,603 A | 12/1984 | Harris |
| 4,496,689 A | 1/1985 | Mitra |
| 4,544,545 A | 10/1985 | Ryan et al. |
| 4,596,556 A | 6/1986 | Morrow et al. |
| 4,640,835 A | 2/1987 | Shimizu et al. |
| 4,670,417 A | 6/1987 | Iwasaki et al. |
| 4,694,778 A | 9/1987 | Learn et al. |
| 4,751,180 A | 6/1988 | Cousens et al. |
| 4,790,824 A | 12/1988 | Morrow et al. |
| 4,791,192 A | 12/1988 | Nakagawa et al. |
| 4,816,397 A | 3/1989 | Boss et al. |
| 4,816,567 A | 3/1989 | Cabilly et al. |
| 4,935,233 A | 6/1990 | Bell et al. |
| 4,941,880 A | 7/1990 | Burns |
| 4,946,778 A | 8/1990 | Ladner et al. |
| 5,013,556 A | 5/1991 | Woodle et al. |
| 5,064,413 A | 11/1991 | McKinnon et al. |
| 5,223,409 A | 6/1993 | Ladner et al. |
| 5,225,539 A | 7/1993 | Winter |
| 5,260,203 A | 11/1993 | Ladner et al. |
| 5,292,658 A | 3/1994 | Cormier et al. |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,418,155 A | 5/1995 | Cormier et al. |
| 5,476,996 A | 12/1995 | Wilson et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,643,763 A | 7/1997 | Dunn et al. |
| 5,648,260 A | 7/1997 | Winter et al. |
| 5,661,016 A | 8/1997 | Lonberg et al. |
| 5,683,888 A | 11/1997 | Campbell |
| 5,693,761 A | 12/1997 | Queen et al. |
| 5,693,762 A | 12/1997 | Queen et al. |
| 5,698,767 A | 12/1997 | Wilson et al. |
| 5,721,367 A | 2/1998 | Kay et al. |
| 5,741,668 A | 4/1998 | Ward et al. |
| 5,770,429 A | 6/1998 | Lonberg et al. |
| 5,777,079 A | 7/1998 | Tsien et al. |
| 5,789,215 A | 8/1998 | Berns et al. |
| 5,789,650 A | 8/1998 | Lonberg et al. |
| 5,804,387 A | 9/1998 | Cormack et al. |
| 5,814,318 A | 9/1998 | Lonberg et al. |
| 5,859,205 A | 1/1999 | Adair et al. |
| 5,874,299 A | 2/1999 | Lonberg et al. |
| 5,874,304 A | 2/1999 | Zolotukhin et al. |
| 5,876,995 A | 3/1999 | Bryan |
| 5,877,397 A | 3/1999 | Lonberg et al. |
| 5,925,558 A | 7/1999 | Tsien et al. |
| 5,939,598 A | 8/1999 | Kucherlapati et al. |
| 5,958,765 A | 9/1999 | Brams et al. |
| 5,981,175 A | 11/1999 | Loring et al. |
| 6,023,010 A | 2/2000 | Krimpenfort et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,255,458 B1 | 7/2001 | Lonberg et al. |
| 6,300,064 B1 | 10/2001 | Knappik et al. |
| 6,407,213 B1 | 6/2002 | Carter et al. |
| 6,673,986 B1 | 1/2004 | Kucherlapati et al. |
| 9,308,257 B2 * | 4/2016 | Sharma, Sr. ............ A61P 35/00 |

FOREIGN PATENT DOCUMENTS

| | | |
|---|---|---|
| EP | 0088046 A2 | 9/1983 |
| EP | 0133988 A2 | 3/1985 |
| EP | 0143949 A1 | 6/1985 |
| EP | 0171496 A2 | 2/1986 |
| EP | 0173494 A2 | 3/1986 |
| EP | 0183070 A2 | 6/1986 |
| EP | 239400 A2 | 9/1987 |
| EP | 244234 A2 | 11/1987 |
| EP | 402226 A1 | 12/1990 |
| EP | 0463151 B1 | 6/1996 |
| EP | 773 288 A2 | 5/1997 |
| EP | 0546073 B1 | 9/1997 |
| EP | 843 961 A1 | 5/1998 |
| GB | 2177096 B | 5/1989 |
| JP | 3 068 180 B2 | 7/2000 |
| JP | 3 068 506 B2 | 7/2000 |
| JP | 3 068 507 B2 | 7/2000 |
| WO | WO-1987/005330 A1 | 9/1987 |
| WO | WO-1988/001649 A1 | 3/1988 |
| WO | WO-1988/009344 A1 | 12/1988 |
| WO | WO-1992/003918 A1 | 3/1992 |
| WO | WO-1992/015673 A1 | 9/1992 |
| WO | WO-1992/022645 A1 | 12/1992 |
| WO | WO-1992/022647 A1 | 12/1992 |
| WO | WO-1992/022670 A1 | 12/1992 |
| WO | WO-1993/012227 A1 | 6/1993 |
| WO | WO-1993/015722 A1 | 8/1993 |
| WO | WO-1994/000569 A1 | 1/1994 |
| WO | WO-1994/002602 A1 | 2/1994 |
| WO | WO-1994/025585 A1 | 11/1994 |
| WO | WO-1995/007463 A1 | 3/1995 |
| WO | WO-1996/014436 A1 | 5/1996 |
| WO | WO-1996/033735 A1 | 10/1996 |
| WO | WO-1996/034096 A1 | 10/1996 |
| WO | WO-1997/013852 A1 | 4/1997 |
| WO | WO-1997/038731 A1 | 10/1997 |
| WO | WO-1998/014605 A1 | 4/1998 |
| WO | WO-1998/024884 A1 | 6/1998 |
| WO | WO-1998/024893 A2 | 6/1998 |
| WO | WO-1998/026277 A2 | 6/1998 |
| WO | WO-1998/052976 A1 | 11/1998 |
| WO | WO-1999/049019 A2 | 9/1999 |
| WO | WO-1999/054440 A1 | 10/1999 |
| WO | WO-2000/006605 A2 | 2/2000 |
| WO | WO-2000/34317 A2 | 6/2000 |
| WO | WO-2000/76310 A1 | 12/2000 |
| WO | WO-2003/47336 A2 | 6/2003 |
| WO | WO-2005/040220 A1 | 5/2005 |
| WO | WO-2006/138181 A2 | 12/2006 |
| WO | WO-2007/042261 A2 | 4/2007 |
| WO | WO-2008/119567 A2 | 10/2008 |
| WO | WO-2010/037838 A2 | 4/2010 |
| WO | WO-2013/026833 A1 | 2/2013 |
| WO | WO-2013/026837 A1 | 2/2013 |
| WO | WO-2014/144722 A2 | 9/2014 |
| WO | WO-2014/151910 A1 | 9/2014 |
| WO | WO-2015/048272 A1 | 4/2015 |

OTHER PUBLICATIONS

U.S. Appl. No. 03/0070185-A1, filed Apr. 10, 2003, Jakobovits et al.
U.S. Appl. No. 07/466,008, Kucherlapati et al.
U.S. Appl. No. 07/574,748, Kay et al.
U.S. Appl. No. 07/575,962, Lonberg et al.
U.S. Appl. No. 07/610,515, Kucherlapati et al.
U.S. Appl. No. 07/810,279.
U.S. Appl. No. 07/853,408.
U.S. Appl. No. 07/904,068, Lonberg et al.
U.S. Appl. No. 07/919,297, Kucherlapati et al.
U.S. Appl. No. 07/922,649.
U.S. Appl. No. 07/990,860.
U.S. Appl. No. 08/031,801.
U.S. Appl. No. 08/053,131.
U.S. Appl. No. 08/096,762.
U.S. Appl. No. 08/112,848, Kucherlapati et al.

(56) References Cited

OTHER PUBLICATIONS

U.S. Appl. No. 08/155,301, Lonberg et al.
U.S. Appl. No. 08/161,739, Lonberg et al.
U.S. Appl. No. 08/165,699, Lonberg et al.
U.S. Appl. No. 08/209,741, Kay et al.
U.S. Appl. No. 08/234,145, Kucherlapati et al.
U.S. Appl. No. 08/376,279, Kucherlapati et al.
U.S. Appl. No. 08/430,938, Kucherlapati et al.
U.S. Appl. No. 08/462,513.
U.S. Appl. No. 08/462,837, Kucherlapati et al.
U.S. Appl. No. 08/463,191, Kucherlapati et al.
U.S. Appl. No. 08/464,582.
U.S. Appl. No. 08/464,584, Kucherlapati et al.
U.S. Appl. No. 08/486,853.
U.S. Appl. No. 08/486,857.
U.S. Appl. No. 08/486,859.
U.S. Appl. No. 08/724,752.
U.S. Appl. No. 08/759,620, Jakobovits et al.
U.S. Appl. No. 14/0302037-A1, filed Oct. 9, 2014, Borges et al.
U.S. Appl. No. 14/0308285-A1, filed Oct. 16, 2014, Yan et al.
Altschul et al., Basic local alignment search tool, *J. Mol. Biol.* 215:403-10 (1990).
Altschul et al., Gapped BLAST and PSI-BLAST: a new generation of protein database search programs, *Nucleic Acids Res.* 25:3389-402 (1997).
Altschul et al., Local alignment statistics, *Methods Enzymol.* 266:460-80 (1996).
Aplin et al., Preparation properties and applications of carbohydrate conjugates of proteins lipids, *CRC Crit. Rev. Biochem.* 10:259-306 (1981).
Arakawa et al., Protein-solvent interactions in pharmaceutical formulations, *Pharm. Red.* 8:285-91 (1991).
Artsaenko et al., Expression of a single-chain Fv antibody against abscisic acid creates a witty phenotype in transgenic tobacco, *Plant J.* 8:745-50 (1995).
Bird et al., Single-Chain antigen-binding proteins, *Science.* 242:423-6 (1988).
Bruhl et al., Depletion of CCR5-expressing cells with bispecific antibodies and chemokine toxins: a new strategy in the treatment of chronic inflammatory diseases and HIV, *J. Immunol.* 166:2420-6 (2001).
Carpenter et al., Rational Design of Stable Lyophilized Protein Formulations: Theory and Practice, Pharmaceutical Biotechnology (2002).
Carter et al., High level *Escherichia coli* expression and production of a bivalent humanized antibody fragment, *Biotechnology.* 10:163-7 (1992).
Chalfie et al., Green flourescent protein as a marker for gene expression, *Science.* 263:802-5 (1994).
Cheadle et al., Cloning and expression of the variable regions of mouse myeloma protein MOPC315 in *E. coli*: recovery of active FV fragments, *Mol. Immunol.* 29:21-30 (1992).
Chen et al., Immunoglobulin gene rearrangement in B cell deficient mice generated by targeted deletion of the JH locus, *International Immunology.* 5::647-656 (1993).
Cheson et al., Report of an international workshop to standardize response criteria for non-Hodgkin's lymphomas. NCI Sponsored International Working Group, *J. Clin. Oncol.* 17:1244 (1999).
Chi et al., Physical stability of proteins in aqueous solution: mechanism and driving forces in nonnative protein aggregation, *Pharm. Res.* 20:1325-36 (2003).
Choi et al., Transgenic mice containing a human heavy chain immunoglobin gene fragment cloned in a yeast artificial chromosome, *Nature Publishing Group.* 4:117-123 (1993).
Chothia et al., Canonical structures for the hypervariable regions of immunoglobulins, *J. Mol. Biol.* 196:901-17 (1987).
Chothia et al., Conformations of immunoglobulin hypervariable regions, *Nature.* 342:877-83 (1989).
Clackson et al., Making antibody fragments using phage display libraries, *Nature.* 352:624-8 (1991).
Cole et al., Monoclonal Antibodies and Cancer Therapy, Alan R Liss, Inc., pp. 77-96 (1985).
Cook et al., The human immunoglobulin VH repertoire, *Immunol. Today.* 16:237-42 (1995).
Creighton, Proteins: Structure and Molecular Properties, W.H. Freeman & Co., San Francisco, pp. 79-86 (1983).
Cunningham et al., High-resolution epitope mapping of hGH-receptor interactions by alanin-scanning mutagenesis, *Science.* 244:1081-5 (1989).
Dall'Acqua et al., Contribution of domain interface residues to the stability of antibody CH3 domain homodimers, *Biochemistry.* 37:9266-73 (1998).
Devereux et al., A comprehensive set of sequence analysis programs for the VAX, *Nucleic Acids Res.* 12:387-95 (1984).
Duksin et al., Relationship of the structure and biological activity of the natural homologues of tunicamycin, *J. Biol. Chem.* 257:3105-3109 (1982).
Edge et al., Deglycosylation of glycoproteins by trifluoromethanesulfonic acid, *Anal. Biochem.* 118:131-7 (1981).
Eppstein et al., Biological activity of liposome-encapsulated murine interferon gamma is mediated by a cell membrane receptor, *Proc. Natl. Acad. Sci. USA.* 82:3688-92 (1985).
Fecker et al., Expression of single-chain antibody fragments (scFV) specific for beet necrotic yellow vein virus coat protein or 25 kDa protein in *Escherichia coli* and Nicotiana benthamiana, *Plant Mol. Biol.* 32:979-86 (1996).
Feng et al., Progressive sequence alignment as a prerequisite to correct phylogenetic trees, *J. Mol. Evol.* 25:351-60 (1987).
Fishwild et al., High-avidity human IGk monoclonal antibodies from a novel strain of minilocus transgenic mice, *Nature Biotechnology.* 14:845-851 (1996).
Gabizon et al., Pharmacokinetics and tissue distribution of doxorubicin encapsulated in stable liposomes with long circulation times, *J. Natl. Cancer Inst.* 81:1484-8 (1989).
George et al., Current Methods in Sequence Comparison and Analysis, Macromolecule Sequencing and Synthesis, Selected Methods and Applications, Alan R Liss, Inc., pp. 127-149 (1988).
Graham et al., Characteristics of a human cell line transformed by DNA from human adenovirus type 5, *J. Gen. Virol.* 36:59-74 (1977).
Green et al., Antigen-specific human monoclonal antibodies from mice engineered with human Ig heavy and light chain YACs, *Nat. Genet.* 7:13-21 (1994).
Green et al., Regulation of B cell development by variable gene complexity in mice reconstituted with human immunoglobulin yeast artificial chromosomes, *J. Exp. Med.* 188:483-95 (1998).
Hakimuddin et al., A chemical method for deglycosylation of proteins, *Archives of Biochemistry and Biophysics.* 259:52-57 (1987).
Harlow et al., Antibodies a Laboratory Manual, Cold Spring Harbor Laboratory (1988).
Harlow et al., Using Antibodies: A Laboratory Manual, Cold Spring Harbor Laboratory Press (1999).
Hawkins et al., Selection of phage antibodies by binding affinity mimicking affinity maturation, *J. Mol. Viol.* 226:889-896 (1992).
Heim et al., Engineering green fluorescent protein for improved brightness, longer wavelengths and fluorescence resonance energy transfer, *Curr. Biol.* 6:178-82 (1996).
Hiatt et al., Production of antibodies in transgenic plants, *Nature.* 342:76-8 (1989).
Higgins et al., Fast and sensitive multiple sequence alignments on a microcomputer, *Comput. Appl. Biosci.* 5:151-3 (1989).
Hollinger et al., "Diabodies": Small bivalent and bispecific antibody fragments, *Proc. Natl. Acad. Sci. USA.* 90:6444-6448 (1993).
Honjo et al., Immunoglobulin Genes, Academic Press, San Diego, CA (2nd ed 1995).
Huston et al., Protein engineering of antibody binding sites: recovery of specific activity in an anti-digoxin single-chain Fv analogue produced *Escherichia coli, Proc. Natl. Acad. Sci. USA.* 85:5879-83 (1988).
Hwang et al., Hepatic uptake and degradation of unilamellar sphingomyelin/cholesterol liposomes: a kinetic study, *Proc. Natl. Acad. Sci. USA.* 77:4030-4 (1980).
Hwang et al., Immunogenicity of engineered antibodies, *Methods.* 36:3-10 (2005).

(56) References Cited

OTHER PUBLICATIONS

Ichiki et al., Regulation of the expression of human C epsilon germline transcript. Identification of a novel IL-4 responsive element, *J. Immunol.* 150:5408-17 (1993).
Jones et al., Replacing the complementarity-determining regions in a human antibody with those from a mouse, *Nature.* 321:522-5 (1986).
Kabat et al., Sequences of Proteins of Immunological Interest, BBN Systems and Technologies, Cambridge MA (5th ed 1991).
Karin et al., Applications and statistics for multiple high-scoring segments in molecular sequences. *Proc. Natl. Acad. Sci. USA.* 90:5873-5787 (1993).
Kendrick et al., Physical stabilization of proteins in aqueous solution, *Pharm. Biotechnol.* 13:61-84 (2002).
Kipriyanov et al., Bispecific tandem diabody for tumor therapy with improved antigen binding and pharmacokinetics, *J. Mol. Biol.* 293:41-56 (1999).
Kohler et al., Continuous cultures of fused cells secreting antibody of predefined specificity, *Nature.* 256:495-7 (1975).
Kontermann et al., Antibody Engineering, Springer (2nd ed. 2010).
Kozbor et al., The production of monoclonal antibodies from human lymphocytes, *Immunol. Today.* 4:72-9 (1983).
Kufer et al., A revival of bispecifc antibodies, *Trends Biotechnol.* 22:238-44 (2004).
Kufer et al., Construction and biological activity of a recombinant bispecific single-chain antibody designed for therapy of minimal residual colorectal cancer, *Cancer Immunol. Immunother.* 45:193-7 (1997).
Langer et al., Biocompatibility of polymeric delivery systems for macromolecules, *J. Biomed. Mater. Res.* 15:167-277 (1981).
Langer, Controlled release of macromolecules, *Chem. Tech.* 12:98-105 (1982).
Leader et al., Protein therapeutics: a summary and pharmacological classification, *Nat. Rev. Drug. Discov.* 7:21-39 (2008).
Little, Recombinant Antibodies for Immunotherapy, Cambridge University Press (2009).
Loffler et al., A recombinant bispecific single-chain antibody, CD19 x CD3, induces rapid and high lymphoma-directed cytotoxicity by unstimulated T lymphocytes, *Blood.* 95:2098-103 (2000).
Lonberg et al., Antigen-specific human antibodies from mice comprising four distinct genetic modifications, *Nature.* 368:856-859 (1994).
Lowman et al., Selecting high-affinity binding proteins by monovalent phage display, *Biochemistry.* 30:10832-8 (1991).
MacCallum et al., Antibody-antigen interactions: contact analysis and binding site topography, *J Mol Biol.* 262:732-45 (1996).
Mack et al., A small bispecific antibody construct expressed as a functional single-chain molecule with high tumor cell cytotoxcity, *Proc. Natl. Acad. Sci. USA.* 92:7021-5 (1995).
Mack et al., Biologic properties of a bispecific single-chain antibody directed against 17-1A (EpCAM) and CD3: tumor cell-dependent T cell stimulation and cytotoxic activity, *J. Immunol.* 158:3965-70 (1997).
Mahler et al., Protein aggregation: pathways, induction factors and analysis, *J. Pharm. Sci.,* 98:2909-34 (2009).
Malmborg et al., BIAcore as a tool in antibody engineering, *J. Immunol. Methods.* 183:7-13 (1995).
Marks et al., By-passing immunization. Human antibodies from V-gene libraries displayed on phage, *J. Mol. Biol.* 222:581-97 (1991).
Martin et al., Irreversible coupling of immunoglobulin fragments to preformed vesicles. An improved method for liposome targeting, *J. Biol. Chem.* 257:286-8 (1982).
Martin et al., Protein Sequence and Structure Analysis of Antibody Variable Domains. In: Antibody Engineering Lab Manual (2010).
Martin et al., Structural families in loops of homologous proteins: automatic classification, modelling and application to antibodies, *J. Mol. Biol.* 263:800-15 (1996).
Mather et al., Culture of testicular cells in hormone-supplemented serum-free medium, *Ann. N. Y Acad. Sci.* 383:44-68 (1982).

Mather et al., Establishment and characterization of two distinct mouse testicular epithelial cell lines, *Biol. Reprod.* 23:243-52 (1980).
Mendez et al., Functional transplant of megabase human immunoglobulin loci recapitulates human antibody response in mice, *Nat. Genet.* 15:146-56 (1997).
Meyer et al., Antimicrobial preservative use in parenteral products: past and present, *J. Pharm. Sci.* 96:3155-67 (2007).
Morrison et al., Chimeric human antibody molecules: mouse antigen-binding domains with human constant region domains, *Proc. Natl. Acad. Sci. USA.* 81:6851-5 (1984).
Morrison et al., Combinatorial alanine-scanning, *Curr. Opin. Chem. Biol.* 5:302-7 (2001).
Morrison, Transfectomas provide novel chimeric antibodies, *Science.* 229:1202-7 (1985).
Needleman et al., A general method applicable to the search for similarities in the amino acid sequence of two proteins, *J.Mol. Biol.* 48:443-53 (1970).
Nolan et al., Fluorescence-activated cell analysis and sorting of viable mammalian cells based on beta-D-galactosidase activity after transduction of *Escherichia coli* lacZ, *Proc. Natl. Acad. Sci. USA.* 85:2603-7 (1988).
Oi et al., Chimeric Antibodies, *Biotechniques.* 4:214 (1986).
Olsson et al., Human-Human monoclonal antibody-producing hybridomas: Technical Aspects, *Methods Enzymol.* 92:3-16 (1983).
Osol, Remington's Pharmaceutical Sciences, Mack Publishing Company, (16th ed. 1980).
Owen et al., Synthesis of a functional anti-phytochrome single-chain Fv protein in transgenic tobacco, *Biotechnology.* 10:790-4 (1992).
Padlan, Anatomy of the antibody molecule, *Mol. Immunol.* 31:169-217 (1994).
Pearson et al., Improved tools for biological sequence comparison, *Proc. Natl. Acad. Sci. USA.* 85:2444-8 (1988).
Presta, Antibody engineering, *Curr. Opin. Biotechnol.* 3:394-8 (1992).
Raag et al., Single-chain FVs, *FASEB J.* 9:73-80 (1995).
Randolph et al., Surfactant-protein interactions, *Pharm. Biotechnol.* 13:159-75 (2002).
Reichmann et al., Reshaping human antibodies for therapy, *Nature.* 332:323-329 (1988).
Roberts, Therapeutic protein aggregation: mechanisms, design, and control, *Trends Biotechnol.* 32:372-80 (2014).
Rosenberg et al., The Pharmacology of Monoclonal Antibodies, Springer-Verlag, pp. 269-315 (1994).
Sambrook et al., Molecular Cloning: A Laboratory Manual, Cold Spring Harbor Laboratory Press, Cold Spring Harbor, New York (2001).
Schier et al., Efficient in vitro affinity maturation of phage antibodies using BIAcore guided selections, *Hum. Antibod. Hybridomas.* 7:97-105 (1996).
Schlereth et al., T-Cell activation and B-cell depletion in chimpanzees treated with a bispecific anti-CD19/anti-CD3 single-shain antibody construct, *Cancer Immunol. Immunother.* 20:1-12 (2005).
Sidman et al., Controlled release of macromolecules and pharmaceuticals from synthetic polypeptides based on glutamic acid, *Biopolymers.* 22:547-56 (1983).
Skerra et al., Assembly of a function immunoglobulin Fv fragment in *Escherichia coli, Science.* 240:1038-41 (1988).
Smith et al., Comparison of Biosequences, *Advances in Applied Mathematics.* 2:482-489 (1981).
Smith, Filamentous fusion phage: novel expression vectors that display cloned antigens on the virion surface, *Science.* 228:1315-7 (1985).
Songsivilai et al., Bispecific antibody: a tool for diagnosis and treatment of disease, *Clin. Exp. Immunol.* 79:315-21 (1990).
Stauber et al., Development and applications of enhanced green fluorescent protein mutants, *Biotechniques.* 24:462-6, 468-71 (1998).
Takeda et al., Construction of chimaeric processed immunoglobulin genes containing mouse variable and human constant region sequences, *Nature.* 314:452-4 (1985).
Taylor et al., A transgenic mouse that expresses a diversity of human sequence heavy and light chain immunoglobulins, *Nucleic Acids Research.* 20:6287-6295 (1992).

(56) References Cited

OTHER PUBLICATIONS

Taylor et al., Human immunoglobulin transgenes undergo rearrangement, somatic mutation and class switching in mice that lack endogenous IgM, *International Immunology.* 6:579-591 (1994).

Teng et al., Construction and testing of mouse-human heteromyelomas for human monoclonal antibody production, *Proc. Natl. Acad. Sci. USA.* 80:7308-12 (1983).

Thotakura et al., Enzymatic deglycosylation of glycoproteins, *Methods Enzymol.* 138:350-9 (1987).

Tomlinson et al., The repertoire of human germline VH sequences reveals about fifty groups of VH segments with different hypervariable loops, *J. Mol. Biol.* 227:776-98 (1992).

Tomlinson et al., The structural repertoire of the human V kappa domain, *EMBO J.* 14:4628-38 (1995).

Tuaillon et al. Human immunoglobulin heavy-chain minilocus recombination in transgenic mice: Gene-segment use in $\mu$ and $\gamma$ transcripts, *Proc. Natl. Acad. Sci. USA.* 90:3720-3724 (1993).

Tuaillon et al., Analysis of direct and inverted DJH rearrangments in a human Ig heavy chain transgenic minilocus, *J. Immunol.* 154:6453-6465 (1995).

Urlaub et al., Isolation of Chinese hamster cell mutants deficient in dihydrofolate reductase activity, *Proc. Natl. Acad. Sci. USA.* 77:4216-20 (1980).

Wang, Instability, Stabilization, and formulation of liquid protein pharmaceuticals, *Int. J. Pharm.* 185:129-88 (1999).

Ward et al., Binding activities of a repertoire of single immunoglobulin variable domains secreted from *Escherichia coli, Nature.* 341:544-6 (1989).

\* cited by examiner

SEQUENCE LISTING

<160> NUMBER OF SEQ ID NOS: 181

<210> SEQ ID NO 1
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VL CDR1

<400> SEQUENCE: 1

Lys Ala Ser Gln Ser Val Asp Tyr Asp Gly Asp Ser Tyr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VL CDR2

-continued

<400> SEQUENCE: 2

Asp Ala Ser Asn Leu Val Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VL CDR3

<400> SEQUENCE: 3

Gln Gln Ser Thr Glu Asp Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH CDR1

<400> SEQUENCE: 4

Ser Tyr Trp Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH CDR2

<400> SEQUENCE: 5

Gln Ile Trp Pro Gly Asp Gly Asp Thr Asn Tyr Asn Gly Lys Phe Lys
1               5                   10                  15

Gly

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH CDR3

<400> SEQUENCE: 6

Arg Glu Thr Thr Thr Val Gly Arg Tyr Tyr Tyr Ala Met Asp Tyr
1               5                   10                  15

<210> SEQ ID NO 7
<211> LENGTH: 111
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: MISC_FEATURE
<223> OTHER INFORMATION: CD19 VL

<400> SEQUENCE: 7

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 8
<211> LENGTH: 124
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 VH

<400> SEQUENCE: 8

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VH CDR1

<400> SEQUENCE: 9

Arg Tyr Thr Met His
1               5
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR2

<400> SEQUENCE: 10

Tyr Ile Asn Pro Ser Arg Gly Tyr Thr Asn Tyr Asn Gln Lys Phe Lys
1               5                   10                  15

Asp

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VH CDR3

<400> SEQUENCE: 11

Tyr Tyr Asp Asp His Tyr Cys Leu Asp Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR1

<400> SEQUENCE: 12

Arg Ala Ser Ser Ser Val Ser Tyr Met Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR2

<400> SEQUENCE: 13

Asp Thr Ser Lys Val Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL CDR3

<400> SEQUENCE: 14

Gln Gln Trp Ser Ser Asn Pro Leu Thr
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VH

<400> SEQUENCE: 15

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD3 VL

<400> SEQUENCE: 16

Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Leu Thr Phe Gly Ala Gly Thr Lys Leu Glu Leu Lys
            100                 105

<210> SEQ ID NO 17
<211> LENGTH: 504
<212> TYPE: PRT

<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19xCD3 scFv BLINCYTO incl linker and his-tag

<400> SEQUENCE: 17

```
Asp Ile Gln Leu Thr Gln Ser Pro Ala Ser Leu Ala Val Ser Leu Gly
1               5                  10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
```

```
                     370                 375                 380
Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys His His His His His His
            500

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L1 I2C

<400> SEQUENCE: 18

Gly Ser Ser Thr Gly Ala Val Thr Ser Gly Asn Tyr Pro Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L2 I2C

<400> SEQUENCE: 19

Gly Thr Lys Phe Leu Ala Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L3 I2C

<400> SEQUENCE: 20

Val Leu Trp Tyr Ser Asn Arg Trp Val
1               5

<210> SEQ ID NO 21
<211> LENGTH: 5
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: CDR-H1 I2C

<400> SEQUENCE: 21

Lys Tyr Ala Met Asn
1               5

<210> SEQ ID NO 22
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H2 I2C

<400> SEQUENCE: 22

Arg Ile Arg Ser Lys Tyr Asn Asn Tyr Ala Thr Tyr Tyr Ala Asp Ser
1               5                   10                  15

Val Lys Asp

<210> SEQ ID NO 23
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H3 I2C

<400> SEQUENCE: 23

His Gly Asn Phe Gly Asn Ser Tyr Ile Ser Tyr Trp Ala Tyr
1               5                   10

<210> SEQ ID NO 24
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH I2C

<400> SEQUENCE: 24

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110
```

Ala Tyr Trp Gly Gln Gly Thr Leu Val Thr Val Ser Ser
                115                 120                 125

<210> SEQ ID NO 25
<211> LENGTH: 109
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL I2C

<400> SEQUENCE: 25

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 26
<211> LENGTH: 249
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH-VL I2C

<400> SEQUENCE: 26

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
            165                 170                 175

Trp Val Gln Gln Lys Pro Gly Gln Ala Pro Arg Gly Leu Ile Gly Gly
        180                 185                 190

Thr Lys Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 27
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 ccVH E11

<400> SEQUENCE: 27

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120

<210> SEQ ID NO 28
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 VH E11

<400> SEQUENCE: 28

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe

-continued

```
                50                  55                  60
Gln Gly Arg Val Thr Met Thr Thr Asp Thr Ser Thr Ser Thr Ala Tyr
 65                  70                  75                  80

Met Glu Ile Arg Asn Leu Gly Gly Asp Thr Ala Val Tyr Tyr Cys
                 85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser
        115                 120

<210> SEQ ID NO 29
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HCDR1 E11

<400> SEQUENCE: 29

Asn Tyr Gly Met Asn
 1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HCDR2 E11

<400> SEQUENCE: 30

Trp Ile Asn Thr Tyr Thr Gly Glu Pro Thr Tyr Ala Asp Lys Phe Gln
 1               5                  10                  15
Gly

<210> SEQ ID NO 31
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33  HCDR3 E11

<400> SEQUENCE: 31

Trp Ser Trp Ser Asp Gly Tyr Tyr Val Tyr Phe Asp Tyr
 1               5                  10

<210> SEQ ID NO 32
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 CCVL E11

<400> SEQUENCE: 32

Asp Ile Val Met Thr Gln Ser Pro Asp Ser Leu Thr Val Ser Leu Gly
 1               5                  10                  15
```

```
Glu Arg Thr Thr Ile Asn Cys Lys Ser Ser Gln Ser Val Leu Asp Ser
            20                  25                  30

Ser Thr Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
 50                  55                  60

Pro Asp Arg Phe Ser Gly Ser Gly Ser Gly Thr Asp Phe Thr Leu Thr
 65                  70                  75                  80

Ile Asp Ser Pro Gln Pro Glu Asp Ser Ala Thr Tyr Tyr Cys Gln Gln
                85                  90                  95

Ser Ala His Phe Pro Ile Thr Phe Gly Cys Gly Thr Arg Leu Glu Ile
            100                 105                 110

Lys

<210> SEQ ID NO 33
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 VL E11

<400> SEQUENCE: 33

Asp Ile Val Met Thr Gln Ser Pro Asp Ser Leu Thr Val Ser Leu Gly
 1               5                  10                  15

Glu Arg Thr Thr Ile Asn Cys Lys Ser Ser Gln Ser Val Leu Asp Ser
            20                  25                  30

Ser Thr Asn Lys Asn Ser Leu Ala Trp Tyr Gln Gln Lys Pro Gly Gln
        35                  40                  45

Pro Pro Lys Leu Leu Leu Ser Trp Ala Ser Thr Arg Glu Ser Gly Ile
 50                  55                  60

Pro Asp Arg Phe Ser Gly Ser Gly Ser Gly Thr Asp Phe Thr Leu Thr
 65                  70                  75                  80

Ile Asp Ser Pro Gln Pro Glu Asp Ser Ala Thr Tyr Tyr Cys Gln Gln
                85                  90                  95

Ser Ala His Phe Pro Ile Thr Phe Gly Gln Gly Thr Arg Leu Glu Ile
            100                 105                 110

Lys

<210> SEQ ID NO 34
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 LCDR1 E11

<400> SEQUENCE: 34

Lys Ser Ser Gln Ser Val Leu Asp Ser Ser Thr Asn Lys Asn Ser Leu
 1               5                  10                  15

Ala

<210> SEQ ID NO 35
<211> LENGTH: 7
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 LCDR2 E11

<400> SEQUENCE: 35

Trp Ala Ser Thr Arg Glu Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 LCDR3 E11

<400> SEQUENCE: 36

Gln Gln Ser Ala His Phe Pro Ile Thr
1               5

<210> SEQ ID NO 37
<211> LENGTH: 250
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HL CC E11

<400> SEQUENCE: 37

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Ser Gly
        115                 120                 125

Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Thr Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser
        195                 200                 205
```

-continued

Gly Ser Gly Thr Asp Phe Thr Leu Thr Ile Asp Ser Pro Gln Pro Glu
        210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys
                245                 250

<210> SEQ ID NO 38
<211> LENGTH: 250
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 HL E11

<400> SEQUENCE: 38

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Lys Leu Leu Leu Ser
            180                 185                 190

Trp Ala Ser Thr Arg Glu Ser Gly Ile Pro Asp Arg Phe Ser Gly Ser
        195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 39
<211> LENGTH: 505
<212> TYPE: PRT
<213> ORGANISM: Artificial Sequence
<220> FEATURE:
<223> OTHER INFORMATION: Synthetic Polypeptide
<220> FEATURE:

<221> NAME/KEY: MISC_FEATURE
<223> OTHER INFORMATION: CD33 CC E11 HL x I2C HL Bispecific molecule

<400> SEQUENCE: 39

```
Gln Val Gln Leu Val Gln Ser Gly Ala Glu Val Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Thr Ala Val Tyr Tyr Cys
                85                  90                  95

Ala Arg Trp Ser Trp Ser Asp Gly Tyr Tyr Val Tyr Phe Asp Tyr Trp
                100                 105                 110

Gly Gln Gly Thr Ser Val Thr Val Ser Ser Gly Gly Gly Gly Ser Gly
                115                 120                 125

Gly Gly Gly Ser Gly Gly Gly Gly Ser Asp Ile Val Met Thr Gln Ser
            130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
        210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
                260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
        290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400
```

-continued

```
Thr Gln Glu Pro Ser Leu Thr Val Ser Pro Gly Thr Val Thr Leu
            405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
            450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
            485                 490                 495

Gly Gly Gly Thr Lys Leu Thr Val Leu
            500                 505

<210> SEQ ID NO 40
<211> LENGTH: 530
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 E11 HL x I2C HL

<400> SEQUENCE: 40

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Glu Ser Val Lys Val Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Lys Phe Gln Gly Arg Val Thr Met Thr Thr Asp Thr Ser Thr Ser
                85                  90                  95

Thr Ala Tyr Met Glu Ile Arg Asn Leu Gly Asp Asp Thr Ala Val
            100                 105                 110

Tyr Tyr Cys Ala Arg Trp Ser Trp Ser Asp Gly Tyr Tyr Val Tyr Phe
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Pro Asp Ser Leu Thr Val Ser Leu Gly Glu Arg Thr Thr
                165                 170                 175

Ile Asn Cys Lys Ser Ser Gln Ser Val Leu Asp Ser Ser Thr Asn Lys
            180                 185                 190

Asn Ser Leu Ala Trp Tyr Gln Gln Lys Pro Gly Gln Pro Pro Lys Leu
        195                 200                 205

Leu Leu Ser Trp Ala Ser Thr Arg Glu Ser Gly Ile Pro Asp Arg Phe
    210                 215                 220

Ser Gly Ser Gly Ser Gly Thr Asp Phe Thr Leu Thr Ile Asp Ser Pro
225                 230                 235                 240
```

```
Gln Pro Glu Asp Ser Ala Thr Tyr Tyr Cys Gln Gln Ser Ala His Phe
                245                 250                 255

Pro Ile Thr Phe Gly Gln Gly Thr Arg Leu Glu Ile Lys Ser Gly Gly
            260                 265                 270

Gly Gly Ser Glu Val Gln Leu Val Glu Ser Gly Gly Gly Leu Val Gln
        275                 280                 285

Pro Gly Gly Ser Leu Lys Leu Ser Cys Ala Ala Ser Gly Phe Thr Phe
    290                 295                 300

Asn Lys Tyr Ala Met Asn Trp Val Arg Gln Ala Pro Gly Lys Gly Leu
305                 310                 315                 320

Glu Trp Val Ala Arg Ile Arg Ser Lys Tyr Asn Asn Tyr Ala Thr Tyr
                325                 330                 335

Tyr Ala Asp Ser Val Lys Asp Arg Phe Thr Ile Ser Arg Asp Asp Ser
            340                 345                 350

Lys Asn Thr Ala Tyr Leu Gln Met Asn Asn Leu Lys Thr Glu Asp Thr
        355                 360                 365

Ala Val Tyr Tyr Cys Val Arg His Gly Asn Phe Gly Asn Ser Tyr Ile
    370                 375                 380

Ser Tyr Trp Ala Tyr Trp Gly Gln Gly Thr Leu Val Thr Val Ser Ser
385                 390                 395                 400

Gly Gly Gly Gly Ser Gly Gly Gly Ser Gly Gly Gly Ser Gln
                405                 410                 415

Thr Val Val Thr Gln Glu Pro Ser Leu Thr Val Ser Pro Gly Gly Thr
            420                 425                 430

Val Thr Leu Thr Cys Gly Ser Ser Thr Gly Ala Val Thr Ser Gly Asn
        435                 440                 445

Tyr Pro Asn Trp Val Gln Gln Lys Pro Gly Gln Ala Pro Arg Gly Leu
    450                 455                 460

Ile Gly Gly Thr Lys Phe Leu Ala Pro Gly Thr Pro Ala Arg Phe Ser
465                 470                 475                 480

Gly Ser Leu Leu Gly Gly Lys Ala Ala Leu Thr Leu Ser Gly Val Gln
                485                 490                 495

Pro Glu Asp Glu Ala Glu Tyr Tyr Cys Val Leu Trp Tyr Ser Asn Arg
            500                 505                 510

Trp Val Phe Gly Gly Gly Thr Lys Leu Thr Val Leu His His His His
        515                 520                 525

His His
    530

<210> SEQ ID NO 41
<211> LENGTH: 993
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD33 CC x I2C-scFc Bispecific HLE molecule

<400> SEQUENCE: 41

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Cys Leu Glu Trp Met
        35                  40                  45
```

Gly Trp Ile Asn Thr Tyr Thr Gly Glu Pro Thr Tyr Ala Asp Lys Phe
 50                  55                  60

Gln Gly Arg Val Thr Met Thr Thr Asp Thr Ser Thr Ser Thr Ala Tyr
 65                  70                  75                  80

Met Glu Ile Arg Asn Leu Gly Gly Asp Asp Thr Ala Val Tyr Tyr Cys
                 85                  90                  95

Ala Arg Trp Ser Trp Ser Asp Gly Tyr Val Tyr Phe Asp Tyr Trp
            100                 105                 110

Gly Gln Gly Thr Ser Val Thr Val Ser Ser Gly Gly Gly Ser Gly
            115                 120                 125

Gly Gly Gly Ser Gly Gly Gly Ser Asp Ile Val Met Thr Gln Ser
130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
            210                 215                 220

Asp Ser Ala Thr Tyr Tyr Cys Gln Gln Ser Ala His Phe Pro Ile Thr
225                 230                 235                 240

Phe Gly Cys Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
                260                 265                 270

Ser Leu Lys Leu Ser Cys Ala Ala Ser Gly Phe Thr Phe Asn Lys Tyr
                275                 280                 285

Ala Met Asn Trp Val Arg Gln Ala Pro Gly Lys Gly Leu Glu Trp Val
290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
                340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
450                 455                 460

-continued

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
            485                 490                 495

Gly Gly Gly Thr Lys Leu Thr Val Leu Gly Gly Gly Asp Lys Thr
                500                 505                 510

His Thr Cys Pro Pro Cys Pro Ala Pro Glu Leu Leu Gly Gly Pro Ser
        515                 520                 525

Val Phe Leu Phe Pro Pro Lys Pro Lys Asp Thr Leu Met Ile Ser Arg
    530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
            565                 570                 575

Lys Thr Lys Pro Cys Glu Glu Gln Tyr Gly Ser Thr Tyr Arg Cys Val
                580                 585                 590

Ser Val Leu Thr Val Leu His Gln Asp Trp Leu Asn Gly Lys Glu Tyr
        595                 600                 605

Lys Cys Lys Val Ser Asn Lys Ala Leu Pro Ala Pro Ile Glu Lys Thr
    610                 615                 620

Ile Ser Lys Ala Lys Gly Gln Pro Arg Glu Pro Gln Val Tyr Thr Leu
625                 630                 635                 640

Pro Pro Ser Arg Glu Glu Met Thr Lys Asn Gln Val Ser Leu Thr Cys
            645                 650                 655

Leu Val Lys Gly Phe Tyr Pro Ser Asp Ile Ala Val Glu Trp Glu Ser
                660                 665                 670

Asn Gly Gln Pro Glu Asn Asn Tyr Lys Thr Thr Pro Pro Val Leu Asp
        675                 680                 685

Ser Asp Gly Ser Phe Phe Leu Tyr Ser Lys Leu Thr Val Asp Lys Ser
    690                 695                 700

Arg Trp Gln Gln Gly Asn Val Phe Ser Cys Ser Val Met His Glu Ala
705                 710                 715                 720

Leu His Asn His Tyr Thr Gln Lys Ser Leu Ser Leu Ser Pro Gly Lys
            725                 730                 735

Gly Gly Gly Gly Ser Gly Gly Gly Ser Gly Gly Gly Gly Ser Gly
                740                 745                 750

Gly Gly Ser Gly Gly Gly Ser Gly Gly Gly Ser Asp Lys
    755                 760                 765

Thr His Thr Cys Pro Pro Cys Pro Ala Pro Glu Leu Leu Gly Gly Pro
770                 775                 780

Ser Val Phe Leu Phe Pro Pro Lys Pro Lys Asp Thr Leu Met Ile Ser
785                 790                 795                 800

Arg Thr Pro Glu Val Thr Cys Val Val Val Asp Val Ser His Glu Asp
            805                 810                 815

Pro Glu Val Lys Phe Asn Trp Tyr Val Asp Gly Val Glu Val His Asn
                820                 825                 830

Ala Lys Thr Lys Pro Cys Glu Glu Gln Tyr Gly Ser Thr Tyr Arg Cys
        835                 840                 845

Val Ser Val Leu Thr Val Leu His Gln Asp Trp Leu Asn Gly Lys Glu
    850                 855                 860

Tyr Lys Cys Lys Val Ser Asn Lys Ala Leu Pro Ala Pro Ile Glu Lys
865                 870                 875                 880

Thr Ile Ser Lys Ala Lys Gly Gln Pro Arg Glu Pro Gln Val Tyr Thr

```
                    885                 890                 895
Leu Pro Pro Ser Arg Glu Glu Met Thr Lys Asn Gln Val Ser Leu Thr
                900                 905                 910

Cys Leu Val Lys Gly Phe Tyr Pro Ser Asp Ile Ala Val Glu Trp Glu
            915                 920                 925

Ser Asn Gly Gln Pro Glu Asn Asn Tyr Lys Thr Thr Pro Pro Val Leu
        930                 935                 940

Asp Ser Asp Gly Ser Phe Phe Leu Tyr Ser Lys Leu Thr Val Asp Lys
945                 950                 955                 960

Ser Arg Trp Gln Gln Gly Asn Val Phe Ser Cys Ser Val Met His Glu
                965                 970                 975

Ala Leu His Asn His Tyr Thr Gln Lys Ser Leu Ser Leu Ser Pro Gly
            980                 985                 990

Lys

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VH CDR1

<400> SEQUENCE: 42

Asn Tyr Gly Met His
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VH CDR2

<400> SEQUENCE: 43

Val Ile Trp Tyr Asp Gly Ser Asp Lys Tyr Tyr Ala Asp Ser Val Arg
1               5                   10                  15
Gly

<210> SEQ ID NO 44
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VH CDR3

<400> SEQUENCE: 44

Asp Gly Tyr Asp Ile Leu Thr Gly Asn Pro Arg Asp Phe Asp Tyr
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: EGFRvIIIxCD3-scFc VL CDR1

<400> SEQUENCE: 45

Arg Ser Ser Gln Ser Leu Val His Ser Asp Gly Asn Thr Tyr Leu Ser
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VL CDR2

<400> SEQUENCE: 46

Arg Ile Ser Arg Arg Phe Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIIIxCD3-scFc VL CDR3

<400> SEQUENCE: 47

Met Gln Ser Thr His Val Pro Arg Thr
1               5

<210> SEQ ID NO 48
<211> LENGTH: 124
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc VH

<400> SEQUENCE: 48

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
                20                  25                  30

Gly Met His Trp Val Arg Gln Ala Pro Gly Lys Cys Leu Glu Trp Val
            35                  40                  45

Ala Val Ile Trp Tyr Asp Gly Ser Asp Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Ile Leu Thr Gly Asn Pro Arg Asp Phe Asp
                100                 105                 110

Tyr Trp Gly Gln Gly Thr Leu Val Thr Val Ser Ser
            115                 120
```

<210> SEQ ID NO 49
<211> LENGTH: 112
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc VL

<400> SEQUENCE: 49

```
Asp Thr Val Met Thr Gln Thr Pro Leu Ser Ser His Val Thr Leu Gly
1               5                   10                  15
Gln Pro Ala Ser Ile Ser Cys Arg Ser Gln Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Arg Ile Ser Arg Arg Phe Ser Gly Val Pro
    50                  55                  60
Asp Arg Phe Ser Gly Ser Gly Ala Gly Thr Asp Phe Thr Leu Glu Ile
65                  70                  75                  80
Ser Arg Val Glu Ala Glu Asp Val Gly Val Tyr Tyr Cys Met Gln Ser
                85                  90                  95
Thr His Val Pro Arg Thr Phe Gly Cys Gly Thr Lys Val Glu Ile Lys
            100                 105                 110
```

<210> SEQ ID NO 50
<211> LENGTH: 251
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc scFv

<400> SEQUENCE: 50

```
Gln Val Gln Leu Val Glu Ser Gly Gly Gly Val Val Gln Ser Gly Arg
1               5                   10                  15
Ser Leu Arg Leu Ser Cys Ala Ala Ser Gly Phe Thr Phe Arg Asn Tyr
            20                  25                  30
Gly Met His Trp Val Arg Gln Ala Pro Gly Lys Cys Leu Glu Trp Val
        35                  40                  45
Ala Val Ile Trp Tyr Asp Gly Ser Asp Lys Tyr Tyr Ala Asp Ser Val
    50                  55                  60
Arg Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Gly Tyr Asp Ile Leu Thr Gly Asn Pro Arg Asp Phe Asp
            100                 105                 110
Tyr Trp Gly Gln Gly Thr Leu Val Thr Val Ser Ser Gly Gly Gly Gly
        115                 120                 125
Ser Gly Gly Gly Ser Gly Gly Gly Ser Asp Thr Val Met Thr
    130                 135                 140
Gln Thr Pro Leu Ser Ser His Val Thr Leu Gly Gln Pro Ala Ser Ile
145                 150                 155                 160
Ser Cys Arg Ser Ser Gln Ser Leu Val His Ser Asp Gly Asn Thr Tyr
                165                 170                 175
```

```
Leu Ser Trp Leu Gln Gln Arg Pro Gly Gln Pro Pro Arg Leu Leu Ile
            180                 185                 190

Tyr Arg Ile Ser Arg Arg Phe Ser Gly Val Pro Asp Arg Phe Ser Gly
        195                 200                 205

Ser Gly Ala Gly Thr Asp Phe Thr Leu Glu Ile Ser Arg Val Glu Ala
    210                 215                 220

Glu Asp Val Gly Val Tyr Tyr Cys Met Gln Ser Thr His Val Pro Arg
225                 230                 235                 240

Thr Phe Gly Cys Gly Thr Lys Val Glu Ile Lys
                245                 250
```

<210> SEQ ID NO 51
<211> LENGTH: 506
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc Bispecific molecule

<400> SEQUENCE: 51

```
Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Cys Leu Glu Trp Val
        35                  40                  45

Ala Val Ile Trp Tyr Asp Gly Ser Asp Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Tyr Asp Ile Leu Thr Gly Asn Pro Arg Asp Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Asp Thr Val Met Thr
    130                 135                 140

Gln Thr Pro Leu Ser Ser His Val Thr Leu Gly Gln Pro Ala Ser Ile
145                 150                 155                 160

Ser Cys Arg Ser Ser Gln Ser Leu Val His Ser Asp Gly Asn Thr Tyr
                165                 170                 175

Leu Ser Trp Leu Gln Gln Arg Pro Gly Gln Pro Pro Arg Leu Leu Ile
            180                 185                 190

Tyr Arg Ile Ser Arg Arg Phe Ser Gly Val Pro Asp Arg Phe Ser Gly
        195                 200                 205

Ser Gly Ala Gly Thr Asp Phe Thr Leu Glu Ile Ser Arg Val Glu Ala
    210                 215                 220

Glu Asp Val Gly Val Tyr Tyr Cys Met Gln Ser Thr His Val Pro Arg
225                 230                 235                 240

Thr Phe Gly Cys Gly Thr Lys Val Glu Ile Lys Ser Gly Gly Gly Gly
                245                 250                 255

Ser Glu Val Gln Leu Val Glu Ser Gly Gly Gly Leu Val Gln Pro Gly
            260                 265                 270
```

Gly Ser Leu Lys Leu Ser Cys Ala Ala Ser Gly Phe Thr Phe Asn Lys
            275                 280                 285

Tyr Ala Met Asn Trp Val Arg Gln Ala Pro Gly Lys Gly Leu Glu Trp
290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Gly Asn Phe Gly Asn Ser Tyr Ile Ser Tyr
            355                 360                 365

Trp Ala Tyr Trp Gly Gln Gly Thr Leu Val Thr Val Ser Ser Gly Gly
            370                 375                 380

Gly Gly Ser Gly Gly Gly Ser Gly Gly Gly Ser Gln Thr Val
385                 390                 395                 400

Val Thr Gln Glu Pro Ser Leu Thr Val Ser Pro Gly Gly Thr Val Thr
                405                 410                 415

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
            435                 440                 445

Gly Thr Lys Phe Leu Ala Pro Gly Thr Pro Ala Arg Phe Ser Gly Ser
            450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
                485                 490                 495

Phe Gly Gly Gly Thr Lys Leu Thr Val Leu
            500                 505

<210> SEQ ID NO 52
<211> LENGTH: 994
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: EGFRvIII_CCxCD3-scFc Bispecific HLE molecule

<400> SEQUENCE: 52

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Arg Asn Tyr
            20                  25                  30

Gly Met His Trp Val Arg Gln Ala Pro Gly Lys Cys Leu Glu Trp Val
        35                  40                  45

Ala Val Ile Trp Tyr Asp Gly Ser Asp Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Asp Ile Leu Thr Gly Asn Pro Arg Asp Phe Asp
            100                 105                 110

-continued

```
Tyr Trp Gly Gln Gly Thr Leu Val Thr Val Ser Ser Gly Gly Gly
            115                 120                 125
Ser Gly Gly Gly Gly Ser Gly Gly Gly Ser Asp Thr Val Met Thr
    130                 135                 140
Gln Thr Pro Leu Ser Ser His Val Thr Leu Gly Gln Pro Ala Ser Ile
145                 150                 155                 160
Ser Cys Arg Ser Ser Gln Ser Leu Val His Ser Asp Gly Asn Thr Tyr
                165                 170                 175
Leu Ser Trp Leu Gln Gln Arg Pro Gly Gln Pro Pro Arg Leu Leu Ile
            180                 185                 190
Tyr Arg Ile Ser Arg Arg Phe Ser Gly Val Pro Asp Arg Phe Ser Gly
            195                 200                 205
Ser Gly Ala Gly Thr Asp Phe Thr Leu Glu Ile Ser Arg Val Glu Ala
            210                 215                 220
Glu Asp Val Gly Val Tyr Tyr Cys Met Gln Ser Thr His Val Pro Arg
225                 230                 235                 240
Thr Phe Gly Cys Gly Thr Lys Val Glu Ile Lys Ser Gly Gly Gly Gly
                245                 250                 255
Ser Glu Val Gln Leu Val Glu Ser Gly Gly Gly Leu Val Gln Pro Gly
                260                 265                 270
Gly Ser Leu Lys Leu Ser Cys Ala Ala Ser Gly Phe Thr Phe Asn Lys
            275                 280                 285
Tyr Ala Met Asn Trp Val Arg Gln Ala Pro Gly Lys Gly Leu Glu Trp
            290                 295                 300
Val Ala Arg Ile Arg Ser Lys Tyr Asn Asn Tyr Ala Thr Tyr Tyr Ala
305                 310                 315                 320
Asp Ser Val Lys Asp Arg Phe Thr Ile Ser Arg Asp Asp Ser Lys Asn
                325                 330                 335
Thr Ala Tyr Leu Gln Met Asn Asn Leu Lys Thr Glu Asp Thr Ala Val
            340                 345                 350
Tyr Tyr Cys Val Arg His Gly Asn Phe Gly Asn Ser Tyr Ile Ser Tyr
            355                 360                 365
Trp Ala Tyr Trp Gly Gln Gly Thr Leu Val Thr Val Ser Ser Gly Gly
            370                 375                 380
Gly Gly Ser Gly Gly Gly Gly Ser Gly Gly Gly Gly Ser Gln Thr Val
385                 390                 395                 400
Val Thr Gln Glu Pro Ser Leu Thr Val Ser Pro Gly Gly Thr Val Thr
                405                 410                 415
Leu Thr Cys Gly Ser Ser Thr Gly Ala Val Thr Ser Gly Asn Tyr Pro
            420                 425                 430
Asn Trp Val Gln Gln Lys Pro Gly Gln Ala Pro Arg Gly Leu Ile Gly
            435                 440                 445
Gly Thr Lys Phe Leu Ala Pro Gly Thr Pro Ala Arg Phe Ser Gly Ser
    450                 455                 460
Leu Leu Gly Gly Lys Ala Ala Leu Thr Leu Ser Gly Val Gln Pro Glu
465                 470                 475                 480
Asp Glu Ala Glu Tyr Tyr Cys Val Leu Trp Tyr Ser Asn Arg Trp Val
                485                 490                 495
Phe Gly Gly Gly Thr Lys Leu Thr Val Leu Gly Gly Gly Asp Lys
                500                 505                 510
Thr His Thr Cys Pro Pro Cys Pro Ala Pro Glu Leu Leu Gly Gly Pro
            515                 520                 525
Ser Val Phe Leu Phe Pro Pro Lys Pro Lys Asp Thr Leu Met Ile Ser
```

```
                530              535            540
Arg Thr Pro Glu Val Thr Cys Val Val Asp Val Ser His Glu Asp
545              550              555              560

Pro Glu Val Lys Phe Asn Trp Tyr Val Asp Gly Val Glu Val His Asn
                565              570              575

Ala Lys Thr Lys Pro Cys Glu Glu Gln Tyr Gly Ser Thr Tyr Arg Cys
                580              585              590

Val Ser Val Leu Thr Val Leu His Gln Asp Trp Leu Asn Gly Lys Glu
                595              600              605

Tyr Lys Cys Lys Val Ser Asn Lys Ala Leu Pro Ala Pro Ile Glu Lys
                610              615              620

Thr Ile Ser Lys Ala Lys Gly Gln Pro Arg Glu Pro Gln Val Tyr Thr
625              630              635              640

Leu Pro Pro Ser Arg Glu Glu Met Thr Lys Asn Gln Val Ser Leu Thr
                645              650              655

Cys Leu Val Lys Gly Phe Tyr Pro Ser Asp Ile Ala Val Glu Trp Glu
                660              665              670

Ser Asn Gly Gln Pro Glu Asn Asn Tyr Lys Thr Thr Pro Pro Val Leu
                675              680              685

Asp Ser Asp Gly Ser Phe Phe Leu Tyr Ser Lys Leu Thr Val Asp Lys
                690              695              700

Ser Arg Trp Gln Gln Gly Asn Val Phe Ser Cys Ser Val Met His Glu
705              710              715              720

Ala Leu His Asn His Tyr Thr Gln Lys Ser Leu Ser Leu Ser Pro Gly
                725              730              735

Lys Gly Gly Gly Gly Ser Gly Gly Gly Gly Ser Gly Gly Gly Gly Ser
                740              745              750

Gly Gly Gly Gly Ser Gly Gly Gly Ser Gly Gly Gly Gly Ser Asp
                755              760              765

Lys Thr His Thr Cys Pro Pro Cys Pro Ala Pro Glu Leu Leu Gly Gly
                770              775              780

Pro Ser Val Phe Leu Phe Pro Pro Lys Pro Lys Asp Thr Leu Met Ile
785              790              795              800

Ser Arg Thr Pro Glu Val Thr Cys Val Val Val Asp Val Ser His Glu
                805              810              815

Asp Pro Glu Val Lys Phe Asn Trp Tyr Val Asp Gly Val Glu Val His
                820              825              830

Asn Ala Lys Thr Lys Pro Cys Glu Glu Gln Tyr Gly Ser Thr Tyr Arg
                835              840              845

Cys Val Ser Val Leu Thr Val Leu His Gln Asp Trp Leu Asn Gly Lys
850              855              860

Glu Tyr Lys Cys Lys Val Ser Asn Lys Ala Leu Pro Ala Pro Ile Glu
865              870              875              880

Lys Thr Ile Ser Lys Ala Lys Gly Gln Pro Arg Glu Pro Gln Val Tyr
                885              890              895

Thr Leu Pro Pro Ser Arg Glu Glu Met Thr Lys Asn Gln Val Ser Leu
                900              905              910

Thr Cys Leu Val Lys Gly Phe Tyr Pro Ser Asp Ile Ala Val Glu Trp
                915              920              925

Glu Ser Asn Gly Gln Pro Glu Asn Asn Tyr Lys Thr Thr Pro Pro Val
                930              935              940

Leu Asp Ser Asp Gly Ser Phe Phe Leu Tyr Ser Lys Leu Thr Val Asp
945              950              955              960
```

-continued

```
Lys Ser Arg Trp Gln Gln Gly Asn Val Phe Ser Cys Ser Val Met His
            965                 970                 975
Glu Ala Leu His Asn His Tyr Thr Gln Lys Ser Leu Ser Leu Ser Pro
        980                 985                 990
Gly Lys

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VH CDR1

<400> SEQUENCE: 53

Asp Tyr Tyr Met Thr
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VH CDR2

<400> SEQUENCE: 54

Tyr Ile Ser Ser Ser Gly Ser Thr Ile Tyr Tyr Ala Asp Ser Val Lys
1               5                   10                  15
Gly

<210> SEQ ID NO 55
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VH CDR3

<400> SEQUENCE: 55

Asp Arg Asn Ser His Phe Asp Tyr
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL CDR1

<400> SEQUENCE: 56

Arg Ala Ser Gln Gly Ile Asn Thr Trp Leu Ala
1               5                   10

<210> SEQ ID NO 57
<211> LENGTH: 7
<212> TYPE: PRT
```

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL CDR2

<400> SEQUENCE: 57

Gly Ala Ser Gly Leu Gln Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL CDR3

<400> SEQUENCE: 58

Gln Gln Ala Lys Ser Phe Pro Arg Thr
1               5

<210> SEQ ID NO 59
<211> LENGTH: 117
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN _5 VH

<400> SEQUENCE: 59

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Arg Asn Ser His Phe Asp Tyr Trp Gly Gln Gly Thr Leu
            100                 105                 110

Val Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 VL

<400> SEQUENCE: 60

Asp Ile Gln Met Thr Gln Ser Pro Ser Ser Val Ser Ala Ser Val Gly

-continued

```
                1               5                  10                 15
Asp Arg Val Thr Ile Thr Cys Arg Ala Ser Gln Gly Ile Asn Thr Trp
                20                 25                 30

Leu Ala Trp Tyr Gln Gln Lys Pro Gly Lys Ala Pro Lys Leu Leu Ile
            35                 40                 45

Tyr Gly Ala Ser Gly Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ala Lys Ser Phe Pro Arg
                85                 90                 95

Thr Phe Gly Gln Gly Thr Lys Val Glu Ile Lys
               100                105
```

<210> SEQ ID NO 61
<211> LENGTH: 239
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5 scFv

<400> SEQUENCE: 61

```
Gln Val Gln Leu Val Glu Ser Gly Gly Gly Leu Val Lys Pro Gly Gly
1               5                  10                 15

Ser Leu Arg Leu Ser Cys Ala Ala Ser Gly Phe Thr Phe Ser Asp Tyr
                20                 25                 30

Tyr Met Thr Trp Ile Arg Gln Ala Pro Gly Lys Gly Leu Glu Trp Leu
            35                 40                 45

Ser Tyr Ile Ser Ser Ser Gly Ser Thr Ile Tyr Tyr Ala Asp Ser Val
        50                 55                 60

Lys Gly Arg Phe Thr Ile Ser Arg Asp Asn Ala Lys Asn Ser Leu Phe
65                 70                 75                 80

Leu Gln Met Asn Ser Leu Arg Ala Glu Asp Thr Ala Val Tyr Tyr Cys
                85                 90                 95

Ala Arg Asp Arg Asn Ser His Phe Asp Tyr Trp Gly Gln Gly Thr Leu
               100                105                110

Val Thr Val Ser Ser Gly Gly Gly Ser Gly Gly Gly Gly Ser Gly
            115                120                125

Gly Gly Gly Ser Asp Ile Gln Met Thr Gln Ser Pro Ser Ser Val Ser
130                135                140

Ala Ser Val Gly Asp Arg Val Thr Ile Thr Cys Arg Ala Ser Gln Gly
145                150                155                160

Ile Asn Thr Trp Leu Ala Trp Tyr Gln Gln Lys Pro Gly Lys Ala Pro
                165                170                175

Lys Leu Leu Ile Tyr Gly Ala Ser Gly Leu Gln Ser Gly Val Pro Ser
            180                185                190

Arg Phe Ser Gly Ser Gly Ser Gly Thr Asp Phe Thr Leu Thr Ile Ser
        195                200                205

Ser Leu Gln Pro Glu Asp Phe Ala Thr Tyr Tyr Cys Gln Gln Ala Lys
            210                215                220

Ser Phe Pro Arg Thr Phe Gly Gln Gly Thr Lys Val Glu Ile Lys
225                230                235
```

```
<210> SEQ ID NO 62
<211> LENGTH: 494
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5xI2C0 bispecific molecule

<400> SEQUENCE: 62

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Leu
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Arg Asn Ser His Phe Asp Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Asp Ile Gln Met Thr Gln Ser Pro Ser Ser Val Ser
130                 135                 140

Ala Ser Val Gly Asp Arg Val Thr Ile Thr Cys Arg Ala Ser Gln Gly
145                 150                 155                 160

Ile Asn Thr Trp Leu Ala Trp Tyr Gln Gln Lys Pro Gly Lys Ala Pro
                165                 170                 175

Lys Leu Leu Ile Tyr Gly Ala Ser Gly Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ala Lys
    210                 215                 220

Ser Phe Pro Arg Thr Phe Gly Gln Gly Thr Lys Val Glu Ile Lys Ser
225                 230                 235                 240

Gly Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
            260                 265                 270

Thr Phe Asn Lys Tyr Ala Met Asn Trp Val Arg Gln Ala Pro Gly Lys
        275                 280                 285

Gly Leu Glu Trp Val Ala Arg Ile Arg Ser Lys Tyr Asn Asn Tyr Ala
    290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
                325                 330                 335

Asp Thr Ala Val Tyr Tyr Cys Val Arg His Gly Asn Phe Gly Asn Ser
            340                 345                 350

Tyr Ile Ser Tyr Trp Ala Tyr Trp Gly Gln Gly Thr Leu Val Thr Val
```

```
                355                 360                 365
Ser Ser Gly Gly Gly Gly Ser Gly Gly Gly Ser Gly Gly Gly
    370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
                405                 410                 415

Gly Asn Tyr Pro Asn Trp Val Gln Gln Lys Pro Gly Gln Ala Pro Arg
                420                 425                 430

Gly Leu Ile Gly Gly Thr Lys Phe Leu Ala Pro Gly Thr Pro Ala Arg
                435                 440                 445

Phe Ser Gly Ser Leu Leu Gly Gly Lys Ala Ala Leu Thr Leu Ser Gly
                450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Gly Thr Lys Leu Thr Val Leu
                485                 490

<210> SEQ ID NO 63
<211> LENGTH: 982
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5xCD3-scFc Bispecific HLE molecule

<400> SEQUENCE: 63

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Thr Trp Ile Arg Gln Ala Pro Gly Lys Gly Leu Glu Trp Leu
                35                  40                  45

Ser Tyr Ile Ser Ser Ser Gly Ser Thr Ile Tyr Tyr Ala Asp Ser Val
                50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Arg Asn Ser His Phe Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Gly Ser Asp Ile Gln Met Thr Gln Ser Pro Ser Ser Val Ser
                130                 135                 140

Ala Ser Val Gly Asp Arg Val Thr Ile Thr Cys Arg Ala Ser Gln Gly
145                 150                 155                 160

Ile Asn Thr Trp Leu Ala Trp Tyr Gln Gln Lys Pro Gly Lys Ala Pro
                165                 170                 175

Lys Leu Leu Ile Tyr Gly Ala Ser Gly Leu Gln Ser Gly Val Pro Ser
                180                 185                 190

Arg Phe Ser Gly Ser Gly Ser Gly Thr Asp Phe Thr Leu Thr Ile Ser
                195                 200                 205

Ser Leu Gln Pro Glu Asp Phe Ala Thr Tyr Tyr Cys Gln Gln Ala Lys
```

```
                    210                 215                 220
Ser Phe Pro Arg Thr Phe Gly Gln Gly Thr Lys Val Glu Ile Lys Ser
225                 230                 235                 240

Gly Gly Gly Gly Ser Glu Val Gln Leu Val Glu Ser Gly Gly Gly Leu
                    245                 250                 255

Val Gln Pro Gly Gly Ser Leu Lys Leu Ser Cys Ala Ala Ser Gly Phe
                260                 265                 270

Thr Phe Asn Lys Tyr Ala Met Asn Trp Val Arg Gln Ala Pro Gly Lys
                275                 280                 285

Gly Leu Glu Trp Val Ala Arg Ile Arg Ser Lys Tyr Asn Asn Tyr Ala
            290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
                325                 330                 335

Asp Thr Ala Val Tyr Tyr Cys Val Arg His Gly Asn Phe Gly Asn Ser
                340                 345                 350

Tyr Ile Ser Tyr Trp Ala Tyr Trp Gly Gln Gly Thr Leu Val Thr Val
            355                 360                 365

Ser Ser Gly Gly Gly Gly Ser Gly Gly Gly Gly Ser Gly Gly Gly Gly
        370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
                405                 410                 415

Gly Asn Tyr Pro Asn Trp Val Gln Gln Lys Pro Gly Gln Ala Pro Arg
                420                 425                 430

Gly Leu Ile Gly Gly Thr Lys Phe Leu Ala Pro Gly Thr Pro Ala Arg
            435                 440                 445

Phe Ser Gly Ser Leu Leu Gly Gly Lys Ala Ala Leu Thr Leu Ser Gly
        450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Gly Thr Lys Leu Thr Val Leu Gly Gly
                485                 490                 495

Gly Gly Asp Lys Thr His Thr Cys Pro Pro Cys Pro Ala Pro Glu Leu
                500                 505                 510

Leu Gly Gly Pro Ser Val Phe Leu Phe Pro Pro Lys Pro Lys Asp Thr
            515                 520                 525

Leu Met Ile Ser Arg Thr Pro Glu Val Thr Cys Val Val Val Asp Val
        530                 535                 540

Ser His Glu Asp Pro Glu Val Lys Phe Asn Trp Tyr Val Asp Gly Val
545                 550                 555                 560

Glu Val His Asn Ala Lys Thr Lys Pro Cys Glu Glu Gln Tyr Gly Ser
                565                 570                 575

Thr Tyr Arg Cys Val Ser Val Leu Thr Val Leu His Gln Asp Trp Leu
                580                 585                 590

Asn Gly Lys Glu Tyr Lys Cys Lys Val Ser Asn Lys Ala Leu Pro Ala
            595                 600                 605

Pro Ile Glu Lys Thr Ile Ser Lys Ala Lys Gly Gln Pro Arg Glu Pro
        610                 615                 620

Gln Val Tyr Thr Leu Pro Pro Ser Arg Glu Glu Met Thr Lys Asn Gln
625                 630                 635                 640
```

```
Val Ser Leu Thr Cys Leu Val Lys Gly Phe Tyr Pro Ser Asp Ile Ala
            645                 650                 655

Val Glu Trp Glu Ser Asn Gly Gln Pro Glu Asn Asn Tyr Lys Thr Thr
        660                 665                 670

Pro Pro Val Leu Asp Ser Asp Gly Ser Phe Phe Leu Tyr Ser Lys Leu
        675                 680                 685

Thr Val Asp Lys Ser Arg Trp Gln Gln Gly Asn Val Phe Ser Cys Ser
690                 695                 700

Val Met His Glu Ala Leu His Asn His Tyr Thr Gln Lys Ser Leu Ser
705                 710                 715                 720

Leu Ser Pro Gly Lys Gly Gly Gly Ser Gly Gly Gly Gly Ser Gly
            725                 730                 735

Gly Gly Ser Gly Gly Gly Gly Ser Gly Gly Gly Gly Ser Gly Gly
        740                 745                 750

Gly Gly Ser Asp Lys Thr His Thr Cys Pro Pro Cys Pro Ala Pro Glu
        755                 760                 765

Leu Leu Gly Gly Pro Ser Val Phe Leu Phe Pro Pro Lys Pro Lys Asp
        770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
            805                 810                 815

Val Glu Val His Asn Ala Lys Thr Lys Pro Cys Glu Glu Gln Tyr Gly
        820                 825                 830

Ser Thr Tyr Arg Cys Val Ser Val Leu Thr Val Leu His Gln Asp Trp
        835                 840                 845

Leu Asn Gly Lys Glu Tyr Lys Cys Lys Val Ser Asn Lys Ala Leu Pro
850                 855                 860

Ala Pro Ile Glu Lys Thr Ile Ser Lys Ala Lys Gly Gln Pro Arg Glu
865                 870                 875                 880

Pro Gln Val Tyr Thr Leu Pro Pro Ser Arg Glu Met Thr Lys Asn
            885                 890                 895

Gln Val Ser Leu Thr Cys Leu Val Lys Gly Phe Tyr Pro Ser Asp Ile
        900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
            965                 970                 975

Ser Leu Ser Pro Gly Lys
            980

<210> SEQ ID NO 64
<211> LENGTH: 982
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: MSLN_5_CCxCD3-scFc Bispecific HLE molecule

<400> SEQUENCE: 64
```

-continued

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Cys Leu Glu Trp Phe
        35                  40                  45

Ser Tyr Ile Ser Ser Ser Gly Gly Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Ser His Phe Asp Tyr Trp Gly Gln Gly Thr Leu
            100                 105                 110

Val Thr Val Ser Ser Gly Gly Gly Ser Gly Gly Gly Gly Ser Gly
    115                 120                 125

Gly Gly Gly Ser Asp Ile Gln Met Thr Gln Ser Pro Ser Ser Val Ser
    130                 135                 140

Ala Ser Val Gly Asp Arg Val Thr Ile Thr Cys Arg Ala Ser Gln Asp
145                 150                 155                 160

Ile Ser Arg Trp Leu Ala Trp Tyr Gln Gln Lys Pro Gly Lys Ala Pro
            165                 170                 175

Lys Leu Leu Ile Ser Ala Ala Ser Arg Leu Gln Ser Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Ile Tyr Tyr Cys Gln Gln Ala Lys
    210                 215                 220

Ser Phe Pro Arg Thr Phe Gly Cys Gly Thr Lys Val Glu Ile Lys Ser
225                 230                 235                 240

Gly Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
            260                 265                 270

Thr Phe Asn Lys Tyr Ala Met Asn Trp Val Arg Gln Ala Pro Gly Lys
            275                 280                 285

Gly Leu Glu Trp Val Ala Arg Ile Arg Ser Lys Tyr Asn Asn Tyr Ala
    290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
            325                 330                 335

Asp Thr Ala Val Tyr Tyr Cys Val Arg His Gly Asn Phe Gly Asn Ser
            340                 345                 350

Tyr Ile Ser Tyr Trp Ala Tyr Trp Gly Gln Gly Thr Leu Val Thr Val
    355                 360                 365

Ser Ser Gly Gly Gly Gly Ser Gly Gly Gly Gly Ser Gly Gly Gly Gly
370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
            405                 410                 415

```
Gly Asn Tyr Pro Asn Trp Val Gln Gln Lys Pro Gly Gln Ala Pro Arg
            420                 425                 430

Gly Leu Ile Gly Gly Thr Lys Phe Leu Ala Pro Gly Thr Pro Ala Arg
            435                 440                 445

Phe Ser Gly Ser Leu Leu Gly Gly Lys Ala Ala Leu Thr Leu Ser Gly
450             455                 460

Val Gln Pro Glu Asp Glu Ala Glu Tyr Tyr Cys Val Leu Trp Tyr Ser
465             470                 475                 480

Asn Arg Trp Val Phe Gly Gly Gly Thr Lys Leu Thr Val Leu Gly Gly
                485                 490                 495

Gly Gly Asp Lys Thr His Thr Cys Pro Pro Cys Pro Ala Pro Glu Leu
            500                 505                 510

Leu Gly Gly Pro Ser Val Phe Leu Phe Pro Pro Lys Pro Lys Asp Thr
            515                 520                 525

Leu Met Ile Ser Arg Thr Pro Glu Val Thr Cys Val Val Val Asp Val
            530                 535                 540

Ser His Glu Asp Pro Glu Val Lys Phe Asn Trp Tyr Val Asp Gly Val
545             550                 555                 560

Glu Val His Asn Ala Lys Thr Lys Pro Cys Glu Glu Gln Tyr Gly Ser
                565                 570                 575

Thr Tyr Arg Cys Val Ser Val Leu Thr Val Leu His Gln Asp Trp Leu
            580                 585                 590

Asn Gly Lys Glu Tyr Lys Cys Lys Val Ser Asn Lys Ala Leu Pro Ala
            595                 600                 605

Pro Ile Glu Lys Thr Ile Ser Lys Ala Lys Gly Gln Pro Arg Glu Pro
610             615                 620

Gln Val Tyr Thr Leu Pro Pro Ser Arg Glu Glu Met Thr Lys Asn Gln
625             630                 635                 640

Val Ser Leu Thr Cys Leu Val Lys Gly Phe Tyr Pro Ser Asp Ile Ala
                645                 650                 655

Val Glu Trp Glu Ser Asn Gly Gln Pro Glu Asn Asn Tyr Lys Thr Thr
            660                 665                 670

Pro Pro Val Leu Asp Ser Asp Gly Ser Phe Phe Leu Tyr Ser Lys Leu
            675                 680                 685

Thr Val Asp Lys Ser Arg Trp Gln Gln Gly Asn Val Phe Ser Cys Ser
            690                 695                 700

Val Met His Glu Ala Leu His Asn His Tyr Thr Gln Lys Ser Leu Ser
705             710                 715                 720

Leu Ser Pro Gly Lys Gly Gly Gly Ser Gly Gly Gly Gly Ser Gly
                725                 730                 735

Gly Gly Gly Ser Gly Gly Gly Gly Ser Gly Gly Gly Gly Ser Gly Gly
            740                 745                 750

Gly Gly Ser Asp Lys Thr His Thr Cys Pro Pro Cys Pro Ala Pro Glu
            755                 760                 765

Leu Leu Gly Gly Pro Ser Val Phe Leu Phe Pro Pro Lys Pro Lys Asp
            770                 775                 780

Thr Leu Met Ile Ser Arg Thr Pro Glu Val Thr Cys Val Val Val Asp
785             790                 795                 800

Val Ser His Glu Asp Pro Glu Val Lys Phe Asn Trp Tyr Val Asp Gly
                805                 810                 815

Val Glu Val His Asn Ala Lys Thr Lys Pro Cys Glu Glu Gln Tyr Gly
            820                 825                 830

Ser Thr Tyr Arg Cys Val Ser Val Leu Thr Val Leu His Gln Asp Trp
```

```
                  835                 840                 845
Leu Asn Gly Lys Glu Tyr Lys Cys Lys Val Ser Asn Lys Ala Leu Pro
    850                 855                 860

Ala Pro Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H1  CDH19 65254.007

<400> SEQUENCE: 65

Ser Tyr Gly Met His
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H2  CDH19 65254.007

<400> SEQUENCE: 66

Phe Ile Trp Tyr Glu Gly Ser Asn Lys Tyr Tyr Ala Glu Ser Val Lys
1               5                   10                  15

Asp

<210> SEQ ID NO 67
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-H3  CDH19 65254.007

<400> SEQUENCE: 67

Arg Ala Gly Ile Ile Gly Thr Ile Gly Tyr Tyr Tyr Gly Met Asp Val
1               5                   10                  15
```

```
<210> SEQ ID NO 68
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L1  CDH19 65254.007

<400> SEQUENCE: 68

Ser Gly Asp Arg Leu Gly Glu Lys Tyr Thr Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L2  CDH19 65254.007

<400> SEQUENCE: 69

Gln Asp Thr Lys Arg Pro Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDR-L3  CDH19 65254.007

<400> SEQUENCE: 70

Gln Ala Trp Glu Ser Ser Thr Val Val
1               5

<210> SEQ ID NO 71
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH  CDH19 65254.007

<400> SEQUENCE: 71

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser
        115                 120                 125

<210> SEQ ID NO 72
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL  CDH19 65254.007

<400> SEQUENCE: 72

Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Glu Lys Tyr Thr
            20                  25                  30

Ser Trp Tyr Gln Gln Arg Pro Gly Gln Ser Pro Leu Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Glu Ser Ser Thr Val Val
                85                  90                  95

Phe Gly Gly Gly Thr Lys Leu Thr Val Leu Ser
            100                 105

<210> SEQ ID NO 73
<211> LENGTH: 247
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH-VL  CDH19 65254.007

<400> SEQUENCE: 73

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Thr Val Val Phe Gly Gly Gly
225                 230                 235                 240

Thr Lys Leu Thr Val Leu Ser
                245

<210> SEQ ID NO 74
<211> LENGTH: 507
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007 x I2C

<400> SEQUENCE: 74

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Thr Val Val Phe Gly Gly Gly
225                 230                 235                 240

Thr Lys Leu Thr Val Leu Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Ala Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu His His His His His
            500                 505

<210> SEQ ID NO 75
<211> LENGTH: 989
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007 x I2C -scFc Bispecific HLE
      molecule

<400> SEQUENCE: 75

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                85                  90                  95
Ala Arg Arg Ala Gly Ile Ile Gly Thr Ile Gly Tyr Tyr Gly Met
            100                 105                 110
Asp Val Trp Gly Gln Gly Thr Thr Val Thr Val Ser Ser Gly Gly Gly
            115                 120                 125
Gly Ser Gly Gly Gly Gly Ser Gly Gly Gly Ser Ser Tyr Glu Leu
        130                 135                 140
Thr Gln Pro Pro Ser Val Ser Val Ser Pro Gly Gln Thr Ala Ser Ile
145                 150                 155                 160
Thr Cys Ser Gly Asp Arg Leu Gly Glu Lys Tyr Thr Ser Trp Tyr Gln
                165                 170                 175
Gln Arg Pro Gly Gln Ser Pro Leu Leu Val Ile Tyr Gln Asp Thr Lys
            180                 185                 190
Arg Pro Ser Gly Ile Pro Glu Arg Phe Ser Gly Ser Asn Ser Gly Asn
            195                 200                 205
Thr Ala Thr Leu Thr Ile Ser Gly Thr Gln Ala Met Asp Glu Ala Asp
        210                 215                 220
Tyr Tyr Cys Gln Ala Trp Glu Ser Ser Thr Val Val Phe Gly Gly Gly
225                 230                 235                 240
Thr Lys Leu Thr Val Leu Ser Gly Gly Gly Ser Glu Val Gln Leu
                245                 250                 255
Val Glu Ser Gly Gly Gly Leu Val Gln Pro Gly Gly Ser Leu Lys Leu
            260                 265                 270
Ser Cys Ala Ala Ser Gly Phe Thr Phe Asn Lys Tyr Ala Met Asn Trp
            275                 280                 285
Val Arg Gln Ala Pro Gly Lys Gly Leu Glu Trp Val Ala Arg Ile Arg
        290                 295                 300
Ser Lys Tyr Asn Asn Tyr Ala Thr Tyr Tyr Ala Asp Ser Val Lys Asp
305                 310                 315                 320
Arg Phe Thr Ile Ser Arg Asp Asp Ser Lys Asn Thr Ala Tyr Leu Gln
                325                 330                 335
Met Asn Asn Leu Lys Thr Glu Asp Thr Ala Val Tyr Tyr Cys Val Arg
            340                 345                 350
His Gly Asn Phe Gly Asn Ser Tyr Ile Ser Tyr Trp Ala Tyr Trp Gly
            355                 360                 365
Gln Gly Thr Leu Val Thr Val Ser Ser Gly Gly Gly Ser Gly Gly
        370                 375                 380
Gly Gly Ser Gly Gly Gly Ser Gln Thr Val Val Thr Gln Glu Pro
385                 390                 395                 400
Ser Leu Thr Val Ser Pro Gly Gly Thr Val Thr Leu Thr Cys Gly Ser
                405                 410                 415
Ser Thr Gly Ala Val Thr Ser Gly Asn Tyr Pro Asn Trp Val Gln Gln
            420                 425                 430
Lys Pro Gly Gln Ala Pro Arg Gly Leu Ile Gly Gly Thr Lys Phe Leu
        435                 440                 445
Ala Pro Gly Thr Pro Ala Arg Phe Ser Gly Ser Leu Leu Gly Gly Lys
            450                 455                 460
Ala Ala Leu Thr Leu Ser Gly Val Gln Pro Glu Asp Glu Ala Glu Tyr
465                 470                 475                 480
Tyr Cys Val Leu Trp Tyr Ser Asn Arg Trp Val Phe Gly Gly Gly Thr
                485                 490                 495
```

-continued

```
Lys Leu Thr Val Leu Gly Gly Gly Asp Lys Thr His Thr Cys Pro
            500                 505                 510
Pro Cys Pro Ala Pro Glu Leu Leu Gly Gly Pro Ser Val Phe Leu Phe
        515                 520                 525
Pro Pro Lys Pro Lys Asp Thr Leu Met Ile Ser Arg Thr Pro Glu Val
        530                 535                 540
Thr Cys Val Val Val Asp Val Ser His Glu Asp Pro Glu Val Lys Phe
545                 550                 555                 560
Asn Trp Tyr Val Asp Gly Val Glu Val His Asn Ala Lys Thr Lys Pro
                565                 570                 575
Cys Glu Glu Gln Tyr Gly Ser Thr Tyr Arg Cys Val Ser Val Leu Thr
            580                 585                 590
Val Leu His Gln Asp Trp Leu Asn Gly Lys Glu Tyr Lys Cys Lys Val
        595                 600                 605
Ser Asn Lys Ala Leu Pro Ala Pro Ile Glu Lys Thr Ile Ser Lys Ala
        610                 615                 620
Lys Gly Gln Pro Arg Glu Pro Gln Val Tyr Thr Leu Pro Pro Ser Arg
625                 630                 635                 640
Glu Glu Met Thr Lys Asn Gln Val Ser Leu Thr Cys Leu Val Lys Gly
                645                 650                 655
Phe Tyr Pro Ser Asp Ile Ala Val Glu Trp Glu Ser Asn Gly Gln Pro
            660                 665                 670
Glu Asn Asn Tyr Lys Thr Thr Pro Pro Val Leu Asp Ser Asp Gly Ser
        675                 680                 685
Phe Phe Leu Tyr Ser Lys Leu Thr Val Asp Lys Ser Arg Trp Gln Gln
        690                 695                 700
Gly Asn Val Phe Ser Cys Ser Val Met His Glu Ala Leu His Asn His
705                 710                 715                 720
Tyr Thr Gln Lys Ser Leu Ser Leu Ser Pro Gly Lys Gly Gly Gly Gly
                725                 730                 735
Ser Gly Gly Gly Gly Ser Gly Gly Gly Gly Ser Gly Gly Gly Gly Ser
            740                 745                 750
Gly Gly Gly Gly Ser Gly Gly Gly Ser Asp Lys Thr His Thr Cys
        755                 760                 765
Pro Pro Cys Pro Ala Pro Glu Leu Leu Gly Gly Pro Ser Val Phe Leu
        770                 775                 780
Phe Pro Pro Lys Pro Lys Asp Thr Leu Met Ile Ser Arg Thr Pro Glu
785                 790                 795                 800
Val Thr Cys Val Val Val Asp Val Ser His Glu Asp Pro Glu Val Lys
                805                 810                 815
Phe Asn Trp Tyr Val Asp Gly Val Glu Val His Asn Ala Lys Thr Lys
            820                 825                 830
Pro Cys Glu Glu Gln Tyr Gly Ser Thr Tyr Arg Cys Val Ser Val Leu
        835                 840                 845
Thr Val Leu His Gln Asp Trp Leu Asn Gly Lys Glu Tyr Lys Cys Lys
        850                 855                 860
Val Ser Asn Lys Ala Leu Pro Ala Pro Ile Glu Lys Thr Ile Ser Lys
865                 870                 875                 880
Ala Lys Gly Gln Pro Arg Glu Pro Gln Val Tyr Thr Leu Pro Pro Ser
                885                 890                 895
Arg Glu Glu Met Thr Lys Asn Gln Val Ser Leu Thr Cys Leu Val Lys
            900                 905                 910
```

```
Gly Phe Tyr Pro Ser Asp Ile Ala Val Glu Trp Glu Ser Asn Gly Gln
            915                 920                 925

Pro Glu Asn Asn Tyr Lys Thr Thr Pro Pro Val Leu Asp Ser Asp Gly
        930                 935                 940

Ser Phe Phe Leu Tyr Ser Lys Leu Thr Val Asp Lys Ser Arg Trp Gln
945                 950                 955                 960

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 76
<211> LENGTH: 987
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007 x I2C -scFc_delGK Bispecific
      HLE molecule

<400> SEQUENCE: 76

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
    210                 215                 220

Tyr Tyr Cys Gln Ala Trp Glu Ser Ser Thr Val Val Phe Gly Gly Gly
225                 230                 235                 240

Thr Lys Leu Thr Val Leu Ser Gly Gly Gly Gly Ser Glu Val Gln Leu
                245                 250                 255

Val Glu Ser Gly Gly Gly Leu Val Gln Pro Gly Gly Ser Leu Lys Leu
            260                 265                 270
```

```
Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
                340                 345                 350

His Gly Asn Phe Gly Asn Ser Tyr Ile Ser Tyr Trp Ala Tyr Trp Gly
                355                 360                 365

Gln Gly Thr Leu Val Thr Val Ser Ser Gly Gly Gly Ser Gly Gly
            370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
                420                 425                 430

Lys Pro Gly Gln Ala Pro Arg Gly Leu Ile Gly Gly Thr Lys Phe Leu
                435                 440                 445

Ala Pro Gly Thr Pro Ala Arg Phe Ser Gly Ser Leu Leu Gly Gly Lys
                450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu Gly Gly Gly Asp Lys Thr His Thr Cys Pro
                500                 505                 510

Pro Cys Pro Ala Pro Glu Leu Leu Gly Gly Pro Ser Val Phe Leu Phe
            515                 520                 525

Pro Pro Lys Pro Lys Asp Thr Leu Met Ile Ser Arg Thr Pro Glu Val
            530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Cys Glu Glu Gln Tyr Gly Ser Thr Tyr Arg Cys Val Ser Val Leu Thr
                580                 585                 590

Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
            610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
            675                 680                 685
```

```
Phe Phe Leu Tyr Ser Lys Leu Thr Val Asp Lys Ser Arg Trp Gln Gln
            690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Gly Gly Ser Gly
                725                 730                 735

Gly Gly Gly Ser Gly Gly Gly Ser Gly Gly Gly Ser Gly Gly
            740                 745                 750

Gly Gly Ser Gly Gly Gly Ser Asp Lys Thr His Thr Cys Pro Pro
            755                 760                 765

Cys Pro Ala Pro Glu Leu Leu Gly Gly Pro Ser Val Phe Leu Phe Pro
770                 775                 780

Pro Lys Pro Lys Asp Thr Leu Met Ile Ser Arg Thr Pro Glu Val Thr
785                 790                 795                 800

Cys Val Val Val Asp Val Ser His Glu Asp Pro Glu Val Lys Phe Asn
                805                 810                 815

Trp Tyr Val Asp Gly Val Glu Val His Asn Ala Lys Thr Lys Pro Cys
                820                 825                 830

Glu Glu Gln Tyr Gly Ser Thr Tyr Arg Cys Val Ser Val Leu Thr Val
            835                 840                 845

Leu His Gln Asp Trp Leu Asn Gly Lys Glu Tyr Lys Cys Lys Val Ser
850                 855                 860

Asn Lys Ala Leu Pro Ala Pro Ile Glu Lys Thr Ile Ser Lys Ala Lys
865                 870                 875                 880

Gly Gln Pro Arg Glu Pro Gln Val Tyr Thr Leu Pro Pro Ser Arg Glu
                885                 890                 895

Glu Met Thr Lys Asn Gln Val Ser Leu Thr Cys Leu Val Lys Gly Phe
            900                 905                 910

Tyr Pro Ser Asp Ile Ala Val Glu Trp Glu Ser Asn Gly Gln Pro Glu
            915                 920                 925

Asn Asn Tyr Lys Thr Thr Pro Pro Val Leu Asp Ser Asp Gly Ser Phe
            930                 935                 940

Phe Leu Tyr Ser Lys Leu Thr Val Asp Lys Ser Arg Trp Gln Gln Gly
945                 950                 955                 960

Asn Val Phe Ser Cys Ser Val Met His Glu Ala Leu His Asn His Tyr
                965                 970                 975

Thr Gln Lys Ser Leu Ser Leu Ser Pro Gly Lys
            980                 985

<210> SEQ ID NO 77
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C -scFc VH

<400> SEQUENCE: 77

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45
```

```
Ala Phe Ile Trp Tyr Glu Gly Ser Asn Lys Tyr Tyr Ala Glu Ser Val
 50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Gly Ile Ile Gly Thr Ile Gly Tyr Tyr Gly Met
                100                 105                 110

Asp Val Trp Gly Gln Gly Thr Thr Val Thr Val Ser Ser
            115                 120                 125

<210> SEQ ID NO 78
<211> LENGTH: 106
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C -scFc VL

<400> SEQUENCE: 78

Ser Tyr Glu Leu Thr Gln Pro Pro Ser Val Ser Val Ser Pro Gly Gln
 1                5                  10                  15

Thr Ala Ser Ile Thr Cys Ser Gly Asp Arg Leu Gly Glu Lys Tyr Thr
                 20                  25                  30

Ser Trp Tyr Gln Gln Arg Pro Gly Gln Ser Pro Leu Leu Val Ile Tyr
             35                  40                  45

Gln Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Glu Ser Ser Thr Val Val
                 85                  90                  95

Phe Gly Cys Gly Thr Lys Leu Thr Val Leu
                100                 105

<210> SEQ ID NO 79
<211> LENGTH: 246
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C -scFc scFv

<400> SEQUENCE: 79

Gln Val Gln Leu Val Glu Ser Gly Gly Gly Val Val Gln Pro Gly Gly
 1                5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Cys Leu Glu Trp Val
             35                  40                  45

Ala Phe Ile Trp Tyr Glu Gly Ser Asn Lys Tyr Tyr Ala Glu Ser Val
 50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
            115                 120                 125

Gly Ser Gly Gly Gly Gly Ser Gly Gly Gly Ser Ser Tyr Glu Leu
        130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
            195                 200                 205

Thr Ala Thr Leu Thr Ile Ser Gly Thr Gln Ala Met Asp Glu Ala Asp
210                 215                 220

Tyr Tyr Cys Gln Ala Trp Glu Ser Ser Thr Val Val Phe Gly Cys Gly
225                 230                 235                 240

Thr Lys Leu Thr Val Leu
            245

<210> SEQ ID NO 80
<211> LENGTH: 501
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C -scFc Bispecific
      molecule

<400> SEQUENCE: 80

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
            115                 120                 125

Gly Ser Gly Gly Gly Gly Ser Gly Gly Gly Ser Ser Tyr Glu Leu
        130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys

```
                180               185               190
Arg Pro Ser Gly Ile Pro Glu Arg Phe Ser Gly Ser Asn Ser Gly Asn
            195               200               205

Thr Ala Thr Leu Thr Ile Ser Gly Thr Gln Ala Met Asp Glu Ala Asp
210               215               220

Tyr Tyr Cys Gln Ala Trp Glu Ser Ser Thr Val Val Phe Gly Cys Gly
225               230               235               240

Thr Lys Leu Thr Val Leu Ser Gly Gly Gly Ser Glu Val Gln Leu
                245               250               255

Val Glu Ser Gly Gly Gly Leu Val Gln Pro Gly Gly Ser Leu Lys Leu
            260               265               270

Ser Cys Ala Ala Ser Gly Phe Thr Phe Asn Lys Tyr Ala Met Asn Trp
        275               280               285

Val Arg Gln Ala Pro Gly Lys Gly Leu Glu Trp Val Ala Arg Ile Arg
            290               295               300

Ser Lys Tyr Asn Asn Tyr Ala Thr Tyr Tyr Ala Asp Ser Val Lys Asp
305               310               315               320

Arg Phe Thr Ile Ser Arg Asp Asp Ser Lys Asn Thr Ala Tyr Leu Gln
                325               330               335

Met Asn Asn Leu Lys Thr Glu Asp Thr Ala Val Tyr Tyr Cys Val Arg
            340               345               350

His Gly Asn Phe Gly Asn Ser Tyr Ile Ser Tyr Trp Ala Tyr Trp Gly
        355               360               365

Gln Gly Thr Leu Val Thr Val Ser Ser Gly Gly Gly Gly Ser Gly Gly
    370               375               380

Gly Gly Ser Gly Gly Gly Gly Ser Gln Thr Val Val Thr Gln Glu Pro
385               390               395               400

Ser Leu Thr Val Ser Pro Gly Gly Thr Val Thr Leu Thr Cys Gly Ser
                405               410               415

Ser Thr Gly Ala Val Thr Ser Gly Asn Tyr Pro Asn Trp Val Gln Gln
            420               425               430

Lys Pro Gly Gln Ala Pro Arg Gly Leu Ile Gly Gly Thr Lys Phe Leu
        435               440               445

Ala Pro Gly Thr Pro Ala Arg Phe Ser Gly Ser Leu Leu Gly Gly Lys
    450               455               460

Ala Ala Leu Thr Leu Ser Gly Val Gln Pro Glu Asp Glu Ala Glu Tyr
465               470               475               480

Tyr Cys Val Leu Trp Tyr Ser Asn Arg Trp Val Phe Gly Gly Gly Thr
                485               490               495

Lys Leu Thr Val Leu
            500

<210> SEQ ID NO 81
<211> LENGTH: 989
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C -scFc Bispecific HLE
      molecule

<400> SEQUENCE: 81

Gln Val Gln Leu Val Glu Ser Gly Gly Gly Val Val Gln Pro Gly Gly
1               5                   10                  15
```

-continued

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Tyr Ala Glu Ser Val
 50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Ser Ser Tyr Glu Leu
        130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
            165                 170                 175

Gln Arg Pro Gly Gln Ser Pro Leu Leu Val Ile Tyr Gln Asp Thr Lys
        180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
210                 215                 220

Tyr Tyr Cys Gln Ala Trp Glu Ser Ser Thr Val Val Phe Gly Cys Gly
225                 230                 235                 240

Thr Lys Leu Thr Val Leu Ser Gly Gly Gly Ser Glu Val Gln Leu
            245                 250                 255

Val Glu Ser Gly Gly Gly Leu Val Gln Pro Gly Gly Ser Leu Lys Leu
        260                 265                 270

Ser Cys Ala Ala Ser Gly Phe Thr Phe Asn Lys Tyr Ala Met Asn Trp
        275                 280                 285

Val Arg Gln Ala Pro Gly Lys Gly Leu Glu Trp Val Ala Arg Ile Arg
        290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
        340                 345                 350

His Gly Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Ser Gly Gly
        370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
```

```
            435                 440                 445
Ala Pro Gly Thr Pro Ala Arg Phe Ser Gly Ser Leu Leu Gly Gly Lys
450                     455                 460

Ala Ala Leu Thr Leu Ser Gly Val Gln Pro Glu Asp Glu Ala Glu Tyr
465                     470                 475                 480

Tyr Cys Val Leu Trp Tyr Ser Asn Arg Trp Val Phe Gly Gly Gly Thr
                    485                 490                 495

Lys Leu Thr Val Leu Gly Gly Gly Asp Lys Thr His Thr Cys Pro
                500                 505                 510

Pro Cys Pro Ala Pro Glu Leu Leu Gly Gly Pro Ser Val Phe Leu Phe
            515                 520                 525

Pro Pro Lys Pro Lys Asp Thr Leu Met Ile Ser Arg Thr Pro Glu Val
        530                 535                 540

Thr Cys Val Val Val Asp Val Ser His Glu Asp Pro Glu Val Lys Phe
545                     550                 555                 560

Asn Trp Tyr Val Asp Gly Val Glu Val His Asn Ala Lys Thr Lys Pro
                    565                 570                 575

Cys Glu Glu Gln Tyr Gly Ser Thr Tyr Arg Cys Val Ser Val Leu Thr
                580                 585                 590

Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
610                     615                 620

Lys Gly Gln Pro Arg Glu Pro Gln Val Tyr Thr Leu Pro Pro Ser Arg
625                     630                 635                 640

Glu Glu Met Thr Lys Asn Gln Val Ser Leu Thr Cys Leu Val Lys Gly
                    645                 650                 655

Phe Tyr Pro Ser Asp Ile Ala Val Glu Trp Glu Ser Asn Gly Gln Pro
                660                 665                 670

Glu Asn Asn Tyr Lys Thr Thr Pro Pro Val Leu Asp Ser Asp Gly Ser
            675                 680                 685

Phe Phe Leu Tyr Ser Lys Leu Thr Val Asp Lys Ser Arg Trp Gln Gln
        690                 695                 700

Gly Asn Val Phe Ser Cys Ser Val Met His Glu Ala Leu His Asn His
705                     710                 715                 720

Tyr Thr Gln Lys Ser Leu Ser Leu Ser Pro Gly Lys Gly Gly Gly Gly
                    725                 730                 735

Ser Gly Gly Gly Gly Ser Gly Gly Gly Ser Gly Gly Gly Gly Ser
                740                 745                 750

Gly Gly Gly Gly Ser Gly Gly Gly Ser Asp Lys Thr His Thr Cys
            755                 760                 765

Pro Pro Cys Pro Ala Pro Glu Leu Leu Gly Gly Pro Ser Val Phe Leu
        770                 775                 780

Phe Pro Pro Lys Pro Lys Asp Thr Leu Met Ile Ser Arg Thr Pro Glu
785                     790                 795                 800

Val Thr Cys Val Val Val Asp Val Ser His Glu Asp Pro Glu Val Lys
                    805                 810                 815

Phe Asn Trp Tyr Val Asp Gly Val Glu Val His Asn Ala Lys Thr Lys
                820                 825                 830

Pro Cys Glu Glu Gln Tyr Gly Ser Thr Tyr Arg Cys Val Ser Val Leu
            835                 840                 845

Thr Val Leu His Gln Asp Trp Leu Asn Gly Lys Glu Tyr Lys Cys Lys
        850                 855                 860
```

```
Val Ser Asn Lys Ala Leu Pro Ala Pro Ile Glu Lys Thr Ile Ser Lys
865                 870                 875                 880

Ala Lys Gly Gln Pro Arg Glu Pro Gln Val Tyr Thr Leu Pro Pro Ser
                885                 890                 895

Arg Glu Glu Met Thr Lys Asn Gln Val Ser Leu Thr Cys Leu Val Lys
            900                 905                 910

Gly Phe Tyr Pro Ser Asp Ile Ala Val Glu Trp Glu Ser Asn Gly Gln
        915                 920                 925

Pro Glu Asn Asn Tyr Lys Thr Thr Pro Pro Val Leu Asp Ser Asp Gly
    930                 935                 940

Ser Phe Phe Leu Tyr Ser Lys Leu Thr Val Asp Lys Ser Arg Trp Gln
945                 950                 955                 960

Gln Gly Asn Val Phe Ser Cys Ser Val Met His Glu Ala Leu His Asn
                965                 970                 975

His Tyr Thr Gln Lys Ser Leu Ser Leu Ser Pro Gly Lys
            980                 985

<210> SEQ ID NO 82
<211> LENGTH: 987
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH19 65254.007_CC x I2C -scFc_delGK Bispecific
      HLE molecule

<400> SEQUENCE: 82

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Phe Ile Trp Tyr Glu Gly Ser Asn Lys Tyr Ala Glu Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly Ile Ile Gly Thr Ile Gly Tyr Tyr Tyr Gly Met
            100                 105                 110

Asp Val Trp Gly Gln Gly Thr Thr Val Thr Val Ser Ser Gly Gly Gly
        115                 120                 125

Gly Ser Gly Gly Gly Gly Ser Gly Gly Gly Gly Ser Ser Tyr Glu Leu
    130                 135                 140

Thr Gln Pro Pro Ser Val Ser Val Ser Pro Gly Gln Thr Ala Ser Ile
145                 150                 155                 160

Thr Cys Ser Gly Asp Arg Leu Gly Glu Lys Tyr Thr Ser Trp Tyr Gln
                165                 170                 175

Gln Arg Pro Gly Gln Ser Pro Leu Leu Val Ile Tyr Gln Asp Thr Lys
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Met Asp Glu Ala Asp
```

```
            210                 215                 220
Tyr Tyr Cys Gln Ala Trp Glu Ser Ser Thr Val Val Phe Gly Cys Gly
225                 230                 235                 240

Thr Lys Leu Thr Val Leu Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Met Asn Trp
                275                 280                 285

Val Arg Gln Ala Pro Gly Lys Gly Leu Glu Trp Val Ala Arg Ile Arg
            290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
                340                 345                 350

His Gly Asn Phe Gly Asn Ser Tyr Ile Ser Tyr Trp Ala Tyr Trp Gly
            355                 360                 365

Gln Gly Thr Leu Val Thr Val Ser Ser Gly Gly Gly Ser Gly Gly
            370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Ala Pro Gly Thr Pro Ala Arg Phe Ser Gly Ser Leu Leu Gly Gly Lys
            450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
                485                 490                 495

Lys Leu Thr Val Leu Gly Gly Gly Gly Asp Lys Thr His Thr Cys Pro
                500                 505                 510

Pro Cys Pro Ala Pro Glu Leu Leu Gly Gly Pro Ser Val Phe Leu Phe
            515                 520                 525

Pro Pro Lys Pro Lys Asp Thr Leu Met Ile Ser Arg Thr Pro Glu Val
            530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
            610                 615                 620

Lys Gly Gln Pro Arg Glu Pro Gln Val Tyr Thr Leu Pro Pro Ser Arg
625                 630                 635                 640
```

```
Glu Glu Met Thr Lys Asn Gln Val Ser Leu Thr Cys Leu Val Lys Gly
            645                 650                 655
Phe Tyr Pro Ser Asp Ile Ala Val Glu Trp Glu Ser Asn Gly Gln Pro
            660                 665                 670
Glu Asn Asn Tyr Lys Thr Thr Pro Pro Val Leu Asp Ser Asp Gly Ser
            675                 680                 685
Phe Phe Leu Tyr Ser Lys Leu Thr Val Asp Lys Ser Arg Trp Gln Gln
            690                 695                 700
Gly Asn Val Phe Ser Cys Ser Val Met His Glu Ala Leu His Asn His
705                 710                 715                 720
Tyr Thr Gln Lys Ser Leu Ser Leu Ser Pro Gly Gly Gly Gly Ser Gly
            725                 730                 735
Gly Gly Gly Ser Gly Gly Gly Ser Gly Gly Gly Gly Ser Gly Gly
            740                 745                 750
Gly Gly Ser Gly Gly Gly Gly Ser Asp Lys Thr His Thr Cys Pro Pro
            755                 760                 765
Cys Pro Ala Pro Glu Leu Leu Gly Gly Pro Ser Val Phe Leu Phe Pro
            770                 775                 780
Pro Lys Pro Lys Asp Thr Leu Met Ile Ser Arg Thr Pro Glu Val Thr
785                 790                 795                 800
Cys Val Val Val Asp Val Ser His Glu Asp Pro Glu Val Lys Phe Asn
            805                 810                 815
Trp Tyr Val Asp Gly Val Glu Val His Asn Ala Lys Thr Lys Pro Cys
            820                 825                 830
Glu Glu Gln Tyr Gly Ser Thr Tyr Arg Cys Val Ser Val Leu Thr Val
            835                 840                 845
Leu His Gln Asp Trp Leu Asn Gly Lys Glu Tyr Lys Cys Lys Val Ser
850                 855                 860
Asn Lys Ala Leu Pro Ala Pro Ile Glu Lys Thr Ile Ser Lys Ala Lys
865                 870                 875                 880
Gly Gln Pro Arg Glu Pro Gln Val Tyr Thr Leu Pro Pro Ser Arg Glu
            885                 890                 895
Glu Met Thr Lys Asn Gln Val Ser Leu Thr Cys Leu Val Lys Gly Phe
            900                 905                 910
Tyr Pro Ser Asp Ile Ala Val Glu Trp Glu Ser Asn Gly Gln Pro Glu
            915                 920                 925
Asn Asn Tyr Lys Thr Thr Pro Pro Val Leu Asp Ser Asp Gly Ser Phe
930                 935                 940
Phe Leu Tyr Ser Lys Leu Thr Val Asp Lys Ser Arg Trp Gln Gln Gly
945                 950                 955                 960
Asn Val Phe Ser Cys Ser Val Met His Glu Ala Leu His Asn His Tyr
            965                 970                 975
Thr Gln Lys Ser Leu Ser Leu Ser Pro Gly Lys
            980                 985
```

<210> SEQ ID NO 83
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH CDR1

<400> SEQUENCE: 83

Asn Ala Arg Met Gly Val Ser
1               5

<210> SEQ ID NO 84
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH CDR2

<400> SEQUENCE: 84

His Ile Phe Ser Asn Asp Glu Lys Ser Tyr Ser Thr Ser Leu Lys Asn
1               5                   10                  15

<210> SEQ ID NO 85
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH CDR3

<400> SEQUENCE: 85

Ile Val Gly Tyr Gly Ser Gly Trp Tyr Gly Phe Phe Asp Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VL CDR1

<400> SEQUENCE: 86

Arg Ala Ser Gln Gly Ile Arg Asn Asp Leu Gly
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VL CDR2

<400> SEQUENCE: 87

Ala Ala Ser Thr Leu Gln Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VL CDR3

<400> SEQUENCE: 88

Leu Gln His Asn Ser Tyr Pro Leu Thr
1               5

<210> SEQ ID NO 89
<211> LENGTH: 124
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc VH

<400> SEQUENCE: 89

Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Gly Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
    50                  55                  60

Leu Lys Asn Arg Leu Thr Ile Ser Lys Asp Ser Ser Lys Thr Gln Val
65                  70                  75                  80

Val Leu Thr Met Thr Asn Val Asp Pro Val Asp Thr Ala Thr Tyr Tyr
                85                  90                  95

Cys Ala Arg Ile Val Gly Tyr Gly Ser Gly Trp Tyr Gly Phe Phe Asp
            100                 105                 110

Tyr Trp Gly Gln Gly Thr Leu Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_ A8-scFc VL

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Cys Gly Thr Lys Val Glu Ile Lys
            100                 105

<210> SEQ ID NO 91
<211> LENGTH: 246

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3- scFv

<400> SEQUENCE: 91
```

Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Gly Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
    50                  55                  60

Leu Lys Asn Arg Leu Thr Ile Ser Lys Asp Ser Ser Lys Thr Gln Val
65                  70                  75                  80

Val Leu Thr Met Thr Asn Val Asp Pro Val Asp Thr Ala Thr Tyr Tyr
            85                  90                  95

Cys Ala Arg Ile Val Gly Tyr Gly Ser Gly Trp Tyr Gly Phe Phe Asp
        100                 105                 110

Tyr Trp Gly Gln Gly Thr Leu Val Thr Val Ser Ser Gly Gly Gly Gly
    115                 120                 125

Ser Gly Gly Gly Gly Ser Gly Gly Gly Gly Ser Asp Ile Gln Met Thr
130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
            165                 170                 175

Gln Lys Pro Gly Lys Ala Pro Lys Arg Leu Ile Tyr Ala Ala Ser Thr
        180                 185                 190

Leu Gln Ser Gly Val Pro Ser Arg Phe Ser Gly Ser Gly Ser Gly Thr
    195                 200                 205

Glu Phe Thr Leu Thr Ile Ser Ser Leu Gln Pro Glu Asp Phe Ala Thr
    210                 215                 220

Tyr Tyr Cys Leu Gln His Asn Ser Tyr Pro Leu Thr Phe Gly Cys Gly
225                 230                 235                 240

Thr Lys Val Glu Ile Lys
            245

```
<210> SEQ ID NO 92
<211> LENGTH: 501
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3 Bispecific molecule

<400> SEQUENCE: 92
```

Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Gly Val Ser Trp Ile Arg Gln Pro Pro Gly Lys Cys Leu Glu
        35                  40                  45

```
Trp Leu Ala His Ile Phe Ser Asn Asp Glu Lys Ser Tyr Ser Thr Ser
 50                  55                  60

Leu Lys Asn Arg Leu Thr Ile Ser Lys Asp Ser Ser Lys Thr Gln Val
 65                  70                  75                  80

Val Leu Thr Met Thr Asn Val Asp Pro Val Asp Thr Ala Thr Tyr Tyr
                 85                  90                  95

Cys Ala Arg Ile Val Gly Tyr Gly Ser Gly Trp Tyr Gly Phe Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Met Thr
130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
            165                 170                 175

Gln Lys Pro Gly Lys Ala Pro Lys Arg Leu Ile Tyr Ala Ala Ser Thr
        180                 185                 190

Leu Gln Ser Gly Val Pro Ser Arg Phe Ser Gly Ser Gly Ser Gly Thr
    195                 200                 205

Glu Phe Thr Leu Thr Ile Ser Ser Leu Gln Pro Glu Asp Phe Ala Thr
210                 215                 220

Tyr Tyr Cys Leu Gln His Asn Ser Tyr Pro Leu Thr Phe Gly Cys Gly
225                 230                 235                 240

Thr Lys Val Glu Ile Lys Ser Gly Gly Gly Ser Glu Val Gln Leu
            245                 250                 255

Val Glu Ser Gly Gly Gly Leu Val Gln Pro Gly Gly Ser Leu Lys Leu
        260                 265                 270

Ser Cys Ala Ala Ser Gly Phe Thr Phe Asn Lys Tyr Ala Met Asn Trp
    275                 280                 285

Val Arg Gln Ala Pro Gly Lys Gly Leu Glu Trp Val Ala Arg Ile Arg
290                 295                 300

Ser Lys Tyr Asn Asn Tyr Ala Thr Tyr Tyr Ala Asp Ser Val Lys Asp
305                 310                 315                 320

Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
        340                 345                 350

His Gly Asn Phe Gly Asn Ser Tyr Ile Ser Tyr Trp Ala Tyr Trp Gly
    355                 360                 365

Gln Gly Thr Leu Val Thr Val Ser Ser Gly Gly Gly Ser Gly Gly
370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
            405                 410                 415

Ser Thr Gly Ala Val Thr Ser Gly Asn Tyr Pro Asn Trp Val Gln Gln
        420                 425                 430

Lys Pro Gly Gln Ala Pro Arg Gly Leu Ile Gly Gly Thr Lys Phe Leu
    435                 440                 445

Ala Pro Gly Thr Pro Ala Arg Phe Ser Gly Ser Leu Leu Gly Gly Lys
450                 455                 460
```

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
            485                 490                 495

Lys Leu Thr Val Leu
            500

<210> SEQ ID NO 93
<211> LENGTH: 989
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: FLT3_7 A8xCD3-scFc Bispecific HLE molecule

<400> SEQUENCE: 93

Gln Val Thr Leu Lys Glu Ser Gly Pro Thr Leu Val Lys Pro Thr Glu
1               5                   10                  15

Thr Leu Thr Leu Thr Cys Thr Leu Ser Gly Phe Ser Leu Asn Asn Ala
            20                  25                  30

Arg Met Gly Val Ser Trp Ile Arg Gln Pro Pro Gly Lys Cys Leu Glu
        35                  40                  45

Trp Leu Ala His Ile Phe Ser Asn Asp Glu Lys Ser Tyr Ser Thr Ser
    50                  55                  60

Leu Lys Asn Arg Leu Thr Ile Ser Lys Asp Ser Ser Lys Thr Gln Val
65                  70                  75                  80

Val Leu Thr Met Thr Asn Val Asp Pro Val Asp Thr Ala Thr Tyr Tyr
                85                  90                  95

Cys Ala Arg Ile Val Gly Tyr Gly Ser Gly Trp Tyr Gly Phe Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Gly Ile Arg Asn Asp Leu Gly Trp Tyr Gln
            165                 170                 175

Gln Lys Pro Gly Lys Ala Pro Lys Arg Leu Ile Tyr Ala Ala Ser Thr
        180                 185                 190

Leu Gln Ser Gly Val Pro Ser Arg Phe Ser Gly Ser Gly Ser Gly Thr
    195                 200                 205

Glu Phe Thr Leu Thr Ile Ser Ser Leu Gln Pro Glu Asp Phe Ala Thr
210                 215                 220

Tyr Tyr Cys Leu Gln His Asn Ser Tyr Pro Leu Thr Phe Gly Cys Gly
225                 230                 235                 240

Thr Lys Val Glu Ile Lys Ser Gly Gly Gly Ser Glu Val Gln Leu
            245                 250                 255

Val Glu Ser Gly Gly Gly Leu Val Gln Pro Gly Gly Ser Leu Lys Leu
        260                 265                 270

Ser Cys Ala Ala Ser Gly Phe Thr Phe Asn Lys Tyr Ala Met Asn Trp
    275                 280                 285

Val Arg Gln Ala Pro Gly Lys Gly Leu Glu Trp Val Ala Arg Ile Arg
290                 295                 300

```
Ser Lys Tyr Asn Asn Tyr Ala Thr Tyr Tyr Ala Asp Ser Val Lys Asp
305                 310                 315                 320

Arg Phe Thr Ile Ser Arg Asp Ser Lys Asn Thr Ala Tyr Leu Gln
            325                 330                 335

Met Asn Asn Leu Lys Thr Glu Asp Thr Ala Val Tyr Tyr Cys Val Arg
            340                 345                 350

His Gly Asn Phe Gly Asn Ser Tyr Ile Ser Tyr Trp Ala Tyr Trp Gly
            355                 360                 365

Gln Gly Thr Leu Val Thr Val Ser Ser Gly Gly Gly Ser Gly Gly
    370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Gly Ser
            405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Ala Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Val Leu Trp Tyr Ser Asn Arg Trp Val Phe Gly Gly Gly Thr
            485                 490                 495

Lys Leu Thr Val Leu Gly Gly Gly Gly Asp Lys Thr His Thr Cys Pro
            500                 505                 510

Pro Cys Pro Ala Pro Glu Leu Leu Gly Gly Pro Ser Val Phe Leu Phe
            515                 520                 525

Pro Pro Lys Pro Lys Asp Thr Leu Met Ile Ser Arg Thr Pro Glu Val
530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
            565                 570                 575

Cys Glu Glu Gln Tyr Gly Ser Thr Tyr Arg Cys Val Ser Val Leu Thr
            580                 585                 590

Val Leu His Gln Asp Trp Leu Asn Gly Lys Glu Tyr Lys Cys Lys Val
        595                 600                 605

Ser Asn Lys Ala Leu Pro Ala Pro Ile Glu Lys Thr Ile Ser Lys Ala
    610                 615                 620

Lys Gly Gln Pro Arg Glu Pro Gln Val Tyr Thr Leu Pro Pro Ser Arg
625                 630                 635                 640

Glu Glu Met Thr Lys Asn Gln Val Ser Leu Thr Cys Leu Val Lys Gly
            645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
            675                 680                 685

Phe Phe Leu Tyr Ser Lys Leu Thr Val Asp Lys Ser Arg Trp Gln Gln
            690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys Gly Gly Gly Gly
```

```
                    725                 730                 735
Ser Gly Gly Gly Gly Ser Gly Gly Gly Ser Gly Gly Gly Gly Ser
                740                 745                 750
Gly Gly Gly Gly Ser Gly Gly Gly Ser Asp Lys Thr His Thr Cys
                755                 760                 765
Pro Pro Cys Pro Ala Pro Glu Leu Leu Gly Gly Pro Ser Val Phe Leu
                770                 775                 780
Phe Pro Pro Lys Pro Lys Asp Thr Leu Met Ile Ser Arg Thr Pro Glu
785                 790                 795                 800
Val Thr Cys Val Val Val Asp Val Ser His Glu Asp Pro Glu Val Lys
                805                 810                 815
Phe Asn Trp Tyr Val Asp Gly Val Glu Val His Asn Ala Lys Thr Lys
                820                 825                 830
Pro Cys Glu Glu Gln Tyr Gly Ser Thr Tyr Arg Cys Val Ser Val Leu
                835                 840                 845
Thr Val Leu His Gln Asp Trp Leu Asn Gly Lys Glu Tyr Lys Cys Lys
850                 855                 860
Val Ser Asn Lys Ala Leu Pro Ala Pro Ile Glu Lys Thr Ile Ser Lys
865                 870                 875                 880
Ala Lys Gly Gln Pro Arg Glu Pro Gln Val Tyr Thr Leu Pro Pro Ser
                885                 890                 895
Arg Glu Glu Met Thr Lys Asn Gln Val Ser Leu Thr Cys Leu Val Lys
                900                 905                 910
Gly Phe Tyr Pro Ser Asp Ile Ala Val Glu Trp Glu Ser Asn Gly Gln
                915                 920                 925
Pro Glu Asn Asn Tyr Lys Thr Thr Pro Pro Val Leu Asp Ser Asp Gly
                930                 935                 940
Ser Phe Phe Leu Tyr Ser Lys Leu Thr Val Asp Lys Ser Arg Trp Gln
945                 950                 955                 960
Gln Gly Asn Val Phe Ser Cys Ser Val Met His Glu Ala Leu His Asn
                965                 970                 975
His Tyr Thr Gln Lys Ser Leu Ser Leu Ser Pro Gly Lys
                980                 985

<210> SEQ ID NO 94
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR1 DLL3_1_CC_delGK

<400> SEQUENCE: 94

Ser Tyr Tyr Trp Ser
1               5

<210> SEQ ID NO 95
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR2 DLL3_1_CC_delGK

<400> SEQUENCE: 95
```

Tyr Val Tyr Tyr Ser Gly Thr Thr Asn Tyr Asn Pro Ser Leu Lys Ser
1               5                   10                  15

<210> SEQ ID NO 96
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR3 DLL3_1_CC_delGK

<400> SEQUENCE: 96

Ile Ala Val Thr Gly Phe Tyr Phe Asp Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR1 DLL3_1_CC_delGK

<400> SEQUENCE: 97

Arg Ala Ser Gln Arg Val Asn Asn Asn Tyr Leu Ala
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR2 DLL3_1_CC_delGK

<400> SEQUENCE: 98

Gly Ala Ser Ser Arg Ala Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR3 DLL3_1_CC_delGK

<400> SEQUENCE: 99

Gln Gln Tyr Asp Arg Ser Pro Leu Thr
1               5

<210> SEQ ID NO 100
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH DLL3_1_CC_delGK

<400> SEQUENCE: 100

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser
            115

<210> SEQ ID NO 101
<211> LENGTH: 108
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL DLL3_1_CC_delGK

<400> SEQUENCE: 101

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Arg Val Asn Asn Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Cys Gly Thr Lys Leu Glu Ile Lys
            100                 105

<210> SEQ ID NO 102
<211> LENGTH: 241
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: DLL3_1_CC_delGK

<400> SEQUENCE: 102

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile

```
                35                  40                  45
Gly Tyr Val Tyr Tyr Ser Gly Thr Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Ile Ala Val Thr Gly Phe Tyr Phe Asp Tyr Trp Gly Gln Gly Thr
                100                 105                 110

Leu Val Thr Val Ser Ser Gly Gly Gly Gly Ser Gly Gly Gly Gly Ser
                115                 120                 125

Gly Gly Gly Gly Ser Glu Ile Val Leu Thr Gln Ser Pro Gly Thr Leu
                130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
                180                 185                 190

Pro Asp Arg Phe Ser Gly Ser Gly Ser Gly Thr Asp Phe Thr Leu Thr
                195                 200                 205

Ile Ser Arg Leu Glu Pro Glu Asp Phe Ala Val Tyr Tyr Cys Gln Gln
210                 215                 220

Tyr Asp Arg Ser Pro Leu Thr Phe Gly Cys Gly Thr Lys Leu Glu Ile
225                 230                 235                 240

Lys

<210> SEQ ID NO 103
<211> LENGTH: 496
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: DLL3_1_CCxCD3_delGK  Bispecific molecule

<400> SEQUENCE: 103

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Cys Leu Glu Trp Ile
             35                  40                  45

Gly Tyr Val Tyr Tyr Ser Gly Thr Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Ile Ala Val Thr Gly Phe Tyr Phe Asp Tyr Trp Gly Gln Gly Thr
                100                 105                 110

Leu Val Thr Val Ser Ser Gly Gly Gly Gly Ser Gly Gly Gly Gly Ser
                115                 120                 125

Gly Gly Gly Gly Ser Glu Ile Val Leu Thr Gln Ser Pro Gly Thr Leu
                130                 135                 140
```

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
            165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
        210                 215                 220

Tyr Asp Arg Ser Pro Leu Thr Phe Gly Cys Gly Thr Lys Leu Glu Ile
225                 230                 235                 240

Lys Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
            435                 440                 445

Ala Arg Phe Ser Gly Ser Leu Leu Gly Gly Lys Ala Ala Leu Thr Leu
        450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

<210> SEQ ID NO 104
<211> LENGTH: 982
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: DLL3_1_CCxCD3-scFc_delGK  Bispecific HLE
      molecule

```
<400> SEQUENCE: 104

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Cys Leu Glu Trp Ile
         35                  40                  45

Gly Tyr Val Tyr Tyr Ser Gly Thr Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Leu Thr Gln Ser Pro Gly Thr Leu
            130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
            210                 215                 220

Tyr Asp Arg Ser Pro Leu Thr Phe Gly Cys Gly Thr Lys Leu Glu Ile
225                 230                 235                 240

Lys Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
            275                 280                 285

Gly Lys Gly Leu Glu Trp Val Ala Arg Ile Arg Ser Lys Tyr Asn Asn
            290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
            355                 360                 365

Thr Val Ser Ser Gly Gly Gly Gly Ser Gly Gly Gly Gly Ser Gly Gly
            370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415
```

```
Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
            485                 490                 495

Gly Gly Gly Gly Asp Lys Thr His Thr Cys Pro Pro Cys Pro Ala Pro
                500                 505                 510

Glu Leu Leu Gly Gly Pro Ser Val Phe Leu Phe Pro Pro Lys Pro Lys
                515                 520                 525

Asp Thr Leu Met Ile Ser Arg Thr Pro Glu Val Thr Cys Val Val Val
    530                 535                 540

Asp Val Ser His Glu Asp Pro Glu Val Lys Phe Asn Trp Tyr Val Asp
545                 550                 555                 560

Gly Val Glu Val His Asn Ala Lys Thr Lys Pro Cys Glu Glu Gln Tyr
            565                 570                 575

Gly Ser Thr Tyr Arg Cys Val Ser Val Leu Thr Val Leu His Gln Asp
                580                 585                 590

Trp Leu Asn Gly Lys Glu Tyr Lys Cys Lys Val Ser Asn Lys Ala Leu
                595                 600                 605

Pro Ala Pro Ile Glu Lys Thr Ile Ser Lys Ala Lys Gly Gln Pro Arg
    610                 615                 620

Glu Pro Gln Val Tyr Thr Leu Pro Pro Ser Arg Glu Glu Met Thr Lys
625                 630                 635                 640

Asn Gln Val Ser Leu Thr Cys Leu Val Lys Gly Phe Tyr Pro Ser Asp
            645                 650                 655

Ile Ala Val Glu Trp Glu Ser Asn Gly Gln Pro Glu Asn Asn Tyr Lys
                660                 665                 670

Thr Thr Pro Pro Val Leu Asp Ser Asp Gly Ser Phe Phe Leu Tyr Ser
                675                 680                 685

Lys Leu Thr Val Asp Lys Ser Arg Trp Gln Gln Gly Asn Val Phe Ser
    690                 695                 700

Cys Ser Val Met His Glu Ala Leu His Asn His Tyr Thr Gln Lys Ser
705                 710                 715                 720

Leu Ser Leu Ser Pro Gly Gly Gly Gly Ser Gly Gly Gly Gly Ser Gly
            725                 730                 735

Gly Gly Gly Ser Gly Gly Gly Gly Ser Gly Gly Gly Gly Ser Gly Gly
                740                 745                 750

Gly Gly Ser Asp Lys Thr His Thr Cys Pro Pro Cys Pro Ala Pro Glu
        755                 760                 765

Leu Leu Gly Gly Pro Ser Val Phe Leu Phe Pro Pro Lys Pro Lys Asp
    770                 775                 780

Thr Leu Met Ile Ser Arg Thr Pro Glu Val Thr Cys Val Val Val Asp
785                 790                 795                 800

Val Ser His Glu Asp Pro Glu Val Lys Phe Asn Trp Tyr Val Asp Gly
            805                 810                 815

Val Glu Val His Asn Ala Lys Thr Lys Pro Cys Glu Glu Gln Tyr Gly
                820                 825                 830
```

```
Ser Thr Tyr Arg Cys Val Ser Val Leu Thr Val Leu His Gln Asp Trp
            835                 840                 845

Leu Asn Gly Lys Glu Tyr Lys Cys Lys Val Ser Asn Lys Ala Leu Pro
    850                 855                 860

Ala Pro Ile Glu Lys Thr Ile Ser Lys Ala Lys Gly Gln Pro Arg Glu
865                 870                 875                 880

Pro Gln Val Tyr Thr Leu Pro Pro Ser Arg Glu Glu Met Thr Lys Asn
                885                 890                 895

Gln Val Ser Leu Thr Cys Leu Val Lys Gly Phe Tyr Pro Ser Asp Ile
            900                 905                 910

Ala Val Glu Trp Glu Ser Asn Gly Gln Pro Glu Asn Asn Tyr Lys Thr
        915                 920                 925

Thr Pro Pro Val Leu Asp Ser Asp Gly Ser Phe Phe Leu Tyr Ser Lys
    930                 935                 940

Leu Thr Val Asp Lys Ser Arg Trp Gln Gln Gly Asn Val Phe Ser Cys
945                 950                 955                 960

Ser Val Met His Glu Ala Leu His Asn His Tyr Thr Gln Lys Ser Leu
                965                 970                 975

Ser Leu Ser Pro Gly Lys
            980

<210> SEQ ID NO 105
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR1 CD19 97-G1RE-C2

<400> SEQUENCE: 105

Ser Tyr Gly Met His
1               5

<210> SEQ ID NO 106
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR2 CD19 97-G1RE-C2

<400> SEQUENCE: 106

Val Ile Ser Tyr Glu Gly Ser Asn Lys Tyr Tyr Ala Glu Ser Val Lys
1               5                   10                  15

Gly

<210> SEQ ID NO 107
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR3 CD19 97-G1RE-C2

<400> SEQUENCE: 107

Asp Arg Gly Thr Ile Phe Gly Asn Tyr Gly Leu Glu Val
1               5                   10
```

<210> SEQ ID NO 108
<211> LENGTH: 122
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CD19 97-G1RE-C2 CC

<400> SEQUENCE: 108

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Val Ile Ser Tyr Glu Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Arg Gly Thr Ile Phe Gly Asn Tyr Gly Leu Glu Val Trp
            100                 105                 110

Gly Gln Gly Thr Thr Val Thr Val Ser Ser
        115                 120
```

<210> SEQ ID NO 109
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR1 CD19 97-G1RE-C2

<400> SEQUENCE: 109

```
Arg Ser Ser Gln Ser Leu Leu His Lys Asn Ala Phe Asn Tyr Leu Asp
1               5                   10                  15
```

<210> SEQ ID NO 110
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR2 CD19 97-G1RE-C2

<400> SEQUENCE: 110

```
Leu Gly Ser Asn Arg Ala Ser
1               5
```

<210> SEQ ID NO 111
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE

<223> OTHER INFORMATION: VL CDR3 CD19 97-G1RE-C2

<400> SEQUENCE: 111

Met Gln Ala Leu Gln Thr Pro Phe Thr
1               5

<210> SEQ ID NO 112
<211> LENGTH: 112
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CD19 97-G1RE-C2 CC

<400> SEQUENCE: 112

Asp Ile Val Met Thr Gln Ser Pro Leu Ser Leu Pro Val Ile Ser Gly
1               5                   10                  15

Glu Pro Ala Ser Ile Ser Cys Arg Ser Gln Ser Leu Leu His Lys
            20                  25                  30

Asn Ala Phe Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Cys Gly Thr Lys Val Asp Ile Lys
            100                 105                 110

<210> SEQ ID NO 113
<211> LENGTH: 525
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CD19 97-G1RE-C2 CC x I2C0

<400> SEQUENCE: 113

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Ile Ser Gly Glu Pro Ala Ser Ile Ser Cys Arg Ser Ser
        35                  40                  45

Gln Ser Leu Leu His Lys Asn Ala Phe Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Phe Thr Phe Gly Cys Gly
        115                 120                 125

Thr Lys Val Asp Ile Lys Gly Gly Gly Gly Ser Gly Gly Gly Gly Ser

```
             130                 135                 140
Gly Gly Gly Gly Ser Gln Val Gln Leu Val Glu Ser Gly Gly Val
145                 150                 155                 160

Val Gln Pro Gly Arg Ser Leu Arg Leu Ser Cys Ala Ala Ser Gly Phe
                165                 170                 175

Thr Phe Ser Ser Tyr Gly Met His Trp Val Arg Gln Ala Pro Gly Lys
            180                 185                 190

Cys Leu Glu Trp Val Ala Val Ile Ser Tyr Glu Gly Ser Asn Lys Tyr
        195                 200                 205

Tyr Ala Glu Ser Val Lys Gly Arg Phe Thr Ile Ser Arg Asp Asn Ser
    210                 215                 220

Lys Asn Thr Leu Tyr Leu Gln Met Asn Ser Leu Arg Asp Glu Asp Thr
225                 230                 235                 240

Ala Val Tyr Tyr Cys Ala Arg Asp Arg Gly Thr Ile Phe Gly Asn Tyr
                245                 250                 255

Gly Leu Glu Val Trp Gly Gln Gly Thr Thr Val Thr Val Ser Ser Gly
            260                 265                 270

Gly Gly Gly Ser Glu Val Gln Leu Val Glu Ser Gly Gly Gly Leu Val
        275                 280                 285

Gln Pro Gly Gly Ser Leu Lys Leu Ser Cys Ala Ala Ser Gly Phe Thr
    290                 295                 300

Phe Asn Lys Tyr Ala Met Asn Trp Val Arg Gln Ala Pro Gly Lys Gly
305                 310                 315                 320

Leu Glu Trp Val Ala Arg Ile Arg Ser Lys Tyr Asn Asn Tyr Ala Thr
                325                 330                 335

Tyr Tyr Ala Asp Ser Val Lys Asp Arg Phe Thr Ile Ser Arg Asp Asp
            340                 345                 350

Ser Lys Asn Thr Ala Tyr Leu Gln Met Asn Asn Leu Lys Thr Glu Asp
        355                 360                 365

Thr Ala Val Tyr Cys Val Arg His Gly Asn Phe Gly Asn Ser Tyr
    370                 375                 380

Ile Ser Tyr Trp Ala Tyr Trp Gly Gln Gly Thr Leu Val Thr Val Ser
385                 390                 395                 400

Ser Gly Gly Gly Gly Ser Gly Gly Gly Gly Ser Gly Gly Gly Gly Ser
                405                 410                 415

Gln Thr Val Thr Gln Glu Pro Ser Leu Thr Val Ser Pro Gly Gly
            420                 425                 430

Thr Val Thr Leu Thr Cys Gly Ser Ser Thr Gly Ala Val Thr Ser Gly
        435                 440                 445

Asn Tyr Pro Asn Trp Val Gln Gln Lys Pro Gly Gln Ala Pro Arg Gly
    450                 455                 460

Leu Ile Gly Gly Thr Lys Phe Leu Ala Pro Thr Pro Ala Arg Phe
465                 470                 475                 480

Ser Gly Ser Leu Leu Gly Gly Lys Ala Ala Leu Thr Leu Ser Gly Val
                485                 490                 495

Gln Pro Glu Asp Glu Ala Glu Tyr Tyr Cys Val Leu Trp Tyr Ser Asn
            500                 505                 510

Arg Trp Val Phe Gly Gly Gly Thr Lys Leu Thr Val Leu
        515                 520                 525

<210> SEQ ID NO 114
<211> LENGTH: 1013
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: CD19 97-G1RE-C2 CC x I2C0-scFc

<400> SEQUENCE: 114

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Ile Ser Gly Glu Pro Ala Ser Ile Ser Cys Arg Ser Ser
        35                  40                  45

Gln Ser Leu Leu His Lys Asn Ala Phe Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Phe Thr Phe Gly Cys Gly
        115                 120                 125

Thr Lys Val Asp Ile Lys Gly Gly Gly Ser Gly Gly Gly Gly Gly Ser
130                 135                 140

Gly Gly Gly Gly Ser Gln Val Gln Leu Val Glu Ser Gly Gly Gly Val
145                 150                 155                 160

Val Gln Pro Gly Arg Ser Leu Arg Leu Ser Cys Ala Ala Ser Gly Phe
                165                 170                 175

Thr Phe Ser Ser Tyr Gly Met His Trp Val Arg Gln Ala Pro Gly Lys
            180                 185                 190

Cys Leu Glu Trp Val Ala Val Ile Ser Tyr Glu Gly Ser Asn Lys Tyr
        195                 200                 205

Tyr Ala Glu Ser Val Lys Gly Arg Phe Thr Ile Ser Arg Asp Asn Ser
    210                 215                 220

Lys Asn Thr Leu Tyr Leu Gln Met Asn Ser Leu Arg Asp Glu Asp Thr
225                 230                 235                 240

Ala Val Tyr Tyr Cys Ala Arg Asp Arg Gly Thr Ile Phe Gly Asn Tyr
                245                 250                 255

Gly Leu Glu Val Trp Gly Gln Gly Thr Thr Val Thr Val Ser Ser Gly
            260                 265                 270

Gly Gly Gly Ser Glu Val Gln Leu Val Glu Ser Gly Gly Gly Leu Val
        275                 280                 285

Gln Pro Gly Gly Ser Leu Lys Leu Ser Cys Ala Ala Ser Gly Phe Thr
    290                 295                 300

Phe Asn Lys Tyr Ala Met Asn Trp Val Arg Gln Ala Pro Gly Lys Gly
305                 310                 315                 320

Leu Glu Trp Val Ala Arg Ile Arg Ser Lys Tyr Asn Asn Tyr Ala Thr
                325                 330                 335

Tyr Tyr Ala Asp Ser Val Lys Asp Arg Phe Thr Ile Ser Arg Asp Asp
            340                 345                 350

Ser Lys Asn Thr Ala Tyr Leu Gln Met Asn Asn Leu Lys Thr Glu Asp
        355                 360                 365

Thr Ala Val Tyr Tyr Cys Val Arg His Gly Asn Phe Gly Asn Ser Tyr
    370                 375                 380
```

-continued

```
Ile Ser Tyr Trp Ala Tyr Trp Gly Gln Gly Thr Leu Val Thr Val Ser
385                 390                 395                 400

Ser Gly Gly Gly Ser Gly Gly Gly Ser Gly Gly Gly Ser
            405                 410                 415

Gln Thr Val Val Thr Gln Glu Pro Ser Leu Thr Val Ser Pro Gly Gly
            420                 425                 430

Thr Val Thr Leu Thr Cys Gly Ser Ser Thr Gly Ala Val Thr Ser Gly
            435                 440                 445

Asn Tyr Pro Asn Trp Val Gln Gln Lys Pro Gly Gln Ala Pro Arg Gly
            450                 455                 460

Leu Ile Gly Gly Thr Lys Phe Leu Ala Pro Gly Thr Pro Ala Arg Phe
465                 470                 475                 480

Ser Gly Ser Leu Leu Gly Gly Lys Ala Ala Leu Thr Leu Ser Gly Val
            485                 490                 495

Gln Pro Glu Asp Glu Ala Glu Tyr Tyr Cys Val Leu Trp Tyr Ser Asn
            500                 505                 510

Arg Trp Val Phe Gly Gly Gly Thr Lys Leu Thr Val Leu Gly Gly Gly
            515                 520                 525

Gly Asp Lys Thr His Thr Cys Pro Pro Cys Pro Ala Pro Glu Leu Leu
530                 535                 540

Gly Gly Pro Ser Val Phe Leu Phe Pro Pro Lys Pro Lys Asp Thr Leu
545                 550                 555                 560

Met Ile Ser Arg Thr Pro Glu Val Thr Cys Val Val Val Asp Val Ser
                565                 570                 575

His Glu Asp Pro Glu Val Lys Phe Asn Trp Tyr Val Asp Gly Val Glu
            580                 585                 590

Val His Asn Ala Lys Thr Lys Pro Cys Glu Glu Gln Tyr Gly Ser Thr
            595                 600                 605

Tyr Arg Cys Val Ser Val Leu Thr Val Leu His Gln Asp Trp Leu Asn
            610                 615                 620

Gly Lys Glu Tyr Lys Cys Lys Val Ser Asn Lys Ala Leu Pro Ala Pro
625                 630                 635                 640

Ile Glu Lys Thr Ile Ser Lys Ala Lys Gly Gln Pro Arg Glu Pro Gln
                645                 650                 655

Val Tyr Thr Leu Pro Pro Ser Arg Glu Glu Met Thr Lys Asn Gln Val
            660                 665                 670

Ser Leu Thr Cys Leu Val Lys Gly Phe Tyr Pro Ser Asp Ile Ala Val
            675                 680                 685

Glu Trp Glu Ser Asn Gly Gln Pro Glu Asn Asn Tyr Lys Thr Thr Pro
            690                 695                 700

Pro Val Leu Asp Ser Asp Gly Ser Phe Phe Leu Tyr Ser Lys Leu Thr
705                 710                 715                 720

Val Asp Lys Ser Arg Trp Gln Gln Gly Asn Val Phe Ser Cys Ser Val
                725                 730                 735

Met His Glu Ala Leu His Asn His Tyr Thr Gln Lys Ser Leu Ser Leu
            740                 745                 750

Ser Pro Gly Lys Gly Gly Gly Gly Ser Gly Gly Gly Ser Gly Gly
            755                 760                 765

Gly Gly Ser Gly Gly Gly Ser Gly Gly Gly Ser Gly Gly Gly
            770                 775                 780

Gly Ser Asp Lys Thr His Thr Cys Pro Pro Cys Pro Ala Pro Glu Leu
785                 790                 795                 800
```

```
Leu Gly Gly Pro Ser Val Phe Leu Phe Pro Pro Lys Pro Lys Asp Thr
                805                 810                 815
Leu Met Ile Ser Arg Thr Pro Glu Val Thr Cys Val Val Val Asp Val
                820                 825                 830
Ser His Glu Asp Pro Glu Val Lys Phe Asn Trp Tyr Val Asp Gly Val
                835                 840                 845
Glu Val His Asn Ala Lys Thr Lys Pro Cys Glu Glu Gln Tyr Gly Ser
                850                 855                 860
Thr Tyr Arg Cys Val Ser Val Leu Thr Val Leu His Gln Asp Trp Leu
865                 870                 875                 880
Asn Gly Lys Glu Tyr Lys Cys Lys Val Ser Asn Lys Ala Leu Pro Ala
                885                 890                 895
Pro Ile Glu Lys Thr Ile Ser Lys Ala Lys Gly Gln Pro Arg Glu Pro
                900                 905                 910
Gln Val Tyr Thr Leu Pro Pro Ser Arg Glu Glu Met Thr Lys Asn Gln
                915                 920                 925
Val Ser Leu Thr Cys Leu Val Lys Gly Phe Tyr Pro Ser Asp Ile Ala
                930                 935                 940
Val Glu Trp Glu Ser Asn Gly Gln Pro Glu Asn Asn Tyr Lys Thr Thr
945                 950                 955                 960
Pro Pro Val Leu Asp Ser Asp Gly Ser Phe Phe Leu Tyr Ser Lys Leu
                965                 970                 975
Thr Val Asp Lys Ser Arg Trp Gln Gln Gly Asn Val Phe Ser Cys Ser
                980                 985                 990
Val Met His Glu Ala Leu His Asn  His Tyr Thr Gln Lys  Ser Leu Ser
                995                 1000                1005
Leu Ser  Pro Gly Lys
    1010

<210> SEQ ID NO 115
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR1 CDH3 G8A 6-B12

<400> SEQUENCE: 115

Ser Tyr Pro Ile Asn
1               5

<210> SEQ ID NO 116
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDR2 CDH3 G8A 6-B12

<400> SEQUENCE: 116

Val Ile Trp Thr Gly Gly Gly Thr Asn Tyr Ala Ser Ser Val Lys Gly
1               5                   10                  15

<210> SEQ ID NO 117
<211> LENGTH: 15
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: VH CDR3 CDH3 G8A 6-B12

<400> SEQUENCE: 117

Ser Arg Gly Val Tyr Asp Phe Asp Gly Arg Gly Ala Met Asp Tyr
1               5                   10                  15

<210> SEQ ID NO 118
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR1 CDH3 G8A 6-B12

<400> SEQUENCE: 118

Lys Ser Ser Gln Ser Leu Leu Tyr Ser Ser Asn Gln Lys Asn Tyr Phe
1               5                   10                  15

Ala

<210> SEQ ID NO 119
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR2 CDH3 G8A 6-B12

<400> SEQUENCE: 119

Trp Ala Ser Thr Arg Glu Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDR3 CDH3 G8A 6-B12

<400> SEQUENCE: 120

Gln Gln Tyr Tyr Ser Tyr Pro Tyr Thr
1               5

<210> SEQ ID NO 121
<211> LENGTH: 123
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VH CDH3 G8A 6-B12

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30
```

```
Pro Ile Asn Trp Val Arg Gln Ala Pro Gly Lys Gly Leu Glu Trp Val
            35                  40                  45

Gly Val Ile Trp Thr Gly Gly Thr Asn Tyr Ala Ser Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Lys Ser Arg Gly Val Tyr Asp Phe Asp Gly Arg Gly Ala Met Asp Tyr
                100                 105                 110

Trp Gly Gln Gly Thr Leu Val Thr Val Ser Ser
            115                 120
```

<210> SEQ ID NO 122
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: VL CDH3 G8A 6-B12

<400> SEQUENCE: 122

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
             20                  25                  30

Ser Asn Gln Lys Asn Tyr Phe Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Tyr Thr Phe Gly Gln Gly Thr Lys Leu Glu Ile
                100                 105                 110

Lys
```

<210> SEQ ID NO 123
<211> LENGTH: 251
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH3 G8A 6-B12 scFv

<400> SEQUENCE: 123

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser Tyr
             20                  25                  30

Pro Ile Asn Trp Val Arg Gln Ala Pro Gly Lys Gly Leu Glu Trp Val
         35                  40                  45

Gly Val Ile Trp Thr Gly Gly Thr Asn Tyr Ala Ser Ser Val Lys
     50                  55                  60
```

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Ser Arg Gly Val Tyr Asp Phe Asp Gly Arg Gly Ala Met Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Gln Lys Asn Tyr
                165                 170                 175

Phe Ala Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Tyr Ser Tyr Pro Tyr
225                 230                 235                 240

Thr Phe Gly Gln Gly Thr Lys Leu Glu Ile Lys
                245                 250

<210> SEQ ID NO 124
<211> LENGTH: 506
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH3 G8A 6-B12 x I2C0 bispecific molecule

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Ile Asn Trp Val Arg Gln Ala Pro Gly Lys Gly Leu Glu Trp Val
        35                  40                  45

Gly Val Ile Trp Thr Gly Gly Thr Asn Tyr Ala Ser Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Ser Arg Gly Val Tyr Asp Phe Asp Gly Arg Gly Ala Met Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Val Met Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Leu Leu Tyr Ser Ser Asn Gln Lys Asn Tyr
            165                 170                 175

Phe Ala Trp Tyr Gln Gln Lys Pro Gly Gln Pro Pro Lys Leu Leu Ile
        180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Tyr Ser Tyr Pro Tyr
225                 230                 235                 240

Thr Phe Gly Gln Gly Thr Lys Leu Glu Ile Lys Ser Gly Gly Gly Gly
            245                 250                 255

Ser Glu Val Gln Leu Val Glu Ser Gly Gly Gly Leu Val Gln Pro Gly
        260                 265                 270

Gly Ser Leu Lys Leu Ser Cys Ala Ala Ser Gly Phe Thr Phe Asn Lys
    275                 280                 285

Tyr Ala Met Asn Trp Val Arg Gln Ala Pro Gly Lys Gly Leu Glu Trp
290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
            325                 330                 335

Thr Ala Tyr Leu Gln Met Asn Asn Leu Lys Thr Glu Asp Thr Ala Val
        340                 345                 350

Tyr Tyr Cys Val Arg His Gly Asn Phe Gly Asn Ser Tyr Ile Ser Tyr
    355                 360                 365

Trp Ala Tyr Trp Gly Gln Gly Thr Leu Val Thr Val Ser Ser Gly Gly
370                 375                 380

Gly Gly Ser Gly Gly Gly Gly Ser Gly Gly Gly Gly Ser Gln Thr Val
385                 390                 395                 400

Val Thr Gln Glu Pro Ser Leu Thr Val Ser Pro Gly Gly Thr Val Thr
            405                 410                 415

Leu Thr Cys Gly Ser Ser Thr Gly Ala Val Thr Ser Gly Asn Tyr Pro
        420                 425                 430

Asn Trp Val Gln Gln Lys Pro Gly Gln Ala Pro Arg Gly Leu Ile Gly
    435                 440                 445

Gly Thr Lys Phe Leu Ala Pro Gly Thr Pro Ala Arg Phe Ser Gly Ser
450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
            485                 490                 495

Phe Gly Gly Gly Thr Lys Leu Thr Val Leu
        500                 505

<210> SEQ ID NO 125
<211> LENGTH: 994
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CDH3 G8A 6-B12 x I2C0 bispecific molecule HLE

<400> SEQUENCE: 125

```
Glu Val Gln Leu Leu Glu Ser Gly Gly Gly Leu Val Gln Pro Gly
1               5                   10                  15

Ser Leu Arg Leu Ser Cys Ala Ala Ser Gly Phe Ser Phe Ser Ser Tyr
            20                  25                  30

Pro Ile Asn Trp Val Arg Gln Ala Pro Gly Lys Gly Leu Glu Trp Val
            35                  40                  45

Gly Val Ile Trp Thr Gly Gly Thr Asn Tyr Ala Ser Ser Val Lys
50                      55                  60

Gly Arg Phe Thr Ile Ser Arg Asp Asn Ser Lys Asn Thr Val Tyr Leu
65                      70                  75                  80

Gln Met Asn Ser Leu Arg Ala Glu Asp Thr Ala Val Tyr Tyr Cys Ala
                85                  90                  95

Lys Ser Arg Gly Val Tyr Asp Phe Asp Gly Arg Gly Ala Met Asp Tyr
                100                 105                 110

Trp Gly Gln Gly Thr Leu Val Thr Val Ser Ser Gly Gly Gly Gly Ser
                115                 120                 125

Gly Gly Gly Gly Ser Gly Gly Gly Ser Asp Ile Val Met Thr Gln
130                     135                 140

Ser Pro Asp Ser Leu Ala Val Ser Leu Gly Glu Arg Ala Thr Ile Asn
145                     150                 155                 160

Cys Lys Ser Ser Gln Ser Leu Leu Tyr Ser Ser Asn Gln Lys Asn Tyr
                165                 170                 175

Phe Ala Trp Tyr Gln Gln Lys Pro Gly Gln Pro Pro Lys Leu Leu Ile
                180                 185                 190

Tyr Trp Ala Ser Thr Arg Glu Ser Gly Val Pro Asp Arg Phe Ser Gly
                195                 200                 205

Ser Gly Ser Gly Thr Asp Phe Thr Leu Thr Ile Ser Ser Leu Gln Ala
                210                 215                 220

Glu Asp Val Ala Val Tyr Tyr Cys Gln Gln Tyr Tyr Ser Tyr Pro Tyr
225                     230                 235                 240

Thr Phe Gly Gln Gly Thr Lys Leu Glu Ile Lys Ser Gly Gly Gly Gly
                245                 250                 255

Ser Glu Val Gln Leu Val Glu Ser Gly Gly Gly Leu Val Gln Pro Gly
                260                 265                 270

Gly Ser Leu Lys Leu Ser Cys Ala Ala Ser Gly Phe Thr Phe Asn Lys
                275                 280                 285

Tyr Ala Met Asn Trp Val Arg Gln Ala Pro Gly Lys Gly Leu Glu Trp
                290                 295                 300

Val Ala Arg Ile Arg Ser Lys Tyr Asn Asn Tyr Ala Thr Tyr Tyr Ala
305                     310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
                340                 345                 350

Tyr Tyr Cys Val Arg His Gly Asn Phe Gly Asn Ser Tyr Ile Ser Tyr
                355                 360                 365

Trp Ala Tyr Trp Gly Gln Gly Thr Leu Val Thr Val Ser Ser Gly Gly
                370                 375                 380

Gly Gly Ser Gly Gly Gly Gly Ser Gly Gly Gly Ser Gln Thr Val
385                     390                 395                 400

Val Thr Gln Glu Pro Ser Leu Thr Val Ser Pro Gly Gly Thr Val Thr
                405                 410                 415
```

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
            435                 440                 445

Gly Thr Lys Phe Leu Ala Pro Gly Thr Pro Ala Arg Phe Ser Gly Ser
450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
            485                 490                 495

Phe Gly Gly Gly Thr Lys Leu Thr Val Leu Gly Gly Gly Gly Asp Lys
            500                 505                 510

Thr His Thr Cys Pro Pro Cys Pro Ala Pro Glu Leu Leu Gly Gly Pro
            515                 520                 525

Ser Val Phe Leu Phe Pro Pro Lys Pro Lys Asp Thr Leu Met Ile Ser
            530                 535                 540

Arg Thr Pro Glu Val Thr Cys Val Val Val Asp Val Ser His Glu Asp
545                 550                 555                 560

Pro Glu Val Lys Phe Asn Trp Tyr Val Asp Gly Val Glu Val His Asn
            565                 570                 575

Ala Lys Thr Lys Pro Cys Glu Glu Gln Tyr Gly Ser Thr Tyr Arg Cys
            580                 585                 590

Val Ser Val Leu Thr Val Leu His Gln Asp Trp Leu Asn Gly Lys Glu
            595                 600                 605

Tyr Lys Cys Lys Val Ser Asn Lys Ala Leu Pro Ala Pro Ile Glu Lys
            610                 615                 620

Thr Ile Ser Lys Ala Lys Gly Gln Pro Arg Glu Pro Gln Val Tyr Thr
625                 630                 635                 640

Leu Pro Pro Ser Arg Glu Glu Met Thr Lys Asn Gln Val Ser Leu Thr
            645                 650                 655

Cys Leu Val Lys Gly Phe Tyr Pro Ser Asp Ile Ala Val Glu Trp Glu
            660                 665                 670

Ser Asn Gly Gln Pro Glu Asn Asn Tyr Lys Thr Thr Pro Pro Val Leu
            675                 680                 685

Asp Ser Asp Gly Ser Phe Phe Leu Tyr Ser Lys Leu Thr Val Asp Lys
            690                 695                 700

Ser Arg Trp Gln Gln Gly Asn Val Phe Ser Cys Ser Val Met His Glu
705                 710                 715                 720

Ala Leu His Asn His Tyr Thr Gln Lys Ser Leu Ser Leu Ser Pro Gly
            725                 730                 735

Lys Gly Gly Gly Gly Ser Gly Gly Gly Gly Ser Gly Gly Gly Gly Ser
            740                 745                 750

Gly Gly Gly Gly Ser Gly Gly Gly Gly Ser Gly Gly Gly Gly Ser Asp
            755                 760                 765

Lys Thr His Thr Cys Pro Pro Cys Pro Ala Pro Glu Leu Leu Gly Gly
            770                 775                 780

Pro Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
            805                 810                 815

Asp Pro Glu Val Lys Phe Asn Trp Tyr Val Asp Gly Val Glu Val His
            820                 825                 830

Asn Ala Lys Thr Lys Pro Cys Glu Glu Gln Tyr Gly Ser Thr Tyr Arg

```
          835                 840                 845
Cys Val Ser Val Leu Thr Val Leu His Gln Asp Trp Leu Asn Gly Lys
    850                 855                 860

Glu Tyr Lys Cys Lys Val Ser Asn Lys Ala Leu Pro Ala Pro Ile Glu
865                 870                 875                 880

Lys Thr Ile Ser Lys Ala Lys Gly Gln Pro Arg Glu Pro Gln Val Tyr
                885                 890                 895

Thr Leu Pro Pro Ser Arg Glu Glu Met Thr Lys Asn Gln Val Ser Leu
            900                 905                 910

Thr Cys Leu Val Lys Gly Phe Tyr Pro Ser Asp Ile Ala Val Glu Trp
        915                 920                 925

Glu Ser Asn Gly Gln Pro Glu Asn Asn Tyr Lys Thr Thr Pro Pro Val
    930                 935                 940

Leu Asp Ser Asp Gly Ser Phe Phe Leu Tyr Ser Lys Leu Thr Val Asp
945                 950                 955                 960

Lys Ser Arg Trp Gln Gln Gly Asn Val Phe Ser Cys Ser Val Met His
                965                 970                 975

Glu Ala Leu His Asn His Tyr Thr Gln Lys Ser Leu Ser Leu Ser Pro
            980                 985                 990

Gly Lys

<210> SEQ ID NO 126
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR1 VH

<400> SEQUENCE: 126

Asn His Ile Ile His
1               5

<210> SEQ ID NO 127
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR2 VH

<400> SEQUENCE: 127

Tyr Ile Asn Pro Tyr Pro Gly Tyr His Ala Tyr Asn Glu Lys Phe Gln
1               5                   10                  15

Gly

<210> SEQ ID NO 128
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR3 VH

<400> SEQUENCE: 128

Asp Gly Tyr Tyr Arg Asp Thr Asp Val Leu Asp Tyr
```

<210> SEQ ID NO 129
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR1 VL

<400> SEQUENCE: 129

Gln Ala Ser Gln Asp Ile Ser Asn Tyr Leu Asn
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR2 VL

<400> SEQUENCE: 130

Tyr Thr Ser Arg Leu His Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CDR3 VL

<400> SEQUENCE: 131

Gln Gln Gly Asn Thr Leu Pro Trp Thr
1               5

<210> SEQ ID NO 132
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) VH

<400> SEQUENCE: 132

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn His
                20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
    50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys

```
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser
            115                 120

<210> SEQ ID NO 133
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) VL

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Thr Gly Val Pro Ser Arg Phe Ser Gly
    50                  55                  60

Ser Gly Ser Gly Thr Asp Phe Thr Phe Thr Ile Ser Ser Leu Glu Pro
65                  70                  75                  80

Glu Asp Ile Ala Thr Tyr Tyr Cys Gln Gln Gly Asn Thr Leu Pro Trp
                85                  90                  95

Thr Phe Gly Cys Gly Thr Lys Leu Glu Ile Lys
            100                 105

<210> SEQ ID NO 134
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) scFv

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
    50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Gly Ser Gly Gly
            115                 120                 125
```

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
                180                 185                 190

Gly Val Pro Ser Arg Phe Ser Gly Ser Gly Ser Gly Thr Asp Phe Thr
                195                 200                 205

Phe Thr Ile Ser Ser Leu Glu Pro Glu Asp Ile Ala Thr Tyr Tyr Cys
210                 215                 220

Gln Gln Gly Asn Thr Leu Pro Trp Thr Phe Gly Cys Gly Thr Lys Leu
225                 230                 235                 240

Glu Ile Lys

<210> SEQ ID NO 135
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) x I2C0 bispecific
      molecule

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
                20                  25                  30

Ile Ile His Trp Val Arg Gln Ala Pro Gly Gln Cys Leu Glu Trp Met
            35                  40                  45

Gly Tyr Ile Asn Pro Tyr Pro Gly Tyr His Ala Tyr Asn Glu Lys Phe
50                  55                  60

Gln Gly Arg Ala Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
                100                 105                 110

Gln Gly Thr Leu Val Thr Val Ser Gly Gly Gly Gly Ser Gly Gly
                115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
                180                 185                 190

Gly Val Pro Ser Arg Phe Ser Gly Ser Gly Ser Gly Thr Asp Phe Thr
                195                 200                 205

Phe Thr Ile Ser Ser Leu Glu Pro Glu Asp Ile Ala Thr Tyr Tyr Cys
210                 215                 220

```
Gln Gln Gly Asn Thr Leu Pro Trp Thr Phe Gly Cys Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 136
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BCMA A7 27-C4-G7 CC (44/100) x I2C0-scFc
      bispecific molecule HLE

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Ile Ile His Trp Val Arg Gln Ala Pro Gly Gln Cys Leu Glu Trp Met
        35                  40                  45

Gly Tyr Ile Asn Pro Tyr Pro Gly Tyr His Ala Tyr Asn Glu Lys Phe
    50                  55                  60
```

-continued

Gln Gly Arg Ala Thr Met Thr Ser Asp Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Tyr Arg Asp Thr Asp Val Leu Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Tyr Thr Ser Arg Leu His Thr
            180                 185                 190

Gly Val Pro Ser Arg Phe Ser Gly Ser Gly Ser Gly Thr Asp Phe Thr
        195                 200                 205

Phe Thr Ile Ser Ser Leu Glu Pro Glu Asp Ile Ala Thr Tyr Tyr Cys
210                 215                 220

Gln Gln Gly Asn Thr Leu Pro Trp Thr Phe Gly Cys Gly Thr Lys Val
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr

```
                485                 490                 495
Val Leu Gly Gly Gly Asp Lys Thr His Thr Cys Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
        530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
                725                 730                 735

Gly Gly Ser Gly Gly Gly Gly Ser Gly Gly Gly Ser Gly Gly Gly
            740                 745                 750

Gly Ser Gly Gly Gly Gly Ser Asp Lys Thr His Thr Cys Pro Pro Cys
        755                 760                 765

Pro Ala Pro Glu Leu Leu Gly Gly Pro Ser Val Phe Leu Phe Pro Pro
    770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910
```

Pro Ser Asp Ile Ala Val Glu Trp Glu Ser Asn Gly Gln Pro Glu Asn
            915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 137
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH CDR1

<400> SEQUENCE: 137

Asp Tyr Tyr Met Tyr
1               5

<210> SEQ ID NO 138
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH CDR2

<400> SEQUENCE: 138

Ile Ile Ser Asp Ala Gly Tyr Tyr Thr Tyr Tyr Ser Asp Ile Ile Lys
1               5                   10                  15

Gly

<210> SEQ ID NO 139
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH CDR3

<400> SEQUENCE: 139

Gly Phe Pro Leu Leu Arg His Gly Ala Met Asp Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL CDR1

<400> SEQUENCE: 140

```
Lys Ala Ser Gln Asn Val Asp Ala Asn Val Ala
1               5                   10
```

<210> SEQ ID NO 141
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL CDR2

<400> SEQUENCE: 141

```
Ser Ala Ser Tyr Val Tyr Trp
1               5
```

<210> SEQ ID NO 142
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VL CDR3

<400> SEQUENCE: 142

```
Gln Gln Tyr Asp Gln Gln Leu Ile Thr
1               5
```

<210> SEQ ID NO 143
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC VH

<400> SEQUENCE: 143

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser
        115                 120
```

<210> SEQ ID NO 144
<211> LENGTH: 107
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: MISC_FEATURE
<223> OTHER INFORMATION: PM 76-B10.17 CC VL

<400> SEQUENCE: 144

Asp Ile Gln Met Thr Gln Ser Pro Ser Leu Ser Ala Ser Val Gly
1               5                   10                  15

Asp Arg Val Thr Ile Thr Cys Lys Ala Ser Gln Asn Val Asp Ala Asn
            20                  25                  30

Val Ala Trp Tyr Gln Gln Lys Pro Gly Gln Ala Pro Lys Ser Leu Ile
        35                  40                  45

Tyr Ser Ala Ser Tyr Val Tyr Trp Asp Val Pro Ser Arg Phe Ser Gly
    50                  55                  60

Ser Ala Ser Gly Thr Asp Phe Thr Leu Thr Ile Ser Ser Val Gln Ser
65                  70                  75                  80

Glu Asp Phe Ala Thr Tyr Tyr Cys Gln Gln Tyr Asp Gln Leu Ile
                85                  90                  95

Thr Phe Gly Cys Gly Thr Lys Leu Glu Ile Lys
                100                 105

<210> SEQ ID NO 145
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC scFv

<400> SEQUENCE: 145

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
                180                 185                 190

Asp Val Pro Ser Arg Phe Ser Gly Ser Ala Ser Gly Thr Asp Phe Thr
                195                 200                 205
```

```
Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys

<210> SEQ ID NO 146
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 bispecific molecule

<400> SEQUENCE: 146

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
```

```
                305                 310                 315                 320
Ile Ser Arg Asp Asp Ser Lys Asn Thr Ala Tyr Leu Gln Met Asn Asn
                    325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
                355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
                435                 440                 445

Thr Pro Ala Arg Phe Ser Gly Ser Leu Leu Gly Gly Lys Ala Ala Leu
                450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 147
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0-scFc bispecific HLE
      molecule

<400> SEQUENCE: 147

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
                20                  25                  30

Tyr Met Tyr Trp Val Arg Gln Ala Pro Gly Lys Cys Leu Glu Trp Val
                35                  40                  45

Ala Ile Ile Ser Asp Ala Gly Tyr Tyr Thr Tyr Tyr Ser Asp Ile Ile
            50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
                100                 105                 110

Gln Gly Thr Leu Val Thr Val Ser Ser Gly Gly Gly Gly Ser Gly Gly
                115                 120                 125

Gly Gly Ser Gly Gly Gly Gly Ser Asp Ile Gln Met Thr Gln Ser Pro
            130                 135                 140

Ser Ser Leu Ser Ala Ser Val Gly Asp Arg Val Thr Ile Thr Cys Lys
```

```
            145                 150                 155                 160
        Ala Ser Gln Asn Val Asp Ala Asn Val Ala Trp Tyr Gln Gln Lys Pro
                        165                 170                 175
        Gly Gln Ala Pro Lys Ser Leu Ile Tyr Ser Ala Ser Tyr Val Tyr Trp
                        180                 185                 190
        Asp Val Pro Ser Arg Phe Ser Gly Ser Ala Ser Gly Thr Asp Phe Thr
                        195                 200                 205
        Leu Thr Ile Ser Ser Val Gln Ser Glu Asp Phe Ala Thr Tyr Tyr Cys
                        210                 215                 220
        Gln Gln Tyr Asp Gln Gln Leu Ile Thr Phe Gly Cys Gly Thr Lys Leu
        225                 230                 235                 240
        Glu Ile Lys Ser Gly Gly Gly Ser Glu Val Gln Leu Val Glu Ser
                        245                 250                 255
        Gly Gly Gly Leu Val Gln Pro Gly Gly Ser Leu Lys Leu Ser Cys Ala
                        260                 265                 270
        Ala Ser Gly Phe Thr Phe Asn Lys Tyr Ala Met Asn Trp Val Arg Gln
                        275                 280                 285
        Ala Pro Gly Lys Gly Leu Glu Trp Val Ala Arg Ile Arg Ser Lys Tyr
                        290                 295                 300
        Asn Asn Tyr Ala Thr Tyr Tyr Ala Asp Ser Val Lys Asp Arg Phe Thr
        305                 310                 315                 320
        Ile Ser Arg Asp Asp Ser Lys Asn Thr Ala Tyr Leu Gln Met Asn Asn
                        325                 330                 335
        Leu Lys Thr Glu Asp Thr Ala Val Tyr Tyr Cys Val Arg His Gly Asn
                        340                 345                 350
        Phe Gly Asn Ser Tyr Ile Ser Tyr Trp Ala Tyr Trp Gly Gln Gly Thr
                        355                 360                 365
        Leu Val Thr Val Ser Ser Gly Gly Gly Ser Gly Gly Gly Gly Ser
                        370                 375                 380
        Gly Gly Gly Gly Ser Gln Thr Val Val Thr Gln Glu Pro Ser Leu Thr
        385                 390                 395                 400
        Val Ser Pro Gly Gly Thr Val Thr Leu Thr Cys Gly Ser Ser Thr Gly
                        405                 410                 415
        Ala Val Thr Ser Gly Asn Tyr Pro Asn Trp Val Gln Gln Lys Pro Gly
                        420                 425                 430
        Gln Ala Pro Arg Gly Leu Ile Gly Gly Thr Lys Phe Leu Ala Pro Gly
                        435                 440                 445
        Thr Pro Ala Arg Phe Ser Gly Ser Leu Leu Gly Gly Lys Ala Ala Leu
        450                 455                 460
        Thr Leu Ser Gly Val Gln Pro Glu Asp Glu Ala Glu Tyr Tyr Cys Val
        465                 470                 475                 480
        Leu Trp Tyr Ser Asn Arg Trp Val Phe Gly Gly Gly Thr Lys Leu Thr
                        485                 490                 495
        Val Leu Gly Gly Gly Gly Asp Lys Thr His Thr Cys Pro Pro Cys Pro
                        500                 505                 510
        Ala Pro Glu Leu Leu Gly Gly Pro Ser Val Phe Leu Phe Pro Pro Lys
                        515                 520                 525
        Pro Lys Asp Thr Leu Met Ile Ser Arg Thr Pro Glu Val Thr Cys Val
                        530                 535                 540
        Val Val Asp Val Ser His Glu Asp Pro Glu Val Lys Phe Asn Trp Tyr
        545                 550                 555                 560
        Val Asp Gly Val Glu Val His Asn Ala Lys Thr Lys Pro Cys Glu Glu
                        565                 570                 575
```

```
Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
            645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
            675                 680                 685

Tyr Ser Lys Leu Thr Val Asp Lys Ser Arg Trp Gln Gln Gly Asn Val
            690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
            725                 730                 735

Gly Gly Ser Gly Gly Gly Gly Ser Gly Gly Gly Ser Gly Gly Gly
            740                 745                 750

Gly Ser Gly Gly Gly Gly Ser Asp Lys Thr His Thr Cys Pro Pro Cys
            755                 760                 765

Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
            805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
            835                 840                 845

His Gln Asp Trp Leu Asn Gly Lys Glu Tyr Lys Cys Lys Val Ser Asn
850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
            885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
            915                 920                 925

Asn Tyr Lys Thr Thr Pro Pro Val Leu Asp Ser Asp Gly Ser Phe Phe
            930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985
```

<210> SEQ ID NO 148
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0-scFc_delGK bispecific
      HLE molecule

<400> SEQUENCE: 148

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350
```

```
Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Ser
    370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Gly Ser Gly Gly Gly Ser Gly Gly Gly Gly Ser
            740                 745                 750

Gly Gly Gly Gly Ser Asp Lys Thr His Thr Cys Pro Pro Cys Pro Ala
        755                 760                 765
```

```
Pro Glu Leu Leu Gly Gly Pro Ser Val Phe Leu Phe Pro Pro Lys Pro
770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
            805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
            835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
                900                 905                 910

Asp Ile Ala Val Glu Trp Glu Ser Asn Gly Gln Pro Glu Asn Asn Tyr
            915                 920                 925

Lys Thr Thr Pro Pro Val Leu Asp Ser Asp Gly Ser Phe Phe Leu Tyr
930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
                980

<210> SEQ ID NO 149
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 CC (103/43)-scFc
      bispecific molecule

<400> SEQUENCE: 149

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125
```

Gly Gly Ser Gly Gly Gly Ser Asp Ile Gln Met Thr Gln Ser Pro
                130             135                 140
Ser Ser Leu Ser Ala Ser Val Gly Asp Arg Val Thr Ile Thr Cys Lys
145                 150                 155                 160
Ala Ser Gln Asn Val Asp Ala Asn Val Ala Trp Tyr Gln Gln Lys Pro
                165                 170                 175
Gly Gln Ala Pro Lys Ser Leu Ile Tyr Ser Ala Ser Tyr Val Tyr Trp
                180                 185                 190
Asp Val Pro Ser Arg Phe Ser Gly Ser Ala Ser Gly Thr Asp Phe Thr
                195                 200                 205
Leu Thr Ile Ser Ser Val Gln Ser Glu Asp Phe Ala Thr Tyr Tyr Cys
210                 215                 220
Gln Gln Tyr Asp Gln Gln Leu Ile Thr Phe Gly Cys Gly Thr Lys Leu
225                 230                 235                 240
Glu Ile Lys Ser Gly Gly Gly Ser Glu Val Gln Leu Val Glu Ser
                245                 250                 255
Gly Gly Gly Leu Val Gln Pro Gly Gly Ser Leu Lys Leu Ser Cys Ala
                260                 265                 270
Ala Ser Gly Phe Thr Phe Asn Lys Tyr Ala Met Asn Trp Val Arg Gln
                275                 280                 285
Ala Pro Gly Lys Gly Leu Glu Trp Val Ala Arg Ile Arg Ser Lys Tyr
                290                 295                 300
Asn Asn Tyr Ala Thr Tyr Tyr Ala Asp Ser Val Lys Asp Arg Phe Thr
305                 310                 315                 320
Ile Ser Arg Asp Asp Ser Lys Asn Thr Ala Tyr Leu Gln Met Asn Asn
                325                 330                 335
Leu Lys Thr Glu Asp Thr Ala Val Tyr Tyr Cys Val Arg His Gly Asn
                340                 345                 350
Phe Gly Asn Ser Tyr Ile Ser Tyr Trp Ala Tyr Cys Gly Gln Gly Thr
                355                 360                 365
Leu Val Thr Val Ser Ser Gly Gly Gly Ser Gly Gly Gly Ser
370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
                405                 410                 415
Ala Val Thr Ser Gly Asn Tyr Pro Asn Trp Val Gln Gln Lys Pro Gly
                420                 425                 430
Gln Cys Pro Arg Gly Leu Ile Gly Gly Thr Lys Phe Leu Ala Pro Gly
                435                 440                 445
Thr Pro Ala Arg Phe Ser Gly Ser Leu Leu Gly Gly Lys Ala Ala Leu
450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Gly Thr Lys Leu Thr
                485                 490                 495

Val Leu

<210> SEQ ID NO 150
<211> LENGTH: 986
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: MISC_FEATURE
<223> OTHER INFORMATION: PM 76-B10.17 CC x I2C0 CC (103/43)-scFc
      bispecific HLE molecule

<400> SEQUENCE: 150

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Ala Asn Val Ala Trp Tyr Gln Gln Lys Pro
            165                 170                 175

Gly Gln Ala Pro Lys Ser Leu Ile Tyr Ser Ala Ser Tyr Val Tyr Trp
        180                 185                 190

Asp Val Pro Ser Arg Phe Ser Gly Ser Ala Ser Gly Thr Asp Phe Thr
    195                 200                 205

Leu Thr Ile Ser Ser Val Gln Ser Glu Asp Phe Ala Thr Tyr Tyr Cys
210                 215                 220

Gln Gln Tyr Asp Gln Leu Ile Thr Phe Gly Cys Gly Thr Lys Leu
225                 230                 235                 240

Glu Ile Lys Ser Gly Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Cys Gly Gln Gly Thr
    355                 360                 365

Leu Val Thr Val Ser Ser Gly Gly Gly Gly Ser Gly Gly Gly Gly Ser
370                 375                 380
```

```
Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
        405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Gly Gly Gly Gly Asp Lys Thr His Thr Cys Pro Pro Cys Pro
        500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
            565                 570                 575

Gln Tyr Gly Ser Thr Tyr Arg Cys Val Ser Val Leu Thr Val Leu His
        580                 585                 590

Gln Asp Trp Leu Asn Gly Lys Glu Tyr Lys Cys Lys Val Ser Asn Lys
    595                 600                 605

Ala Leu Pro Ala Pro Ile Glu Lys Thr Ile Ser Lys Ala Lys Gly Gln
610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
            645                 650                 655

Ser Asp Ile Ala Val Glu Trp Glu Ser Asn Gly Gln Pro Glu Asn Asn
        660                 665                 670

Tyr Lys Thr Thr Pro Pro Val Leu Asp Ser Asp Gly Ser Phe Phe Leu
    675                 680                 685

Tyr Ser Lys Leu Thr Val Asp Lys Ser Arg Trp Gln Gln Gly Asn Val
690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
            725                 730                 735

Gly Gly Ser Gly Gly Gly Gly Ser Gly Gly Gly Gly Ser Gly Gly Gly
        740                 745                 750

Gly Ser Gly Gly Gly Gly Ser Asp Lys Thr His Thr Cys Pro Pro Cys
    755                 760                 765

Pro Ala Pro Glu Leu Leu Gly Gly Pro Ser Val Phe Leu Phe Pro Pro
    770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
```

```
                    805                 810                 815
Tyr Val Asp Gly Val Glu Val His Asn Ala Lys Thr Lys Pro Cys Glu
                820                 825                 830

Glu Gln Tyr Gly Ser Thr Tyr Arg Cys Val Ser Val Leu Thr Val Leu
            835                 840                 845

His Gln Asp Trp Leu Asn Gly Lys Glu Tyr Lys Cys Lys Val Ser Asn
        850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 151
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.17 CC x I2C0 CC (103/43)-scFc_delGK
      bispecific HLE molecule

<400> SEQUENCE: 151

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Ala Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160
```

```
Ala Ser Gln Asn Val Asp Ala Asn Val Ala Trp Tyr Gln Gln Lys Pro
            165                 170                 175
Gly Gln Ala Pro Lys Ser Leu Ile Tyr Ser Ala Ser Tyr Val Tyr Trp
            180                 185                 190
Asp Val Pro Ser Arg Phe Ser Gly Ser Ala Ser Gly Thr Asp Phe Thr
            195                 200                 205
Leu Thr Ile Ser Ser Val Gln Ser Glu Asp Phe Ala Thr Tyr Tyr Cys
            210                 215                 220
Gln Gln Tyr Asp Gln Leu Ile Thr Phe Gly Cys Gly Thr Lys Leu
225                 230                 235                 240
Glu Ile Lys Ser Gly Gly Gly Ser Glu Val Gln Leu Val Glu Ser
            245                 250                 255
Gly Gly Gly Leu Val Gln Pro Gly Gly Ser Leu Lys Leu Ser Cys Ala
            260                 265                 270
Ala Ser Gly Phe Thr Phe Asn Lys Tyr Ala Met Asn Trp Val Arg Gln
            275                 280                 285
Ala Pro Gly Lys Gly Leu Glu Trp Val Ala Arg Ile Arg Ser Lys Tyr
            290                 295                 300
Asn Asn Tyr Ala Thr Tyr Tyr Ala Asp Ser Val Lys Asp Arg Phe Thr
305                 310                 315                 320
Ile Ser Arg Asp Asp Ser Lys Asn Thr Ala Tyr Leu Gln Met Asn Asn
            325                 330                 335
Leu Lys Thr Glu Asp Thr Ala Val Tyr Tyr Cys Val Arg His Gly Asn
            340                 345                 350
Phe Gly Asn Ser Tyr Ile Ser Tyr Trp Ala Tyr Cys Gly Gln Gly Thr
            355                 360                 365
Leu Val Thr Val Ser Ser Gly Gly Gly Ser Gly Gly Gly Gly Ser
            370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
            405                 410                 415
Ala Val Thr Ser Gly Asn Tyr Pro Asn Trp Val Gln Gln Lys Pro Gly
            420                 425                 430
Gln Cys Pro Arg Gly Leu Ile Gly Gly Thr Lys Phe Leu Ala Pro Gly
            435                 440                 445
Thr Pro Ala Arg Phe Ser Gly Ser Leu Leu Gly Gly Lys Ala Ala Leu
            450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Gly Thr Lys Leu Thr
            485                 490                 495
Val Leu Gly Gly Gly Gly Asp Lys Thr His Thr Cys Pro Pro Cys Pro
            500                 505                 510
Ala Pro Glu Leu Leu Gly Gly Pro Ser Val Phe Leu Phe Pro Pro Lys
            515                 520                 525
Pro Lys Asp Thr Leu Met Ile Ser Arg Thr Pro Glu Val Thr Cys Val
            530                 535                 540
Val Val Asp Val Ser His Glu Asp Pro Glu Val Lys Phe Asn Trp Tyr
545                 550                 555                 560
Val Asp Gly Val Glu Val His Asn Ala Lys Thr Lys Pro Cys Glu Glu
            565                 570                 575
Gln Tyr Gly Ser Thr Tyr Arg Cys Val Ser Val Leu Thr Val Leu His
```

-continued

```
                580                 585                 590
    Gln Asp Trp Leu Asn Gly Lys Glu Tyr Lys Cys Lys Val Ser Asn Lys
                    595                 600                 605
    Ala Leu Pro Ala Pro Ile Glu Lys Thr Ile Ser Lys Ala Lys Gly Gln
        610                 615                 620
    Pro Arg Glu Pro Gln Val Tyr Thr Leu Pro Pro Ser Arg Glu Glu Met
    625                 630                 635                 640
    Thr Lys Asn Gln Val Ser Leu Thr Cys Leu Val Lys Gly Phe Tyr Pro
                    645                 650                 655
    Ser Asp Ile Ala Val Glu Trp Glu Ser Asn Gly Gln Pro Glu Asn Asn
                660                 665                 670
    Tyr Lys Thr Thr Pro Pro Val Leu Asp Ser Asp Gly Ser Phe Phe Leu
            675                 680                 685
    Tyr Ser Lys Leu Thr Val Asp Lys Ser Arg Trp Gln Gln Gly Asn Val
        690                 695                 700
    Phe Ser Cys Ser Val Met His Glu Ala Leu His Asn His Tyr Thr Gln
    705                 710                 715                 720
    Lys Ser Leu Ser Leu Ser Pro Gly Gly Gly Gly Ser Gly Gly Gly Gly
                    725                 730                 735
    Ser Gly Gly Gly Gly Ser Gly Gly Gly Gly Ser Gly Gly Gly Gly Ser
                740                 745                 750
    Gly Gly Gly Gly Ser Asp Lys Thr His Thr Cys Pro Pro Cys Pro Ala
            755                 760                 765
    Pro Glu Leu Leu Gly Gly Pro Ser Val Phe Leu Phe Pro Pro Lys Pro
        770                 775                 780
    Lys Asp Thr Leu Met Ile Ser Arg Thr Pro Glu Val Thr Cys Val Val
    785                 790                 795                 800
    Val Asp Val Ser His Glu Asp Pro Glu Val Lys Phe Asn Trp Tyr Val
                    805                 810                 815
    Asp Gly Val Glu Val His Asn Ala Lys Thr Lys Pro Cys Glu Glu Gln
                820                 825                 830
    Tyr Gly Ser Thr Tyr Arg Cys Val Ser Val Leu Thr Val Leu His Gln
            835                 840                 845
    Asp Trp Leu Asn Gly Lys Glu Tyr Lys Cys Lys Val Ser Asn Lys Ala
        850                 855                 860
    Leu Pro Ala Pro Ile Glu Lys Thr Ile Ser Lys Ala Lys Gly Gln Pro
    865                 870                 875                 880
    Arg Glu Pro Gln Val Tyr Thr Leu Pro Pro Ser Arg Glu Glu Met Thr
                    885                 890                 895
    Lys Asn Gln Val Ser Leu Thr Cys Leu Val Lys Gly Phe Tyr Pro Ser
                900                 905                 910
    Asp Ile Ala Val Glu Trp Glu Ser Asn Gly Gln Pro Glu Asn Asn Tyr
            915                 920                 925
    Lys Thr Thr Pro Pro Val Leu Asp Ser Asp Gly Ser Phe Phe Leu Tyr
        930                 935                 940
    Ser Lys Leu Thr Val Asp Lys Ser Arg Trp Gln Gln Gly Asn Val Phe
    945                 950                 955                 960
    Ser Cys Ser Val Met His Glu Ala Leu His Asn His Tyr Thr Gln Lys
                    965                 970                 975
    Ser Leu Ser Leu Ser Pro Gly Lys
                    980

<210> SEQ ID NO 152
```

```
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH CDR1

<400> SEQUENCE: 152

Asp Tyr Tyr Met Tyr
1               5

<210> SEQ ID NO 153
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH CDR2

<400> SEQUENCE: 153

Ile Ile Ser Asp Gly Gly Tyr Tyr Thr Tyr Tyr Ser Asp Ile Ile Lys
1               5                   10                  15

Gly

<210> SEQ ID NO 154
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH CDR3

<400> SEQUENCE: 154

Gly Phe Pro Leu Leu Arg His Gly Ala Met Asp Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL CDR1

<400> SEQUENCE: 155

Lys Ala Ser Gln Asn Val Asp Thr Asn Val Ala
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL CDR2

<400> SEQUENCE: 156

Ser Ala Ser Tyr Val Tyr Trp
1               5
```

<210> SEQ ID NO 157
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL CDR3

<400> SEQUENCE: 157

Gln Gln Tyr Asp Gln Gln Leu Ile Thr
1               5

<210> SEQ ID NO 158
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VH

<400> SEQUENCE: 158

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser
        115                 120

<210> SEQ ID NO 159
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC VL

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ser Leu Ile
        35                  40                  45

Tyr Ser Ala Ser Tyr Val Tyr Trp Asp Val Pro Ser Arg Phe Ser Gly
    50                  55                  60

```
Ser Ala Ser Gly Thr Asp Phe Thr Leu Thr Ile Ser Ser Val Gln Ser
 65                  70                  75                  80

Glu Asp Phe Ala Thr Tyr Tyr Cys Gln Gln Tyr Asp Gln Gln Leu Ile
                 85                  90                  95

Thr Phe Gly Gly Gly Thr Lys Leu Glu Ile Lys
            100                 105
```

<210> SEQ ID NO 160
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC scFv

<400> SEQUENCE: 160

```
Gln Val Gln Leu Val Glu Ser Gly Gly Gly Leu Val Lys Pro Gly Glu
 1               5                  10                  15

Ser Leu Arg Leu Ser Cys Ala Ala Ser Gly Phe Thr Phe Ser Asp Tyr
                 20                  25                  30

Tyr Met Tyr Trp Val Arg Gln Ala Pro Gly Lys Gly Leu Glu Trp Val
             35                  40                  45

Ala Ile Ile Ser Asp Gly Gly Tyr Tyr Thr Tyr Tyr Ser Asp Ile Ile
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
                 85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
            210                 215                 220

Gln Gln Tyr Asp Gln Gln Leu Ile Thr Phe Gly Gly Gly Thr Lys Leu
225                 230                 235                 240

Glu Ile Lys
```

<210> SEQ ID NO 161
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 bispecific molecule

<400> SEQUENCE: 161

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
            165                 170                 175

Gly Gln Ala Pro Lys Ser Leu Ile Tyr Ser Ala Ser Tyr Val Tyr Trp
        180                 185                 190

Asp Val Pro Ser Arg Phe Ser Gly Ser Ala Ser Gly Thr Asp Phe Thr
    195                 200                 205

Leu Thr Ile Ser Ser Val Gln Ser Glu Asp Phe Ala Thr Tyr Tyr Cys
210                 215                 220

Gln Gln Tyr Asp Gln Leu Ile Thr Phe Gly Gly Gly Thr Lys Leu
225                 230                 235                 240

Glu Ile Lys Ser Gly Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Trp Gly Gln Gly Thr
    355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
```

-continued

```
                405                 410                 415
Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 162
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc bispecific HLE
      molecule

<400> SEQUENCE: 162

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Gly Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Gly Gly Thr Lys Leu
225                 230                 235                 240

Glu Ile Lys Ser Gly Gly Gly Gly Ser Glu Val Gln Leu Val Glu Ser
```

```
              245                 250                 255
Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670
```

```
Tyr Lys Thr Thr Pro Pro Val Leu Asp Ser Asp Gly Ser Phe Phe Leu
            675                 680                 685

Tyr Ser Lys Leu Thr Val Asp Lys Ser Arg Trp Gln Gln Gly Asn Val
        690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
            725                 730                 735

Gly Gly Ser Gly Gly Gly Gly Ser Gly Gly Gly Gly Ser Gly Gly Gly
            740                 745                 750

Gly Ser Gly Gly Gly Gly Ser Asp Lys Thr His Thr Cys Pro Pro Cys
            755                 760                 765

Pro Ala Pro Glu Leu Leu Gly Gly Pro Ser Val Phe Leu Phe Pro Pro
            770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
                820                 825                 830

Glu Gln Tyr Gly Ser Thr Tyr Arg Cys Val Ser Val Leu Thr Val Leu
            835                 840                 845

His Gln Asp Trp Leu Asn Gly Lys Glu Tyr Lys Cys Lys Val Ser Asn
850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
            915                 920                 925

Asn Tyr Lys Thr Thr Pro Pro Val Leu Asp Ser Asp Gly Ser Phe Phe
            930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 163
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc_delGK bispecific
      HLE molecule

<400> SEQUENCE: 163

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
```

-continued

```
                20                  25                  30
Tyr Met Tyr Trp Val Arg Gln Ala Pro Gly Lys Gly Leu Glu Trp Val
            35                  40                  45

Ala Ile Ile Ser Asp Gly Gly Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
        100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
        180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
        210                 215                 220

Gln Gln Tyr Asp Gln Gln Leu Ile Thr Phe Gly Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
        370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
        435                 440                 445
```

```
Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Gly Ser Gly Gly Gly Ser Gly Gly Gly Gly Ser
            740                 745                 750

Gly Gly Gly Gly Ser Asp Lys Thr His Thr Cys Pro Pro Cys Pro Ala
        755                 760                 765

Pro Glu Leu Leu Gly Gly Pro Ser Val Phe Leu Phe Pro Pro Lys Pro
    770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
        835                 840                 845

Asp Trp Leu Asn Gly Lys Glu Tyr Lys Cys Lys Val Ser Asn Lys Ala
    850                 855                 860
```

```
Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
                900                 905                 910

Asp Ile Ala Val Glu Trp Glu Ser Asn Gly Gln Pro Glu Asn Asn Tyr
                915                 920                 925

Lys Thr Thr Pro Pro Val Leu Asp Ser Asp Gly Ser Phe Phe Leu Tyr
                930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
                980

<210> SEQ ID NO 164
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific molecule

<400> SEQUENCE: 164

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
                20                  25                  30

Tyr Met Tyr Trp Val Arg Gln Ala Pro Gly Lys Gly Leu Glu Trp Val
            35                  40                  45

Ala Ile Ile Ser Asp Gly Gly Tyr Tyr Thr Tyr Tyr Ser Asp Ile Ile
        50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
                180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
        210                 215                 220
```

```
Gln Gln Tyr Asp Gln Gln Leu Ile Thr Phe Gly Gly Thr Lys Leu
225                 230                 235                 240

Glu Ile Lys Ser Gly Gly Gly Gly Ser Glu Val Gln Leu Val Glu Ser
            245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu

<210> SEQ ID NO 165
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific HLE molecule

<400> SEQUENCE: 165

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60
```

-continued

```
Lys Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
                 85                  90                  95

Ala Arg Gly Phe Pro Leu Leu Arg His Gly Ala Met Asp Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
210                 215                 220

Gln Gln Tyr Asp Gln Gln Leu Ile Thr Phe Gly Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480
```

```
Leu Trp Tyr Ser Asn Arg Trp Val Phe Gly Gly Thr Lys Leu Thr
                485                 490                 495

Val Leu Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
        530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
            610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
            690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Gly Ser Gly Gly
                725                 730                 735

Gly Gly Ser Gly Gly Gly Gly Ser Gly Gly Gly Gly Ser Gly Gly Gly
            740                 745                 750

Gly Ser Gly Gly Gly Gly Ser Asp Lys Thr His Thr Cys Pro Pro Cys
        755                 760                 765

Pro Ala Pro Glu Leu Leu Gly Gly Pro Ser Val Phe Leu Phe Pro Pro
    770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
```

```
                        900             905             910
Pro Ser Asp Ile Ala Val Glu Trp Glu Ser Asn Gly Gln Pro Glu Asn
            915             920             925

Asn Tyr Lys Thr Thr Pro Pro Val Leu Asp Ser Asp Gly Ser Phe Phe
        930             935             940

Leu Tyr Ser Lys Leu Thr Val Asp Lys Ser Arg Trp Gln Gln Gly Asn
945             950             955             960

Val Phe Ser Cys Ser Val Met His Glu Ala Leu His Asn His Tyr Thr
                965             970             975

Gln Lys Ser Leu Ser Leu Ser Pro Gly Lys
            980             985

<210> SEQ ID NO 166
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc_delGK
      bispecific HLE molecule

<400> SEQUENCE: 166

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Gly Thr Lys Leu
225                 230                 235                 240

Glu Ile Lys Ser Gly Gly Gly Gly Ser Glu Val Gln Leu Val Glu Ser
                245                 250                 255
```

```
Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
```

```
                675                 680                 685
Tyr Ser Lys Leu Thr Val Asp Lys Ser Arg Trp Gln Gln Gly Asn Val
            690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Ser Gly Gly Gly Ser Gly Gly Gly Ser
            740                 745                 750

Gly Gly Gly Gly Ser Asp Lys Thr His Thr Cys Pro Pro Cys Pro Ala
            755                 760                 765

Pro Glu Leu Leu Gly Gly Pro Ser Val Phe Leu Phe Pro Pro Lys Pro
        770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
        835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
    930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
            980

<210> SEQ ID NO 167
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH CDR1

<400> SEQUENCE: 167

Asp Tyr Tyr Met Tyr
1               5

<210> SEQ ID NO 168
<211> LENGTH: 17
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH CDR2

<400> SEQUENCE: 168

Ile Ile Ser Asp Gly Gly Tyr Tyr Thr Tyr Tyr Ser Asp Ile Ile Lys
1               5                   10                  15

Gly

<210> SEQ ID NO 169
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH CDR3

<400> SEQUENCE: 169

Gly Phe Pro Leu Leu Arg His Gly Ala Met Asp Tyr
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL CDR1

<400> SEQUENCE: 170

Lys Ala Ser Gln Asn Val Asp Thr Asn Val Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL CDR2

<400> SEQUENCE: 171

Ser Ala Ser Tyr Val Tyr Trp
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL CDR3

<400> SEQUENCE: 172

Gln Gln Tyr Asp Gln Gln Leu Ile Thr
1               5
```

```
<210> SEQ ID NO 173
<211> LENGTH: 121
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VH

<400> SEQUENCE: 173

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser
        115                 120

<210> SEQ ID NO 174
<211> LENGTH: 107
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc VL

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Lys Ser Leu Ile
        35                  40                  45

Tyr Ser Ala Ser Tyr Val Tyr Trp Asp Val Pro Ser Arg Phe Ser Gly
    50                  55                  60

Ser Ala Ser Gly Thr Asp Phe Thr Leu Thr Ile Ser Ser Val Gln Ser
65                  70                  75                  80

Glu Asp Phe Ala Thr Tyr Tyr Cys Gln Gln Tyr Asp Gln Gln Leu Ile
                85                  90                  95

Thr Phe Gly Cys Gly Thr Lys Leu Glu Ile Lys
            100                 105

<210> SEQ ID NO 175
<211> LENGTH: 243
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

<223> OTHER INFORMATION: PM 76-B10.11 CC x I2C0-scFc scFv

<400> SEQUENCE: 175

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys

<210> SEQ ID NO 176
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc bispecific molecule

<400> SEQUENCE: 176

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Lys Ala Glu Asp Thr Ala Val Tyr Tyr Cys
                 85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
            130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
            210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu
```

<210> SEQ ID NO 177
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc bispecific HLE
      molecule

<400> SEQUENCE: 177

```
Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
```

```
              340                 345                 350
Phe Gly Asn Ser Tyr Ile Ser Tyr Trp Ala Tyr Trp Gly Gln Gly Thr
            355                 360                 365
Leu Val Thr Val Ser Ser Gly Gly Gly Ser Gly Gly Gly Gly Ser
        370                 375                 380
Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
                405                 410                 415
Ala Val Thr Ser Gly Asn Tyr Pro Asn Trp Val Gln Gln Lys Pro Gly
            420                 425                 430
Gln Ala Pro Arg Gly Leu Ile Gly Gly Thr Lys Phe Leu Ala Pro Gly
        435                 440                 445
Thr Pro Ala Arg Phe Ser Gly Ser Leu Leu Gly Gly Lys Ala Ala Leu
    450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Gly Thr Lys Leu Thr
                485                 490                 495
Val Leu Gly Gly Gly Asp Lys Thr His Thr Cys Pro Pro Cys Pro
            500                 505                 510
Ala Pro Glu Leu Leu Gly Gly Pro Ser Val Phe Leu Phe Pro Pro Lys
        515                 520                 525
Pro Lys Asp Thr Leu Met Ile Ser Arg Thr Pro Glu Val Thr Cys Val
    530                 535                 540
Val Val Asp Val Ser His Glu Asp Pro Glu Val Lys Phe Asn Trp Tyr
545                 550                 555                 560
Val Asp Gly Val Glu Val His Asn Ala Lys Thr Lys Pro Cys Glu Glu
                565                 570                 575
Gln Tyr Gly Ser Thr Tyr Arg Cys Val Ser Val Leu Thr Val Leu His
            580                 585                 590
Gln Asp Trp Leu Asn Gly Lys Glu Tyr Lys Cys Lys Val Ser Asn Lys
        595                 600                 605
Ala Leu Pro Ala Pro Ile Glu Lys Thr Ile Ser Lys Ala Lys Gly Gln
    610                 615                 620
Pro Arg Glu Pro Gln Val Tyr Thr Leu Pro Pro Ser Arg Glu Glu Met
625                 630                 635                 640
Thr Lys Asn Gln Val Ser Leu Thr Cys Leu Val Lys Gly Phe Tyr Pro
                645                 650                 655
Ser Asp Ile Ala Val Glu Trp Glu Ser Asn Gly Gln Pro Glu Asn Asn
            660                 665                 670
Tyr Lys Thr Thr Pro Pro Val Leu Asp Ser Asp Gly Ser Phe Phe Leu
        675                 680                 685
Tyr Ser Lys Leu Thr Val Asp Lys Ser Arg Trp Gln Gln Gly Asn Val
    690                 695                 700
Phe Ser Cys Ser Val Met His Glu Ala Leu His Asn His Tyr Thr Gln
705                 710                 715                 720
Lys Ser Leu Ser Leu Ser Pro Gly Lys Gly Gly Gly Gly Ser Gly
                725                 730                 735
Gly Gly Ser Gly Gly Gly Gly Ser Gly Gly Gly Gly Ser Gly Gly Gly
            740                 745                 750
Gly Ser Gly Gly Gly Gly Ser Asp Lys Thr His Thr Cys Pro Pro Cys
        755                 760                 765
```

```
Pro Ala Pro Glu Leu Leu Gly Gly Pro Ser Val Phe Leu Phe Pro Pro
        770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 178
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0-scFc_delGK bispecific
      HLE molecule

<400> SEQUENCE: 178

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Gly Ser Gly Gly
```

-continued

```
                115                 120                 125
Gly Gly Ser Gly Gly Gly Ser Asp Ile Gln Met Thr Gln Ser Pro
            130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
            195                 200                 205

Leu Thr Ile Ser Ser Val Gln Ser Glu Asp Phe Ala Thr Tyr Tyr Cys
            210                 215                 220

Gln Gln Tyr Asp Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
            290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Gly Ser Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
            515                 520                 525

Pro Lys Asp Thr Leu Met Ile Ser Arg Thr Pro Glu Val Thr Cys Val
            530                 535                 540
```

```
Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
    610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Gly Ser Gly Gly Gly Gly Ser Gly Gly Gly Gly Ser
            740                 745                 750

Gly Gly Gly Gly Ser Asp Lys Thr His Thr Cys Pro Pro Cys Pro Ala
        755                 760                 765

Pro Glu Leu Leu Gly Gly Pro Ser Val Phe Leu Phe Pro Pro Lys Pro
770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
        835                 840                 845

Asp Trp Leu Asn Gly Lys Glu Tyr Lys Cys Lys Val Ser Asn Lys Ala
    850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
    930                 935                 940

Ser Lys Leu Thr Val Asp Lys Ser Arg Trp Gln Gln Gly Asn Val Phe
945                 950                 955                 960
```

```
Ser Cys Ser Val Met His Glu Ala Leu His Asn His Tyr Thr Gln Lys
                965                 970                 975
Ser Leu Ser Leu Ser Pro Gly Lys
            980

<210> SEQ ID NO 179
<211> LENGTH: 498
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific molecule

<400> SEQUENCE: 179

Gln Val Gln Leu Val Glu Ser Gly Gly Gly Leu Val Lys Pro Gly Glu
1               5                   10                  15
Ser Leu Arg Leu Ser Cys Ala Ala Ser Gly Phe Thr Phe Ser Asp Tyr
            20                  25                  30
Tyr Met Tyr Trp Val Arg Gln Ala Pro Gly Lys Cys Leu Glu Trp Val
        35                  40                  45
Ala Ile Ile Ser Asp Gly Gly Tyr Tyr Thr Tyr Tyr Ser Asp Ile Ile
    50                  55                  60
Lys Gly Arg Phe Thr Ile Ser Arg Asp Asn Ala Lys Asn Ser Leu Tyr
65                  70                  75                  80
Leu Gln Met Asn Ser Leu Lys Ala Glu Asp Thr Ala Val Tyr Tyr Cys
                85                  90                  95
Ala Arg Gly Phe Pro Leu Leu Arg His Gly Ala Met Asp Tyr Trp Gly
            100                 105                 110
Gln Gly Thr Leu Val Thr Val Ser Ser Gly Gly Gly Ser Gly Gly
        115                 120                 125
Gly Gly Ser Gly Gly Gly Ser Asp Ile Gln Met Thr Gln Ser Pro
    130                 135                 140
Ser Ser Leu Ser Ala Ser Val Gly Asp Arg Val Thr Ile Thr Cys Lys
145                 150                 155                 160
Ala Ser Gln Asn Val Asp Thr Asn Val Ala Trp Tyr Gln Gln Lys Pro
                165                 170                 175
Gly Gln Ala Pro Lys Ser Leu Ile Tyr Ser Ala Ser Tyr Val Tyr Trp
            180                 185                 190
Asp Val Pro Ser Arg Phe Ser Gly Ser Ala Ser Gly Thr Asp Phe Thr
        195                 200                 205
Leu Thr Ile Ser Ser Val Gln Ser Glu Asp Phe Ala Thr Tyr Tyr Cys
    210                 215                 220
Gln Gln Tyr Asp Gln Leu Ile Thr Phe Gly Cys Gly Thr Lys Leu
225                 230                 235                 240
Glu Ile Lys Ser Gly Gly Gly Ser Glu Val Gln Leu Val Glu Ser
                245                 250                 255
Gly Gly Gly Leu Val Gln Pro Gly Gly Ser Leu Lys Leu Ser Cys Ala
            260                 265                 270
Ala Ser Gly Phe Thr Phe Asn Lys Tyr Ala Met Asn Trp Val Arg Gln
        275                 280                 285
Ala Pro Gly Lys Gly Leu Glu Trp Val Ala Arg Ile Arg Ser Lys Tyr
    290                 295                 300
Asn Asn Tyr Ala Thr Tyr Tyr Ala Asp Ser Val Lys Asp Arg Phe Thr
305                 310                 315                 320
```

-continued

```
Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
            355                 360                 365

Leu Val Thr Val Ser Ser Gly Gly Gly Ser Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu

<210> SEQ ID NO 180
<211> LENGTH: 986
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc
      bispecific HLE molecule

<400> SEQUENCE: 180

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
            35                  40                  45

Ala Ile Ile Ser Asp Gly Gly Tyr Tyr Thr Tyr Tyr Ser Asp Ile Ile
50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
            85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Gly Ser Asp Ile Gln Met Thr Gln Ser Pro
            130                 135                 140

Ser Ser Leu Ser Ala Ser Val Gly Asp Arg Val Thr Ile Thr Cys Lys
145                 150                 155                 160
```

```
Ala Ser Gln Asn Val Asp Thr Asn Val Ala Trp Tyr Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
                195                 200                 205

Leu Thr Ile Ser Ser Val Gln Ser Glu Asp Phe Ala Thr Tyr Tyr Cys
        210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Cys Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Cys Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575
```

-continued

```
Gln Tyr Gly Ser Thr Tyr Arg Cys Val Ser Val Leu Thr Val Leu His
                580                 585                 590

Gln Asp Trp Leu Asn Gly Lys Glu Tyr Lys Cys Lys Val Ser Asn Lys
            595                 600                 605

Ala Leu Pro Ala Pro Ile Glu Lys Thr Ile Ser Lys Ala Lys Gly Gln
610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Lys Gly Gly Gly Ser Gly Gly
                725                 730                 735

Gly Gly Ser Gly Gly Gly Ser Gly Gly Gly Ser Gly Gly Gly
            740                 745                 750

Gly Ser Gly Gly Gly Ser Asp Lys Thr His Thr Cys Pro Pro Cys
        755                 760                 765

Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Cys Glu
            820                 825                 830

Glu Gln Tyr Gly Ser Thr Tyr Arg Cys Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Glu Glu
                885                 890                 895

Met Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985
```

-continued

```
<210> SEQ ID NO 181
<211> LENGTH: 984
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: PM 76-B10.11 CC x I2C0 CC (103/43)-scFc_delGK
      bispecific HLE molecule

<400> SEQUENCE: 181

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Cys Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Gln Lys Pro
                165                 170                 175

Gly Gln Ala Pro Lys Ser Leu Ile Tyr Ser Ala Ser Tyr Val Tyr Trp
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Gln Gln Leu Ile Thr Phe Gly Cys Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350
```

-continued

```
Phe Gly Asn Ser Tyr Ile Ser Tyr Trp Ala Tyr Cys Gly Gln Gly Thr
                355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Cys Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Gly Asp Lys Thr His Thr Cys Pro Pro Cys Pro
            500                 505                 510

Ala Pro Glu Leu Leu Gly Gly Pro Ser Val Phe Leu Phe Pro Pro Lys
        515                 520                 525

Pro Lys Asp Thr Leu Met Ile Ser Arg Thr Pro Glu Val Thr Cys Val
    530                 535                 540

Val Val Asp Val Ser His Glu Asp Pro Glu Val Lys Phe Asn Trp Tyr
545                 550                 555                 560

Val Asp Gly Val Glu Val His Asn Ala Lys Thr Lys Pro Cys Glu Glu
                565                 570                 575

Gln Tyr Gly Ser Thr Tyr Arg Cys Val Ser Val Leu Thr Val Leu His
            580                 585                 590

Gln Asp Trp Leu Asn Gly Lys Glu Tyr Lys Cys Lys Val Ser Asn Lys
        595                 600                 605

Ala Leu Pro Ala Pro Ile Glu Lys Thr Ile Ser Lys Ala Lys Gly Gln
610                 615                 620

Pro Arg Glu Pro Gln Val Tyr Thr Leu Pro Pro Ser Arg Glu Glu Met
625                 630                 635                 640

Thr Lys Asn Gln Val Ser Leu Thr Cys Leu Val Lys Gly Phe Tyr Pro
                645                 650                 655

Ser Asp Ile Ala Val Glu Trp Glu Ser Asn Gly Gln Pro Glu Asn Asn
            660                 665                 670

Tyr Lys Thr Thr Pro Pro Val Leu Asp Ser Asp Gly Ser Phe Phe Leu
        675                 680                 685

Tyr Ser Lys Leu Thr Val Asp Lys Ser Arg Trp Gln Gln Gly Asn Val
    690                 695                 700

Phe Ser Cys Ser Val Met His Glu Ala Leu His Asn His Tyr Thr Gln
705                 710                 715                 720

Lys Ser Leu Ser Leu Ser Pro Gly Gly Gly Gly Ser Gly Gly Gly Gly
                725                 730                 735

Ser Gly Gly Gly Gly Ser Gly Gly Gly Gly Ser Gly Gly Gly Gly Ser
            740                 745                 750

Gly Gly Gly Gly Ser Asp Lys Thr His Thr Cys Pro Pro Cys Pro Ala
        755                 760                 765

Pro Glu Leu Leu Gly Gly Pro Ser Val Phe Leu Phe Pro Pro Lys Pro
```

```
            770                 775                 780
Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
                820                 825                 830

Tyr Gly Ser Thr Tyr Arg Cys Val Ser Val Leu Thr Val Leu His Gln
                835                 840                 845

Asp Trp Leu Asn Gly Lys Glu Tyr Lys Cys Lys Val Ser Asn Lys Ala
        850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
                900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
        930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
                980
```

PHARMACEUTICAL COMPOSITION COMPRISING BISPECIFIC ANTIBODY CONSTRUCTS FOR IMPROVED STORAGE AND ADMINISTRATION

BACKGROUND

Protein therapeutics including protein-based pharmaceuticals already have a significant role in almost every field of medicine and are among the fastest growing therapeutic agents in (pre)clinical development and as commercial products (Leader, *Nature Reviews Drug Discovery* 2008 Jan. 7, 21-39). In comparison with small chemical drugs, protein pharmaceuticals have high specificity and activity at relatively low concentrations, and typically provide for therapy of high impact diseases such as various cancers, autoimmune diseases, and metabolic disorders (Roberts, *Trends Biotechnol.* 2014 July; 32(7):372-80, Wang, *Int J Pharm.* 1999 Aug. 20; 185(2):129-88).

Protein-based pharmaceuticals, such as recombinant proteins, can now be obtained in high purity when first manufactured due to advances in commercial scale purification processes. However, proteins are only marginally stable and are highly susceptible to degradation, both chemical and physical. Chemical degradation refers to modifications involving covalent bonds, such as deamidation, oxidation, cleavage or formation of new disulfide bridges, hydrolysis, isomerization, or deglycosylation. Physical degradation includes protein unfolding, undesirable adsorption to surfaces, and aggregation. Dealing with these physical and chemical instabilities is one of the most challenging tasks in the development of protein pharmaceuticals (Chi et al., Pharm Res, Vol. 20, No. 9, September 2003, pp. 1325-1336, Roberts, Trends Biotechnol. 2014 July; 32(7):372-80).

Interesting protein-based pharmaceuticals include bispecific antibody constructs such as BiTE® (bispecific T cell engager) antibody constructs which are recombinant protein constructs made from two flexibly linked antibody derived binding domains. One binding domain of BiTE® antibody constructs is specific for a selected tumor-associated surface antigen on target cells; the second binding domain is specific for CD3, a subunit of the T cell receptor complex on T cells. By their particular design BiTE® antibody constructs are uniquely suited to transiently connect T cells with target cells and, at the same time, potently activate the inherent cytolytic potential of T cells against target cells. An important further development of the first generation of BiTE® antibody constructs (see WO 99/54440 and WO 2005/040220) developed into the clinic as AMG 103 and AMG 110 was the provision of bispecific antibody constructs binding to a context independent epitope at the N-terminus of the CD3ε chain (WO 2008/119567). BiTE® antibody constructs binding to this elected epitope do not only show cross-species specificity for human and *Callithrix jacchus*, *Saguinus oedipus* or *Saimiri sciureus* CD3ε chain, but also, due to recognizing this specific epitope instead of previously described epitopes for CD3 binders in bispecific T cell engaging molecules, do not unspecifically activate T cells to the same degree as observed for the previous generation of T cell engaging antibodies. This reduction in T cell activation was connected with less or reduced T cell redistribution in patients, which was identified as a risk for side effects.

Antibody constructs as described in WO 2008/119567 are likely to suffer from rapid clearance from the body; thus, whilst they are able to reach most parts of the body rapidly, and are quick to produce and easier to handle, their in vivo applications may be limited by their brief persistence in vivo. Prolonged administration by continuous intravenous infusion is used to achieve therapeutic effects because of the short in vivo half life of this small, single chain molecule. However, such continuous intravenous infusions are classified as inconvenient for the patients, for example, because the infusion bags have to be exchanged frequently, at least every second day, in order to avoid microbial contamination and, thus, side effects like sepsis.

The addition of preservatives is envisaged as one solution to this problem. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives is challenging. Preservatives almost always have a destabilizing effect (aggregation) on proteins, and this has become a major factor in limiting their use in protein formulations. Therefore, most protein drugs today have been formulated for single-use only. Only few preservative-comprising formulations were so far possible, such as human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol. Several aspects need to be considered during the formulation and development of preserved dosage forms. The effective preservative concentration in the drug product must be optimized. This requires testing a given preservative in the dosage form with concentration ranges that confer antimicrobial effectiveness without compromising protein stability. An important point to note is that preservative effectiveness should be demonstrated in the final formulation containing the active drug and all excipient components.

Hence, it is an objective of the present invention to provide improved pharmaceutical compositions comprising bispecific antibody constructs which are preferably preserved in such a way that continuous infusions may be conducted at longer intervals, i.e. to enhance patient comfort, and at the same time are stable both during storage and administration. However, a suitable preserved pharmaceutical composition comprising a bispecific antibody construct would be of advantage also for such bispecific antibody constructs which do not require continuous infusion over days but just a few hours because also infusions of these half life extended (HLE) bispecific antibody constructs may take several hours within which time the risk of microbial contamination and thus, infection, should be reduced. At the same time, also recovery of the pharmaceutical composition and the bispecific antibody construct comprised therein is also an object of the present invention.

An increased half-life is generally useful in in vivo applications of immunoglobulins, especially antibodies and most especially antibody fragments of small size. Approaches described in the art to achieve such effect comprise the fusion of the small bispecific antibody construct to larger proteins, which preferably do not interfere with the therapeutic effect of the BiTE® antibody construct. Examples for such further developments of bispecific T cell engagers comprise bispecifc Fc-molecules e.g. described in US 2014/0302037, US 2014/0308285, WO 2014/144722, WO 2014/151910 and WO 2015/048272.

However, avoiding protein aggregation is a major obstacle when aiming for preservation. Protein aggregation represents a major event of physical instability of proteins and occurs due to the inherent tendency to minimize the thermodynamically unfavorable interaction between the solvent and hydrophobic protein residues. It is particularly problematic because it is encountered routinely during refolding, purification, sterilization, shipping, and storage processes. Aggregation can occur even under solution conditions where the protein native state is highly thermodynamically favored (e.g., neutral pH and 37° C.) and in the absence of stresses (Chi et al., Pharm Res, Vol. 20, No. 9, September 2003, pp. 1325-1336, Roberts, Trends Biotechnol. 2014 July; 32(7):372-80, Wang, Int J Pharm. 1999 Aug. 20; 185(2):129-88, Mahler J Pharm Sci. 2009 September; 98(9):2909-34).

Also half-life extended antibody constructs such as of bispecific T cell engagers comprising a half-life extending modality such as Fc-molecules have to be protected against protein aggregation and/or other degradation events. Protein aggregation is problematic because it can impair biological activity of the therapeutic proteins. Moreover, aggregation of proteins leads to undesirable aesthetics of the drug product, and decreases product yield due to elaborate purification steps that are required to remove the aggregates from the end product. More recently, there has also been growing concern and evidence that the presence of aggregated proteins (even humanized or fully human proteins) can significantly increase the risk that a patient will develop an immune response to the active protein monomer, resulting in the formation of neutralizing antibodies and drug resistance, or other adverse side effects (Mahler J Pharm Sci. 2009 September; 98(9):2909-34.

In general, several efforts have been reported in the literature to minimize protein aggregation by various mechanisms. Proteins can be stabilized and thus protected from aggregate formation and other chemical changes by modifying their primary structure, thereby increasing interior hydrophobicity and reducing outer hydrophobicity. However, genetic engineering of proteins may result in impaired functionality and/or increased immunogenicity. Another approach focuses on the dissociation of aggregates (referred to as "disaggregation") to recover functional, native monomers by using various mechanisms such as temperature, pressure, pH, and salts. Currently, protein aggregates are removed as impurities mainly in the polishing steps of downstream processing. However, in cases of high levels of high-molecular weight (HMW), removing significant amount of HMW not only results in substantial yield loss but also makes the design of a robust downstream process challenging (Chi et al., Pharm Res, Vol. 20, No. 9, September 2003, pp. 1325-1336).

Preserving a bispecific antibody construct formulation over a wide concentration range while maintaining its stability and ensuring its quantitative recovery from the administration container poses serious challenges. There is a need in the art for optimized pharmaceutical compositions that provide for enhanced stabilization of preserved therapeutic protein formulations. It is the object of the present invention to comply with this need, both with regard to non half-life extended bispecific antibody constructs and half-life extended bispecific antibody constructs such as of bispecific T cell engagers comprising a half-life extending modality such as Fc-molecules.

SUMMARY

The safe, quantitative and optionally prolonged administration of protein-based pharmaceuticals such as bispecific antibody constructs including bispecific T cell engaging antibody constructs, typically via the i.v. route, is challenging. To this end, in the context of the present invention, a pharmaceutical composition is provided, comprising i. a bispecific antibody construct, binding to a target cell surface antigen via a first binding domain and to the T cell surface antigen CD3 via a second binding domain, wherein the chain antibody construct is present in a concentration in the range from 0.5 µg/ml to 20 mg/ml, preferably 0.5 µg/ml to 10 or 5 mg/ml.

ii. at least one preservative selected from benzyl alcohol, chlorobutanol, phenol, meta-cresol, methylparaben, phenoxyethanol, propylparaben and thiomerosal at a concentration effective to inhibit the growth of microbes, iii. a diluent, wherein the bispecific antibody construct is stable.

It is envisaged in the context of the present invention that the bispecific antibody construct is present at a concentration in the range selected from the list consisting of (a) 0.5 to 200 µg/ml at a pH of 6.5 to 7.5, or
(b) 0.5 to 1000 µg/ml at a pH of 4.0 to 6.0, or
(c) 0.5 µg to 2 mg in the presence of a CD3 binding domain stabilizing agent, preferably citrate, at a pH of 4.0 to 7.5 or
(d) 0.5 µg to 20 mg, preferably 0.5 µg to 10 or 5 mg/ml at a pH of 4.0 to 7.5, wherein the bispecific antibody comprises a third binding domain which comprises two polypeptide monomers, each comprising a hinge, a CH2 and a CH3 domain, wherein said two polypeptide monomers are fused to each other via a peptide linker, and wherein said third binding domain comprises in an amino to carboxyl order:

hinge-CH2-CH3-linker-hinge-CH2-CH3.

It is also envisaged in the context of the present invention that the pharmaceutical composition comprises a bispecific antibody construct which is a bispecific single chain antibody construct.

It is further envisaged in the context of the present invention that the bispecific antibody construct is present in a concentration in the range of 1.0 to 20 mg/ml, or 1.0 to 10 mg/ml, or 1.0 µg/ml to 5 mg/ml or 1.0 µg/ml to 4 mg/ml or 1.0 µg/ml to 3 mg/ml, or 1.0 µg/ml to 2 mg/ml or 1.0 µg/ml to 1 mg/ml or 1.5 to 5 mg/ml or 1.5 µg/ml to 4 mg/ml or 1.5 µg/ml to 3 mg/ml, or 1.5 µg/ml to 2 mg/ml or 1.5 µg/ml to 1 mg/ml or 1.5 to 200 µg/ml.

It is also envisaged in the context of the present invention that the at least one preservative is present in a concentration in the range from 0.001 to 1.0% (w/v).

It is even more envisaged in the context of the present invention that the preservative is present in a concentration in the range from 0.009 to 0.9% (w/v), preferably 0.11 to 0.9%, or 0.5 to 0.75% (w/v) or 0.6 to 0.74% (w/v).

It is envisaged in the context of the present invention that the diluent is a buffer comprising a salt selected from the group consisting of phosphate, acetate, citrate, succinate and tartrate, and/or wherein the buffer comprises histidine, glycine, TRIS glycine, Tris, or mixtures thereof.

It is further envisaged in the context of the present invention that the diluent is a buffer selected from the group consisting of potassium phosphate, acetic acid/sodium acetate, citric acid/sodium citrate, succinic acid/sodium succinate, tartaric acid/sodium tartrate, and histidine/histidine HCl or mixtures thereof.

It is also envisaged in the context of the present invention that the diluent is a buffer present at a concentration in the range of 0.1 to 150 mM, preferably in the range of 0.25 to 50 mM.

It is even more envisaged in the context of the present invention that the diluent is a buffer comprising citrate at a concentration the range of 0.25 to 50 mM.

It is envisaged in the context of the present invention that the pH of the composition is in the range of 4.0 to 8.0, preferably in the range of pH 4.0 to 5.0 or pH 6.5 to 7.5, or preferably at pH 7.0.

It is further envisaged in the context of the present invention that the pharmaceutical composition further comprises one or more excipients selected from the group consisting of sucrose, trehalose, mannitol, sorbitol, arginine, lysine, polysorbate 20, polysorbate 80, poloxamer 188, pluronic and combinations thereof.

It is also envisaged in the context of the present invention that the pharmaceutical composition further comprises polysorbate, preferably polysorbate 80, and/or lysine HCL.

It is further envisaged in the context of the present invention that the pharmaceutical composition does not comprise polysorbate, preferably polysorbate 80, and/or lysine HCL if the concentration of the bispecific antibody construct is at least 10 μg/ml, preferably 15 μg/ml or 20 μg/ml.

It is even more envisaged in the context of the present invention that the first binding domain of the bispecific antibody construct binds to at least one target cell surface antigen selected from the group consisting of CD19, CD33, EGFRvIII, MSLN, CDH19, FLT3, DLL3, CDH3, BCMA and PSMA.

It is envisaged in the context of the present invention that the first binding domain comprises a VH region comprising CDR-H1, CDR-H2 and CDR-H3 and a VL region comprising CDR-L1, CDR-L2 and CDR-L3 selected from the group consisting of:

(a) CDR-H1 as depicted in SEQ ID NO: 1, CDR-H2 as depicted in SEQ ID NO: 2, CDR-H3 as depicted in SEQ ID NO: 3, CDR-L1 as depicted in SEQ ID NO: 4, CDR-L2 as depicted in SEQ ID NO: 5 and CDR-L3 as depicted in SEQ ID NO: 6, (b) CDR-H1 as depicted in SEQ ID NO: 29, CDR-H2 as depicted in SEQ ID NO: 30, CDR-H3 as depicted in SEQ ID NO: 31, CDR-L1 as depicted in SEQ ID NO: 34, CDR-L2 as depicted in SEQ ID NO: 35 and CDR-L3 as depicted in SEQ ID NO: 36, (c) CDR-H1 as depicted in SEQ ID NO: 42, CDR-H2 as depicted in SEQ ID NO: 43, CDR-H3 as depicted in SEQ ID NO: 44, CDR-L1 as depicted in SEQ ID NO: 45, CDR-L2 as depicted in SEQ ID NO: 46 and CDR-L3 as depicted in SEQ ID NO: 47, (d) CDR-H1 as depicted in SEQ ID NO: 53, CDR-H2 as depicted in SEQ ID NO: 54, CDR-H3 as depicted in SEQ ID NO: 55, CDR-L1 as depicted in SEQ ID NO: 56, CDR-L2 as depicted in SEQ ID NO: 57 and CDR-L3 as depicted in SEQ ID NO: 58, (e) CDR-H1 as depicted in SEQ ID NO: 65, CDR-H2 as depicted in SEQ ID NO: 66, CDR-H3 as depicted in SEQ ID NO: 67, CDR-L1 as depicted in SEQ ID NO: 68, CDR-L2 as depicted in SEQ ID NO: 69 and CDR-L3 as depicted in SEQ ID NO: 70, (f) CDR-H1 as depicted in SEQ ID NO: 83, CDR-H2 as depicted in SEQ ID NO: 84, CDR-H3 as depicted in SEQ ID NO: 85, CDR-L1 as depicted in SEQ ID NO: 86, CDR-L2 as depicted in SEQ ID NO: 87 and CDR-L3 as depicted in SEQ ID NO: 88, (g) CDR-H1 as depicted in SEQ ID NO: 94, CDR-H2 as depicted in SEQ ID NO: 95, CDR-H3 as depicted in SEQ ID NO: 96, CDR-L1 as depicted in SEQ ID NO: 97, CDR-L2 as depicted in SEQ ID NO: 98 and CDR-L3 as depicted in SEQ ID NO: 99, (h) CDR-H1 as depicted in SEQ ID NO: 105, CDR-H2 as depicted in SEQ ID NO: 106, CDR-H3 as depicted in SEQ ID NO: 107, CDR-L1 as depicted in SEQ ID NO: 109, CDR-L2 as depicted in SEQ ID NO: 110 and CDR-L3 as depicted in SEQ ID NO: 111, (i) CDR-H1 as depicted in SEQ ID NO: 115, CDR-H2 as depicted in SEQ ID NO: 116, CDR-H3 as depicted in SEQ ID NO: 117, CDR-L1 as depicted in SEQ ID NO: 118, CDR-L2 as depicted in SEQ ID NO: 119 and CDR-L3 as depicted in SEQ ID NO: 120, (j) CDR-H1 as depicted in SEQ ID NO: 126, CDR-H2 as depicted in SEQ ID NO: 127, CDR-H3 as depicted in SEQ ID NO: 128, CDR-L1 as depicted in SEQ ID NO: 129, CDR-L2 as depicted in SEQ ID NO: 130 and CDR-L3 as depicted in SEQ ID NO: 131, (k) CDR-H1 as depicted in SEQ ID NO: 137, CDR-H2 as depicted in SEQ ID NO: 138, CDR-H3 as depicted in SEQ ID NO: 139, CDR-L1 as depicted in SEQ ID NO: 140, CDR-L2 as depicted in SEQ ID NO: 141 and CDR-L3 as depicted in SEQ ID NO: 142, (l) CDR-H1 as depicted in SEQ ID NO: 152, CDR-H2 as depicted in SEQ ID NO: 153, CDR-H3 as depicted in SEQ ID NO: 154, CDR-L1 as depicted in SEQ ID NO: 155, CDR-L2 as depicted in SEQ ID NO: 156 and CDR-L3 as depicted in SEQ ID NO: 157, and (m) CDR-H1 as depicted in SEQ ID NO: 167, CDR-H2 as depicted in SEQ ID NO: 168, CDR-H3 as depicted in SEQ ID NO: 169, CDR-L1 as depicted in SEQ ID NO: 107, CDR-L2 as depicted in SEQ ID NO: 171 and CDR-L3 as depicted in SEQ ID NO: 172.

It is further envisaged in the context of the present invention that the bispecific antibody construct is provided with a half-life extending (HLE) moiety, preferably a scFc domain.

It is also envisaged in the context of the present invention that the pharmaceutical composition is liquid, lyophilized or frozen liquid.

It is even more envisaged in the context of the present invention that the composition comprises <5% of multimers of the bispecific antibody construct, preferably <1%.

It is envisaged in the context of the present invention that the multimers are dimers.

It is further envisaged in the context of the present invention that the composition comprises <5% of multimers of the bispecific antibody construct, preferably <1% for a time period of at least 4 days, preferably at least 10 days, more preferably at least 14 days at room temperature.

It is also envisaged in the context of the present invention that the pharmaceutical composition is filled in a plastic administration container preferably made of EVA, polyolefin, and/or PVC.

It is even more envisaged in the context of the present invention that the bispecific single chain antibody construct is recovered by at least 90%, preferably at least 95, 96, 97, 98 or even at least 99% from the dilution from the plastic administration container comprising at least one of the buffers and/or excipients according to claims 6 to 13.

It is envisaged in the context of the present invention that the pharmaceutical composition comprises at least 0.25 mM citrate, at least 0.0125 mM lysine and/or at least 0.001% polysorbate 80 at a pH of 6.5 to 7.5.

It is further envisaged that the pharmaceutical composition in the context of the present invention is a storage solution stored at −50° C., preferably at −40, −30° C. or −20° C.

It is also envisaged in the context of the present invention that the pharmaceutical composition provided as a storage solution stored at −50° C., preferably at −40, −30° C. or −20° C. comprises the bispecific antibody comprising a third binding domain which comprises two polypeptide monomers, each comprising a hinge, a CH2 and a CH3 domain, wherein said two polypeptide monomers are fused to each other via a peptide linker, and wherein said third binding domain comprises in an amino to carboxyl order:

hinge-CH2-CH3-linker-hinge-CH2-CH3.

It is further envisaged in the context of the present invention that the bispecific antibody construct is provided as a lyophilisate, the lyophilisate preferably comprising a lyoprotector, a buffer and/or a surfactant, and wherein the lyophilisate is reconstituted by a diluent, comprising a preservative and preferably comprising a buffer and/or an excipient.

It is especially envisaged in the context of the present invention that the pharmaceutical composition is stored until use as solution, as solution in frozen state or as lyophilisate, and is then administered, optionally after dilution or reconstitution, without the need of adding further excipients selected from preservatives, stabilizers or surfactants.

It is also envisaged in the context of the present invention that the pharmaceutical composition is for use in the treatment of a malignant disease.

Even more envisaged in the context of the present invention is a method for the treatment or amelioration of a malignant disease, comprising the step of administering to a subject in need thereof the pharmaceutical composition according to the present invention, or produced according to the method of the present invention.

It is envisaged in the context of the present invention that the pharmaceutical composition according to the present invention is administered intravenously, preferably continuously, for 1 to 24 hours, preferably 1 to 10 or 2 to 5 hours.

It is further envisaged in the context of the present invention that the pharmaceutical composition according to the present invention is administered intravenously continuously for 2 to 14 days, preferably for 2 to 10 days, most preferably for 4 to 7 days.

Also envisaged in the context of the present invention is a kit comprising the bispecific antibody construct as a lyophilisate, the lyophilisate preferably comprising a lyoprotector, a buffer and/or a surfactant, and a diluent, comprising a preservative and preferably comprising a buffer and/or an excipient according to the present invention.

DESCRIPTION OF THE FIGURES

FIGS. 6E and 6F show the effect of citrate and benzyl alcohol individually and FIGS. 6G and 6H in combination, each at a bispecific antibody construct or single domain concentration of 600 µg/ml each. The results are the same for anti-CD3 domain, CD33×CD3 bispecific antibody constructs, FAPα, and EGFRvIII×CD3 bispecific antibody constructs.

DETAILED DESCRIPTION

Figure 1:
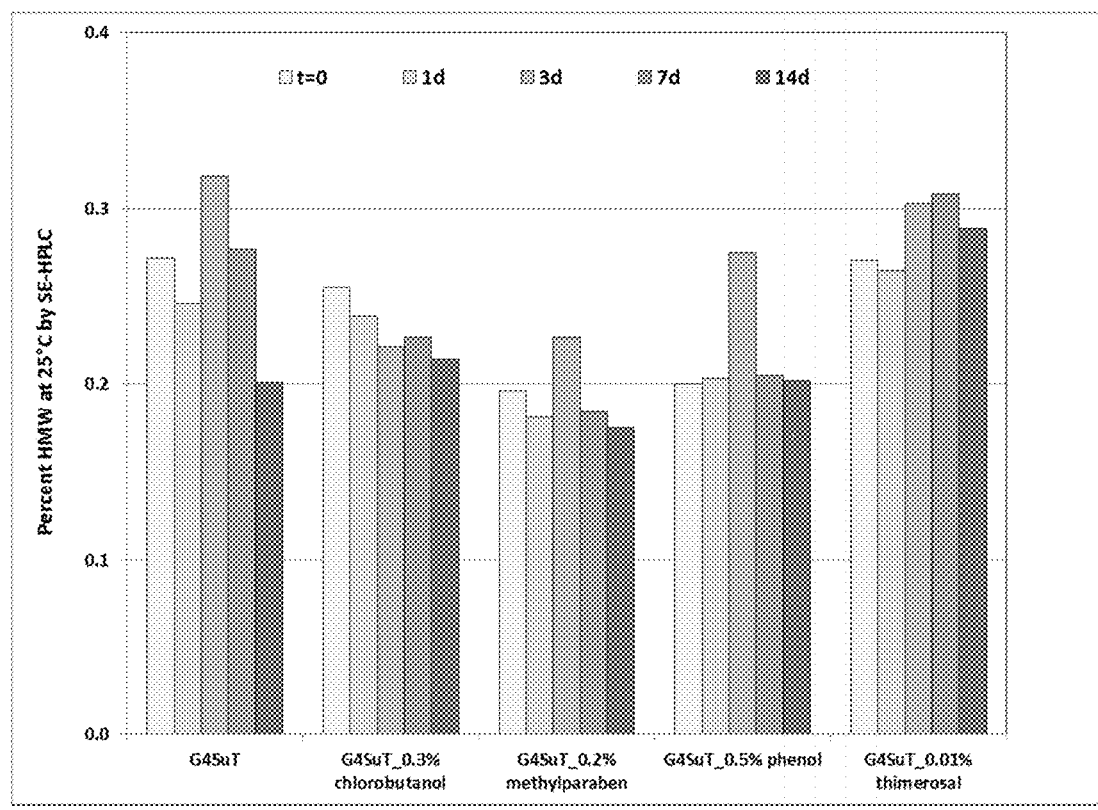
FIG. 1: Stability diagram as per percentile high molecular weight (HMW) species of CD19×CD3 bispecific antibody constructs as determined by SEC-HPLC for preservatives chlorobutanol, methylparaben, phenol and thiomerosal at 25° C. and pH 4.
Figure 2:
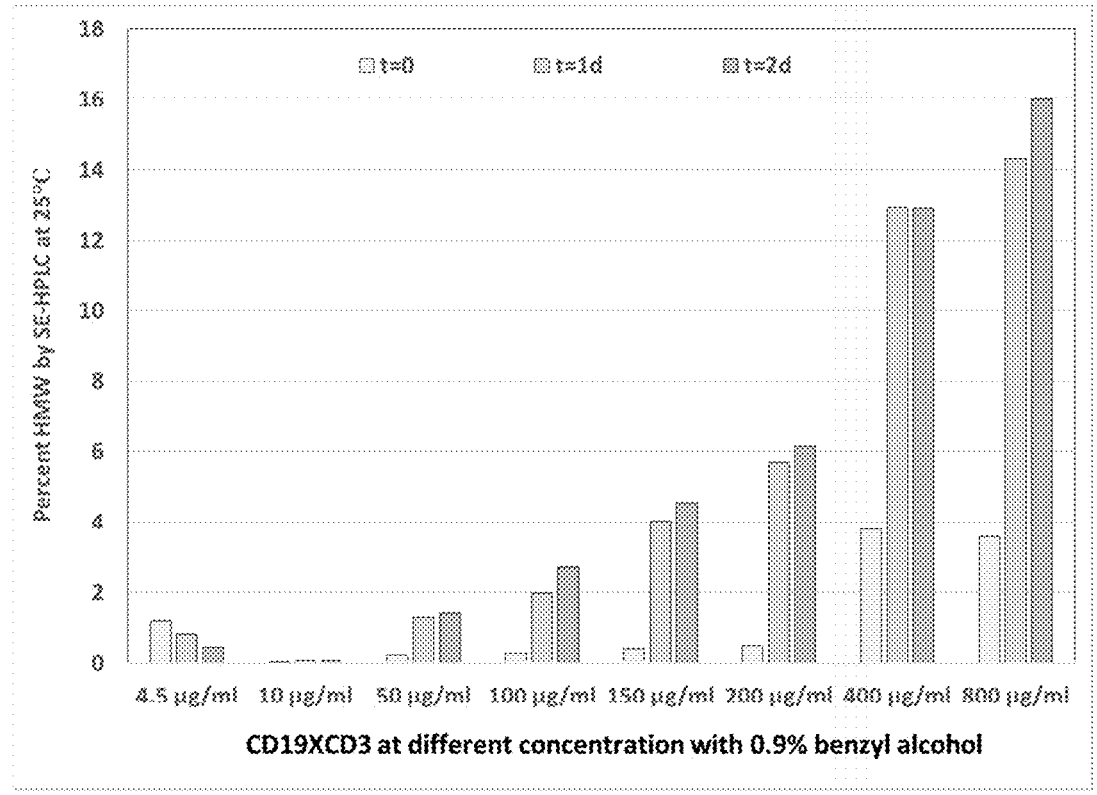
FIG. 2: Stability diagram as per percentile high molecular weight (HMW) species of CD19×CD3 bispecific antibody constructs as determined by SEC-HPLC for preservative benzyl alcohol depending on CD19×CD3 bispecific antibody constructs concentration at 25° C. and pH 7.

A general concept underlying the present invention is the surprising finding that the stability of a pharmaceutical composition, both in liquid and frozen state, comprising a bispecific antibody construct according to the present invention is improved by the addition of a preservative to the liquid pharmaceutical composition, typically depending on concentration of the bispecific antibody construct and the preservative. It has been surprisingly found that a pharmaceutical composition which comprises a bispecific antibody construct, which is preferably a single chain antibody construct such as a BiTE® antibody construct, both when comprising a third domain as defined herein, i.e. being a half live extended (HLE) bispecific antibody construct or not, if present at a certain concentration of about 0.5 µg/ml to 5 mg/ml is not only stable in the presence of a preservative but may be even stabilized by this preservative. This is particularly surprising as it was known in the art that preservatives such as benzyl alcohol, m-cresol and phenoxyethanol promote the aggregation of proteins such as antibodies. However, depending for example on the bispecific antibody concentration type, and optionally the pH and the presence of a further complementing stabilizing agent, the pharmaceutical composition according to the present invention is stable. Therein, the first binding domain as described herein (targeting domain) is of less importance because the stabilizing action of a preservative and optional further stabilizing complementing excipient, such as citrate, is primarily associated with interaction with the second binding domain (CD3 binding domain). Advantageously, the preservative may serve to physically and microbiologically stabilize the pharmaceutical composition during storage, e.g. in frozen state, and—after optional pH adjustment and/or dilution—when administered. Hence, conveniently the same pharmaceutical composition may be used, despite optional pH adjustment, e.g. from low pH such as 4.0 to 6.5 to a neutral pH from 6.5 to 7.5, and dilution for the purpose of i.v. administration. Throughout, the bispecific antibody construct concentration is, however, in range of 0.5 µg/ml to 5 mg/ml, or in some circumstances, in the range of 0.3 µg/ml to 10, 20, or even 30 mg/ml. Thereby, pharmaceutical composition comprising containers such as i.v. infusion bags may be only required to be exchanged with longer time intervals such as 3, 4, 5, 6, 7, 8, 9, 10, 11, 12, 13 or even 14 days due to reduced lack of microbial contamination, which significantly increases patient comfort.

Stabilizing and microbiologically effective preservatives include but are not limited to benzyl alcohol, chlorobutanol, methylparaben, phenol and thierosal. Useful preservatives for formulating pharmaceutical compositions generally include antimicrobials (e.g. anti-bacterial or anti-fungal agents), anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide). Antimicrobial preservatives are substances which are used to extend the shelf-life of medicines by reducing microbial proliferation. Preservatives that particularly useful for formulating the pharmaceutical composition of the invention include benzyl alcohol, chlorobutanol, phenol, meta-cresol, methylparaben, phenoxyethanol, propylparaben thiomerosal. The structure and typical concentration for the use of these preservatives are described in Table 1 of Meyer et al. J Pharm Sci. 96(12), 3155.

The aforementioned preservatives may be present in the pharmaceutical composition in different concentrations. For instance, benzyl alcohol may be present in a concentration ranging between 0.2 and 1.1% (w/v), preferably 0.5 to 0.9% (v/v), chlorobutanol in a concentration ranging between 0.3-0.5% (w/v), phenol in a concentration ranging between 0.07 and 0.5% (w/v), meta-cresol in a concentration ranging between 0.17 and 0-32% (w/v) or thiomerosal in a concentration ranging between 0.003 to 0.01% (w/v). Preferred concentrations for methylparaben are in the range of 0.05 and 0.5% (w/v), for phenoxyethanol in the range of 0.1 and 3% (w/v) and for propylparaben in the range of 0.05 and 0.5% (w/v).

Without wanting to be bound by theory, preservatives such as benzyl alcohol, bind to dimerization sites of bispecific antibody constructs such as CD19×CD3 bispecific antibody construct at an appropriate concentration and, thus, reduce the possibility of forming dimers or other multimers. Thereby, the aggregation risk is significantly reduced, for example in CD19×CD3, BCMA×CD3, PSAM×CD3, CD33×CD3 or EGFRvIII×CD3 bispecific antibody construct. This is in particular surprising, because several regions of unfolding suggest that a preservative such as benzyl alcohol is destabilizing the bispecific antibody construct's monomer which should lead to increased dimer/aggregate formation. However, some of these regions overlap with regions likely being involved with dimer formation. This regional unfolding may be disrupting the dimer formation with conversion back to monomer and an overall stabilizing effect as long as the bispecific antibody concentration remains within certain limits.

In certain embodiments, a buffer and/or excipient may be employed to increase the stability of the bispecific antibody construct in the presence of a preservative in a pharmaceutical composition for i.v. administration according to the present invention. Such an excipient is referred to herein as complementing stabilizing agent which interacts with the CD3 binding domain. In specific embodiments, for example at a neutral pH and/or the bispecific antibody construct not having the third binding domain as described herein and being present in the pharmaceutical composition in a higher concentration, e.g. above 50, 100, 150, 200, 250, 300, 350, 400, 450, 500, 550, 600, 650, 700, 750, 800, 850, 900, 950 or 1000 µg/ml, typically at least 50 µg/ml or 200 µg/ml, such complementing stabilizing agent may be preferred to ensure the stability of the bispecific antibody construct in the presence of a preservative. This may be the case, for example, for bispecific antibody constructs without a third binding domain as described herein, e.g. CD33×CD3 bispecific antibody construct. It is envisaged that no such complementing stabilizing agents such as citrate are required if the bispecific antibody construct concentration is, for example, 200, 150, 100 or 50 µg/ml or lower. However, other buffers/excipients such as polysorbate, e.g. polysorbate 80 may be preferred at a concentration of 20, 15 or 10 µg/ml of bispecific antibody construct in order to allow for quantitative recovery, i.e. the loss e.g. due to adsorption to the administration container is low and the percentile recovered amount corresponds to at least 90, 91, 92, 93, 94, 95, 96, 97, 98, 99, or even 99.5% This is of particular advantage as excessive excipients are saved both for practical (handling) as for medical reasons (allergies, side-effects).

A low pH complements to the stabilization of the bispecific antibody construct by a preservative also at a higher concentration than at a neutral pH, which is why a pharmaceutical composition comprising higher concentrations, such as at least 200, 300, 400, 500, 600, 700, 800, 900 or 1000 µg/ml, is stable, i.e. shows preferably a low percentile HMW concentration below 5, 4, 3, 2, 1 or even 0.5%.

Buffers and/or excipients used in certain embodiments for stabilizing the bispecific antibody construct in the presence of a preservative may include but is not limited to citrate, lysine and polysorbate 80. Any of these compounds individually or in any combination or a comparable compound as to its function or structure may be used to obtain a stabilizing effect for the bispecific antibody construct in the presence of a preservative according to the present invention and/or increase recovery, also in the absence of a preservative where the latter is not needed for stability or microbiologic stability.

The buffers and/or excipients used in certain embodiments for stabilizing the bispecific antibody construct in the presence of a preservative may also and/or concurrently be surprisingly used to improve the recovery of the bispecific antibody construct from the (plastic) container which is used to administer the pharmaceutical composition to the patient. As the drugs according to the present invention are typically dosed at very low concentration, e.g. adsorption to the administration container such as an i.v. infusion bag, may have significant influence on the effective dosing. Therefore, it is very beneficial that the addition of such buffers and/or excipients may increase the recovery of the drug from the container. For example, the addition of a combination of citrate, lysine and/or polysorbate 80 to the pharmaceutical composition to the administered to the patient may increase recovery by up to 250% compared to the drug concentration in the absence of these compounds. Relatively low amounts, e.g. of at least 0.25 to 1 mM citrate, 0.0125 M lysine and/or 0.001% polysorbate 80 may be sufficient to this end. This translates to 1% of IVSS solution to be administered to the patient which may be sufficient. Even better results may be obtained with higher amounts such as 2, 3, 4, 5, 6, 7, 8, 9 or 10% IVSS. 4% IVSS may be preferred. However, not all components of IVSS may be required to obtain the effect of improved recovery. E.g. polysorbate alone may sufficiently reduce drug adsorption to the administration container. Said aspect of the present invention contributes to improved dose reliability for very potent drugs such as bispecific antibody constructs. Hence, patient safety is also improved by the present invention.

However, over a certain threshold, such buffers and/or excipients may not be required any more to improve the recovery. Such a threshold is, for example, 10 µg/ml, 15 µg/ml or 20 µg/ml, preferably 15 µg/ml. However, generally, a pharmaceutical composition is preferred which comprises at least a surfactant as excipient with regard to recovery, such as polysorbate, especially polysorbate 80.

In another aspect of the present invention, based onHDX findings, preservatives such as benzyl alcohol may specifically destabilize the second binding domain (anti-CD3 domain) of bispecific antibody constructs according to the present invention by (hydrophobic) interaction, if the bispecific antibody construct is present above a certain threshold which depends on the absence of presence of the third binding domain according to the present invention and/or the pH of the pharmaceutical composition. Typically, the threshold is higher if a third binding domain as described herein is present and/or the pH is acidic such as pH 4.0 to 6.5. Without wanting to be bound by theory, such bispecific antibody construct destabilization may be associated with increased conformational dynamics which in turn can generally be associated with reduced molecule stability. However, it was surprisingly found herein that buffers and/or excipients such as citrate comprising buffers or excipients may counter-balances that destabilizing effect. The counteracting effects between such buffers and/or excipients and the preservative may apply to all bispecific antibody constructs (with regard to the conformation) having an anti-CD3 domain characterized by CDRS represented in SEQ ID Nos 18 to 23. As it has been seen with regard to such bispecific antibody constructs, at lower concentrations (e.g. below 50 µg/ml), no stabilizing excipient is required in the presence of a preservative such as benzyl alcohol, when the preservative such as benzyl alcohol may surprisingly have stabilizing properties by itself due to the suppression or reduction of dimers. Typically, this is not to be the case at higher concentrations, e.g. at higher concentration than 200 µg/ml, provided the pharmaceutical composition has a pH above 6.5 and/or the bispecific antibody construct comprises a third domain as described herein. In case of a destabilizing effect of the preservative outweighs its stabilizing effect based on the bispecific antibody construct concentration, an excipient such as citrate may be used as additional and complementing stabilizing excipient. Hence, the addition of an additional stabilizing agent such as citrate allows for a more versatile use (concentration range) of bispecific antibody constructs in the presence of a preservative such as benzyl alcohol.

It is alternatively envisaged in the context of the present invention that the pharmaceutical composition is, for example, for infusion over 7 days using Bacteriostatic 0.9% Sodium Chloride, USP (containing 0.9% benzyl alcohol). It is in particular envisaged that this option is available for patients weighing greater than or equal to a certain threshold for security reasons. Such a threshold may be 20, 22 or 25 kg.

It is envisaged in a specific embodiment in the context of the present invention, that the bispecific antibody construct according to the present invention is supplied in a single-dose vial as a sterile, preservative-free, white to off-white lyophilized powder for intravenous administration. Each single-dose vial of a CD19×CD3 antibody construct contains 35 mcg bispecific antibody construct according to the present invention, citric acid monohydrate (3.35 mg), lysine hydrochloride (23.23 mg), polysorbate 80 (0.64 mg), trehalose dihydrate (95.5 mg), and sodium hydroxide to adjust pH to 7.0. After reconstitution with 3 mL of 0.9% Sodium Chloride, USP (containing 0.9% benzyl alcohol), the resulting concentration is 12.5 mcg/mL bispecific antibody construct according to the present invention. I.v. Solution Stabilizer (IVSS) is supplied in a single-dose vial as a sterile, preservative-free, colorless to slightly yellow, clear solution. Each single-dose vial of IV Solution Stabilizer contains citric acid monohydrate (52.5 mg), lysine hydrochloride (2283.8 mg), polysorbate 80 (10 mg), sodium hydroxide to adjust pH to 7.0, and water for injection.

Within the present invention, the term "stability" or "stabilization" relates to the stability of the pharmaceutical composition in total and in particular to the stability of the active ingredient (i.e. the bispecific single chain antibody construct) itself, specifically during formulation, filling, shipment, storage and administration. The terms "stability" or "stable" in the context of the pharmaceutical composition of the invention and the bispecific single chain antibody construct particularly refers to the reduction or prevention of the formation of protein aggregates (HMWS). Specifically, the term "stability" also relates to the colloidal stability of the bispecific (single chain) antibody constructs comprised within the pharmaceutical composition described herein.

"Colloidal stability" is the ability of colloidal particles (such as proteins) to remain dispersed in liquids for a prolonged period of time (days to years). When stability with respect to preservation is concerned, the term microbiologic stability is used.

The term "(protein) aggregate" as used herein generally encompasses protein species of higher molecular weight such as "oligomers" or "multimers" instead of the desired defined species (e.g., a monomer). The term is used interchangeably herein with the terms "high molecular weight species" and "HMWS". Protein aggregates may generally differ in size (ranging from small (dimers) to large assemblies (subvisible or even visible particles) and from the nanometer to micrometer range in diameter), morphology (approximately spherical to fibrillar), protein structure (native vs. non-native/denatured), type of intermolecular bonding (covalent vs. non-covalent), reversibility and solubility. Soluble aggregates cover the size range of roughly 1 to 100 nm, and protein particulates cover subvisible (~0.1-100 .m) and visible (>100 .m) ranges. All of the aforementioned types protein aggregates are generally encompassed by the term. The term "(protein) aggregate" thus refers to all kinds physically-associated or chemically linked non-native species of two or more protein monomers.

The term "protein aggregation" or "non-native aggregation" thus denotes the process(es) by which protein molecules assemble into complexes composed of two or more proteins, with the individual proteins denoted as the monomer. There are multiple pathways leading to protein aggregation that can be induced by a wide variety of conditions, including temperature, mechanical stress such as shaking and stirring, pumping, freezing and/or thawing and formulation.

An increase in temperature accelerates chemical reactions such as oxidation and deamidation of proteins, which can in turn promote aggregation. Higher temperature also directly influences conformation of proteins on the quaternary, tertiary, and secondary structure level, and can lead to temperature-induced unfolding that can promote aggregation. Temperatures referred to in the present application typically are deep freezing temperature for long term storage of delicate protein-based pharmaceuticals (−70° C.), regular freezing temperature (−20° C.), refrigeration temperature (4° C.), room temperature (25° C.) and physiologic temperature (37° C.).

Hence, it was surprising to find that the addition of a preservative to the pharmaceutical composition of the present invention may suppress frozen state aggregation with regard to the bispecific antibody constructs of the present invention. Such bispecific antibody constructs ca, accordingly, be stored at −50° C., −40° C., or preferably even at −30° or −20° C. instead of −70° C. without showing frozen state aggregation, i.e. the presence of aggregates such as high molecular weight (HMW) species remains below 1% or even below 0.8%, 0.6%, 0.4% or even below 0.3% over a storage time of at least 1 month, such as 1, 2, 3, 4, 5, 6, 12 or 24 months. Advantageously, energy may be saved when −70° C. storage can be replaced by storage at a higher freezing storage temperature or −70° C. storage capacity can be allocated to other more delicate storing items. At the same time, transportation challenges are reduced if only a storage temperature in the regular freeze instead of the deep freeze range is required to store the pharmaceutical composition according to the present invention. Without wanting to be bound by theory, the frozen state aggregates are likely formed due to hydrophobic interactions between specific regions of the first binding domain and the second binding domain of the bispecific antibody construct. The addition of a preservative such as benzyl alcohol, may keep frozen state aggregation low, e.g. below 1% of HMW species with respect to the total amount of bispecific antibody construct in (frozen) solution, by binding to a hydrophobic patch in the second binding domain of the bispecific antibody construct according to the present invention. This is in particular true for bispecific antibody constructs comprising a third domain according to the present invention, such as a scFc HLE domain.

Preferably, the frozen state storage pharmaceutical composition has a pH in the range of pH 4.0 to 6.5, preferably 4.2 to 4.8. Before administration to a patient, the pH may be increased for better i.v. compatibility. However, typically, the pharmaceutical composition may be used without the need of removing particular components such as excipients before administration. Accordingly, the preservative which has functioned as a physical stabilizing agent during e.g. frozen state storage, may subsequently act as stabilizing agent in the liquid administered pharmaceutical composition, optionally after dilution and/or pH adjustment, and may also serve as a preservative to ensure microbiologic stability of the pharmaceutical composition according to the present invention.

Protein denaturation and aggregation can occur during freeze/thawing due to complex physical and chemical changes such as creation of new ice/solution interfaces, adsorption to container surfaces, cryoconcentration of the protein and solutes, and pH changes due to crystallization of buffer components.

An increase in protein concentration can also enhance the formation of protein aggregates. At high protein concentrations, macromolecular crowding occurs, a term used to describe the effect of high total volume occupancy by macromolecular solutes upon the behavior of each macromolecular species in that solution. According to this excluded volume theory, self-assembly and thus potentially aggregation may be favored.

Antimicrobial preservatives, such as benzyl alcohol and phenol, are known in liquid formulations to ensure sterility during its shelf life, and in addition required in multidose formulations and certain drug delivery systems, e.g., injection pens, minipumps and topical applications. Many preservatives have been reported to induce protein aggregation, although the underlying mechanism is not well understood. It has been proposed that preservatives bind to and populate unfolded protein states that are prone to aggregation.

Advantageously, the pharmaceutical compositions of the invention are envisaged to be stable, i.e. to remain free or substantially free from protein aggregates even when subjected to stress, in particular thermal stress, storage, surface-induced stress (such as freeze/thaw cycles, foaming), concentration (by ultra- and diafiltration) or being mixed with organic compounds such as antimicrobial preservatives. Preferably, the pharmaceutical compositions may have similar or even improved characteristics as compared to the compositions having a low pH that have been evaluated in the appended Examples. Pharmaceutical compositions of the invention are preferably homogenous solutions of protein-based pharmaceuticals such as dispersed monomeric bispecific single chain antibody constructs with extended half-life.

The skilled person will appreciate that even though the pharmaceutical composition effectively provides for stabilization of the active ingredient (i.e. reduces or inhibits formation of protein aggregates of the bispecific single chain antibody construct), some aggregates or conformers may occasionally form, however without substantially compromising overall usability of the pharmaceutical composition. In this context "substantially free" of aggregates means that the amount of aggregates remains lower than 10%, 9%, 8%, 7%, 6%, 5%, 4%, 3%, 2% or 1% (w/v), particularly also when being subjected to environmental stress, e.g. as evaluated in the appended Examples.

Methods for determining the presence of soluble and insoluble protein aggregates have been, inter alia, reviewed by Mahler et al., *J Pharm Sci.* 2009 September; 98(9):2909-34. Formation of soluble protein aggregates can be evaluated by size exclusion ultra high performance liquid chromatography (SE-UPLC) as described in the appended Examples. SEC is one of the most used analytical methods for the detection and quantification of protein aggregates. SEC analysis allows both for sizing of aggregates, and their quantification. SEQ-UPLC allows for the selective and rapid separation of macromolecules based on their shape and size (hydrodynamic radius) in a molecular weight range of about 5-1000 kDa.

Protein solutions show an optical property, called opalescence or turbidity. The optical property of a solution is a function of the particles present to scatter and absorb light. Proteins are natural colloids and the turbidity of aqueous formulations depends on protein concentration, the presence of nondissolved particles, particle size and particle number per volume unit. Turbidity can be measured by UV-Vis spectroscopy as optical density in the 340-360 nm range and be used to detect both soluble and insoluble aggregates.

Moreover, the inspection of samples by visual means is still an important aspect of assessing protein aggregates. Visual evaluation for the absence or presence of visible aggregates is preferably performed according to Deutscher Arzneimittel Codex (DAC) Test 5.

As set out elsewhere herein, it is envisaged pharmaceutical composition of the invention—most likely by the action of a low pH and optionally further stabilizing agents comprised therein—favor an increased colloidal stability of the bispecific single chain antibody constructs, and thus exhibit a reduced or even absent liquid-liquid phase separation (LLPS). LLPS is a thermodynamically driven event, in which a homogenous protein solution separates into a protein-poor phase (usually the top layer) and a protein-rich phase (usually the bottom layer) with decreasing temperatures. LLPS is typically fully reversible simply by mixing the two phases and raising the temperature of the solution. The occurrence of LLPS has been attributed to short-range attractive protein-protein interactions—making it a measure of strength of protein-protein attraction. Pharmaceutical compositions comprising 3-cyclodextrins according to the invention have been found to comprise higher concentrations of the bispecific single chain antibody construct in the LLPS protein-poor phase, as compared to pharmaceutical compositions not comprising 3-cyclodextrins. Accordingly, pharmaceutical compositions of the invention are envisaged to exhibit reduced LLPS or no LLPS at all when compared to controls, and thus promoting an increased colloidal stability of the bispecific single chain antibody constructs of the present invention. LLPS can be induced and the protein content of the different phases can be examined as described in the appended Examples.

Environmental stress can, in particular due to thermal and/or chemical denaturation, also lead to conformational changes, which may in turn favor aggregation. Surprisingly, the present inventors found that bispecific single chain antibody constructs are also stabilized with regard to conformational changes as evaluated by measuring intrinsic fluorescence emission intensity of aromatic amino acids. The pharmaceutical composition of the present invention therefore preferably also reduces or inhibits the formation of conformers (i.e. non-native, abnormally folded protein species).

As explained previously, the stable pharmaceutical composition of the present invention comprises a bispecific single chain antibody construct, binding to a target cell surface antigen via a first binding domain and to the T Cell surface antigen CD3 via a second binding domain.

The term "antibody construct" refers to a molecule in which the structure and/or function is/are based on the structure and/or function of an antibody, e.g., of a full-length or whole immunoglobulin molecule and/or is/are drawn from the variable heavy chain (VH) and/or variable light chain (VL) domains of an antibody or fragment thereof. An antibody construct is hence capable of binding to its specific target or antigen. Furthermore, the binding domain of an antibody construct according to the invention comprises the minimum structural requirements of an antibody which allow for the target binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region), preferably of all six CDRs. An alternative approach to define the minimal structure requirements of an antibody is the definition of the epitope of the antibody within the structure of the specific target, respectively, the protein domain of the target protein composing the epitope region (epitope cluster) or by reference to an specific antibody competing with the epitope of the defined antibody. The antibodies on which the constructs according to the invention are based include for example monoclonal, recombinant, chimeric, deimmunized, humanized and human antibodies.

The binding domain of an antibody construct according to the invention may e.g. comprise the above referred groups of CDRs. Preferably, those CDRs are comprised in the framework of an antibody light chain variable region (VL) and an antibody heavy chain variable region (VH); however, it does not have to comprise both. Fd fragments, for example, have two VH regions and often retain some antigen-binding function of the intact antigen-binding domain. Additional examples for the format of antibody fragments, antibody variants or binding domains include (1) a Fab fragment, a monovalent fragment having the VL, VH, CL and CH1 domains; (2) a F(ab')$_2$ fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv), the latter being preferred (for example, derived from an scFV-library). Examples for embodiments of antibody constructs according to the invention are e.g. described in WO 00/006605, WO 2005/040220, WO 2008/119567, WO 2010/037838, WO 2013/026837, WO 2013/026833, US 2014/0308285, US 2014/0302037, WO 2014/144722, WO 2014/151910, and WO 2015/048272.

Also within the definition of "binding domain" or "domain which binds" are fragments of full-length antibodies, such as VH, VHH, VL, (s)dAb, Fv, Fd, Fab, Fab', F(ab')2 or "r IgG" ("half antibody"). Antibody constructs according to the invention may also comprise modified fragments of antibodies, also called antibody variants, such as scFv, di-scFv or bi(s)-scFv, scFv-Fc, scFv-zipper, scFab, $Fab_2$, $Fab_3$, diabodies, single chain diabodies, tandem diabodies (Tandab's), tandem di-scFv, tandem tri-scFv, "multibodies" such as triabodies or tetrabodies, and single domain antibodies such as nanobodies or single variable domain antibodies comprising merely one variable domain, which might be VHH, VH or VL, that specifically bind an antigen or epitope independently of other V regions or domains.

As used herein, the terms "single-chain Fv," "single-chain antibodies" or "scFv" refer to single polypeptide chain antibody fragments that comprise the variable regions from both the heavy and light chains, but lack the constant regions. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International Patent Application Publication No. WO 88/01649; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041. In specific embodiments, single-chain antibodies can also be bispecific, multispecific, human, and/or humanized and/or synthetic.

Furthermore, the definition of the term "antibody construct" includes monovalent, bivalent and polyvalent/multivalent constructs and, thus, bispecific constructs, specifically binding to only two antigenic structure, as well as polyspecific/multispecific constructs, which specifically bind more than two antigenic structures, e.g. three, four or more, through distinct binding domains. Moreover, the definition of the term "antibody construct" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter alia in Harlow and Lane, Antibodies a laboratory manual, CSHL Press (1988) and Using Antibodies: a laboratory manual, CSHL Press (1999), Kontermann and Dübel, Antibody Engineering, Springer, 2nd ed. 2010 and Little, Recombinant Antibodies for Immunotherapy, Cambridge University Press 2009.

The term "bispecific" as used herein refers to an antibody construct which is "at least bispecific", i.e., it comprises at least a first binding domain and a second binding domain, wherein the first binding domain binds to one antigen or target (here: the target cell surface antigen), and the second binding domain binds to another antigen or target (here: CD3). Accordingly, antibody constructs according to the invention comprise specificities for at least two different antigens or targets. For example, the first domain does preferably not bind to an extracellular epitope of CD3ε of one or more of the species as described herein. The term "target cell surface antigen" refers to an antigenic structure expressed by a cell and which is present at the cell surface such that it is accessible for an antibody construct as described herein. It may be a protein, preferably the extracellular portion of a protein, or a carbohydrate structure, preferably a carbohydrate structure of a protein, such as a glycoprotein. It is preferably a tumor antigen. The term "bispecific antibody construct" of the invention also encompasses multispecific antibody constructs such as trispecific antibody constructs, the latter ones including three binding domains, or constructs having more than three (e.g. four, five . . . ) specificities.

Given that the antibody constructs according to the invention are (at least) bispecific, they do not occur naturally and they are markedly different from naturally occurring products. A "bispecific" antibody construct or immunoglobulin is hence an artificial hybrid antibody or immunoglobulin having at least two distinct binding sides with different specificities. Bispecific antibody constructs can be produced by a variety of methods including fusion of hybridomas or linking of Fab' fragments. See, e.g., Songsivilai & Lachmann, Clin. Exp. Immunol. 79:315-321 (1990).

The at least two binding domains and the variable domains (VH/VL) of the antibody construct of the present invention may or may not comprise peptide linkers (spacer peptides). The term "peptide linker" comprises in accordance with the present invention an amino acid sequence by which the amino acid sequences of one (variable and/or binding) domain and another (variable and/or binding) domain of the antibody construct of the invention are linked with each other. The peptide linkers can also be used to fuse the third domain to the other domains of the antibody construct of the invention. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody construct of the invention.

The antibody constructs of the present invention are preferably "in vitro generated antibody constructs". This term refers to an antibody construct according to the above definition where all or part of the variable region (e.g., at least one CDR) is generated in a non-immune cell selection, e.g., an in vitro phage display, protein chip or any other method in which candidate sequences can be tested for their ability to bind to an antigen. This term thus preferably excludes sequences generated solely by genomic rearrangement in an immune cell in an animal. A "recombinant antibody" is an antibody made through the use of recombinant DNA technology or genetic engineering.

The term "monoclonal antibody" (mAb) or monoclonal antibody construct as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic side or determinant on the antigen, in contrast to conventional (polyclonal) antibody preparations which typically include different antibodies directed against different determinants (or epitopes). In addition to their specificity, the monoclonal antibodies are advantageous in that they are synthesized by the hybridoma culture, hence uncontaminated by other immunoglobulins. The modifier "monoclonal" indicates the character of the antibody as being obtained from a substantially homogeneous population of antibodies, and is not to be construed as requiring production of the antibody by any particular method.

For the preparation of monoclonal antibodies, any technique providing antibodies produced by continuous cell line cultures can be used. For example, monoclonal antibodies to be used may be made by the hybridoma method first described by Koehler et al., Nature, 256: 495 (1975), or may be made by recombinant DNA methods (see, e.g., U.S. Pat. No. 4,816,567). Examples for further techniques to produce human monoclonal antibodies include the trioma technique, the human B-cell hybridoma technique (Kozbor, Immunology Today 4 (1983), 72) and the EBV-hybridoma technique (Cole et al., Monoclonal Antibodies and Cancer Therapy, Alan R. Liss, Inc. (1985), 77-96).

Hybridomas can then be screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the relevant antigen may be used as the immunogen, e.g., recombinant antigen, naturally occurring forms, any variants or fragments thereof, as well as an antigenic peptide thereof. Surface plasmon resonance as employed in the BIAcore system can be used to increase the efficiency of phage antibodies which bind to an epitope of a target cell surface antigen, (Schier, Human Antibodies Hybridomas 7 (1996), 97-105; Malmborg, J. Immunol. Methods 183 (1995), 7-13).

Another exemplary method of making monoclonal antibodies includes screening protein expression libraries, e.g., phage display or ribosome display libraries. Phage display is described, for example, in Ladner et al., U.S. Pat. No. 5,223,409; Smith (1985) Science 228:1315-1317, Clackson et al., Nature, 352: 624-628 (1991) and Marks et al., J. Mol. Biol., 222: 581-597 (1991).

In addition to the use of display libraries, the relevant antigen can be used to immunize a non-human animal, e.g., a rodent (such as a mouse, hamster, rabbit or rat). In one embodiment, the non-human animal includes at least a part of a human immunoglobulin gene. For example, it is possible to engineer mouse strains deficient in mouse antibody production with large fragments of the human Ig (immunoglobulin) loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, and WO 96/33735.

A monoclonal antibody can also be obtained from a non-human animal, and then modified, e.g., humanized, deimmunized, rendered chimeric etc., using recombinant DNA techniques known in the art. Examples of modified antibody constructs include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dübel (2010), loc. cit. and Little (2009), loc. cit.).

In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. The in vitro affinity maturation has successfully been used to optimize antibodies, antibody constructs, and antibody fragments. Random mutations inside the CDRs are introduced using radiation, chemical mutagens or error-prone PCR. In addition, the genetic diversity can be increased by chain shuffling. Two or three rounds of mutation and selection using display methods like phage display usually results in antibody fragments with affinities in the low nanomolar range.

A preferred type of an amino acid substitutional variation of the antibody constructs involves substituting one or more hypervariable region residues of a parent antibody (e. g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sides (e. g. 6-7 sides) are mutated to generate all possible amino acid substitutions at each side. The antibody variants thus generated are displayed in a monovalent fashion from filamentous phage particles as fusions to the gene III product of M13 packaged within each particle. The phage-displayed variants are then screened for their biological activity (e. g. binding affinity) as herein disclosed. In order to identify candidate hypervariable region sides for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domain and, e.g., human target cell surface antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human constant region sequences. A variety of approaches for making chimeric antibodies have been described. See e.g., Morrison et al., Proc. Natl. Acad. Sci U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 0171496; EP 0173494; and GB 2177096.

An antibody, antibody construct, antibody fragment or antibody variant may also be modified by specific deletion of human T cell epitopes (a method called "deimmunization") by the methods disclosed for example in WO 98/52976 or WO 00/34317. Briefly, the heavy and light chain variable domains of an antibody can be analyzed for peptides that bind to MHC class II; these peptides represent potential T cell epitopes (as defined in WO 98/52976 and WO 00/34317). For detection of potential T cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences are disclosed e.g. in Tomlinson, et al. (1992) J. Mol. Biol. 227:776-798; Cook, G. P. et al. (1995) Immunol. Today Vol. 16 (5): 237-242; and Tomlinson et al. (1995) EMBO J. 14: 14:4628-4638. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, for example as described in U.S. Pat. No. 6,300,064.

"Humanized" antibodies, antibody constructs, variants or fragments thereof (such as Fv, Fab, Fab', F(ab')2 or other antigen-binding subsequences of antibodies) are antibodies or immunoglobulins of mostly human sequences, which contain (a) minimal sequence(s) derived from non-human immunoglobulin. For the most part, humanized antibodies are human immunoglobulins (recipient antibody) in which residues from a hypervariable region (also CDR) of the recipient are replaced by residues from a hypervariable region of a non-human (e.g., rodent) species (donor antibody) such as mouse, rat, hamster or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody may also comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

Humanized antibodies may also be produced using transgenic animals such as mice that express human heavy and light chain genes, but are incapable of expressing the endogenous mouse immunoglobulin heavy and light chain genes. Winter describes an exemplary CDR grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

A humanized antibody can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982, and EP 239 400).

The term "human antibody", "human antibody construct" and "human binding domain" includes antibodies, antibody constructs and binding domains having antibody regions such as variable and constant regions or domains which correspond substantially to human germline immunoglobulin sequences known in the art, including, for example, those described by Kabat et al. (1991) (loc. cit.). The human antibodies, antibody constructs or binding domains of the invention may include amino acid residues not encoded by human germline immunoglobulin sequences (e.g., mutations introduced by random or side-specific mutagenesis in vitro or by somatic mutation in vivo), for example in the CDRs, and in particular, in CDR3. The human antibodies, antibody constructs or binding domains can have at least one, two, three, four, five, or more positions replaced with an amino acid residue that is not encoded by the human germline immunoglobulin sequence. The definition of human antibodies, antibody constructs and binding domains as used herein, however, also contemplates "fully human antibodies", which include only non-artificially and/or genetically altered human sequences of antibodies as those can be derived by using technologies or systems such as the Xenomouse. Preferably, a "fully human antibody" does not include amino acid residues not encoded by human germline immunoglobulin sequences.

In some embodiments, the antibody constructs of the invention are "isolated" or "substantially pure" antibody constructs. "Isolated" or "substantially pure", when used to describe the antibody constructs disclosed herein, means an antibody construct that has been identified, separated and/or recovered from a component of its production environment. Preferably, the antibody construct is free or substantially free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. The antibody constructs may e.g constitute at least about 5%, or at least about 50% by weight of the total protein in a given sample. It is understood that the isolated protein may constitute from 5% to 99.9% by weight of the total protein content, depending on the circumstances. The polypeptide may be made at a significantly higher concentration through the use of an inducible promoter or high expression promoter, such that it is made at increased concentration levels. The definition includes the production of an antibody construct in a wide variety of organisms and/or host cells that are known in the art. In preferred embodiments, the antibody construct will be purified (1) to a degree sufficient to obtain at least 15 residues of N-terminal or internal amino acid sequence by use of a spinning cup sequenator, or (2) to homogeneity by SDS- PAGE under non-reducing or reducing conditions using Coomassie blue or, preferably, silver stain. Ordinarily, however, an isolated antibody construct will be prepared by at least one purification step.

The term "binding domain" characterizes in connection with the present invention a domain which (specifically) binds to/interacts with/recognizes a given target epitope or a given target side on the target molecules (antigens), e.g. CD33 and CD3, respectively. The structure and function of the first binding domain (recognizing e.g. CD33), and preferably also the structure and/or function of the second binding domain (recognizing CD3), is/are based on the structure and/or function of an antibody, e.g. of a full-length or whole immunoglobulin molecule and/or is/are drawn from the variable heavy chain (VH) and/or variable light chain (VL) domains of an antibody or fragment thereof. Preferably the first binding domain is characterized by the presence of three light chain CDRs (i.e. CDR1, CDR2 and CDR3 of the VL region) and/or three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold.

According to the present invention, binding domains are in the form of one or more polypeptides. Such polypeptides may include proteinaceous parts and non-proteinaceous parts (e.g. chemical linkers or chemical cross-linking agents such as glutaraldehyde). Proteins (including fragments thereof, preferably biologically active fragments, and peptides, usually having less than 30 amino acids) comprise two or more amino acids coupled to each other via a covalent peptide bond (resulting in a chain of amino acids).

The term "polypeptide" as used herein describes a group of molecules, which usually consist of more than 30 amino acids. Polypeptides may further form multimers such as dimers, trimers and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is effected e.g. by post-translational modifications like glycosylation, acetylation, phosphorylation and the like. A "peptide", "polypeptide" or "protein" when referred to herein may also be chemically modified such as pegylated. Such modifications are well known in the art and described herein below.

Preferably the binding domain which binds to the target cell surface antigen and/or the binding domain which binds to CD3ε is/are human binding domains. Antibodies and antibody constructs comprising at least one human binding domain avoid some of the problems associated with antibodies or antibody constructs that possess non-human such as rodent (e.g. murine, rat, hamster or rabbit) variable and/or constant regions. The presence of such rodent derived proteins can lead to the rapid clearance of the antibodies or antibody constructs or can lead to the generation of an immune response against the antibody or antibody construct by a patient. In order to avoid the use of rodent derived antibodies or antibody constructs, human or fully human antibodies/antibody constructs can be generated through the introduction of human antibody function into a rodent so that the rodent produces fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the use of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies or antibody constructs are expected to minimize the immunogenic and allergic responses intrinsic to mouse or mouse-derivatized mAbs and thus to increase the efficacy and safety of the administered antibodies/antibody constructs. The use of fully human antibodies or antibody constructs can be expected to provide a substantial advantage in the treatment of chronic and recurring human diseases, such as inflammation, autoimmunity, and cancer, which require repeated compound administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with the generation of the first XenoMouse mouse strains (see Green et al. Nature Genetics 7:13-21 (1994)). The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. The human Ig containing YACs proved to be compatible with the mouse system for both rearrangement and expression of antibodies and were capable of substituting for the inactivated mouse Ig genes. This was demonstrated by their ability to induce B cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620.

The production of the XenoMouse mice is further discussed and delineated in U.S. patent application Ser. No. 07/466,008, Ser. No. 07/610,515, Ser. No. 07/919,297, Ser. No. 07/922,649, Ser. No. 08/031,801, Ser. No. 08/112,848, Ser. No. 08/234,145, Ser. No. 08/376,279, Ser. No. 08/430,938, Ser. No. 08/464,584, Ser. No. 08/464,582, Ser. No. 08/463,191, Ser. No. 08/462,837, Ser. No. 08/486,853, Ser. No. 08/486,857, Ser. No. 08/486,859, Ser. No. 08/462,513, Ser. No. 08/724,752, and Ser. No. 08/759,620; and U.S. Pat. Nos. 6,162,963; 6,150,584; 6,114,598; 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998), EP 0 463 151 B1, WO 94/02602, WO 96/34096, WO 98/24893, WO 00/76310, and WO 03/47336.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806; 5,625,825; 5,625,126; 5,633,425; 5,661,016; 5,770,429; 5,789,650; 5,814,318; 5,877,397; 5,874,299; and 6,255,458 each to Lonberg and Kay, U.S. Pat. Nos. 5,591,669 and 6,023,010 to Krimpenfort and Berns, U.S. Pat. Nos. 5,612,205; 5,721,367; and 5,789,215 to Berns et al., and U.S. Pat. No. 5,643,763 to Choi and Dunn, and GenPharm International U.S. patent application Ser. No. 07/574,748, Ser. No. 07/575,962, Ser. No. 07/810,279, Ser. No. 07/853,408, Ser. No. 07/904,068, Ser. No. 07/990,860, Ser. No. 08/053,131, Ser. No. 08/096,762, Ser. No. 08/155,301, Ser. No. 08/161,739, Ser. No. 08/165,699, Ser. No. 08/209,741. See also EP 0 546 073 B1, WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175. See further Taylor et al. (1992), Chen et al. (1993), Tuaillon et al. (1993), Choi et al. (1993), Lonberg et al. (1994), Taylor et al. (1994), and Tuaillon et al. (1995), Fishwild et al. (1996).

Kirin has also demonstrated the generation of human antibodies from mice in which, through microcell fusion, large pieces of chromosomes, or entire chromosomes, have been introduced. See European Patent Application Nos. 773 288 and 843 961. Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996; 5,698,767; and 5,958,765.

Human anti-mouse antibody (HAMA) responses have led the industry to prepare chimeric or otherwise humanized antibodies. It is however expected that certain human anti-chimeric antibody (HACA) responses will be observed, particularly in chronic or multi-dose utilizations of the antibody. Thus, it would be desirable to provide antibody constructs comprising a human binding domain against the target cell surface antigen and a human binding domain against CD3ε in order to vitiate concerns and/or effects of HAMA or HACA response.

The terms "(specifically) binds to", (specifically) recognizes", "is (specifically) directed to", and "(specifically) reacts with" mean in accordance with this invention that a binding domain interacts or specifically interacts with a given epitope or a given target side on the target molecules (antigens), here: target cell surface antigen and CD3ε, respectively.

The term "epitope" refers to a side on an antigen to which a binding domain, such as an antibody or immunoglobulin, or a derivative, fragment or variant of an antibody or an immunoglobulin, specifically binds. An "epitope" is antigenic and thus the term epitope is sometimes also referred to herein as "antigenic structure" or "antigenic determinant". Thus, the binding domain is an "antigen interaction side". Said binding/interaction is also understood to define a "specific recognition".

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically a conformational epitope comprises an increased number of amino acids relative to a linear epitope. With regard to recognition of conformational epitopes, the binding domain recognizes a three-dimensional structure of the antigen, preferably a peptide or protein or fragment thereof (in the context of the present invention, the antigenic structure for one of the binding domains is comprised within the target cell surface antigen protein). For example, when a protein molecule folds to form a three-dimensional structure, certain amino acids and/or the polypeptide backbone forming the conformational epitope become juxtaposed enabling the antibody to recognize the epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

A method for epitope mapping is described in the following: When a region (a contiguous amino acid stretch) in the human target cell surface antigen protein is exchanged/replaced with its corresponding region of a non-human and non-primate target cell surface antigen (e.g., mouse target cell surface antigen, but others like chicken, rat, hamster, rabbit etc. might also be conceivable), a decrease in the binding of the binding domain is expected to occur, unless the binding domain is cross-reactive for the non-human, non-primate target cell surface antigen used. Said decrease is preferably at least 10%, 20%, 30%, 40%, or 50%; more preferably at least 60%, 70%, or 80%, and most preferably 90%, 95% or even 100% in comparison to the binding to the respective region in the human target cell surface antigen protein, whereby binding to the respective region in the human target cell surface antigen protein is set to be 100%. It is envisaged that the aforementioned human target cell surface antigen/non-human target cell surface antigen chimeras are expressed in CHO cells. It is also envisaged that the human target cell surface antigen/non-human target cell surface antigen chimeras are fused with a transmembrane domain and/or cytoplasmic domain of a different membrane-bound protein such as EpCAM.

In an alternative or additional method for epitope mapping, several truncated versions of the human target cell surface antigen extracellular domain can be generated in order to determine a specific region that is recognized by a binding domain. In these truncated versions, the different extracellular target cell surface antigen domains/sub-domains or regions are stepwise deleted, starting from the N-terminus. It is envisaged that the truncated target cell surface antigen versions may be expressed in CHO cells. It is also envisaged that the truncated target cell surface antigen versions may be fused with a transmembrane domain and/or cytoplasmic domain of a different membrane-bound protein such as EpCAM. It is also envisaged that the truncated target cell surface antigen versions may encompass a signal peptide domain at their N-terminus, for example a signal peptide derived from mouse IgG heavy chain signal peptide. It is furthermore envisaged that the truncated target cell surface antigen versions may encompass a v5 domain at their N-terminus (following the signal peptide) which allows verifying their correct expression on the cell surface. A decrease or a loss of binding is expected to occur with those truncated target cell surface antigen versions which do not encompass any more the target cell surface antigen region that is recognized by the binding domain. The decrease of binding is preferably at least 10%, 20%, 30%, 40%, 50%; more preferably at least 60%, 70%, 80%, and most preferably 90%, 95% or even 100%, whereby binding to the entire human target cell surface antigen protein (or its extracellular region or domain) is set to be 100.

A further method to determine the contribution of a specific residue of a target cell surface antigen to the recognition by an antibody construct or binding domain is alanine scanning (see e.g. Morrison K L & Weiss G A. Cur Opin Chem Biol. 2001 June; 5(3):302-7), where each residue to be analyzed is replaced by alanine, e.g. via site-directed mutagenesis. Alanine is used because of its non-bulky, chemically inert, methyl functional group that nevertheless mimics the secondary structure references that many of the other amino acids possess. Sometimes bulky amino acids such as valine or leucine can be used in cases where conservation of the size of mutated residues is desired. Alanine scanning is a mature technology which has been used for a long period of time.

The interaction between the binding domain and the epitope or the region comprising the epitope implies that a binding domain exhibits appreciable affinity for the epitope/the region comprising the epitope on a particular protein or antigen (here: target cell surface antigen and CD3, respectively) and, generally, does not exhibit significant reactivity with proteins or antigens other than the target cell surface antigen or CD3. "Appreciable affinity" includes binding with an affinity of about $10^{-6}$ M (KD) or stronger. Preferably, binding is considered specific when the binding affinity is about $10^{-12}$ to $10^{-8}$ M, $10^{-12}$ to $10^{-9}$ M, $10^{-12}$ to $10^{-10}$ M, $10^{-11}$ to $10^{-8}$ M, preferably of about $10^{-11}$ to $10^{-9}$ M. Whether a binding domain specifically reacts with or binds to a target can be tested readily by, inter alia, comparing the reaction of said binding domain with a target protein or antigen with the reaction of said binding domain with proteins or antigens other than the target cell surface antigen or CD3. Preferably, a binding domain of the invention does not essentially or substantially bind to proteins or antigens other than the target cell surface antigen or CD3 (i.e., the first binding domain is not capable of binding to proteins other than the target cell surface antigen and the second binding domain is not capable of binding to proteins other than CD3). It is an envisaged characteristic of the antibody constructs according to the present invention to have superior affinity characteristics in comparison to other HLE formats. Such a superior affinity, in consequence, suggests a prolonged half-life in vivo. The longer half-life of the antibody constructs according to the present invention may reduce the duration and frequency of administration which typically contributes to improved patient compliance. This is of particular importance as the antibody constructs of the present invention are particularly beneficial for highly weakened or even multimorbide cancer patients.

The term "does not essentially/substantially bind" or "is not capable of binding" means that a binding domain of the present invention does not bind a protein or antigen other than the target cell surface antigen or CD3, i.e., does not show reactivity of more than 30%, preferably not more than 20%, more preferably not more than 10%, particularly preferably not more than 9%, 8%, 7%, 6% or 5% with proteins or antigens other than the target cell surface antigen or CD3, whereby binding to the target cell surface antigen or CD3, respectively, is set to be 100%.

Specific binding is believed to be effected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-side with its specific antigen may result in a simple binding of said side to the antigen. Moreover, the specific interaction of the antigen-interaction-side with its specific antigen may alternatively or additionally result in the initiation of a signal, e.g. due to the induction of a change of the conformation of the antigen, an oligomerization of the antigen, etc.

The term "variable" refers to the portions of the antibody or immunoglobulin domains that exhibit variability in their sequence and that are involved in determining the specificity and binding affinity of a particular antibody (i.e., the "variable domain(s)"). The pairing of a variable heavy chain (VH) and a variable light chain (VL) together forms a single antigen-binding side.

Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding side (see Kabat et al., loc. cit.).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding side is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding side. H3, for example, can be as short as two amino acid residues or greater than 26 amino acids.

In a classical full-length antibody or immunoglobulin, each light (L) chain is linked to a heavy (H) chain by one covalent disulfide bond, while the two H chains are linked to each other by one or more disulfide bonds depending on the H chain isotype. The CH domain most proximal to VH is usually designated as CH1. The constant ("C") domains are not directly involved in antigen binding, but exhibit various effector functions, such as antibody-dependent, cell-mediated cytotoxicity and complement activation. The Fc region of an antibody is comprised within the heavy chain constant domains and is for example able to interact with cell surface located Fc receptors.

The sequence of antibody genes after assembly and somatic mutation is highly varied, and these varied genes are estimated to encode $10^{10}$ different antibody molecules (Immunoglobulin Genes, $2^{nd}$ ed., eds. Jonio et al., Academic Press, San Diego, CA, 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

The term "Fc portion" or "Fc monomer" means in connection with this invention a polypeptide comprising at least one domain having the function of a CH2 domain and at least one domain having the function of a CH3 domain of an immunoglobulin molecule. As apparent from the term "Fc monomer", the polypeptide comprising those CH domains is a "polypeptide monomer". An Fc monomer can be a polypeptide comprising at least a fragment of the constant region of an immunoglobulin excluding the first constant region immunoglobulin domain of the heavy chain (CH1), but maintaining at least a functional part of one CH2 domain and a functional part of one CH3 domain, wherein the CH2 domain is amino terminal to the CH3 domain. In a preferred aspect of this definition, an Fc monomer can be a polypeptide constant region comprising a portion of the Ig-Fc hinge region, a CH2 region and a CH3 region, wherein the hinge region is amino terminal to the CH2 domain. It is envisaged that the hinge region of the present invention promotes dimerization. Such Fc polypeptide molecules can be obtained by papain digestion of an immunoglobulin region (of course resulting in a dimer of two Fc polypeptide), for example and not limitation. In another aspect of this definition, an Fc monomer can be a polypeptide region comprising a portion of a CH2 region and a CH3 region. Such Fc polypeptide molecules can be obtained by pepsin digestion of an immunoglobulin molecule, for example and not limitation. In one embodiment, the polypeptide sequence of an Fc monomer is substantially similar to an Fc polypeptide sequence of: an $IgG_1$ Fc region, an $IgG_2$ Fc region, an $IgG_3$ Fc region, an $IgG_4$ Fc region, an IgM Fc region, an IgA Fc region, an IgD Fc region and an IgE Fc region. (See, e.g., Padlan, Molecular Immunology, 31(3), 169-217 (1993)). Because there is some variation between immunoglobulins, and solely for clarity, Fc monomer refers to the last two heavy chain constant region immunoglobulin domains of IgA, IgD, and IgG, and the last three heavy chain constant region immunoglobulin domains of IgE and IgM. As mentioned, the Fc monomer can also include the flexible hinge N-terminal to these domains. For IgA and IgM, the Fc monomer may include the J chain. For IgG, the Fc portion comprises immunoglobulin domains CH2 and CH3 and the hinge between the first two domains and CH2. Although the boundaries of the Fc portion may vary an example for a human IgG heavy chain Fc portion comprising a functional hinge, CH2 and CH3 domain can be defined e.g. to comprise residues D231 (of the hinge domain—corresponding to D234 in Table 1 below)) to P476, respectively L476 (for $IgG_4$) of the carboxyl-terminus of the CH3 domain, wherein the numbering is according to Kabat. The two Fc portions or Fc monomers, which are fused to each other via a peptide linker define the third domain of the antibody construct of the invention, which may also be defined as scFc domain.

In one embodiment of the invention it is envisaged that a scFc domain as disclosed herein, respectively the Fc monomers fused to each other are comprised only in the third domain of the antibody construct. In line with the present invention an IgG hinge region can be identified by analogy using the Kabat numbering as set forth in Table 1. In line with the above, it is envisaged that a hinge domain/region of the present invention comprises the amino acid residues corresponding to the IgG, sequence stretch of D234 to P243 according to the Kabat numbering. It is likewise envisaged that a hinge domain/region of the present invention comprises or consists of the IgG1 hinge sequence DKTHTCPPCP (SEQ ID NO: 1449) (corresponding to the stretch D234 to P243 as shown in Table 1 below—variations of said sequence are also envisaged provided that the hinge region still promotes dimerization). In a preferred embodiment of the invention the glycosylation site at Kabat position 314 of the CH2 domains in the third domain of the antibody construct is removed by a N314X substitution, wherein X is any amino acid excluding Q. Said substitution is preferably a N314G substitution. In a more preferred embodiment, said CH2 domain additionally comprises the following substitutions (position according to Kabat) V321C and R309C (these substitutions introduce the intra domain cysteine disulfide bridge at Kabat positions 309 and 321). It is also envisaged that the third domain of the antibody construct of the invention comprises or consists in an amino to carboxyl order: DKTHTCPPCP (SEQ ID NO: 1449) (i.e. hinge) —CH2-CH3-linker-DKTHTCPPCP (SEQ ID NO: 1449) (i.e. hinge) —CH2-CH3. The peptide linker of the aforementioned antibody construct is in a preferred embodiment characterized by the amino acid sequence Gly-Gly-Gly-Gly-Ser, i.e. $Gly_4Ser$ (SEQ ID NO: 1), or polymers thereof, i.e. $(Gly_4Ser)x$, where x is an integer of 5 or greater (e.g. 5, 6, 7, 8 etc. or greater), 6 being preferred ((Gly4Ser)6). Said construct may further comprise the aforementioned substitutions N314X, preferably N314G, and/or the further substitutions V321C and R309C. In a preferred embodiment of the antibody constructs of the invention as defined herein before, it is envisaged that the second domain binds to an extracellular epitope of the human and/or the *Macaca* CD3ε chain.

TABLE 1

Kabat numbering of the amino acid residues of the hinge region

| IMGT numbering for the hinge | IgG₁ amino acid translation | Kabat numbering |
| --- | --- | --- |
| 1 | (E) | 226 |
| 2 | P | 227 |
| 3 | K | 228 |
| 4 | S | 232 |
| 5 | C | 233 |
| 6 | D | 234 |
| 7 | K | 235 |
| 8 | T | 236 |
| 9 | H | 237 |
| 10 | T | 238 |
| 11 | C | 239 |
| 12 | P | 240 |
| 13 | P | 241 |
| 14 | C | 242 |
| 15 | P | 243 |

In further embodiments of the present invention, the hinge domain/region comprises or consists of the IgG2 subtype hinge sequence ERKCCVECPPCP (SEQ ID NO: 1450), the IgG3 subtype hinge sequence ELKTPLDTTHTCPRCP (SEQ ID NO: 1451) or ELKTPLGDTTHTCPRCP (SEQ ID NO: 1458), and/or the IgG4 subtype hinge sequence ESKYGPPCPSCP (SEQ ID NO: 1452). The IgG1 subtype hinge sequence may be the following one EPKSCDKTHTCPPCP (as shown in Table 1 and SEQ ID NO: 1459). These core hinge regions are thus also envisaged in the context of the present invention.

The location and sequence of the IgG CH2 and IgG CD3 domain can be identified by analogy using the Kabat numbering as set forth in Table 2:

TABLE 2

Kabat numbering of the amino acid residues of the IgG CH2 and CH3 region

| IgG subtype | CH2 aa translation | CH2 Kabat numbering | CH3 aa translation | CH3 Kabat numbering |
|---|---|---|---|---|
| IgG$_1$ | APE . . . KAK | 244 . . . 360 | GQP . . . PGK | 361 . . . 478 |
| IgG$_2$ | APP . . . KTK | 244 . . . 360 | GQP . . . PGK | 361 . . . 478 |
| IgG$_3$ | APE . . . KTK | 244 . . . 360 | GQP . . . PGK | 361 . . . 478 |
| IgG$_4$ | APE . . . KAK | 244 . . . 360 | GQP . . . LGK | 361 . . . 478 |

In one embodiment of the invention the emphasized bold amino acid residues in the CH3 domain of the first or both Fc monomers are deleted.

The peptide linker, by whom the polypeptide monomers ("Fc portion" or "Fc monomer") of the third domain are fused to each other, preferably comprises at least 25 amino acid residues (25, 26, 27, 28, 29, 30 etc.). More preferably, this peptide linker comprises at least 30 amino acid residues (30, 31, 32, 33, 34, 35 etc.). It is also preferred that the linker comprises up to 40 amino acid residues, more preferably up to 35 amino acid residues, most preferably exactly 30 amino acid residues. A preferred embodiment of such peptide linker is characterized by the amino acid sequence Gly-Gly-Gly-Gly-Ser, i.e. Gly$_4$Ser (SEQ ID NO: 1), or polymers thereof, i.e. (Gly$_4$Ser)x, where x is an integer of 5 or greater (e.g. 6, 7 or 8). Preferably the integer is 6 or 7, more preferably the integer is 6.

In the event that a linker is used to fuse the first domain to the second domain, or the first or second domain to the third domain, this linker is preferably of a length and sequence sufficient to ensure that each of the first and second domains can, independently from one another, retain their differential binding specificities. For peptide linkers which connect the at least two binding domains (or two variable domains) in the antibody construct of the invention, those peptide linkers are preferred which comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or one amino acid(s), wherein Gly-rich linkers are preferred. A preferred embodiment of the peptide linker for a fusion the first and the second domain is depicted in SEQ ID NO:1. A preferred linker embodiment of the peptide linker for a fusion the second and the third domain is a (Gly)$_4$-linker, respectively G$_4$-linker.

A particularly preferred "single" amino acid in the context of one of the above described "peptide linker" is Gly. Accordingly, said peptide linker may consist of the single amino acid Gly. In a preferred embodiment of the invention a peptide linker is characterized by the amino acid sequence Gly-Gly-Gly-Gly-Ser, i.e. Gly$_4$Ser (SEQ ID NO: 1), or polymers thereof, i.e. (Gly$_4$Ser)x, where x is an integer of 1 or greater (e.g. 2 or 3). Preferred linkers are depicted in SEQ ID NOs: 1 to 12. The characteristics of said peptide linker, which comprise the absence of the promotion of secondary structures, are known in the art and are described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which furthermore do not promote any secondary structures are preferred. The linkage of said domains to each other can be provided, e.g., by genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, New York, 2001).

In a preferred embodiment of the antibody construct or the present invention the first and second domain form an antibody construct in a format selected from the group consisting of (scFv)$_2$, scFv-single domain mAb, diabody and oligomers of any of the those formats According to a particularly preferred embodiment, and as documented in the appended examples, the first and the second domain of the antibody construct of the invention is a "bispecific single chain antibody construct", more preferably a bispecific "single chain Fv" (scFv). Although the two domains of the Fv fragment, VL and VH, are coded for by separate genes, they can be joined, using recombinant methods, by a synthetic linker—as described hereinbefore—that enables them to be made as a single protein chain in which the VL and VH regions pair to form a monovalent molecule; see e.g., Huston et al. (1988) Proc. Natl. Acad. Sci USA 85:5879-5883). These antibody fragments are obtained using conventional techniques known to those with skill in the art, and the fragments are evaluated for function in the same manner as are whole or full-length antibodies. A single-chain variable fragment (scFv) is hence a fusion protein of the variable region of the heavy chain (VH) and of the light chain (VL) of immunoglobulins, usually connected with a short linker peptide of about ten to about 25 amino acids, preferably about 15 to 20 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and introduction of the linker.

Bispecific single chain antibody constructs are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103, Brühl, Immunol., (2001), 166, 2420-2426, Kipriyanov, J. Mol. Biol., (1999), 293, 41-56. Techniques described for the production of single chain antibodies (see, inter alia, U.S. Pat. No. 4,946,778, Kontermann and Dübel (2010), loc. cit. and Little (2009), loc. cit.) can be adapted to produce single chain antibody constructs specifically recognizing (an) elected target(s).

Bivalent (also called divalent) or bispecific single-chain variable fragments (bi-scFvs or di-scFvs having the format (scFv)$_2$ can be engineered by linking two scFv molecules (e.g. with linkers as described hereinbefore). If these two scFv molecules have the same binding specificity, the resulting (scFv)$_2$ molecule will preferably be called bivalent (i.e. it has two valences for the same target epitope). If the two scFv molecules have different binding specificities, the resulting (scFv)$_2$ molecule will preferably be called bispecific. The linking can be done by producing a single peptide chain with two VH regions and two VL regions, yielding tandem scFvs (see e.g. Kufer P. et al., (2004) Trends in Biotechnology 22(5):238-244). Another possibility is the creation of scFv molecules with linker peptides that are too short for the two variable regions to fold together (e.g. about five amino acids), forcing the scFvs to dimerize. This type is known as diabodies (see e.g. Hollinger, Philipp et al., (July 1993) Proceedings of the National Academy of Sciences of the United States of America 90 (14): 6444-8).

In line with this invention either the first, the second or the first and the second domain may comprise a single domain antibody, respectively the variable domain or at least the CDRs of a single domain antibody. Single domain antibodies comprise merely one (monomeric) antibody variable domain which is able to bind selectively to a specific antigen, independently of other V regions or domains. The first single domain antibodies were engineered from havy chain antibodies found in camelids, and these are called $V_HH$ fragments. Cartilaginous fishes also have heavy chain antibodies (IgNAR) from which single domain antibodies called $V_{NAR}$ fragments can be obtained. An alternative approach is to split the dimeric variable domains from common immunoglobulins e.g. from humans or rodents into monomers, hence obtaining VH or VL as a single domain Ab. Although most research into single domain antibodies is currently based on heavy chain variable domains, nanobodies derived from light chains have also been shown to bind specifically to target epitopes. Examples of single domain antibodies are called sdAb, nanobodies or single variable domain antibodies.

A (single domain mAb)$_2$ is hence a monoclonal antibody construct composed of (at least) two single domain monoclonal antibodies, which are individually selected from the group comprising $V_H$, $V_L$, $V_HH$ and $V_{NAR}$. The linker is preferably in the form of a peptide linker. Similarly, an "scFv-single domain mAb" is a monoclonal antibody construct composed of at least one single domain antibody as described above and one scFv molecule as described above. Again, the linker is preferably in the form of a peptide linker.

Whether or not an antibody construct competes for binding with another given antibody construct can be measured in a competition assay such as a competitive ELISA or a cell-based competition assay. Avidin-coupled microparticles (beads) can also be used. Similar to an avidin-coated ELISA plate, when reacted with a biotinylated protein, each of these beads can be used as a substrate on which an assay can be performed. Antigen is coated onto a bead and then precoated with the first antibody. The second antibody is added and any additional binding is determined. Possible means for the read-out includes flow cytometry.

T cells or T lymphocytes are a type of lymphocyte (itself a type of white blood cell) that play a central role in cell-mediated immunity. There are several subsets of T cells, each with a distinct function. T cells can be distinguished from other lymphocytes, such as B cells and NK cells, by the presence of a T cell receptor (TCR) on the cell surface. The TCR is responsible for recognizing antigens bound to major histocompatibility complex (MHC) molecules and is composed of two different protein chains. In 95% of the T cells, the TCR consists of an alpha ($\alpha$) and beta ($\beta$) chain. When the TCR engages with antigenic peptide and MHC (peptide/MHC complex), the T lymphocyte is activated through a series of biochemical events mediated by associated enzymes, co-receptors, specialized adaptor molecules, and activated or released transcription factors.

The CD3 receptor complex is a protein complex and is composed of four chains. In mammals, the complex contains a CD3γ (gamma) chain, a CD3δ (delta) chain, and two CD3ε (epsilon) chains. These chains associate with the T cell receptor (TCR) and the so-called ζ (zeta) chain to form the T cell receptor CD3 complex and to generate an activation signal in T lymphocytes. The CD3γ (gamma), CD3δ (delta), and CD3ε (epsilon) chains are highly related cell-surface proteins of the immunoglobulin superfamily containing a single extracellular immunoglobulin domain. The intracellular tails of the CD3 molecules contain a single conserved motif known as an immunoreceptor tyrosine-based activation motif or ITAM for short, which is essential for the signaling capacity of the TCR. The CD3 epsilon molecule is a polypeptide which in humans is encoded by the CD3E gene which resides on chromosome 11. The most preferred epitope of CD3 epsilon is comprised within amino acid residues 1-27 of the human CD3 epsilon extracellular domain. It is envisaged that antibody constructs according to the present invention typically and advantageously show less unspecific T cell activation, which is not desired in specific immunotherapy. This translates to a reduced risk of side effects.

The redirected lysis of target cells via the recruitment of T cells by a multispecific, at least bispecific, antibody construct involves cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO 2007/042261.

Cytotoxicity mediated by antibody constructs of the invention can be measured in various ways. Effector cells can be e.g. stimulated enriched (human) CD8 positive T cells or unstimulated (human) peripheral blood mononuclear cells (PBMC). If the target cells are of macaque origin or express or are transfected with macaque target cell surface antigen which is bound by the first domain, the effector cells should also be of macaque origin such as a macaque T cell line, e.g. 4119LnPx. The target cells should express (at least the extracellular domain of) the target cell surface antigen, e.g. human or macaque target cell surface antigen. Target cells can be a cell line (such as CHO) which is stably or transiently transfected with target cell surface antigen, e.g. human or macaque target cell surface antigen. Alternatively, the target cells can be a target cell surface antigen positive natural expresser cell line. Usually $EC_{50}$ values are expected to be lower with target cell lines expressing higher levels of target cell surface antigen on the cell surface. The effector to target cell (E:T) ratio is usually about 10:1, but can also vary. Cytotoxic activity of target cell surface antigen×CD3 bispecific antibody constructs can be measured in a $^{51}$Cr-release assay (incubation time of about 18 hours) or in a in a FACS-based cytotoxicity assay (incubation time of about 48 hours). Modifications of the assay incubation time (cytotoxic reaction) are also possible. Other methods of measuring cytotoxicity are well-known to the skilled person and comprise MTT or MTS assays, ATP-based assays including bioluminescent assays, the sulforhodamine B (SRB) assay, WST assay, clonogenic assay and the ECIS technology.

The cytotoxic activity mediated by target cell surface antigen×CD3 bispecific antibody constructs of the present invention is preferably measured in a cell-based cytotoxicity assay. It may also be measured in a $^{51}$Cr-release assay. It is represented by the $EC_{50}$ value, which corresponds to the half maximal effective concentration (concentration of the antibody construct which induces a cytotoxic response halfway between the baseline and maximum). Preferably, the $EC_{50}$ value of the target cell surface antigen×CD3 bispecific antibody constructs is ≤5000 pM or ≤4000 pM, more preferably <3000 pM or <2000 pM, even more preferably <1000 pM or 5500 pM, even more preferably 5400 pM or <300 pM, even more preferably <200 pM, even more preferably <100 pM, even more preferably <50 pM, even more preferably <20 pM or <10 pM, and most preferably <5 pM.

The above given $EC_{50}$ values can be measured in different assays. The skilled person is aware that an $EC_{50}$ value can be expected to be lower when stimulated/enriched CD8+ T cells are used as effector cells, compared with unstimulated PBMC. It can furthermore be expected that the $EC_{50}$ values are lower when the target cells express a high number of the target cell surface antigen compared with a low target expression rat. For example, when stimulated/enriched human CD8+ T cells are used as effector cells (and either target cell surface antigen transfected cells such as CHO cells or target cell surface antigen positive human cell lines are used as target cells), the $EC_{50}$ value of the target cell surface antigen×CD3 bispecific antibody construct is preferably <1000 pM, more preferably <500 pM, even more preferably <250 pM, even more preferably <100 pM, even more preferably <50 pM, even more preferably <10 pM, and most preferably <5 pM. When human PBMCs are used as effector cells, the $EC_{50}$ value of the target cell surface antigen×CD3 bispecific antibody construct is preferably <5000 pM or <4000 pM (in particular when the target cells are target cell surface antigen positive human cell lines), more preferably <2000 pM (in particular when the target cells are target cell surface antigen transfected cells such as CHO cells), more preferably <1000 pM or 5500 pM, even more preferably <200 pM, even more preferably <150 pM, even more preferably <100 pM, and most preferably <50 pM, or lower. When a macaque T cell line such as LnPx4119 is used as effector cells, and a macaque target cell surface antigen transfected cell line such as CHO cells is used as target cell line, the $EC_{50}$ value of the target cell surface antigen×CD3 bispecific antibody construct is preferably <2000 pM or <1500 pM, more preferably <1000 pM or 5500 pM, even more preferably <300 pM or <250 pM, even more preferably <100 pM, and most preferably <50 pM.

Preferably, the target cell surface antigen×CD3 bispecific antibody constructs of the present invention do not induce/mediate lysis or do not essentially induce/mediate lysis of target cell surface antigen negative cells such as CHO cells. The term "do not induce lysis", "do not essentially induce lysis", "do not mediate lysis" or "do not essentially mediate lysis" means that an antibody construct of the present invention does not induce or mediate lysis of more than 30%, preferably not more than 20%, more preferably not more than 10%, particularly preferably not more than 9%, 8%, 7%, 6% or 5% of target cell surface antigen negative cells, whereby lysis of a target cell surface antigen positive human cell line is set to be 100%. This usually applies for concentrations of the antibody construct of up to 500 nM. The skilled person knows how to measure cell lysis without further ado. Moreover, the present specification teaches specific instructions how to measure cell lysis.

The difference in cytotoxic activity between the monomeric and the dimeric isoform of individual target cell surface antigen×CD3 bispecific antibody constructs is referred to as "potency gap". This potency gap can e.g. be calculated as ratio between $EC_{50}$ values of the molecule's monomeric and dimeric form. Potency gaps of the target cell surface antigen×CD3 bispecific antibody constructs of the present invention are preferably <5, more preferably <4, even more preferably <3, even more preferably <2 and most preferably <1.

The first and/or the second (or any further) binding domain(s) of the antibody construct of the invention is/are preferably cross-species specific for members of the mammalian order of primates. Cross-species specific CD3 binding domains are, for example, described in WO 2008/119567. According to one embodiment, the first and/or second binding domain, in addition to binding to human target cell surface antigen and human CD3, respectively, will also bind to target cell surface antigen/CD3 of primates including (but not limited to) new world primates (such as *Callithrix jacchus, Saguinus* Oedipus or *Saimiri sciureus*), old world primates (such baboons and macaques), gibbons, and non-human homininae.

In one embodiment of the antibody construct of the invention the first domain binds to human target cell surface antigen and further binds to macaque target cell surface antigen, such as target cell surface antigen of *Macaca fascicularis*, and more preferably, to macaque target cell surface antigen expressed on the surface macaque cells. The affinity of the first binding domain for macaque target cell surface antigen is preferably <15 nM, more preferably <10 nM, even more preferably <5 nM, even more preferably <1 nM, even more preferably 50.5 nM, even more preferably 50.1 nM, and most preferably 50.05 nM or even <0.01 nM.

Preferably the affinity gap of the antibody constructs according to the invention for binding macaque target cell surface antigen versus human target cell surface antigen [ma target cell surface antigen:hu target cell surface antigen] (as determined e.g. by BiaCore or by Scatchard analysis) is <100, preferably <20, more preferably <15, further preferably <10, even more preferably <8, more preferably <6 and most preferably <2. Preferred ranges for the affinity gap of the antibody constructs according to the invention for binding macaque target cell surface antigen versus human target cell surface antigen are between 0.1 and 20, more preferably between 0.2 and 10, even more preferably between 0.3 and 6, even more preferably between 0.5 and 3 or between 0.5 and 2.5, and most preferably between 0.5 and 2 or between 0.6 and 2.

The second (binding) domain of the antibody construct of the invention binds to human CD3 epsilon and/or to *Macaca* CD3 epsilon. In a preferred embodiment the second domain further bind to *Callithrix jacchus, Saguinus* Oedipus or *Saimiri sciureus* CD3 epsilon. *Callithrix jacchus* and *Saguinus oedipus* are both new world primate belonging to the family of Callitrichidae, while *Saimiri sciureus* is a new world primate belonging to the family of Cebidae.

It is preferred for the antibody construct of the present invention that the second domain which binds to an extracellular epitope of the human and/or the *Macaca* CD3 on the comprises a VL region comprising CDR-L1, CDR-L2 and CDR-L3 selected from:
  (a) CDR-L1 as depicted in SEQ ID NO: 27 of WO 2008/119567, CDR-L2 as depicted in SEQ ID NO: 28 of WO 2008/119567 and CDR-L3 as depicted in SEQ ID NO: 29 of WO 2008/119567;
  (b) CDR-L1 as depicted in SEQ ID NO: 117 of WO 2008/119567, CDR-L2 as depicted in SEQ ID NO: 118 of WO 2008/119567 and CDR-L3 as depicted in SEQ ID NO: 119 of WO 2008/119567; and
  (c) CDR-L1 as depicted in SEQ ID NO: 153 of WO 2008/119567, CDR-L2 as depicted in SEQ ID NO: 154 of WO 2008/119567 and CDR-L3 as depicted in SEQ ID NO: 155 of WO 2008/119567.

In an also preferred embodiment of the antibody construct of the present invention, the second domain which binds to an extracellular epitope of the human and/or the *Macaca* CD3 epsilon chain comprises a VH region comprising CDR-H 1, CDR-H2 and CDR-H3 selected from:
  (a) CDR-H1 as depicted in SEQ ID NO: 12 of WO 2008/119567, CDR-H2 as depicted in SEQ ID NO: 13 of WO 2008/119567 and CDR-H3 as depicted in SEQ ID NO: 14 of WO 2008/119567;
  (b) CDR-H1 as depicted in SEQ ID NO: 30 of WO 2008/119567, CDR-H2 as depicted in SEQ ID NO: 31 of WO 2008/119567 and CDR-H3 as depicted in SEQ ID NO: 32 of WO 2008/119567;

(c) CDR-H1 as depicted in SEQ ID NO: 48 of WO 2008/119567, CDR-H2 as depicted in SEQ ID NO: 49 of WO 2008/119567 and CDR-H3 as depicted in SEQ ID NO: 50 of WO 2008/119567;

(d) CDR-H1 as depicted in SEQ ID NO: 66 of WO 2008/119567, CDR-H2 as depicted in SEQ ID NO: 67 of WO 2008/119567 and CDR-H3 as depicted in SEQ ID NO: 68 of WO 2008/119567;

(e) CDR-H1 as depicted in SEQ ID NO: 84 of WO 2008/119567, CDR-H2 as depicted in SEQ ID NO: 85 of WO 2008/119567 and CDR-H3 as depicted in SEQ ID NO: 86 of WO 2008/119567;

(f) CDR-H1 as depicted in SEQ ID NO: 102 of WO 2008/119567, CDR-H2 as depicted in SEQ ID NO: 103 of WO 2008/119567 and CDR-H3 as depicted in SEQ ID NO: 104 of WO 2008/119567;

(g) CDR-H1 as depicted in SEQ ID NO: 120 of WO 2008/119567, CDR-H2 as depicted in SEQ ID NO: 121 of WO 2008/119567 and CDR-H3 as depicted in SEQ ID NO: 122 of WO 2008/119567;

(h) CDR-H1 as depicted in SEQ ID NO: 138 of WO 2008/119567, CDR-H2 as depicted in SEQ ID NO: 139 of WO 2008/119567 and CDR-H3 as depicted in SEQ ID NO: 140 of WO 2008/119567;

(i) CDR-H1 as depicted in SEQ ID NO: 156 of WO 2008/119567, CDR-H2 as depicted in SEQ ID NO: 157 of WO 2008/119567 and CDR-H3 as depicted in SEQ ID NO: 158 of WO 2008/119567; and (j) CDR-H1 as depicted in SEQ ID NO: 174 of WO 2008/119567, CDR-H2 as depicted in SEQ ID NO: 175 of WO 2008/119567 and CDR-H3 as depicted in SEQ ID NO: 176 of WO 2008/119567.

In a preferred embodiment of the antibody construct of the invention the above described three groups of VL CDRs are combined with the above described ten groups of VH CDRs within the second binding domain to form (30) groups, each comprising CDR-L 1-3 and CDR-H 1-3.

It is preferred for the antibody construct of the present invention that the second domain which binds to CD3 comprises a VL region selected from the group consisting of a VL region as depicted in SEQ ID NO: 17, 21, 35, 39, 53, 57, 71, 75, 89, 93, 107, 111, 125, 129, 143, 147, 161, 165, 179 or 183 of WO 2008/119567 or as depicted in the present sequence listing as SEQ ID NO: 16 or 25.

It is also preferred that the second domain which binds to CD3 comprises a VH region selected from the group consisting of a VH region as depicted in SEQ ID NO: 15, 19, 33, 37, 51, 55, 69, 73, 87, 91, 105, 109, 123, 127, 141, 145, 159, 163, 177 or 181 of WO 2008/119567 or as depicted in the present sequence listing as SEQ ID NO: 15 or 24.

More preferably, the antibody construct of the present invention is characterized by a second domain which binds to CD3 comprising a VL region and a VH region selected from the group consisting of:

(a) a VL region as depicted in SEQ ID NO: 17 or 21 of WO 2008/119567 and a VH region as depicted in SEQ ID NO: 15 or 19 of WO 2008/119567;

(b) a VL region as depicted in SEQ ID NO: 35 or 39 of WO 2008/119567 and a VH region as depicted in SEQ ID NO: 33 or 37 of WO 2008/119567;

(c) a VL region as depicted in SEQ ID NO: 53 or 57 of WO 2008/119567 and a VH region as depicted in SEQ ID NO: 51 or 55 of WO 2008/119567;

(d) a VL region as depicted in SEQ ID NO: 71 or 75 of WO 2008/119567 and a VH region as depicted in SEQ ID NO: 69 or 73 of WO 2008/119567;

(e) a VL region as depicted in SEQ ID NO: 89 or 93 of WO 2008/119567 and a VH region as depicted in SEQ ID NO: 87 or 91 of WO 2008/119567;

(f) a VL region as depicted in SEQ ID NO: 107 or 111 of WO 2008/119567 and a VH region as depicted in SEQ ID NO: 105 or 109 of WO 2008/119567;

(g) a VL region as depicted in SEQ ID NO: 125 or 129 of WO 2008/119567 and a VH region as depicted in SEQ ID NO: 123 or 127 of WO 2008/119567;

(h) a VL region as depicted in SEQ ID NO: 143 or 147 of WO 2008/119567 and a VH region as depicted in SEQ ID NO: 141 or 145 of WO 2008/119567;

(i) a VL region as depicted in SEQ ID NO: 161 or 165 of WO 2008/119567 and a VH region as depicted in SEQ ID NO: 159 or 163 of WO 2008/119567; and (j) a VL region as depicted in SEQ ID NO: 179 or 183 of WO 2008/119567 and a VH region as depicted in SEQ ID NO: 177 or 181 of WO 2008/119567.

Also preferred in connection with the antibody construct of the present invention is a second domain which binds to CD3 comprising a VL region as depicted in SEQ ID NO: 16 or 25 and a VH region as depicted in the present sequence listing as SEQ ID NO: 15 or 24.

According to a preferred embodiment of the antibody construct of the present invention, the first and/or the second domain have the following format: The pairs of VH regions and VL regions are in the format of a single chain antibody (scFv). The VH and VL regions are arranged in the order VH-VL or VL-VH. It is preferred that the VH-region is positioned N-terminally of a linker sequence, and the VL-region is positioned C-terminally of the linker sequence.

A preferred embodiment of the above described antibody construct of the present invention is characterized by the second domain which binds to CD3 comprising an amino acid sequence selected from the group consisting of SEQ ID NOs: 23, 25, 41, 43, 59, 61, 77, 79, 95, 97, 113, 115, 131, 133, 149, 151, 167, 169, 185 or 187 of WO 2008/119567 or depicted in the present sequence listing as SEQ ID NO: 26.

Covalent modifications of the antibody constructs are also included within the scope of this invention, and are generally, but not always, done post-translationally. For example, several types of covalent modifications of the antibody construct are introduced into the molecule by reacting specific amino acid residues of the antibody construct with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking the antibody constructs of the present invention to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates as described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antibody constructs included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody construct is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the amino acid sequence of an antibody construct is preferably altered through changes at the DNA level, particularly by mutating the DNA encoding the polypeptide at preselected bases such that codons are generated that will translate into the desired amino acids.

Another means of increasing the number of carbohydrate moieties on the antibody construct is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, 1981, CRC Crit. Rev. Biochem., pp. 259-306.

Removal of carbohydrate moieties present on the starting antibody construct may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

Other modifications of the antibody construct are also contemplated herein. For example, another type of covalent modification of the antibody construct comprises linking the antibody construct to various non-proteinaceous polymers, including, but not limited to, various polyols such as polyethylene glycol, polypropylene glycol, polyoxyalkylenes, or copolymers of polyethylene glycol and polypropylene glycol, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antibody construct, e.g. in order to facilitate the addition of polymers such as PEG.

In some embodiments, the covalent modification of the antibody constructs of the invention comprises the addition of one or more labels. The labelling group may be coupled to the antibody construct via spacer arms of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following examples include, but are not limited to:

a) isotopic labels, which may be radioactive or heavy isotopes, such as radioisotopes or radionuclides (e.g., $^{3}$H, $^{14}$C, $^{15}$N, $^{35}$S, $^{89}$Zr, $^{90}$Y, $^{99}$Tc, $^{111}$In, $^{125}$I, $^{131}$I)

b) magnetic labels (e.g., magnetic particles)

c) redox active moieties d) optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluores or proteinaceous fluores e) enzymatic groups (e.g. horseradish peroxidase, β-galactosidase, luciferase, alkaline phosphatase)

f) biotinylated groups g) predetermined polypeptide epitopes recognized by a secondary reporter (e.g., leucine zipper pair sequences, binding sides for secondary antibodies, metal binding domains, epitope tags, etc.)

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, OR), FITC, Rhodamine, and Texas Red (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland.

Suitable proteinaceous fluorescent labels also include, but are not limited to, green fluorescent protein, including a *Renilla, Ptilosarcus*, or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658; 5,418,155; 5,683,888; 5,741,668; 5,777,079; 5,804,387; 5,874,304; 5,876,995; 5,925,558).

The antibody construct of the invention may also comprise additional domains, which are e.g. helpful in the isolation of the molecule or relate to an adapted pharmacokinetic profile of the molecule. Domains helpful for the isolation of an antibody construct may be selected from peptide motives or secondarily introduced moieties, which can be captured in an isolation method, e.g. an isolation column. Non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. Strepll-tag) and His-tag. All herein disclosed antibody constructs characterized by the identified CDRs may comprise a His-tag domain, which is generally known as a repeat of consecutive His residues in the amino acid sequence of a molecule, preferably of five, and more preferably of six His residues (hexa-histidine). The His-tag may be located e.g. at the N- or C-terminus of the antibody construct, preferably it is located at the C-terminus. Most preferably, a hexa-histidine tag (HHHHHH) (SEQ ID NO:16) is linked via peptide bond to the C-terminus of the antibody construct according to the invention. Additionally, a conjugate system of PLGA-PEG-PLGA may be combined with a poly-histidine tag for sustained release application and improved pharmacokinetic profile.

Amino acid sequence modifications of the antibody constructs described herein are also contemplated. For example, it may be desirable to improve the binding affinity and/or other biological properties of the antibody construct. Amino acid sequence variants of the antibody constructs are prepared by introducing appropriate nucleotide changes into the antibody constructs nucleic acid, or by peptide synthesis. All of the below described amino acd sequence modifications should result in an antibody construct which still retains the desired biological activity (binding to the target cell surface antigen and to CD3) of the unmodified parental molecule.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, His, Met, Phe, Ser, Thr, Trp, and Tyr).

Amino acid modifications include, for example, deletions from, and/or insertions into, and/or substitutions of, residues within the amino acid sequences of the antibody constructs. Any combination of deletion, insertion, and substitution is made to arrive at the final construct, provided that the final construct possesses the desired characteristics. The amino acid changes also may alter post-translational processes of the antibody constructs, such as changing the number or position of glycosylation sites.

For example, 1, 2, 3, 4, 5, or 6 amino acids may be inserted, substituted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted, substituted or deleted in each of the FRs. Preferably, amino acid sequence insertions into the antibody construct include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. Corresponding modifications may also performed within the third domain of the antibody construct of the invention. An insertional variant of the antibody construct of the invention includes the fusion to the N-terminus or to the C-terminus of the antibody construct of an enzyme or the fusion to a polypeptide.

The sites of greatest interest for substitutional mutagenesis include (but are not limited to) the CDRs of the heavy and/or light chain, in particular the hypervariable regions, but FR alterations in the heavy and/or light chain are also contemplated. The substitutions are preferably conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

A useful method for identification of certain residues or regions of the antibody constructs that are preferred locations for mutagenesis is called "alanine scanning mutagenesis" as described by Cunningham and Wells in Science, 244: 1081-1085 (1989). Here, a residue or group of target residues within the antibody construct is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions are then refined by introducing further or other variants at, or for, the sites of substitution. Thus, while the site or region for introducing an amino acid sequence variation is predetermined, the nature of the mutation per se needs not to be predetermined. For example, to analyze or optimize the performance of a mutation at a given site, alanine scanning or random mutagenesis may be conducted at a target codon or region, and the expressed antibody construct variants are screened for the optimal combination of desired activity. Techniques for making substitution mutations at predetermined sites in the DNA having a known sequence are well known, for example, M13 primer mutagenesis and PCR mutagenesis. Screening of the mutants is done using assays of antigen binding activities, such as the target cell surface antigen or CD3 binding.

Generally, if amino acids are substituted in one or more or all of the CDRs of the heavy and/or light chain, it is preferred that the then-obtained "substituted" sequence is at least 60% or 65%, more preferably 70% or 75%, even more preferably 80% or 85%, and particularly preferably 90% or 95% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the antibody construct may have different degrees of identity to their substituted sequences, e.g., CDRL1 may have 80%, while CDRL3 may have 90%.

Preferred substitutions (or replacements) are conservative substitutions. However, any substitution (including non-conservative substitution or one or more from the "exemplary substitutions" listed in Table 3, below) is envisaged as long as the antibody construct retains its capability to bind to the target cell surface antigen via the first domain and to CD3, respectively CD3 epsilon, via the second domain and/or its CDRs have an identity to the then substituted sequence (at least 60% or 65%, more preferably 70% or 75%, even more preferably 80% or 85%, and particularly preferably 90% or 95% identical to the "original" CDR sequence).

Conservative substitutions are shown in Table 3 under the heading of "preferred substitutions". If such substitutions result in a change in biological activity, then more substantial changes, denominated "exemplary substitutions" in Table 3, or as further described below in reference to amino acid classes, may be introduced and the products screened for a desired characteristic.

TABLE 3

Amino acid substitutions

| Original | Exemplary Substitutions | Preferred Substitutions |
| --- | --- | --- |
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | Ala | ala |
| His (H) | asn, gln, lys, arg | arg |
| Ile (I) | leu, val, met, ala, phe | leu |
| Leu (L) | norleucine, ile, val, met, ala | ile |
| Lys (K) | arg, gln, asn | arg |
| Met (M) | leu, phe, ile | leu |
| Phe (F) | leu, val, ile, ala, tyr | tyr |
| Pro (P) | Ala | ala |
| Ser (S) | Thr | thr |
| Thr (T) | Ser | ser |
| Trp (W) | tyr, phe | tyr |
| Tyr (Y) | trp, phe, thr, ser | phe |
| Val (V) | ile, leu, met, phe, ala | leu |

Substantial modifications in the biological properties of the antibody construct of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr, asn, gin; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the antibody construct may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs or VH/VL sequences are at least 60% to the sequences depicted herein, and more typically with preferably increasing homologies or identities of at least 65% or 70%, more preferably at least 75% or 80%, even more preferably at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs or VH/VL sequences and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%. Thus, a "variant CDR" or a "variant VH/VL region" is one with the specified homology, similarity, or identity to the parent CDR/VH/VL of the invention, and shares biological function, including, but not limited to, at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR or VH/VL.

In one embodiment, the percentage of identity to human germline of the antibody constructs according to the invention is ≥70% or ≥75%, more preferably ≥80% or ≥85%, even more preferably ≥90%, and most preferably ≥91%, ≥92%, ≥93%, ≥94%, ≥95% or even ≥96%. Identity to human antibody germline gene products is thought to be an important feature to reduce the risk of therapeutic proteins to elicit an immune response against the drug in the patient during treatment. Hwang & Foote ("IImmunogenicity of engineered antibodies"; Methods 36 (2005) 3-10) demonstrate that the reduction of non-human portions of drug antibody constructs leads to a decrease of risk to induce anti-drug antibodies in the patients during treatment. By comparing an exhaustive number of clinically evaluated antibody drugs and the respective immunogenicity data, the trend is shown that humanization of the V-regions of antibodies makes the protein less immunogenic (average 5.1% of patients) than antibodies carrying unaltered non-human V regions (average 23.59% of patients). A higher degree of identity to human V-region based protein therapeutics in the form of antibody constructs. For this purpose of determining the germline identity, the V-regions of VL can be aligned with the amino acid sequences of human germline V segments and J segments (http://vbase.mrc-cpe.cam.ac.uk/) using Vector NTI software and the amino acid sequence calculated by dividing the identical amino acid residues by the total number of amino acid residues of the VL in percent. The same can be for the VH segments (http://vbase.mrc-cpe.cam.ac.uk/) with the exception that the VH CDR3 may be excluded due to its high diversity and a lack of existing human germline VH CDR3 alignment partners. Recombinant techniques can then be used to increase sequence identity to human antibody germline genes.

In a further embodiment, the bispecific antibody constructs of the present invention exhibit high monomer yields under standard research scale conditions, e.g., in a standard two-step purification process. Preferably the monomer yield of the antibody constructs according to the invention is ≥0.25 mg/L supernatant, more preferably ≥0.5 mg/L, even more preferably ≥1 mg/L, and most preferably ≥3 mg/L supernatant.

Likewise, the yield of the dimeric antibody construct isoforms and hence the monomer percentage (i.e., monomer:(monomer+dimer)) of the antibody constructs can be determined. The productivity of monomeric and dimeric antibody constructs and the calculated monomer percentage can e.g. be obtained in the SEC purification step of culture supernatant from standardized research-scale production in roller bottles. In one embodiment, the monomer percentage of the antibody constructs is ≥80%, more preferably ≥85%, even more preferably ≥90%, and most preferably ≥95%.

In one embodiment, the antibody constructs have a preferred plasma stability (ratio of EC50 with plasma to EC50 w/o plasma) of <5 or <4, more preferably <3.5 or <3, even more preferably <2.5 or <2, and most preferably <1.5 or <1. The plasma stability of an antibody construct can be tested by incubation of the construct in human plasma at 37° C. for 24 hours followed by EC50 determination in a $^{51}$chromium release cytotoxicity assay. The effector cells in the cytotoxicity assay can be stimulated enriched human CD8 positive T cells. Target cells can e.g. be CHO cells transfected with the human target cell surface antigen. The effector to target cell (E:T) ratio can be chosen as 10:1. The human plasma pool used for this purpose is derived from the blood of healthy donors collected by EDTA coated syringes. Cellular components are removed by centrifugation and the upper plasma phase is collected and subsequently pooled. As control, antibody constructs are diluted immediately prior to the cytotoxicity assay in RPMI-1640 medium. The plasma stability is calculated as ratio of EC50 (after plasma incubation) to EC50 (control).

It is furthermore preferred that the monomer to dimer conversion of antibody constructs of the invention is low. The conversion can be measured under different conditions and analyzed by high performance size exclusion chromatography. For example, incubation of the monomeric isoforms of the antibody constructs can be carried out for 7 days at 37° C. and concentrations of e.g. 100 μg/ml or 250 μg/ml in an incubator. Under these conditions, it is preferred that the antibody constructs of the invention show a dimer percentage that is 55%, more preferably 54%, even more preferably <3%, even more preferably <2.5%, even more preferably <2%, even more preferably <1.5%, and most preferably <1% or 50.5% or even 0%.

It is also preferred that the bispecific antibody constructs of the present invention present with very low dimer conversion after a number of freeze/thaw cycles. For example, the antibody construct monomer is adjusted to a concentration of 250 μg/ml e.g. in generic formulation buffer and subjected to three freeze/thaw cycles (freezing at −80° C. for 30 min followed by thawing for 30 min at room temperature), followed by high performance SEC to determine the percentage of initially monomeric antibody construct, which had been converted into dimeric antibody construct. Preferably the dimer percentages of the bispecific antibody constructs are ≤5%, more preferably 54%, even more preferably <3%, even more preferably <2.5%, even more preferably <2%, even more preferably <1.5%, and most preferably <1% or even ≤0.5%, for example after three freeze/thaw cycles.

The bispecific antibody constructs of the present invention preferably show a favorable thermostability with aggregation temperatures ≥45° C. or ≥50° C., more preferably ≥52° C. or ≥54° C., even more preferably ≥56° C. or ≥57° C., and most preferably ≥58° C. or ≥59° C. The thermostability parameter can be determined in terms of antibody aggregation temperature as follows: Antibody solution at a concentration 250 μg/ml is transferred into a single use cuvette and placed in a Dynamic Light Scattering (DLS) device. The sample is heated from 40° C. to 70° C. at a heating rate of 0.5° C./min with constant acquisition of the measured radius. Increase of radius indicating melting of the protein and aggregation is used to calculate the aggregation temperature of the antibody.

Alternatively, temperature melting curves can be determined by Differential Scanning Calorimetry (DSC) to determine intrinsic biophysical protein stabilities of the antibody constructs. These experiments are performed using a MicroCal LLC (Northampton, MA, U.S.A) VP-DSC device. The energy uptake of a sample containing an antibody construct is recorded from 20° C. to 90° C. compared to a sample containing only the formulation buffer. The antibody constructs are adjusted to a final concentration of 250 μg/ml e.g. in SEC running buffer. For recording of the respective melting curve, the overall sample temperature is increased stepwise. At each temperature T energy uptake of the sample and the formulation buffer reference is recorded. The difference in energy uptake Cp (kcal/mole/° C.) of the sample minus the reference is plotted against the respective temperature. The melting temperature is defined as the temperature at the first maximum of energy uptake.

The target cell surface antigen×CD3 bispecific antibody constructs of the invention are also envisaged to have a turbidity (as measured by OD340 after concentration of purified monomeric antibody construct to 2.5 mg/ml and over night incubation) of <0.2, preferably of <0.15, more preferably of <0.12, even more preferably of <0.1, and most preferably of <0.08.

In a further embodiment the antibody construct according to the invention is stable at acidic pH. The more tolerant the antibody construct behaves at unphysiologic pH such as pH 5.5 (a pH which is required to run e.g. a cation exchange chromatography) or below, such as pH 4.0 to 5.5, the higher is the recovery of the antibody construct eluted from an ion exchange column relative to the total amount of loaded protein. Recovery of the antibody construct from an ion (e.g., cation) exchange column at pH 5.5 is preferably ≥30%, more preferably ≥40%, more preferably ≥50%, even more preferably ≥60%, even more preferably ≥70%, even more preferably ≥80%, even more preferably ≥90%, even more preferably ≥95%, and most preferably ≥99%.

It is furthermore envisaged that the bispecific antibody constructs of the present invention exhibit therapeutic efficacy or anti-tumor activity. This can e.g. be assessed in a study as disclosed in the following example of an advanced stage human tumor xenograft model:

The skilled person knows how to modify or adapt certain parameters of this study, such as the number of injected tumor cells, the site of injection, the number of transplanted human T cells, the amount of bispecific antibody constructs to be administered, and the timelines, while still arriving at a meaningful and reproducible result. Preferably, the tumor growth inhibition T/C [%] is <70 or <60, more preferably <50 or <40, even more preferably <30 or <20 and most preferably <10 or <5 or even <2.5.

In a preferred embodiment of the antibody construct of the invention the antibody construct is a single chain antibody construct.

Also in a preferred embodiment the antibody construct of the invention comprises in a HLE domain with an amino to carboxyl order:

hinge-CH2-CH3-linker-hinge-CH2-CH3.

Also in one embodiment of the invention the CH2 domain of one or preferably each (both) polypeptide monomers of the third domain comprises an intra domain cysteine disulfide bridge. As known in the art the term "cysteine disulfide bridge" refers to a functional group with the general structure R—S—S—R. The linkage is also called an SS-bond or a disulfide bridge and is derived by the coupling of two thiol groups of cysteine residues. It is particularly preferred for the antibody construct of the invention that the cysteines forming the cysteine disulfide bridge in the mature antibody construct are introduced into the amino acid sequence of the CH2 domain corresponding to 309 and 321 (Kabat numbering).

In one embodiment of the invention a glycosylation site in Kabat position 314 of the CH2 domain is removed. It is preferred that this removal of the glycosylation site is achieved by a N314X substitution, wherein X is any amino acid excluding Q. Said substitution is preferably a N314G substitution. In a more preferred embodiment, said CH2 domain additionally comprises the following substitutions (position according to Kabat) V321C and R309C (these substitutions introduce the intra domain cysteine disulfide bridge at Kabat positions 309 and 321).

It is assumed that the preferred features of the antibody construct of the invention compared e.g. to the bispecific heteroFc antibody construct known in the art (figure ib) may be inter alia related to the introduction of the above described modifications in the CH2 domain. Thus, it is preferred for the construct of the invention that the CH2 domains in the third domain of the antibody construct of the invention comprise the intra domain cysteine disulfide bridge at Kabat positions 309 and 321 and/or the glycosylation site at Kabat position 314 is removed by a N314X substitution as above, preferably by a N314G substitution.

In a further preferred embodiment of the invention the CH2 domains in the third domain of the antibody construct of the invention comprise the intra domain cysteine disulfide bridge at Kabat positions 309 and 321 and the glycosylation site at Kabat position 314 is removed by a N314G substitution.

In one embodiment the invention provides an antibody construct, wherein:
(i) the first domain comprises two antibody variable domains and the second domain comprises two antibody variable domains;
(ii) the first domain comprises one antibody variable domain and the second domain comprises two antibody variable domains;
(iii) the first domain comprises two antibody variable domains and the second domain comprises one antibody variable domain; or
(iv) the first domain comprises one antibody variable domain and the second domain comprises one antibody variable domain.

Accordingly, the first and the second domain may be binding domains comprising each two antibody variable domains such as a VH and a VL domain. Examples for such binding domains comprising two antibody variable domains where described herein above and comprise e.g. Fv fragments, scFv fragments or Fab fragments described herein above. Alternatively either one or both of those binding domains may comprise only a single variable domain. Examples for such single domain binding domains where described herein above and comprise e.g. nanobodies or single variable domain antibodies comprising merely one variable domain, which might be VHH, VH or VL, that specifically bind an antigen or epitope independently of other V regions or domains.

In a preferred embodiment of the antibody construct of the invention first and second domain are fused to the third domain via a peptide linker. Preferred peptide linker have been described herein above and are characterized by the amino acid sequence Gly-Gly-Gly-Gly-Ser, i.e. $Gly_4Ser$, or polymers thereof, i.e. $(Gly_4Ser)x$, where x is an integer of 1 or greater (e.g. 2 or 3).

In one aspect of the invention the target cell surface antigen bound by the first domain is a tumor antigen, an antigen specific for an immunological disorder or a viral antigen. The term "tumor antigen" as used herein may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. Non-limiting examples of tumor antigens as used herein are CD19, CD33, EGFRvIII, MSLN, CDH19, FLT3, DLL3, CDH3, BCMA and PSMA.

It is envisaged that the antibody construct of the invention the tumor antigen is selected from the group consisting of CD19, CD33, EGFRvIII, MSLN, CDH19, FLT3, DLL3, CDH3, BCMA and PSMA.

In the context of the present invention, an example for a bispecific antibody construct directed against CD19 is an antibody construct having the CDRs as depicted in SEQ ID NOs: 1 to 6. The CD3 binding domain is characterized by the CDRs as depicted in SEQ ID NOs 9 to 14. A particular example in the context of the present invention is a CD19× CD3 bispecific antibody construct. In the context of the present invention, an example for a bispecific HLE antibody construct directed against CD19 is an antibody construct having the CDRs as depicted in SEQ ID NOs: 102 to 104 and 106 to 108. A particular example in the context of the present invention is a BCMA×CD3 bispecific antibody construct. In the context of the present invention, an example for a bispecific antibody construct directed against CD33 is an antibody construct having the CDRs as depicted in SEQ ID NOs: 29 to 31 and 34 to 36. A particular example in the context of the present invention is a CD33×CD3 bispeciifc antibody construct. In the context of the present invention, an example for a bispecific HLE antibody construct directed against CD33 is an antibody construct having the CDRs as depicted in SEQ ID NOs: 29 to 31 and 34 to 36. A particular example in the context of the present invention is a CD33×CD3 bispecific antibody construct comprising a third domain for HLE. In the context of the present invention, an example for a bispecific antibody construct directed against EGFRvIII is an antibody construct having the CDRs as depicted in SEQ ID NOs: 42 to 47. A particular example in the context of the present invention is a EGFRvIII×CD3 bispecific antibody construct.

In one aspect the antibody construct of the invention is characterized by having an amino acid sequence selected from the group consisting of:

| | |
|---|---|
| (a) SEQ ID NOs: 37 to 41; | CD33 |
| (b) SEQ ID NOs: 51 and 52; | EGFRvIII |
| (c) SEQ ID NOs: 62, 63 and 64; | MSLN |
| (d) SEQ ID NOs: 74 to 82 | CDH19 |
| (e) SEQ ID NOs: 103 and 103 | DLL3 |
| (f) SEQ ID NOs: 17, 113 and 114 | CD19 |
| (g) SEQ ID NOs: 92 and 93 | FLT3 |
| (h) SEQ ID NOs: 124 and 125 | CDH3 |
| (i) SEQ ID NOs: 135 and 136 | BCMA |
| (j) SEQ ID Nos: 146 to 151, 161 to 168 and 176 to 181 | PSMA |

Any of the foregoing bispecific antibody constructs may or may not be provided with a third domain, which is a half life extending domain, which preferably is a scFc domain or a heteroFc domain or an albumin binding domain.

The invention further provides a polynucleotide/nucleic acid molecule encoding an antibody construct of the invention. A polynucleotide is a biopolymer composed of 13 or more nucleotide monomers covalently bonded in a chain. DNA (such as cDNA) and RNA (such as mRNA) are examples of polynucleotides with distinct biological function. Nucleotides are organic molecules that serve as the monomers or subunits of nucleic acid molecules like DNA or RNA. The nucleic acid molecule or polynucleotide can be double stranded and single stranded, linear and circular. It is preferably comprised in a vector which is preferably comprised in a host cell. Said host cell is, e.g. after transformation or transfection with the vector or the polynucleotide of the invention, capable of expressing the antibody construct. For that purpose the polynucleotide or nucleic acid molecule is operatively linked with control sequences.

The genetic code is the set of rules by which information encoded within genetic material (nucleic acids) is translated into proteins. Biological decoding in living cells is accomplished by the ribosome which links amino acids in an order specified by mRNA, using tRNA molecules to carry amino acids and to read the mRNA three nucleotides at a time. The code defines how sequences of these nucleotide triplets, called codons, specify which amino acid will be added next during protein synthesis. With some exceptions, a three-nucleotide codon in a nucleic acid sequence specifies a single amino acid. Because the vast majority of genes are encoded with exactly the same code, this particular code is often referred to as the canonical or standard genetic code. While the genetic code determines the protein sequence for a given coding region, other genomic regions can influence when and where these proteins are produced.

Furthermore, the invention provides a vector comprising a polynucleotide/nucleic acid molecule of the invention. A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding side. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding side is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density.

Moreover, the invention provides a host cell transformed or transfected with the polynucleotide/nucleic acid molecule or with the vector of the invention. As used herein, the terms "host cell" or "recipient cell" are intended to include any individual cell or cell culture that can be or has/have been recipients of vectors, exogenous nucleic acid molecules, and polynucleotides encoding the antibody construct of the present invention; and/or recipients of the antibody construct itself. The introduction of the respective material into the cell is carried out by way of transformation, transfection and the like. The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell, but is still included within the scope of the term as used herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

The antibody construct of the invention can be produced in bacteria. After expression, the antibody construct of the invention is isolated from the *E. coli* cell paste in a soluble fraction and can be purified through, e.g., affinity chromatography and/or size exclusion. Final purification can be carried out similar to the process for purifying antibody expressed e.g., in CHO cells.

In addition to prokaryotes, eukaryotic microbes such as filamentous fungi or yeast are suitable cloning or expression hosts for the antibody construct of the invention. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such as *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus; yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger.*

Suitable host cells for the expression of glycosylated antibody construct of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, *petunia*, tomato, *Arabidopsis* and tobacco can also be used as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL5 1); TRI cells (Mather et al., Annals N. Y Acad. Sci. (1982) 383: 44-68); MRC 5 cells; FS4 cells; and a human hepatoma line (Hep G2).

In a further embodiment the invention provides a process for the production of an antibody construct of the invention, said process comprising culturing a host cell of the invention under conditions allowing the expression of the antibody construct of the invention and recovering the produced antibody construct from the culture.

As used herein, the term "culturing" refers to the in vitro maintenance, differentiation, growth, proliferation and/or propagation of cells under suitable conditions in a medium. The term "expression" includes any step involved in the production of an antibody construct of the invention including, but not limited to, transcription, post-transcriptional modification, translation, post-translational modification, and secretion.

When using recombinant techniques, the antibody construct can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody construct of the invention prepared from the host cells can be recovered or purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromato-focusing, SDS-PAGE, and ammonium sulfate precipitation are also available depending on the antibody to be recovered. Where the antibody construct of the invention comprises a CH3 domain, the Bakerbond ABX resin (J. T. Baker, Phillipsburg, NJ) is useful for purification.

Affinity chromatography is a preferred purification technique. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose.

Moreover, the invention provides a pharmaceutical composition comprising an antibody construct of the invention or an antibody construct produced according to the process of the invention. It is preferred for the pharmaceutical composition of the invention that the homogeneity of the antibody construct is ≥80%, more preferably ≥81%, ≥82%, ≥83%, ≥84%, or ≥85%, further preferably ≥86%, ≥87%, ≥88%, ≥89%, or ≥90%, still further preferably, ≥91%, ≥92%, ≥93%, ≥94%, or ≥95% and most preferably ≥96%, ≥97%, ≥98% or ≥99%.

As used herein, the term "pharmaceutical composition" relates to a composition which is suitable for administration to a patient, preferably a human patient. The particularly preferred pharmaceutical composition of this invention comprises one or a plurality of the antibody construct(s) of the invention, preferably in a therapeutically effective amount. Preferably, the pharmaceutical composition further comprises suitable formulations of one or more (pharmaceutically effective) carriers, stabilizers, excipients, diluents, solubilizers, surfactants, emulsifiers, preservatives and/or adjuvants. Acceptable constituents of the composition are preferably nontoxic to recipients at the dosages and concentrations employed. Pharmaceutical compositions of the invention include, but are not limited to, liquid, frozen, and lyophilized compositions.

The inventive compositions may comprise a pharmaceutically acceptable carrier. In general, as used herein, "pharmaceutically acceptable carrier" means any and all aqueous and non-aqueous solutions, sterile solutions, solvents, buffers, e.g. phosphate buffered saline (PBS) solutions, water, suspensions, emulsions, such as oil/water emulsions, various types of wetting agents, liposomes, dispersion media and coatings, which are compatible with pharmaceutical administration, in particular with parenteral administration. The use of such media and agents in pharmaceutical compositions is well known in the art, and the compositions comprising such carriers can be formulated by well-known conventional methods.

Certain embodiments provide pharmaceutical compositions comprising the antibody construct of the invention and further one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

In certain embodiments, the pharmaceutical composition may contain formulation materials for the purpose of modifying, maintaining or preserving, e.g., the pH, osmolarity, viscosity, clarity, color, isotonicity, odor, sterility, stability, rate of dissolution or release, adsorption or penetration of the composition (see, REMINGTON'S PHARMACEUTICAL SCIENCES, 18" Edition, (A. R. Genrmo, ed.), 1990, Mack Publishing Company). In such embodiments, suitable formulation materials may include, but are not limited to:

amino acids such as glycine, alanine, glutamine, asparagine, threonine, proline, 2-phenylalanine, including charged amino acids, preferably lysine, lysine acetate, arginine, glutamate and/or histidine
antimicrobials such as antibacterial and antifungal agents
antioxidants such as ascorbic acid, methionine, sodium sulfite or sodium hydrogen-sulfite;
buffers, buffer systems and buffering agents which are used to maintain the composition at an of about 5.5, to 7.5, preferably 6.5 to 7; examples of buffers are borate, citrates, phosphates or other organic acids, succinate, phosphate, histidine and acetate;
non-aqueous solvents such as propylene glycol, polyethylene glycol, vegetable oils such as olive oil, and injectable organic esters such as ethyl oleate;
aqueous carriers including water, alcoholic/aqueous solutions, emulsions or suspensions, including saline and buffered media;
biodegradable polymers such as polyesters;
bulking agents such as mannitol or glycine;
chelating agents such as ethylenediamine tetraacetic acid (EDTA);
isotonic and absorption delaying agents;
complexing agents such as caffeine, polyvinylpyrrolidone, beta-cyclodextrin or hydroxypropyl-beta-cyclodextrin)
fillers;
monosaccharides; disaccharides; and other carbohydrates (such as glucose, mannose or dextrins); carbohydrates may be non-reducing sugars, preferably trehalose, sucrose, octasulfate, sorbitol or xylitol;
(low molecular weight) proteins, polypeptides or proteinaceous carriers such as human or bovine serum albumin, gelatin or immunoglobulins, preferably of human origin;
coloring and flavouring agents;
sulfur containing reducing agents, such as glutathione, thioctic acid, sodium thioglycolate, thioglycerol, [alpha]-monothioglycerol, and sodium thio sulfate
diluting agents;
emulsifying agents;
hydrophilic polymers such as polyvinylpyrrolidone)
salt-forming counter-ions such as sodium;
preservatives such as antimicrobials, anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide);
metal complexes such as Zn-protein complexes;
solvents and co-solvents (such as glycerin, propylene glycol or polyethylene glycol);
sugars and sugar alcohols, such as trehalose, sucrose, octasulfate, mannitol, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; and polyhydric sugar alcohols;
suspending agents;
surfactants or wetting agents such as pluronics, PEG, sorbitan esters, polysorbates such as polysorbate 20, polysorbate, triton, tromethamine, lecithin, cholesterol, tyloxapal; surfactants may be detergents, preferably with a molecular weight of >1.2 KD and/or a polyether, preferably with a molecular weight of >3 KD; non-limiting examples for preferred detergents are Tween 20, Tween 40, Tween 60, Tween 80 and Tween 85; non-limiting examples for preferred polyethers are PEG 3000, PEG 3350, PEG 4000 and PEG 5000;
stability enhancing agents such as sucrose or sorbitol;
tonicity enhancing agents such as alkali metal halides, preferably sodium or potassium chloride, mannitol sorbitol;
parenteral delivery vehicles including sodium chloride solution, Ringer's dextrose, dextrose and sodium chloride, lactated Ringer's, or fixed oils;
intravenous delivery vehicles including fluid and nutrient replenishers, electrolyte replenishers (such as those based on Ringer's dextrose).

It is evident to those skilled in the art that the different constituents of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

It is envisaged that the composition of the invention might comprise, in addition to the polypeptide of the invention defined herein, further biologically active agents, depending on the intended use of the composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art. It is also envisaged that the antibody construct of the present invention is applied in a co-therapy, i.e., in combination with another anti-cancer medicament.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibody construct of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In certain embodiments, the antibody construct of the invention compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the antibody construct of the invention may be formulated as a lyophilizate using appropriate excipients such as sucrose.

When parenteral administration is contemplated, the therapeutic compositions for use in this invention may be provided in the form of a pyrogen-free, parenterally acceptable aqueous solution comprising the desired antibody construct of the invention in a pharmaceutically acceptable vehicle. A particularly suitable vehicle for parenteral injection is sterile distilled water in which the antibody construct of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody construct.

Additional pharmaceutical compositions will be evident to those skilled in the art, including formulations involving the antibody construct of the invention in sustained- or controlled-delivery/release formulations. Techniques for formulating a variety of other sustained- or controlled- delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949.

The antibody construct may also be entrapped in microcapsules prepared, for example, by coacervation techniques or by interfacial polymerization (for example, hydroxymethylcellulose or gelatine-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Another aspect of the invention includes self-buffering antibody construct of the invention formulations, which can be used as pharmaceutical compositions, as described in international patent application WO 06138181A2 (PCT/US2006/022599). A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution" in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions", Pharm Biotechnol. 13: 159-75 (2002), see particularly the parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic". Destabilizing solutes are referred to as "chaotropic". Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the antibody construct of the invention formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations. Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the antibody construct of the invention formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the antibody construct of the invention formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard. Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The biological activity of the pharmaceutical composition defined herein can be determined for instance by cytotoxicity assays, as described in the following examples, in WO99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition of the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R I, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4):1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Half-life" means the time where 50% of an administered drug are eliminated through biological processes, e.g. metabolism, excretion, etc. By "hepatic first-pass metabolism" is meant the propensity of a drug to be metabolized upon first contact with the liver, i.e. during its first pass through the liver. "Volume of distribution" means the degree of retention of a drug throughout the various compartments of the body, like e.g. intracellular and extracellular spaces, tissues and organs, etc. and the distribution of the drug within these compartments. "Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma. "Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of bispecific antibody constructs exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12).

In a preferred aspect of the invention the pharmaceutical composition is stable for at least four weeks at about −20° C. As apparent from the appended examples the quality of an antibody construct of the invention vs. the quality of corresponding state of the art antibody constructs may be tested using different systems. Those tests are understood to be in line with the "ICH Harmonised Tripartite Guideline: *Stability Testing of Biotechnological/Biological Products Q5C and Specifications: Test procedures and Acceptance Criteria for Biotech Biotechnological/Biological Products Q6B*" and, thus are elected to provide a stability-indicating profile that provides certainty that changes in the identity, purity and potency of the product are detected. It is well accepted that the term purity is a relative term. Due to the effect of glycosylation, deamidation, or other heterogeneities, the absolute purity of a biotechnological/biological product should be typically assessed by more than one method and the purity value derived is method-dependent. For the purpose of stability testing, tests for purity should focus on methods for determination of degradation products.

For the assessment of the quality of a pharmaceutical composition comprising an antibody construct of the invention may be analyzed e.g. by analyzing the content of soluble aggregates in a solution (HMWS per size exclusion). It is preferred that stability for at least four weeks at about −20° C. is characterized by a content of less than 1.5% HMWS, preferably by less than 1% HMWS.

Other examples for the assessment of the stability of an antibody construct of the invention in form of a pharmaceutical composition are provided in the appended examples 4-12. In those examples embodiments of antibody constructs of the invention are tested with respect to different stress conditions in different pharmaceutical formulations and the results compared with other half-life extending (HLE) formats of bispecific T cell engaging antibody construct known from the art. In general, it is envisaged that antibody constructs provided with the specific FC modality according to the present invention are typically more stable over a broad range of stress conditions such as temperature and light stress, both compared to antibody constructs provided with different HLE formats and without any HLE format (e.g. "canonical" antibody constructs). Said temperature stability may relate both to decreased (below room temperature including freezing) and increased (above room temperature including temperatures up to or above body temperature) temperature. As the person skilled in the art will acknowledge, such improved stability with regard to stress, which is hardly avoidable in clinical practice, makes the antibody construct safer because less degradation products will occur in clinical practice. In consequence, said increased stability means increased safety.

Hydrogen-deuterium exchange (HDX) is a chemical reaction in which a covalently bonded hydrogen atom is replaced by a deuterium atom, or vice versa. It can be applied most easily to exchangeable protons and deuterons, where such a transformation occurs in the presence of a suitable deuterium source, without any catalyst. The method gives information about the solvent accessibility of various parts of the molecule, and thus the tertiary structure of the protein.

One embodiment provides the antibody construct of the invention or the antibody construct produced according to the process of the invention for use in the prevention, treatment or amelioration of a proliferative disease, a tumorous disease, a viral disease or an immunological disorder.

The formulations described herein are useful as pharmaceutical compositions in the treatment, amelioration and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

The term "amelioration" as used herein refers to any improvement of the disease state of a patient having a tumor or cancer or a metastatic cancer as specified herein below, by the administration of an antibody construct according to the invention to a subject in need thereof. Such an improvement may also be seen as a slowing or stopping of the progression of the tumor or cancer or metastatic cancer of the patient. The term "prevention" as used herein means the avoidance of the occurrence or re-occurrence of a patient having a tumor or cancer or a metastatic cancer as specified herein below, by the administration of an antibody construct according to the invention to a subject in need thereof.

The term "disease" refers to any condition that would benefit from treatment with the antibody construct or the pharmaceutic composition described herein. This includes chronic and acute disorders or diseases including those pathological conditions that predispose the mammal to the disease in question.

A "neoplasm" is an abnormal growth of tissue, usually but not always forming a mass. When also forming a mass, it is commonly referred to as a "tumor". Neoplasms or tumors or can be benign, potentially malignant (pre-cancerous), or malignant. Malignant neoplasms are commonly called cancer. They usually invade and destroy the surrounding tissue and may form metastases, i.e., they spread to other parts, tissues or organs of the body. Hence, the term "metatstatic cancer" encompasses metastases to other tissues or organs than the one of the original tumor. Lymphomas and leukemias are lymphoid neoplasms. For the purposes of the present invention, they are also encompassed by the terms "tumor" or "cancer".

The term "viral disease" describes diseases, which are the result of a viral infection of a subject.

The term "immunological disorder" as used herein describes in line with the common definition of this term immunological disorders such as autoimmune diseases, hypersensitivities, immune deficiencies.

In one embodiment the invention provides a method for the treatment or amelioration of a proliferative disease, a tumorous disease, a viral disease or an immunological disorder, comprising the step of administering to a subject in need thereof the antibody construct of the invention, or produced according to the process of the invention.

The terms "subject in need" or those "in need of treatment" includes those already with the disorder, as well as those in which the disorder is to be prevented. The subject in need or "patient" includes human and other mammalian subjects that receive either prophylactic or therapeutic treatment.

The antibody construct of the invention will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed in accordance with the invention for delivery by any suitable route of administration. In the context of the present invention, the routes of administration preferably are parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions and the antibody construct of this invention are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163.

In particular, the present invention provides for an uninterrupted administration of the suitable composition. As a non-limiting example, uninterrupted or substantially uninterrupted, i.e. continuous administration may be realized by a small pump system worn by the patient for metering the influx of therapeutic agent into the body of the patient. The pharmaceutical composition comprising the antibody construct of the invention can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the antibody constructs of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may also be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

The compositions of the present invention can be administered to the subject at a suitable dose which can be determined e.g. by dose escalating studies by administration of increasing doses of the antibody construct of the invention exhibiting cross-species specificity described herein to non-chimpanzee primates, for instance macaques. As set forth above, the antibody construct of the invention exhibiting cross-species specificity described herein can be advantageously used in identical form in preclinical testing in non-chimpanzee primates and as drug in humans. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts or doses effective for this use will depend on the condition to be treated (the indication), the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted according to the judgment of the attending physician such that it can be administered to the patient once or over a series of administrations, and in order to obtain the optimal therapeutic effect.

A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of an antibody construct of the invention preferably results in a decrease in severity of disease symptoms, an increase in frequency or duration of disease symptom-free periods or a prevention of impairment or disability due to the disease affliction. For treating target cell antigen-expressing tumors, a therapeutically effective amount of the antibody construct of the invention, e.g. an anti-target cell antigen/anti-CD3 antibody construct, preferably inhibits cell growth or tumor growth by at least about 20%, at least about 40%, at least about 50%, at least about 60%, at least about 70%, at least about 80%, or at least about 90% relative to untreated patients. The ability of a compound to inhibit tumor growth may be evaluated in an animal model predictive of efficacy The pharmaceutical composition can be administered as a sole therapeutic or in combination with additional therapies such as anti-cancer therapies as needed, e.g. other proteinaceous and non-proteinaceous drugs. These drugs may be administered simultaneously with the composition comprising the antibody construct of the invention as defined herein or separately before or after administration of said antibody construct in timely defined intervals and doses.

The term "effective and non-toxic dose" as used herein refers to a tolerable dose of an inventive antibody construct which is high enough to cause depletion of pathologic cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

Finally, the invention provides a kit comprising an antibody construct of the invention or produced according to the process of the invention, a pharmaceutical composition of the invention, a polynucleotide of the invention, a vector of the invention and/or a host cell of the invention.

In the context of the present invention, the term "kit" means two or more components—one of which corresponding to the antibody construct, the pharmaceutical composition, the vector or the host cell of the invention—packaged together in a container, recipient or otherwise. A kit can hence be described as a set of products and/or utensils that are sufficient to achieve a certain goal, which can be marketed as a single unit.

The kit may comprise one or more recipients (such as vials, ampoules, containers, syringes, bottles, bags) of any appropriate shape, size and material (preferably waterproof, e.g. plastic or glass) containing the antibody construct or the pharmaceutical composition of the present invention in an appropriate dosage for administration (see above). The kit may additionally contain directions for use (e.g. in the form of a leaflet or instruction manual), means for administering the antibody construct of the present invention such as a syringe, pump, infuser or the like, means for reconstituting the antibody construct of the invention and/or means for diluting the antibody construct of the invention.

The invention also provides kits for a single-dose administration unit. The kit of the invention may also contain a first recipient comprising a dried/lyophilized antibody construct and a second recipient comprising an aqueous formulation. In certain embodiments of this invention, kits containing single-chambered and multi-chambered pre-filled syringes (e.g., liquid syringes and lyosyringes) are provided.

The pharmaceutical composition of the invention further comprises a buffer, which may be selected from the group consisting of potassium phosphate, acetic acid/sodium acetate, citric acid/sodium citrate, succinic acid/sodium succinate, tartaric acid/sodium tartrate, histidine/histidine HCl, glycine, Tris, glutamate, acetate and mixtures thereof, and in particular from potassium phosphate, citric acid/sodium citrate, succinic acid, histidine, glutamate, acetate and combinations thereof.

Suitable buffer concentrations encompass concentrations of about 200 mM or less, such as about 190, 180, 170, 160, 150, 140, 130, 120, 110, 100, 80, 70, 60, 50, 40, 30, 20, 10 or 5 mM. The skilled person will be readily able to adjust the buffer concentrations in order to provide for stability of the pharmaceutical composition as described herein. Envisaged buffer concentrations in the pharmaceutical composition of the invention specifically rangefrom about 5 to about 200 mM, preferably from about 5 to about 100 mM, and more preferably from about 10 to about 50 mM.

As used herein, the term "pharmaceutical composition" relates to a composition which is suitable for administration to a subject in need thereof. The terms "subject" or "individual" or "animal" or "patient" are used interchangeably herein to refer to any subject, particularly a mammalian subject, for whom administration of the pharmaceutical composition of the invention is desired. Mammalian subjects include humans, non-human primates, dogs, cats, guinea pigs, rabbits, rats, mice, horses, cattle, cows, and the like, with humans being preferred. The pharmaceutical composition of the present invention is stable and pharmaceutically acceptable, i.e. capable of eliciting the desired therapeutic effect without causing any undesirable local or systemic effects in the subject to which the pharmaceutical composition is administered. Pharmaceutically acceptable compositions of the invention may in particular be sterile and/or pharmaceutically inert. Specifically, the term "pharmaceutically acceptable" can mean approved by a regulatory agency or other generally recognized pharmacopoeia for use in animals, and more particularly in humans.

The pharmaceutical composition of the invention comprises one or a plurality of the bispecific single chain antibody construct(s) described herein, preferably in a therapeutically effective amount, a β-cyclodextrin and a buffer. By "therapeutically effective amount" is meant an amount of said construct that elicits the desired therapeutic effect. Therapeutic efficacy and toxicity can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions that exhibit large therapeutic indices are generally preferred.

The composition may comprise a β-cyclodextrin and the buffer described previously. The pharmaceutical composition may optionally comprise one or more further excipients as long as they do not reduce or abolish its advantageous properties as described herein, and in particular its stability.

Excipients can be used in the invention for a wide variety of purposes, such as adjusting physical, chemical, or biological properties of formulations, such as adjustment of viscosity, and or processes of the invention to further improve effectiveness and or to further stabilize such formulations and processes against degradation and spoilage due to, for instance, stresses that occur during manufacturing, shipping, storage, pre-use preparation, administration, and thereafter. The term "excipient" generally includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers.

It is evident to those skilled in the art that the different excipients of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

Polyols are useful stabilizing agents in both liquid and lyophilized formulations to protect proteins from physical and chemical degradation processes, and are also useful for adjusting the tonicity of formulations. Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Mannitol is commonly used to ensure structural stability of the cake in lyophilized formulations. It ensures structural stability to the cake. It is generally used with a lyoprotectant, e.g., sucrose. Sorbitol and sucrose are commonly used agents for adjusting tonicity and as stabilizers to protect against freeze-thaw stresses during transport or the preparation of bulks during the manufacturing process. PEG is useful to stabilize proteins and as a cryoprotectant.

Surfactants routinely are used to prevent, minimize, or reduce surface adsorption. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Commonly used surfactants include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration.

Antioxidants can—to some extent—prevent deleterious oxidation of proteins in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations are preferably water-soluble and maintain their activity throughout the shelf life of a product. EDTA is a useful example.

Metal ions can act as protein co-factors and enable the formation of protein coordination complexes. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. Ca+2 ions (up to 100 mM) can increase the stability of human deoxyribonuclease. Mg+2, Mn+2, and Zn+2, however, can destabilize rhDNase. Similarly, Ca+2 and Sr+2 can stabilize Factor VIII, it can be destabilized by Mg+2, Mn+2 and Zn+2, Cu+2 and Fe+2, and its aggregation can be increased by Al+3 ions.

Salts may be used in accordance with the invention to, for example, adjust the ionic strength and/or the isotonicity of the pharmaceutical formulation and/or to further improve the solubility and/or physical stability of the antibody construct or other ingredient. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility. Ionic species differ in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the pharmaceutical composition as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Particularly useful excipients for formulating the pharmaceutical composition include sucrose, trehalose, mannitol, sorbitol, arginine, lysine, polysorbate 20, polysorbate 80, poloxamer 188, pluronic and combinations thereof. Said excipients may be present in the pharmaceutical composition in different concentrations, as long as the composition exhibits the desirable properties as exemplified herein, and in particular promotes stabilization of the contained bispecific single chain antibody constructs. For instance, sucrose may be present in the pharmaceutical composition in a concentration between 2% (w/v) and 12% (w/v), i.e. in a concentration of 12% (w/v), 11% (w/v), 10% (w/v), 9% (w/v), 8% (w/v), 7% (w/v), 6% (w/v), 5% (w/v), 4% (w/v), 3% (w/v) or 2% (w/v). Preferred sucrose concentrations range between 4% (w/v) and 10% (w/v) and more preferably between 6% (w/v) and 10% (w/v). Polysorbate 80 may be present in the pharmaceutical composition in a concentration between 0.001% (w/v) and 0.5% (w/v), i.e. in a concentration of 0.5% (w/v), 0.2% (w/v), 0.1% (w/v), 0.08% (w/v), 0.05% (w/v), 0.02% (w/v), 0.01% (w/v), 0.008% (w/v), 0.005% (w/v), 0.002% (w/v) or 0.001% (w/v). Preferred Polysorbate 80 concentrations range between 0.002% (w/v) and 0.5% (w/v), and preferably between 0.005% (w/v) and 0.02% (w/v).

However, it is also conceivable that the pharmaceutical composition does not comprise any preservatives. In particular, the present invention inter alia provides a pharmaceutical composition comprising one or more preservatives, comprising a bispecific antibody construct, which is preferably a single chain, in a concentration of about 0.5 mg/ml to 50 mg/ml, and a buffer wherein the antibody construct is stable. potassium phosphate in concentration of about 10 mM, and further sucrose in concentration of about 8% (w/v) of and polysorbate 80 in concentration of about 0.01% (w/v) at a pH of about 6.0.

The pharmaceutical compositions of the invention can be formulated in various forms, e.g. in solid, liquid, frozen, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts.

Generally, various storage and/or dosage forms are conceivable for the pharmaceutical composition of the invention, depending, i.a., on the intended route of administration, delivery format and desired dosage (see, for example, Remington's Pharmaceutical Sciences, 22nd edition, Oslo, A., Ed., (2012)). The skilled person will be aware that such choice of a particular dosage form may for example influence the physical state, stability, rate of in vivo release and rate of in vivo clearance of the antibody construct of the invention.

For instance, the primary vehicle or carrier in a pharmaceutical composition may be either aqueous or non-aqueous in nature. A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles.

When parenteral administration is contemplated, the therapeutic compositions of the invention may be provided in the form of a pyrogen-free, parenterally acceptable aqueous solution comprising the desired antibody construct in a pharmaceutically acceptable vehicle. A particularly suitable vehicle for parenteral injection is sterile distilled water in which the antibody construct is formulated as a sterile, isotonic solution, properly preserved. The preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. Hyaluronic acid may also be used, having the effect of promoting sustained duration in the circulation. Implantable drug delivery devices may be used to introduce the desired antibody construct.

Sustained- or controlled-delivery/release formulations are also envisaged herein. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949. The antibody construct may also be entrapped in microcapsules prepared, for example, by coacervation techniques or by interfacial polymerization (for example, hydroxymethylcellulose or gelatine-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 22nd edition, Oslo, A., Ed., (2012).

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

It is envisaged that the composition of the invention might comprise, in addition to the bispecific single chained antibody construct defined herein, further biologically active agents, depending on the intended use of the composition. Such agents might be in particular drugs acting on tumors and/or malignant cells, but other active agents are also conceivable depending on the intended use of the pharmaceutical composition, including agents acting on on the gastro-intestinal system, drugs inhibiting immunoreactions (e.g. corticosteroids), drugs modulating the inflammatory response, drugs acting on the circulatory system and/or agents such as cytokines known in the art. It is also envisaged that the pharmaceutical composition of the present invention is applied in a co-therapy, i.e., in combination with another anti-cancer medicament.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. E.g., lyophilized compositions may be reconstituted in, e.g., bacteriostatic water for injection (BWFI), physiological saline, phosphate buffered saline (PBS), or the same formulation the protein had been in prior to lyophilization.

The pharmaceutical composition of the invention may in general be formulated for delivery by any suitable route of administration. In the context of the present invention, the routes of administration include, but are not limited totopical routes (such as epicutaneous, inhalational, nasal, opthalmic, auricular/aural, vaginal, mucosal); enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions described herein are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163.

The pharmaceutical composition of the invention can also be administered uninterruptedly. As a non-limiting example, uninterrupted or substantially uninterrupted, i.e. continuous administration may be realized by a small pump system worn by the patient for metering the influx of the antibody construct into the body of the patient. The pharmaceutical composition can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the pharmaceutical composition of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The skilled person will readily understand that the pharmaceutical composition of the invention may in general comprise any of the aforementioned excipients, or additional active agents, or may be provided in any suitable form as long as it is stable and preferably exhibits the same advantageous properties as the pharmaceutical compositions comprising 3-cyclodextrins that have been evaluated in the appended Examples. The skilled person will readily be able to adjust the various components so as to provide a pharmaceutical composition that is stable, i.e. is preferably substantially free from aggregates and/or conformers of the bispecific single chain antibody fragments comprised within.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following examples, offered for illustrative purposes only. The examples are not intended to limit the scope of the present invention in any way.

EXAMPLES

Example 1

In order to investigate the compatibility of known preservatives with a representative bispecific antibody construct according to the present invention, CD19×CD3 bispecific antibody construct was formulated in the presence of respective known preservatives with parameters as set out in Table 4.

TABLE 4

Formulation parameters for testing preservative compatibility with a CD19×CD3 bispecific antibody construct.

| Formulation name | pH | Protein (mg/mL) | Buffer (mM) | Sucrose (%) | Preservatives (w/v) | Polysorbate 80 (%) |
|---|---|---|---|---|---|---|
| G4SuT | 4.0 | 0.8 | 10 mM glutamate | 9 | NA | 0.01 |
| G4SuT_CH | 4.0 | 0.8 | 10 mM glutamate | 9 | 0.3% chorobutanol | 0.01 |
| G4SuT_ME | 4.0 | 0.8 | 10 mM glutamate | 9 | 0.2% methylparaben | 0.01 |
| G4SuT_PH | 4.0 | 0.8 | 10 mM glutamate | 9 | 0.5% phenol | 0.01 |
| G4SuT_TH | 4.0 | 0.8 | 10 mM glutamate | 9 | 0.01% thimerosal | 0.01 |

The formulation parameters used were previously found to efficiently stabilize bispecific antibody constructs. Hence, any difference in comparison to the negative control without preservative (G4SuT) should become even more evident. The chosen preservative concentrations reflected standard concentrations employed in the art. The respective formulations were stored at 25° C. for 14 days and examined on day 0, 1, 3, 7 and 14 by size exclusion chromatography (SEC-HPLC). As it can be seen from FIG. 1, some formulations tested, including controls containing 0% preservative, showed a decrease in the percent high molecular weight (HMW) species over time at both 25° C. This is the case for chlorobutanol and methylparabene, which indicates that these preservative do not destabilize the protein drug and do not induce aggregation or even reduce aggregation. Upon the addition of phenol, HMW values overall remain constant which also points to a compatibility of phenol with the tested bispecific antibody construct under the given experimental conditions. Thimerosal appeared less suitable due to an observed slight increase in HWM over time. The re-equilibration from HMW to main peak may in part be due to dilution from the drug product concentration to the IV bag concentration. It can be generally concluded that at a low pH in the range of 4.0 to 6.5, such as 4.0, a bispecific antibody construct of the present invention remains stable or is stabilized by a preservative such as, for example, chlorobutanol or methylparaben, or also by benzyl alcohol. The low pH complements to the stabilization of the bispecific antibody construct, which is why a pharmaceutical composition comprising higher concentrations, such as at least 200, 300, 400, 500, 600, 700, 800, 900 or 1000 µg/ml, is stable, i.e. shows low percentile HMW concentration.

Example 2

As a further known preservative, benzyl alcohol was tested for compatibility with representative bispecific antibody construct according to the present invention, CD19×CD3 bispecific antibody construct. In order to better mimic a clinical application situation, a physiologic pH of 7 was chosen as a challenging environment, as typically bispecific antibody constructs as described herein are less protected from aggregation in a pH7 environment compared to a pH 4 environment. An overall tendency towards aggregation would have to be expected. In detail, a dilution row of the CD19×CD3 antibody construct from 4.5 to 800 µg/ml was prepared, reflecting typical clinical application concentrations and those which may exceed it. The benzyl alcohol concentration of 0.9% was chosen in line with commercial and regulatory approved 0.9% Sodium Chloride, USP (containing 0.9% benzyl alcohol). Compatibility was examined by determining the percentage of undesired HMW species by size exclusion chromatography (SEC-HPLC) after 0, 1 and 2 days at 25° C., an ambient temperature also prevalent in a clinical setting. As can be seen in FIG. 1, the aggregation rate, expressed by percentage of undesired HMW species, is dependent on the concentration of the bispecific antibody construct, in the present case CD19×CD3 bispecific antibody construct. Concentratioins below 50 µg/ml surprisingly do not show an increase of HMW species. As it can be seen from the HMW percentage values at the 4.5 µg/ml concentration, HMW species even show reversibility back to monomer. Hence, it was observed that below a threshold of about 50 µg/ml representative CD19×CD3 bispecific antibody construct shows almost no HMW species upon contact with a preservative such as benzyl alcohol and that HMW percentage remains below 2% even after 2 days of storage. Also at a concentration below 200 µg/ml the initial HMW concentration is very low (below 1%) and remains significantly below 5% even after 2 days of storage. As CD19×CD3 bispecific antibody construct according to the present invention is a more sensitive bispecific antibody construct in terms of stability, other constructs show even lower HMW percentages at respective bispecific antibody construct concentration and stable in the presence of representative preservative benzyl alcohol even in the absence of any further complementing stabilizers and at a physiologic pH 7 and a temperature of 25° C. relevant for the clinical application.

Example 3

Figure 3A:
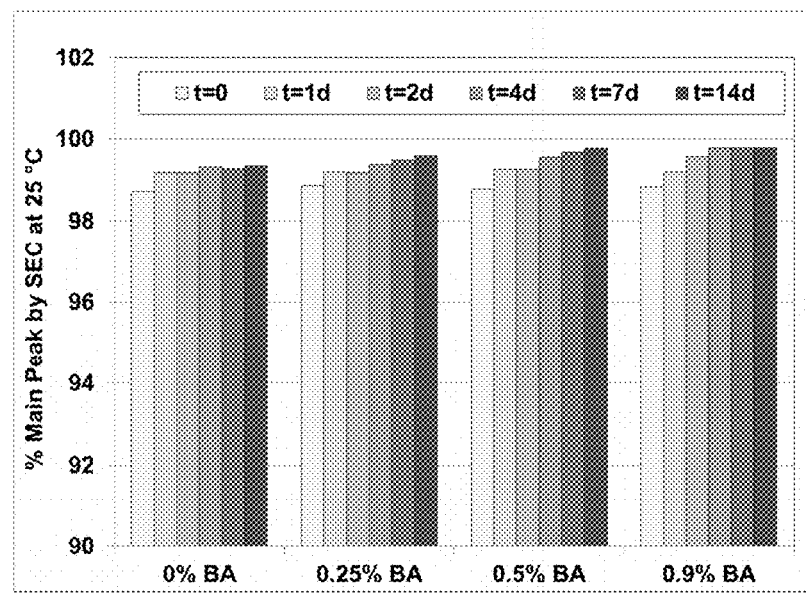
FIG. 3: Stability diagram as per percentile main peak (A) and high molecular weight (HMW) species of CD19×CD3 bispecific antibody constructs as determined by SEC-HPLC for preservative benzyl alcohol depending on preservative concentration at 25° C. (B), and depending on administration container material (C). Stability diagram as per percentile main peak (monomer) of CD19×CD3 bispecific antibody constructs as determined by SEC-HPLC for preservative benzyl alcohol depending on preservative concentration at 25° C. depending on administration container material (D).
Figure 3B:
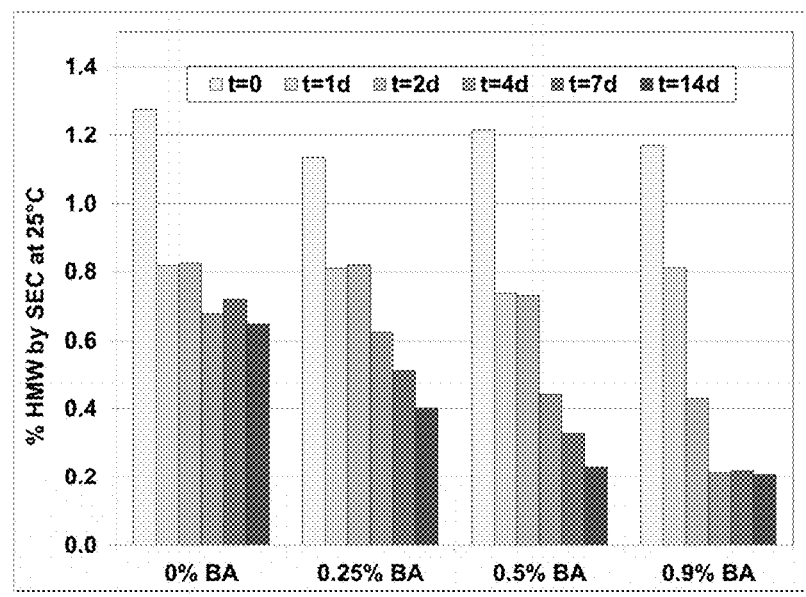

HMW species reversibility back to monomer was further examined over a period of 14 days by SEC-HPLC for representative CD19×CD3 bispecific antibody construct in the presence of representative preservative benzyl alcohol and at a physiologic pH 7 both at a temperature of 4 and 25° C., covering refrigeration and administration in a clinical setting. Concentration of said construct was 4 µg/ml, respectively. Benzyl alcohol concentration was 0.25, 0.5 and 0.9%, respectively. As can be seen from FIG. 3A, at 4° C. the HMW percentage drops from day 0 to day 7 but them does not change significantly from day 7 to day 14. HMW values for formulations comprising benzyl alcohol are slightly lower than those without indicating a stabilizing effect. This effect is even more prominent at 25° C. (see FIG. 3B). The higher the benzyl alcohol concentration and the longer the observation time, the lower is the HMW percentage. This result confirms that HMW species even show reversibility back to monomer in the presence of representative preservative benzyl alcohol, preferably at a higher but regulatory acceptable concentration (0.9%).

Within the same experimental conditions, a potential influence of the infusion bag material was likewise examined. IV bags were prepared containing 1900 ng/mL of Blincyto for the microbial growth study which is the anticipated administration concentration for a 7 day IV bag. IV bags prepared for the stability study bracketed the administration concentration and contained Blincyto at either 4500 ng/mL or 1900 ng/mL. The higher concentration was needed to be above the LOQ for the stability indicating assays, SE-HPLC and CE-HPLC.

Both studies utilized 250 mL IV bags. The microbial growth study was evaluated using empty EVA IV bags only. These bags were prepared in a sterile environment and were prepared for microbe inoculation and growth testing during 14 days of incubation at room temperature. The stability study evaluated both EVA and polyolefin IV bags. Saline filled polyolefin IV bags were drained prior to use. After the Blincyto containing infusion solutions were prepared, both IV bag types were placed at 4° C. for 10 days, to simulate the maximum storage time at the clinic, followed by 14 days of incubation at 25° C. and 37° C. Accordingly, infusion bag material ethyl vinyl acetate (EVA) and a polyolefin were compared for any difference in BiTE® stability in terms of percentile HMW species.

Figure 3C:
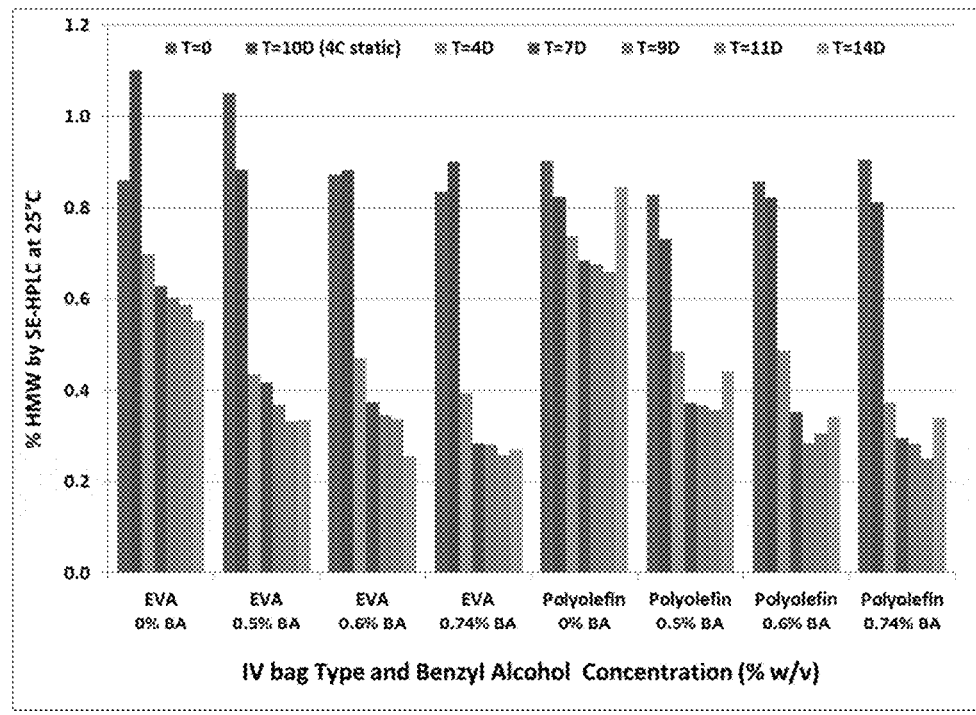
Figure 3D:
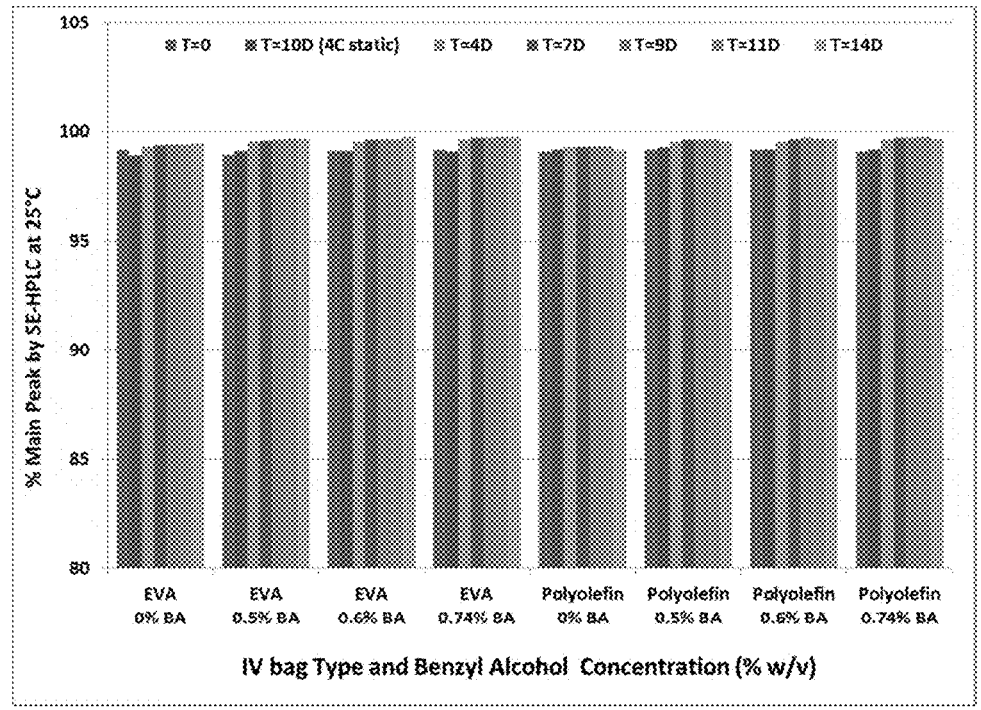

The respective formulations therein comprised 4 µg/ml CD19×CD3 bispecific antibody construct and a benzyl alcohol concentration of 0%, 0.5%, 0.6% or 0.74% were kept for 0, 4, 7, 9, 11 or 14 days at 25° C. with one sample at 4° C. for 10 d as a static control. As can be seen from FIG. 3C, the formulations comprising benzyl alcohol showed overall improved stability, and even decreasing HMW values indicating reversibility back to monomer, in particular dependent on the preservative concentration. This trend was slightly more consistently observed for EVA than for polyolefine. Accordingly, the percentile main peak as an indicator for the monomer, i.e. the non-aggregated and active bispecific antibody construct, increases with higher concentration of preservative and over the examined time (see FIG. 3D). Generally, the presence of benzyl alcohol appeared to increase the rate of the re-equilibration especially during incubation at 25° C. Overall, there were no meaningful differences between the two types of IV bag materials tested.

Example 4

Figure 4:
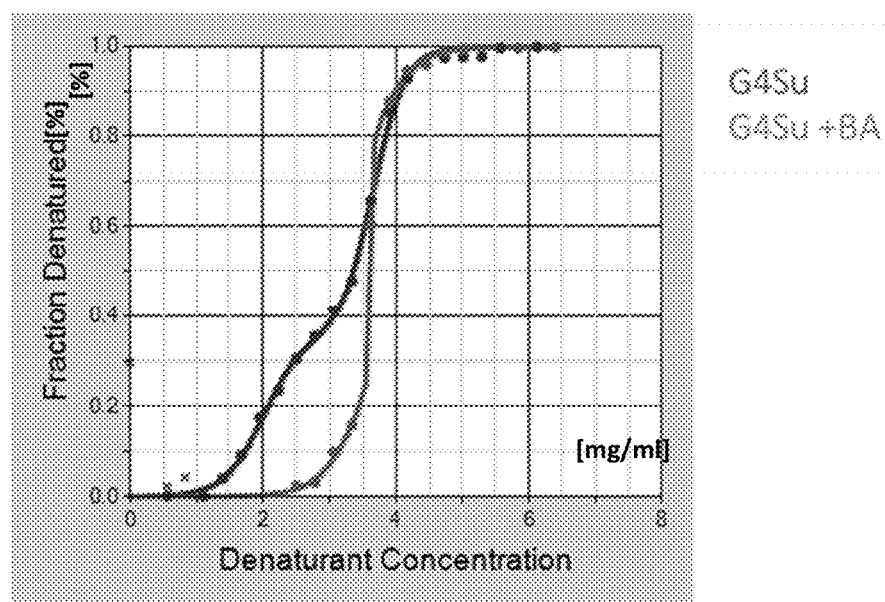
FIG. 4: Denaturation diagram of CD19×CD3 bispecific antibody constructs at a concentration of 1 mg/ml in presence or absence of preservative benzyl alcohol as determined by fluorescence spectrometry at pH 4.

Improved stability of a representative bispecific antibody construct of the present invention conferred by a preservative such as benzyl alcohol was further examined by a denaturation assay using fluorescence as detection means. Experimental conditions comprised guanidinium chloride as denaturant which concentration was plotted on the x-axis (see FIG. 4). Incubation time was 2.5 hours at 25° C. at near-physiologic pH 7. Fluorescence excitation was set to 280 nm and the emission scan was run from 300 to 400 nm. The percentile denatured fraction was calculated from the fluoresces assay as standard in the art. The result can be seen in FIG. 4. The grey curve represents the formulation comprising benzyl alcohol, the black curve the formulation without preservative. The grey curve shows a shift to the right in the bottom portion of the curve. This means that it takes more denaturant to unfold this region, i.e. the CD3 domain, which translates into improved stability conferred by the preservative.

Example 5

This example was a microbial challenge study in support of CD19×CD3 bispecific antibody construct drug product (DP) administered via an intravenous (IV) bag. The study was performed to evaluate the ability of different concentrations (0.5%-0.74%) of benzyl alcohol (BeOH) to reduce or eliminate microbial growth in IV bags holding blinatumomab infusion solution containing benzyl alcohol, CD19×CD3 bispecific antibody construct DP, and intravenous solution stabilizer (IVSS) kept at 20-25° C. for up to 14 days.

Results obtained from the study demonstrate that benzyl alcohol at the assessed concentration is capable of inhibiting the growth of the six evaluated microorganisms. The antimicrobial efficacy on the Gram negative bacteria assessed in the study (*E. coli, P. aeruginosa*, and *E. cloacae*) is apparent. These microorganisms could grow to 106 CFU/mL in blinatumomab infusion solution without BeOH but the growth was completely inhibited by all three assessed concentrations. The effect on the Gram positive bacteria (*S. aureus* and *M. luteus*) and yeast (*C. albicans*) assessed in the study is not as obvious as it was on Gram negative bacteria, mainly due to blinatumomab infusion solution not supporting the growth of Gram positive bacteria and yeast. A gradual decrease in titers for the 0.0% BeOH positive controls of these microorganisms, with low to no recoverable titer toward the end of the assessed period, was observed. Nevertheless, the antimicrobial efficacy for benzyl alcohol on these microorganisms can be demonstrated by the difference in duration required to have the challenged inoculum completely inactivated or inhibited in BeOH treated samples.

The study was carried out to evaluate the growth of six different microorganisms in IV bags filled with 109 mL of CD19×CD3 bispecific antibody construct infusion solution containing benzyl alcohol (BeOH, at a final concentration of 0.0%, 0.5%, 0.6% or 0.74%), CD19×CD3 bispecific antibody construct DP, and IVSS. The prepared IV bags were held at 20-25° C. for up to 14 days.

The bacteria and yeast selected for the study are representative of known human pathogens commonly isolated from nosocomial infections. These microorganisms include *Candida albicans* (ATCC 10231), *Enterobacter cloacae* (ATCC 13047), *Escherichia coli* (ATCC 8739), *Micrococcus luteus* (ATCC 4698), *Pseudomonas aeruginosa* (ATCC 9027), and *Staphylococcus aureus* (ATCC 6538).

The blinatumomab DP formulation contains 1.91 µg/mL blinatumomab in 25 mM citric acid monohydrate, 200 mM L-lysine-monohydrochloride, 15% (w/v) trehalose dehydrate, 0.1% (w/v) polysorbate 80 at pH 7.0. The formulation for IVSS is 25 mM citric acid monohydrate, 1.25 M L-lysine monohydrochloride, 0.1% (w/v) polysorbate 80 at pH 7.0.

Test Articles: The test articles assessed in the study were blinatumomab infusion solution filled in IV bags containing 1.91 µg/mL conc. blinatumomab in a total volume of 109 mL/bag. The solution was made up by the addition of 2.2 mL IVSS, 16.8 mL of pooled reconstituted blinatumomab DP (210 µg), and a combined total volume of 90 mL of saline solution and saline solution with 0.9% benzyl alcohol (basaline). The four different levels of BeOH (0.0%, 0.5%, 0.6% and 0.74%) assessed in the study were achieved by adding different amounts of saline and basaline. For example, the bag with 0.0% BeOH (positive control) was prepared by adding 90 mL of saline, while the bag with 0.6% BeOH was prepared by adding 18 mL saline and 72 mL 0.9% bsaline, to the 2.2 mL IVSS and 16.8 mL blinatumomab DP. Refer to Appendix A for more details. Note that the illustration for 0.0% BeOH positive control in FIG. 1 (Schematic of IV Bag Preparation) of Appendix A of this report and in the same illustration in FIG. 4 of Appendix D inadvertently stated the final BeOH concentration to be 0.5%, instead of 0.0%. This is a typographic error and has no impact on the study outcome.

A total of 24 CD19×CD3 bispecific antibody construct infusion solution filled IV bags were assessed to evaluate the effect of four levels of benzyl alcohol on the aforementioned six different microorganisms (6×4=24). An approximate 1 mL of inoculum containing <1×104 CFU microbes was inoculated through the injection port into each bag that yielded an initial microbial load at ~1×102 CFU/mL. After inoculation, the sampling port on the bag was cleaned with sterile IPA and the bag was mixed briefly and then incubated at 20-25° C.

Negative controls: Three IV bags containing blinatumomab infusion solutions at the three levels of BeOH (0.5%, 0.6% and 0.74%) without challenged microorganisms were incubated along with challenged test articles to serve as a negative control. Additional assay negative controls assessed in the study including 0.1% peptone water (PEPW) and phosphate buffered saline (PHSS). These negative controls must be negative for growth at all times. Refer to Appendix A for more details.

Sampling and titration procedures: At each time point of 0-hour, 4-day, 8-day, 10-day, 12-day and 14 day, a 3 mL aliquot was collected from each assessed bag and titrated.

Sample titration was performed by membrane filtration in duplicate of 1 mL aliquots for each timed sample. Additional dilutions were performed to obtain countable results (<300 CFU/plate).

The effect of BeOH on the challenged microorganisms is graphically displayed in FIG. 1 through FIG. 6. In general, Gram negative (G−) bacteria assessed in the study (*E. coli, P. aeruginosa*, and *E. cloacae*) grew and maintained viability in blinatumomab infusion solution (without BeOH) much better than Gram positive (G+) bacteria (*S. aureus* and *M. luteus*) and yeast (*C. albicans*). The 0.0% BeOH positive control of all three assessed G-bacteria grew to 106 CFU/mL on Day 8 and maintained at the level through the end of the study (14 days), FIGS. 5A, 5B and 5C. In contrast, growth of the inoculated G-bacteria (100 CFU/mL) was inhibited (or inactivated) at the presence of BeOH. There were no recoverable *P. aeruginosa* on Day 4 and beyond (FIG. 5B) and no recoverable *E. coli* or *E. cloacae* on Day 10 and beyond at all three BeOH conc. (FIG. 5A and FIG. 5C, respectively).

Figure 5A:
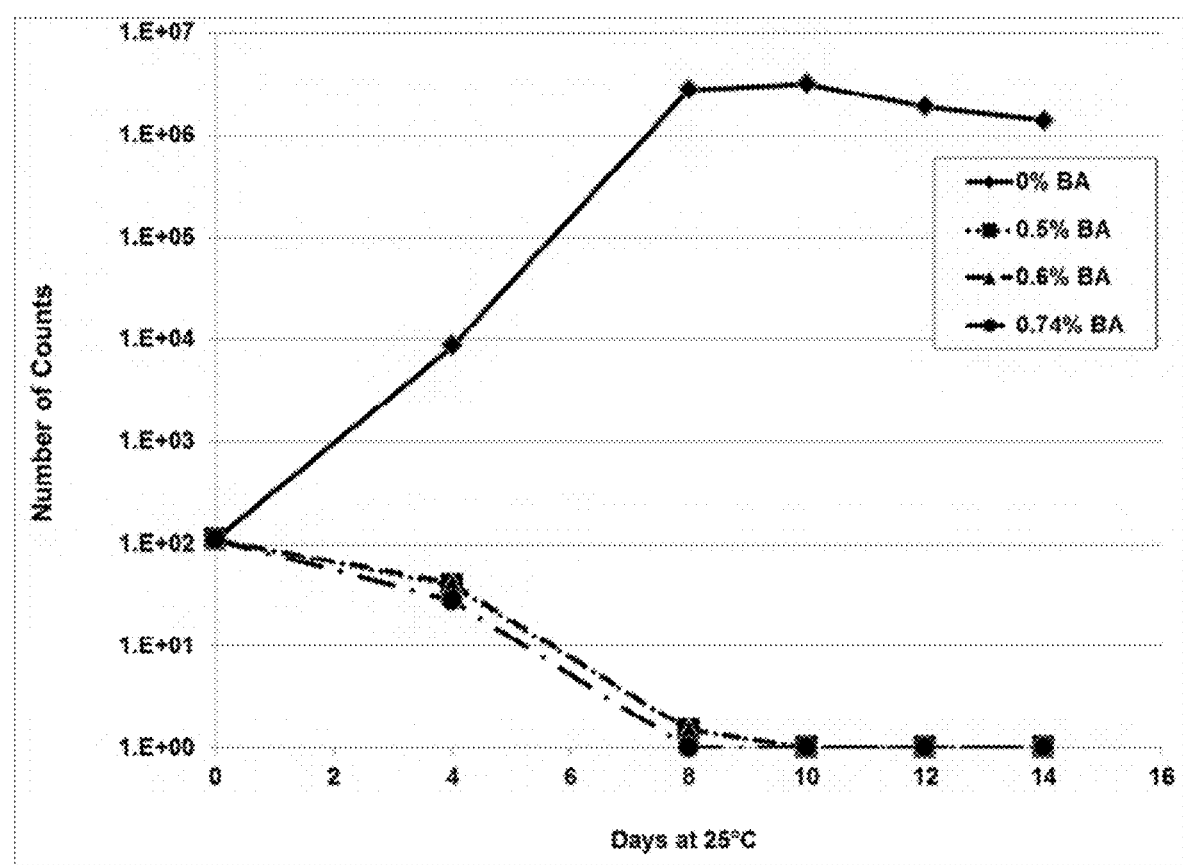
FIGS. 5A-5F: Microbial growth diagrams for E. coli (FIG. 5A), P. arugenosa (FIG. 5B), E. cloace, (FIG. 5C), S. aureus (FIG. 5D), M. luteus (FIG. 5E) and C. albicans (FIG. 5F) in formulations comprising CD19×CD3 bispecific antibody constructs and 0, 0.5, 0.6 or 0.7% benzyl alcohol.
Figure 5B:
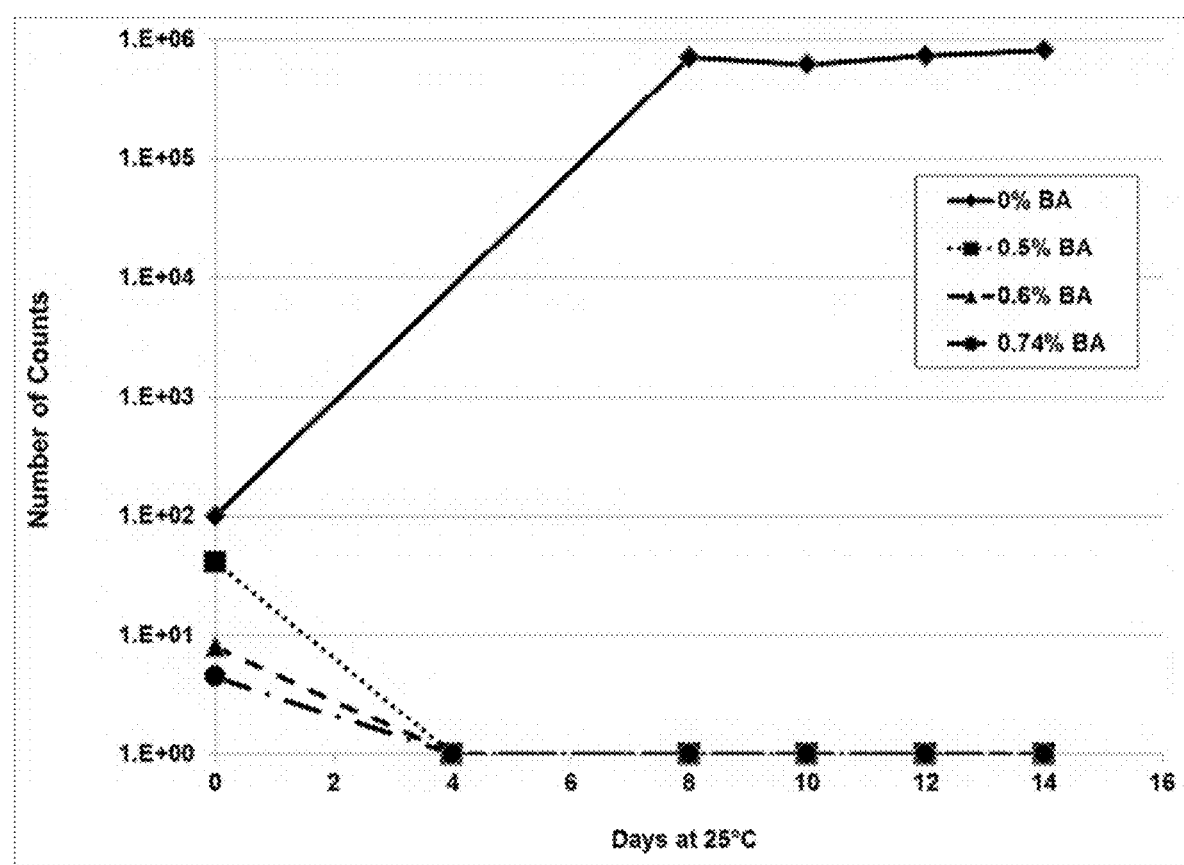
Figure 5C:
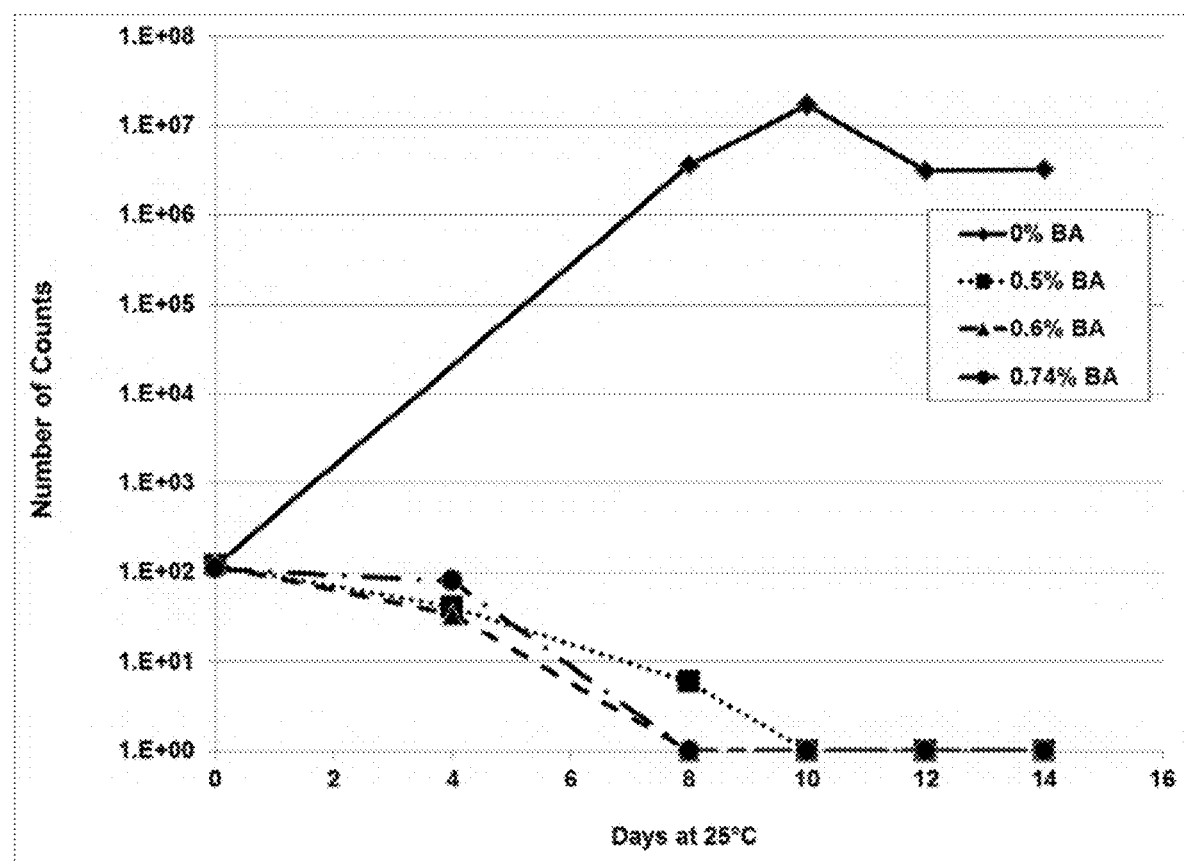
Figure 5D:
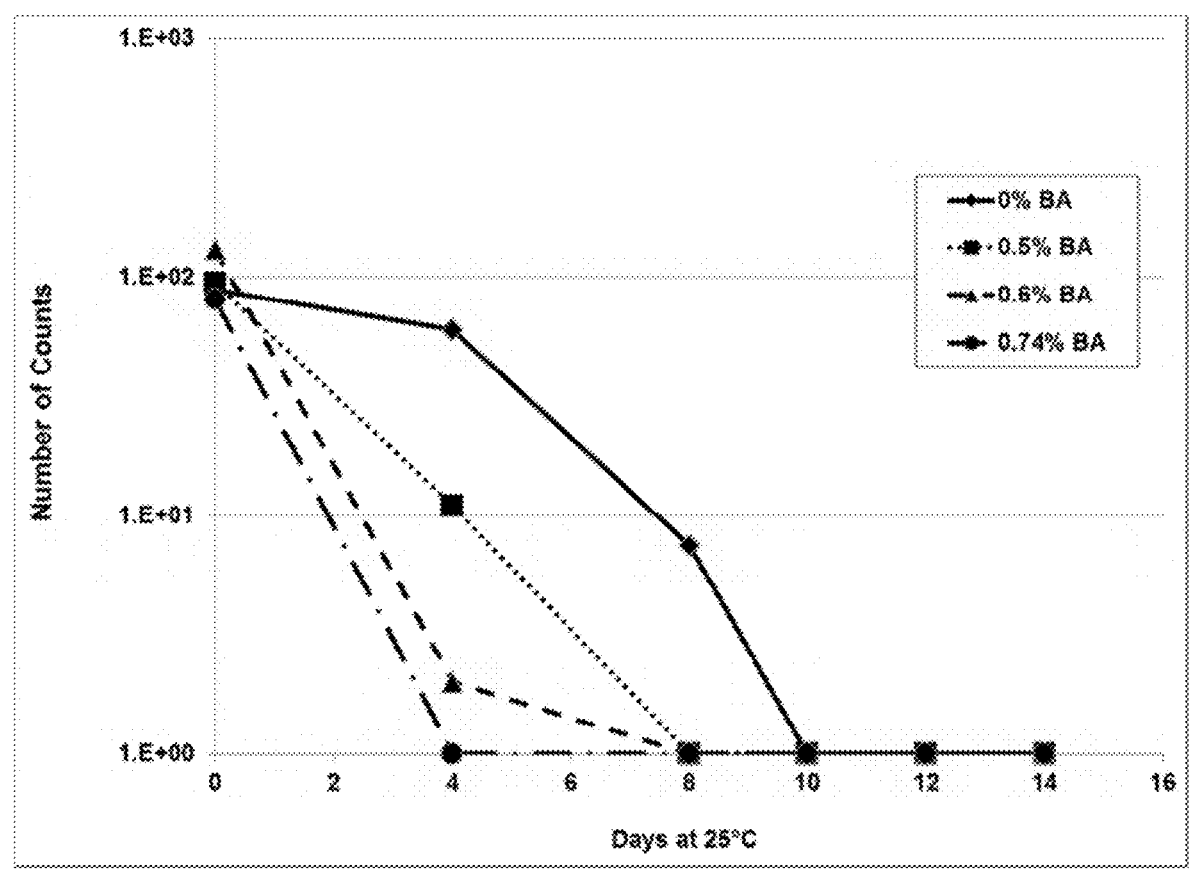
Figure 5E:
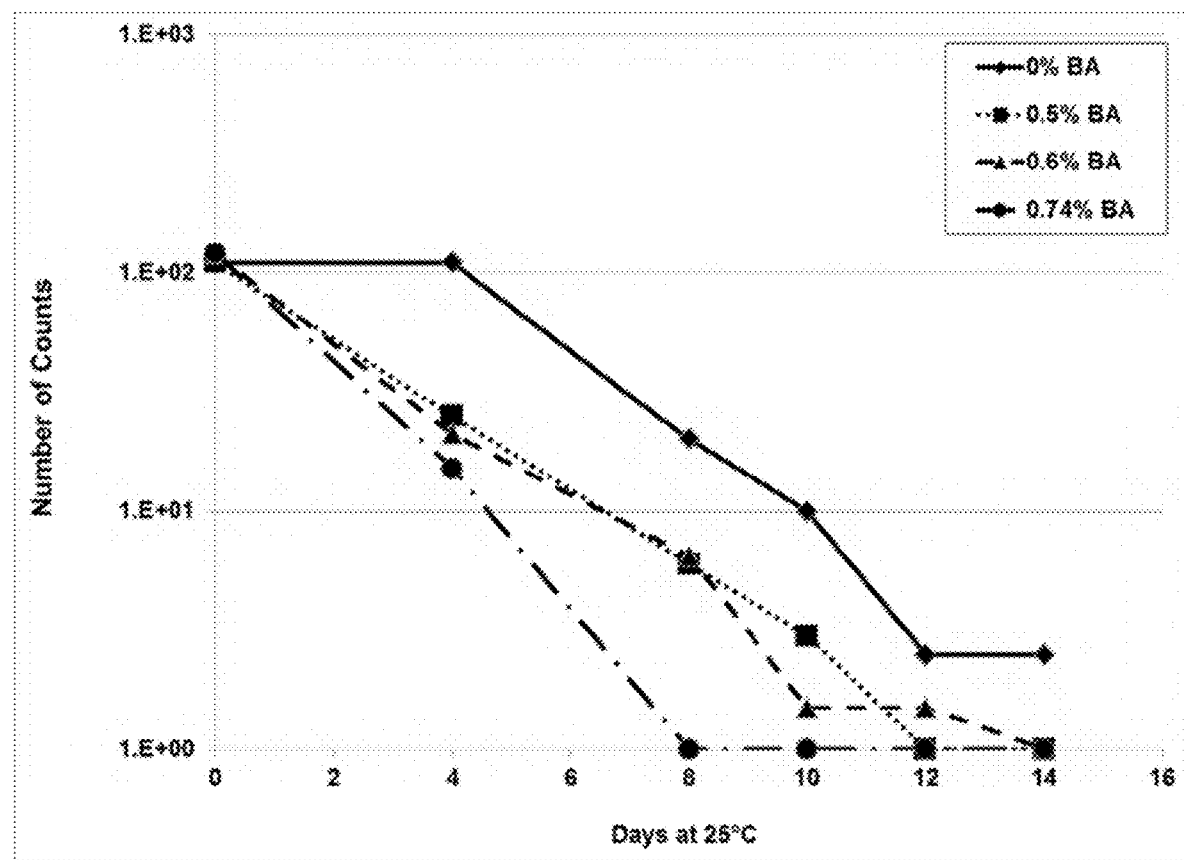
Figure 5F:
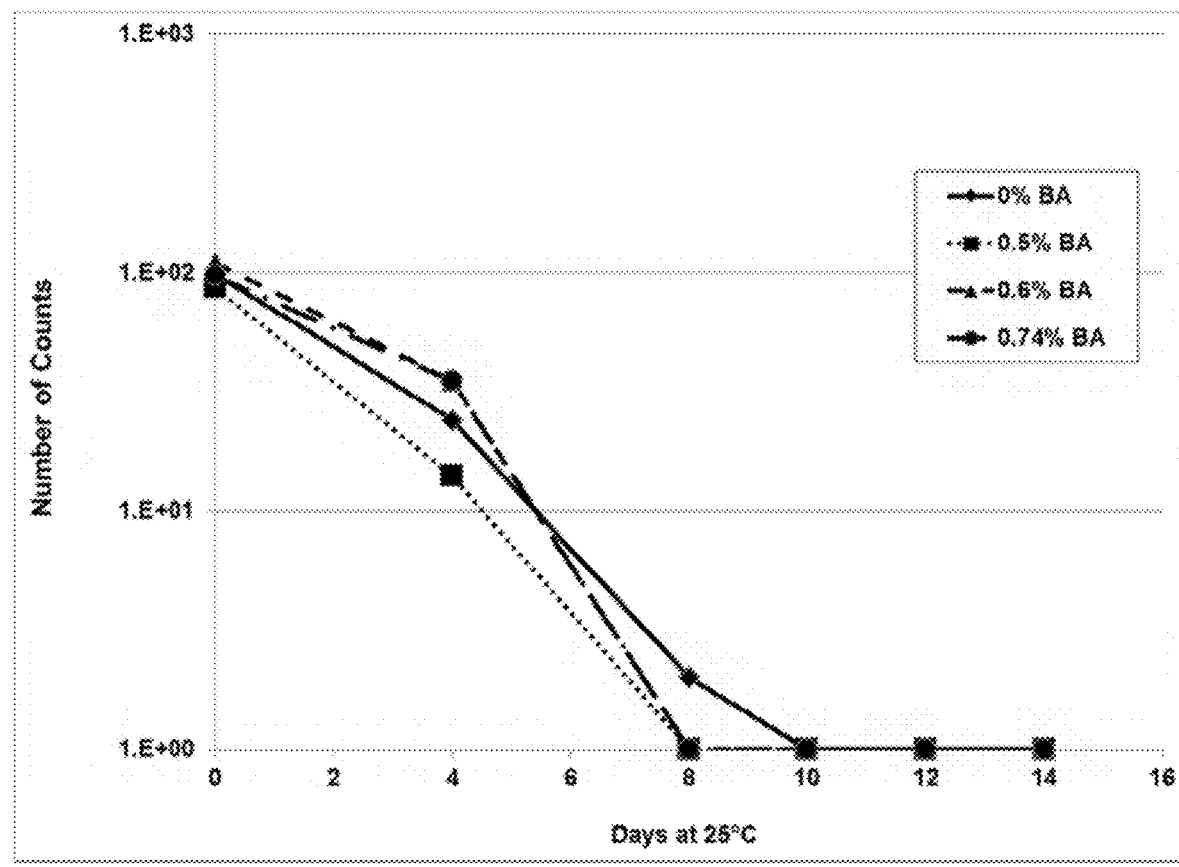

Unlike G-bacteria, the growth of G+ bacteria (*S. aureus* and *M. luteus*) or *C. albicans* was not supported by blinatumomab infusion solution (with or without BeOH), FIGS. 5D, 5E and 5F, respectively. A gradual decrease in titers of G+ bacteria and *C. albicans* in 0.0% BeOH positive control timed samples was observed, with low to no recoverable titer toward the end of the study. In as much, the antimicrobial efficacy of BeOH on these microorganisms, although still noticeable, is not as obvious as it was observed on G-bacteria. The effect can be demonstrated that the challenged microorganisms are completely inactivated or inhibited in BeOH treated samples sooner than the 0.0% BeOH controls. For *S. aureus*, the challenged inoculum became unrecoverable on Day 4 and beyond at 0.74% BeOH, on Day 8 at 0.5% or 0.6% BeOH, versus on Day 10 for the positive control (FIG. 5D). Similarly, the challenged *M. luteus* was unrecoverable on Day 8 at 0.74% BeOH, on Day 14 at 0.5% or 0.6% BeOH, and the positive control still has low recoverable microbes on Day 14 (FIG. 5E); and the challenged *C. albicans* was unrecoverable on Day 8 at all three levels of BeOH and on Day 10 for the positive control (FIG. 5F). Hence, robust antimicrobial activity in the tested formulations could be demonstrated.

Example 6

It was the aim of this experiment to prove additional stabilizing effects by buffers and/or excipients used in a formulation comprising a bispecific antibody construct of the present invention and a preservative. Model anti-FAPα domain, isolated anti-CD3 domain (I2C, as typically used throughout all example bispecific antibody constructs), CD33×CD3 bispecific antibody construct and EGFRvIII×CD3 bispecific antibody construct were examined. For FAPα, anti-CD3 domain, and CD33×CD3 bispecific antibody construct, the experimental procedure was same. Firstly, the protein samples were dialyzed into Tris-phosphate buffer (35 mM Tris, 17.5 mM phosphate, pH 6.0) and (35 mM Tris, 17.5 mM phosphate, 50 mM citrate, pH 6.0), respectively. The protein concentration was adjusted to 0.3 mg/mL after dialysis. Secondly, the Hydrogen-deuterium exchange (HDX) reaction was initiated by 1 to 5 dilution of the protein samples into the corresponding D20 buffer with exact same composition. Thirdly, the HDX reaction was quenched after 10s, 1 min, 10 min, 1 hr, 4 hr, and 12 hr, and then the quenched protein samples were analyzed by mass spectrometry. For FAPa, the HDX reaction was done at 4° C., 25° C., and 37° C. The HDX reaction was done at 37° C. for CD33×CD3 bispecific antibody construct AMG330 and anti-CD3. For the assessment of antibody construct stability in the presence of benzyl alcohol, the benzyl alcohol was added to the protein sample directly at the concentration of 0.9%. For EGFRvIII×CD3 bispecific antibody construct, the protein samples was dialyzed into (a) 10 mM KH2PO4, 2% Sucrose, 4% Manitol pH 6 and (b) 10 mM KH2PO4, 2% Sucrose, 4% Manitol, 50 mm Citrate pH 6, respectively. The protein concentration was adjusted to 1 mg/mL after dialysis. Secondly, the HDX reaction was initiated by 1 to 5 dilution of the protein samples into the corresponding D20 buffer with exact same composition. Thirdly, the HDX reaction was quenched after 10s, 10 min, 2 hr, 8 hr, 16 hr, 24 hr, and then the quenched protein samples were analyzed by mass spectrometry. The experiment was done at 25° C.

Figure 6A:
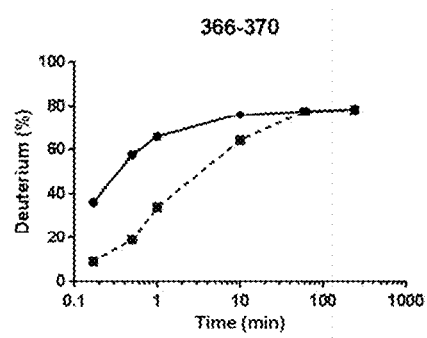
FIGS. 6A-6H: Stabilization effects of citrate—where applicable in the presence of benzyl alcohol—on FAPα (FIG. 6A), anti-CD3 domain wherein the peptide 108-112 in anti-CD3 domain (YISYW) corresponds to the peptide 367-370 in FAPα (FIG. 6B), CD33×CD3 bispecific antibody constructs wherein the peptide 364-368 in CD33×CD3 bispecific antibody constructs (YISYW) corresponds to the peptide 366-370 in FAPα (FIG. 6C), and EGFRvIII×CD3 bispecific antibody constructs wherein the peptide 365-369 in EGFRvIII×CD3 bispecific antibody constructs (YISYW) corresponds to the peptide 366-370 in FAPα (FIG. 6D).
Figure 6B:
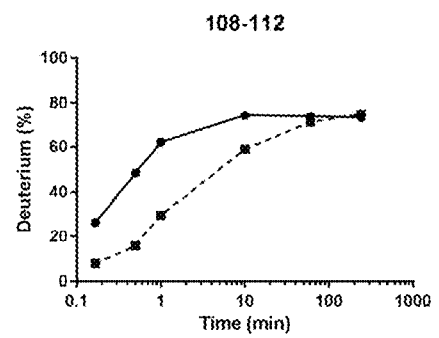
Figure 6C:
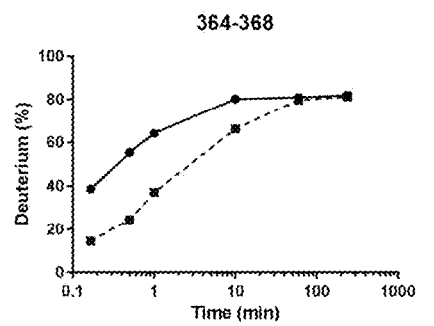
Figure 6D:
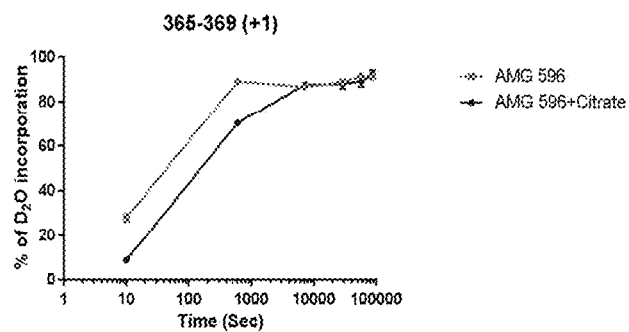

The figures show the stabilization effects of citrate—where applicable in the presence of benzyl alcohol—on FAPα (FIG. 6A), anti-CD3 domain wherein the peptide 108-112 in anti-CD3 domain (YISYW) corresponds to the peptide 367-370 in FAPα (FIG. 6B), CD33×CD3 bispecific antibody construct wherein the peptide 364-368 in CD33× CD3 bispecific antibody construct (YISYW) corresponds to the peptide 366-370 in FAPα (FIG. 6C), and EGFRvIII× CD3 bispecific antibody construct wherein the peptide 365-369 in EGFRvIII bispecific antibody construct (YISYW) corresponds to the peptide 366-370 in FAPα (FIG. 6D). Accordingly, the citrate stabilization effects on CDR-H3 region (YISYW) of anti-CD3 domain for different BiTE molecules can be observed. For FAPα, anti-CD3, and CD33×CD3 bispecific antibody construct, the experimental conditions are identical, and the stabilization effects are equivalent. For EGFRvIII×CD3 bispecific antibody construct, the experiment was done at slightly different condition as laid out above, but the stabilization effect is likewise given. Hence, citrate is shown to be able to stabilize bispecific antibody constructs in the presence of a preservative where required.

Figure 6E:
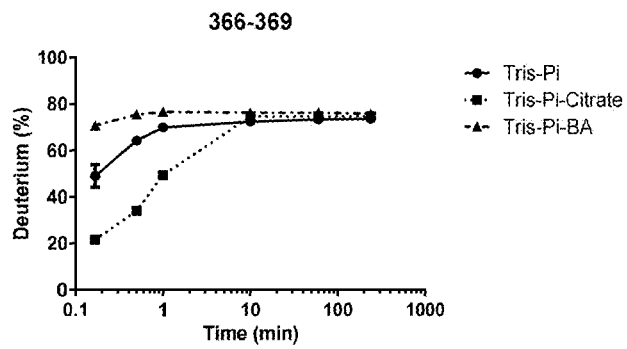
Figure 6F:
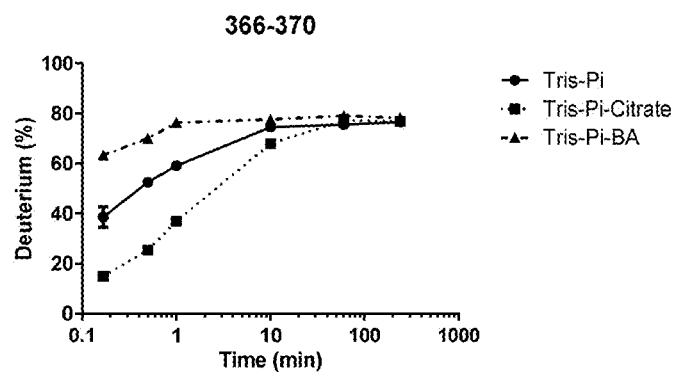
Figure 6G:
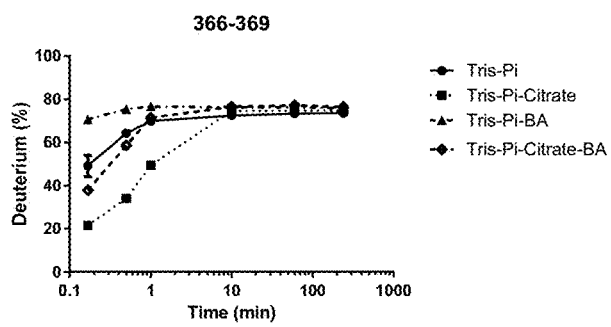
Figure 6H:
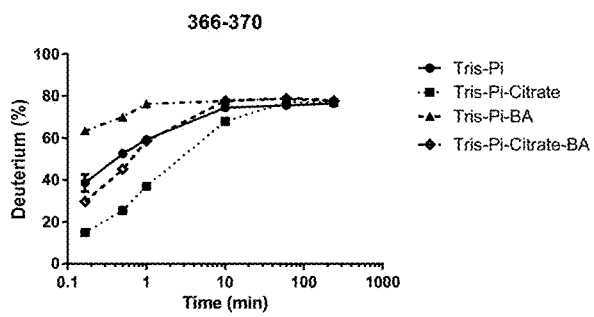

Further, the effects of citrate and benzyl alcohol for FAPa, AMG 330, AMG 596, and isolated CD3 binder itself were tested. The results for each examined construct show the similar effects. Here, it is shown that citrate and benzyl alcohol may have counteracting effects on the region of residues 366-370 (YISYW). FIGS. 6E and 6F show the individual effects of citrate and benzyl alcohol. For example, the addition of citrate (slide squares) to the formulation of Tris-phosphate (slide circles), reduces the conformational dynamics of this region. As a comparison, the addition of benzyl alcohol (slide triangles) to the formulation of Tris-phosphate, it increases the conformational dynamics of this region. FIGS. 6G and 6H show the counteracting effects of citrate and benzyl alcohol. The additions of both citrate and benzyl alcohol (empty diamonds), the conformational dynamics has been restored back to that in the formulation of Tris-phosphate (solid circles), indicating that citrate and benzyl alcohol counteract each other. Accordingly, citrate may serve as a complementing stabilizing agent to counteract destabilizing action of a preservative in case the bispecific antibody construct is higher than what the stabilizing effects (anti-dimerization effect) of the preservative such as benzyl alcohol can balance.

Example 7

This example is directed to the improvement of low-concentrated bispecific antibody construct such as BiTE® recovery from IV infusion bags. Low BiTE® concentration is typically necessary as a result of the high potency of BiTE® antibody constructs. During IV bag compatibility studies, EGFRvIII×CD3 bispecific antibody constructis diluted to very low concentrations into a 0.9% (v/v) saline solution for administration through continuous intravenous infusion. The lowest cohort dosing for FIH clinical studies, requires the protein concentration to be around 80 ng/mL. Analysis of EGFRvIII×CD3 bispecific antibody constructrecovery at this extremely low concentration required some ingenuity and adaptation of a fairly standard reversed phase chromatography method to maximize the signal from the protein.

An early study investigating recovery of EGFRvIII×CD3 bispecific antibody constructwith and without the addition of intravenous stabilizing solution IVSS comprising 25 mM citrate, 1.25 M lysine and 0.1% polysorbate at pH 7 led to the observation that under the same preparation protocols, the signal from the protein that was diluted in saline in the presence of IVSS was substantially higher than the signal from the protein that was diluted into saline in the absence of IVSS. A single IVSS concentration of 4% (v/v) was being utilized for this study.

Figure 7A:
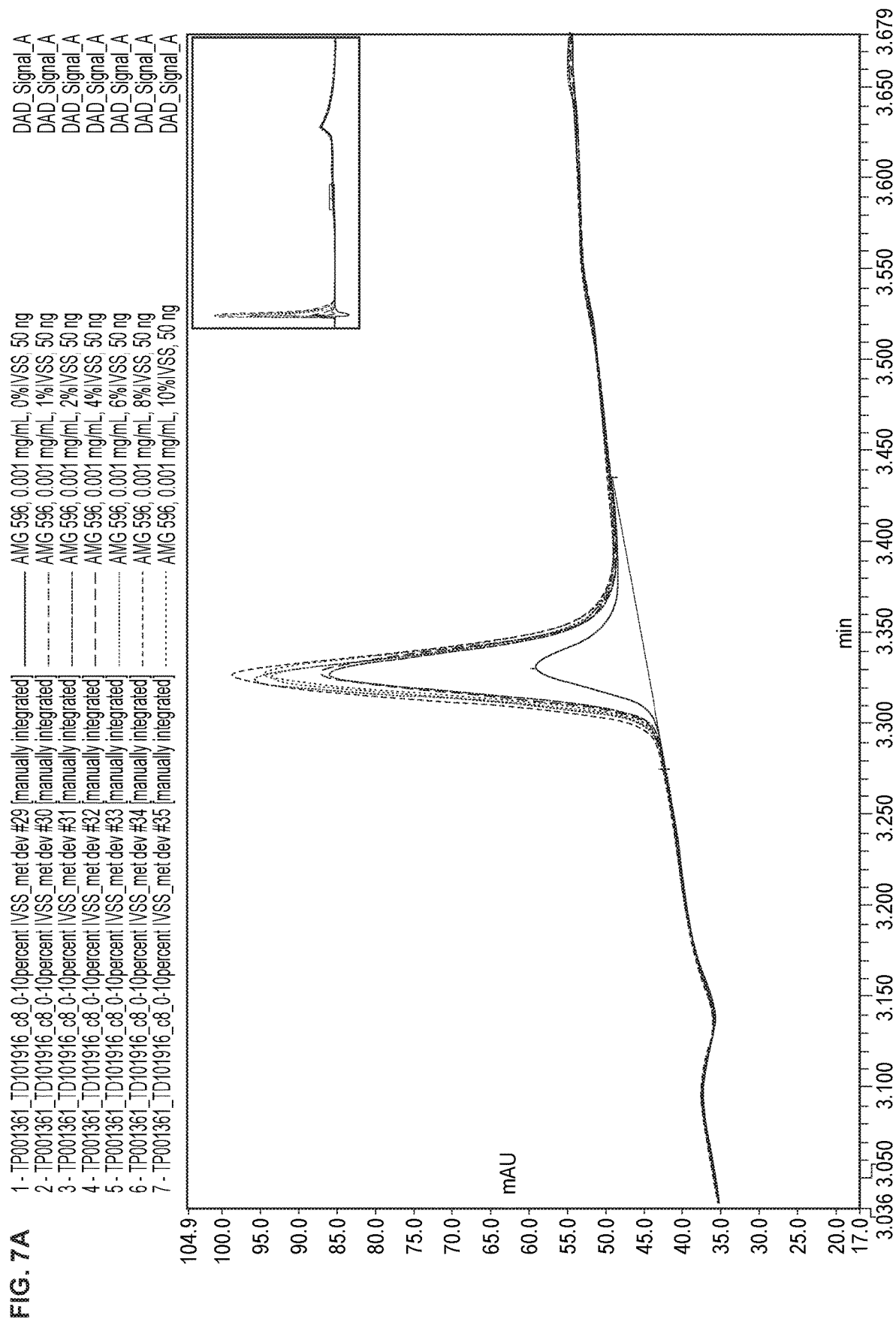
FIGS. 7A-7B: Reversed phase chromatogram after 50 µL injections of EGFRvIII×CD3 non-HLE bispecific antibody construct on a C8 column diluted to 1 µg/mL in 0 to 10% IVSS, respectively, in 0.9% saline (FIG. 7A). The peak area for each eluted EGFRvIII×CD3 non-HLE bispecific antibody construct sample is plotted as a function of the percentile IVSS concentration [% IVSS] included in the dilution solution (FIG. 7B).

To try and understand the discrepancy in signal a short study was designed to compare the protein peak area recorded upon elution from a C8 column using 215 nm absorbance as the recorded signal. The following protocol briefly describes the experiment performed. A stock of EGFRvIII×CD3 bispecific antibody construct with a concentration of 2 mg/mL was serially diluted 2000 fold to 1 μg/mL in Eppendorf tubes using 0.9% saline with either 0%, 1%, 2%, 4%, 6%, 8%, or 10% (v/v) IVSS as the diluent. The dilutions were performed on the same stock EGFRvIII×CD3 bispecific antibody construct aliquot using the following dilution scheme: 1:10→1:10→1:10→1:2. 50 μL of each EGFRvIII×CD3 bispecific antibody construct sample with nominal concentrations of 1 μg/mL were loaded onto a C8 column and eluted using reversed phase chromatography Chromatograms were recorded using 215 nm absorbance. The peak height and area was recorded for each sample for comparison. The raw data generated is presented below in FIG. 7A. The peak area for each EGFRvIII×CD3 bispecific antibody construct sample is plotted as a function of the % IVSS included in the dilution solution below in FIG. 2.

Figure 7B:
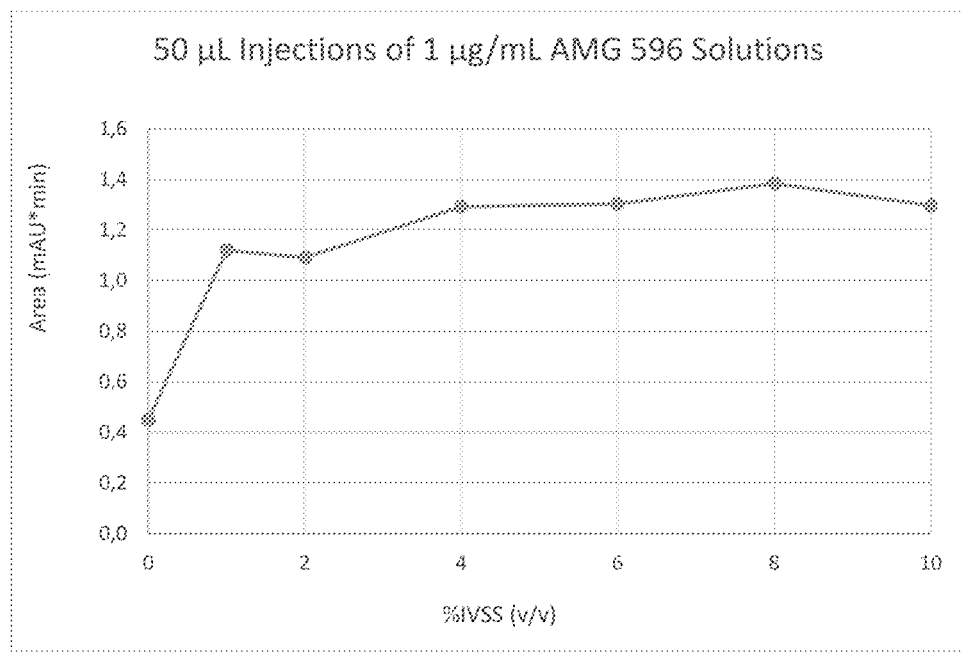
Figure 8A:
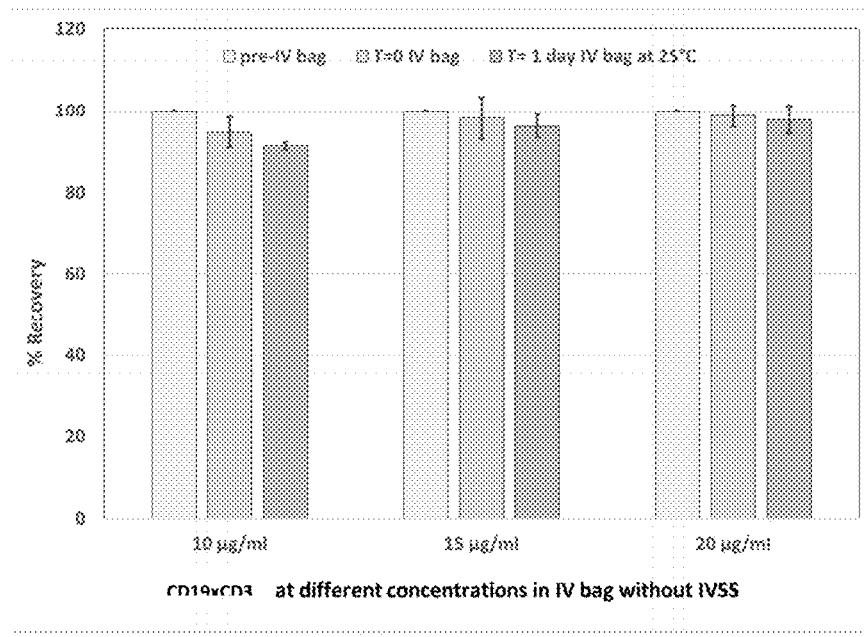
FIGS. 8A-8C: Impact and necessity of excipients with regard to percentile recovery are assessed. Observed over 24 hours at 25° C., no addition of a combination of citrate, lysine and polysorbate 80 (combination abbreviated herein as IVSS) is needed to ensure quantitative CD19×CD3 bispecific antibody construct recovery if the construct concentration is at least 15 µg/ml (FIG. 8A). The agent which facilitates quantitative recovery is polysorbate 80, while non-surfactant excipients are not needed for this effect (FIG. 8B). 0.002% polysorbate 80 ensure CD19×CD3 bispecific antibody construct recovery in IV bag even at very low concentrations of 1 and 0.05 µg/ml (FIG. 8C). 0.02% polysorbate 80 corresponds to the typical concentration in IVSS.
Figure 8B:
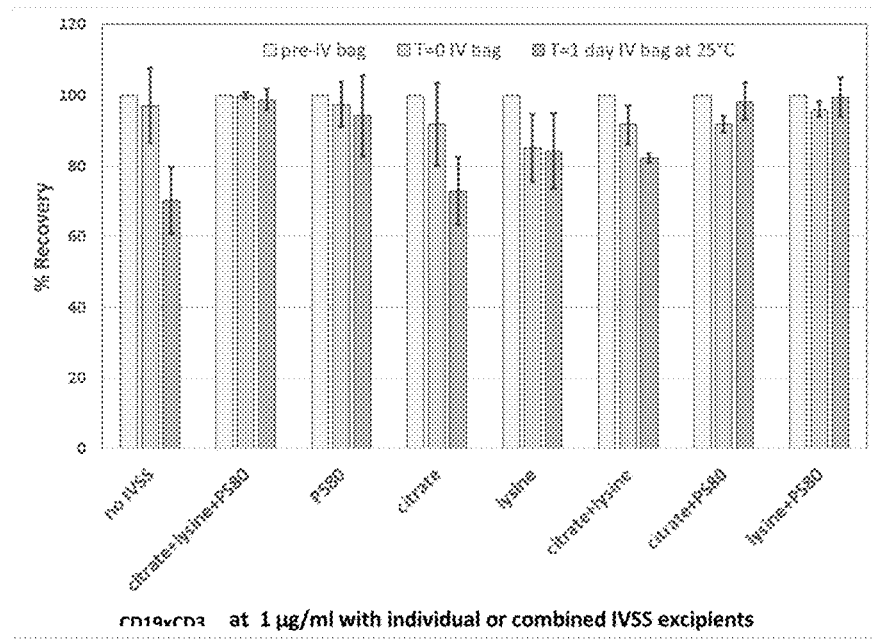
Figure 8C:
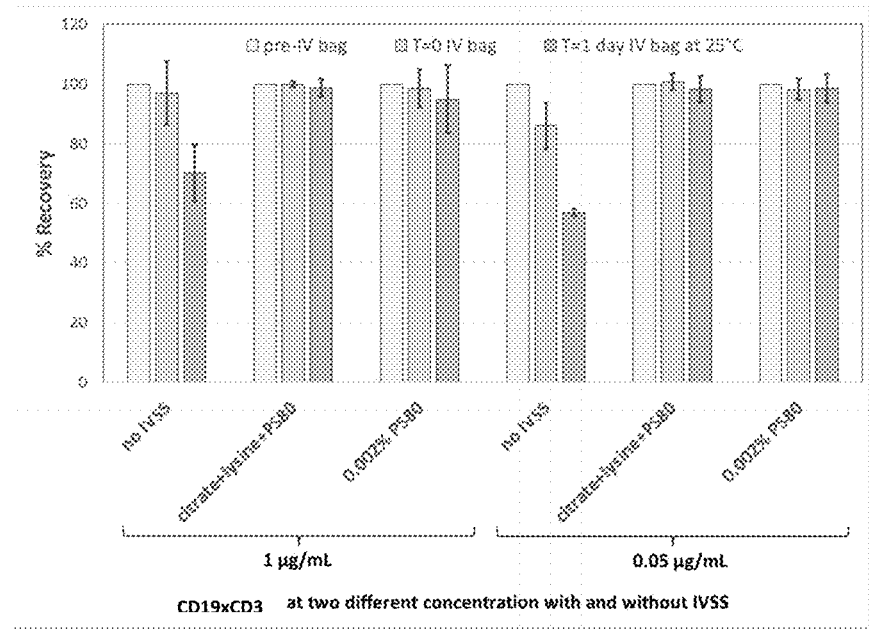
Figure 9:
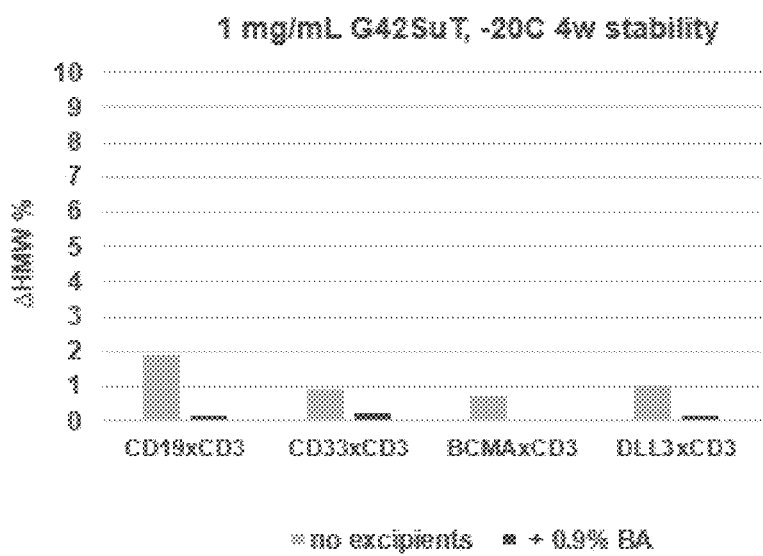
FIG. 9: Preservative benzyl alcohol improves frozen stability of pharmaceutical compositions comprising CD19×CD3, CD33×CD3, BCMA×CD3 and DLL3×CD3 bispecific antibody constructs comprising a third domain (HLE domain) at a concentration of 1 mg/ml at pH 4 as shown after storage over 4 weeks at −20° C.
Figure 10:
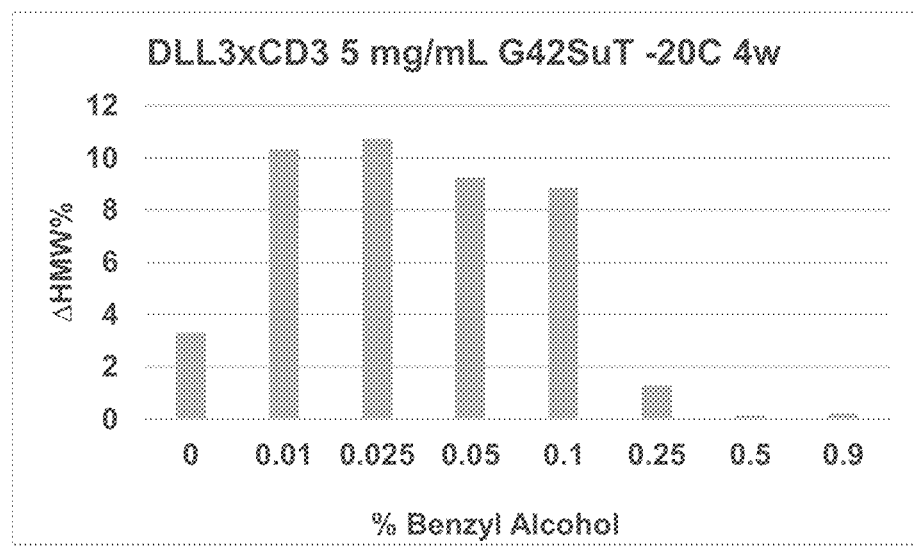
FIG. 10: Stabilizing effect by preservative benzyl alcohol with regard to frozen stability is best in a concentration above 0.1% and ensures a reduction in HMW species even at high concentrations of bispecific antibody construct of 5 mg/ml as exemplified with DLL3×CD3 at pH 4 after storage at −20° C. over 4 weeks.

From FIG. 7B, it is clear that the addition of 1% (v/v) IVSS to the saline diluent has a significant impact on the recovery of EGFRvIII×CD3 bispecific antibody construct, increasing EGFRvIII×CD3 bispecific antibody constructrecovery by approximately 250%. With the addition of between 4%-10% (v/v) IVSS to the saline diluent, the recovery of EGFRvIII×CD3 bispecific antibody constructis constant, as assessed by elution peak height and area, indicating full recovery of the molecule has been obtained at 4% (v/v) IVSS.

As the samples of EGFRvIII×CD3 bispecific antibody constructwere all prepared and analyzed under identical conditions, with the % IVSS in the saline diluent being the only variable between samples, it is logical to conclude that the amounts of protein loaded onto the column varied between the 0% IVSS, 1-2% IVSS, and 4-10% IVSS samples as a result of loss of protein; presumably through adsorption to surfaces the molecule came in contact with during processing. Conversely, the increased recovery of EGFRvIII×CD3 bispecific antibody construct in the presence of IVSS solution, is presumably a result of blocking EGFRvIII×CD3 bispecific antibody construct surface adsorption during processing. This understanding can be used in various drug product administration steps to ensure accurate delivery of the active drug product.

TABLE 5

| | | Sequence table | | | |
|---|---|---|---|---|---|
| 1 | CD19 VL CDR1 | artificial | aa | KASQSVDYDGDSYLN | |
| 2 | CD19 VL CDR2 | artificial | aa | DASNLVS | |
| 3 | CD19 VL CDR3 | artificial | aa | QQSTEDPWT | |
| 4 | CD19 VH CDR1 | artificial | aa | SYWMN | |

TABLE 5-continued

Sequence table

| 5 | CD19 VH CDR2 | artificial | aa | QIWPGDGDTNYNGKFKG |
|---|---|---|---|---|
| 6 | CD19 VH CDR3 | artificial | aa | RETTTVGRYYYAMDY |
| 7 | CD19 VL | artificial | aa | DIQLTQSPASLAVSLGQRATISCKASQSVDYDGDSYLNWY QQIPGQPPKWYDASNLVSGIPPRFSGSGSGTDFTLNIHP VEKVDAATYHCQQSTEDPWTFGGGTKLEIK |
| 8 | CD19 VH | artificial | aa | QVQLQQSGAELVRPGSSVKISCKASGYAFSSYWMNWVK QRPGQGLEWIGQIWPGDGDTNYNGKFKGKATLTADESS STAYMQLSSLASEDSAVYFCARRETTTVGRYYYAMDYWG QGTTVTVSS |
| 9 | CD3 VH CDR1 | artificial | aa | RYTMH |
| 10 | CD3 VH CDR2 | artificial | aa | YINPSRGYTNYNQKFKD |
| 11 | CD3 VH CDR3 | artificial | aa | YYDDHYCLDY |
| 12 | CD3 VL CDR1 | artificial | aa | RASSSVSYMN |
| 13 | CD3 VL CDR2 | artificial | aa | DTSKVAS |
| 14 | CD3 VL CDR3 | artificial | aa | QQWSSNPLT |
| 15 | CD3 VH | artificial | aa | DIKLQQSGAELARPGASVKMSCKTSGYTFTRYTMHWVK QRPGQGLEWIGYINPSRGYTNYNQKFKDKATLTTDKSSST AYMQLSSLTSEDSAVYYCARYYDDHYCLDYWGQGTTLTV SS |
| 16 | CD3 VL | artificial | aa | VDDIQLTQSPAIMSASPGEKVTMTCRASSSVSYMNWYQ QKSGTSPKRWIYDTSKVASGVPYRFSGSGSGTSYSLTISSM EAEDAATYYCQQWSSNPLTFGAGTKLELK |
| 17 | CD19xCD3 scFv BLINCYTO incl linker and his-tag | artificial | aa | DIQLTQSPASLAVSLGQRATISCKASQSVDYDGDSYLNWY QQIPGQPPKWYDASNLVSGIPPRFSGSGSGTDFTLNIHP VEKVDAATYHCQQSTEDPWTFGGGTKLEIKGGGGSGGGG SGGGGSQVQLQQSGAELVRPGSSVKISCKASGYAFSSY WMNWVKQRPGQGLEWIGQIWPGDGDTNYNGKFKGK ATLTADESSSTAYMQLSSLASEDSAVYFCARRETTTVGRYY YAMDYWGQGTTVTVSSGGGGSDIKLQQSGAELARPGAS VKMSCKTSGYTFTRYTMHWVKQRPGQGLEWIGYINPSR GYTNYNQKFKDKATLTTDKSSSTAYMQLSSLTSEDSAVYY CARYYDDHYCLDYWGQGTTLTVSSVEGGSGGSGGSGGS GGVDDIQLTQSPAIMSASPGEKVTMTCRASSSVSYMNW YQQKSGTSPKRWIYDTSKVASGVPYRFSGSGSGTSYSLTIS SMEAEDAATYYCQQWSSNPLTFGAGTKLELKHHHHHH |
| 18 | CDR-L1 I2C | artificial | aa | GSSTGAVTSGNYPN |
| 19 | CDR-L2 I2C | artificial | aa | GTKFLAP |
| 20 | CDR-L3 I2C | artificial | aa | VLWYSNRWV |
| 21 | CDR-H1 I2C | artificial | aa | KYAMN |
| 22 | CDR-H2 I2C | artificial | aa | RIRSKYNNYATYYADSVKD |
| 23 | CDR-H3 I2C | artificial | aa | HGNFGNSYISYWAY |
| 24 | VH I2C | artificial | aa | EVQLVESGGGLVQPGGSLKLSCAASGFTFNKYAMNWVR QAPGKGLEWVARIRSKYNNYATYYADSVKDRFTISRDDSK NTAYLQMNNLKTEDTAVYYCVRHGNFGNSYISYWAYW GQGTLVTVSS |
| 25 | VL I2C | artificial | aa | QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVL |

TABLE 5-continued

Sequence table

| 26 | VH-VL I2C | artificial | aa | EVQLVESGGGLVQPGGSLKLSCAASGFTFNKYAMNWVR QAPGKGLEWVARIRSKYNNYATYYADSVKDRFTISRDDSK NTAYLQMNNLKTEDTAVYYCVRHGNFGNSYISYWAYW GQGTLVTVSSGGGGSGGGGSGGGGSQTVVTQEPSLTVS PGGTVTLTCGSSTGAVTSGNYPNWVQQKPGQAPRGLIG GTKFLAPGTPARFSGSLLGGKAALTLSGVQPEDEAEYYCV LWYSNRWVFGGGTKLTVL |
| --- | --- | --- | --- | --- |
| 27 | CD33 ccVH E11 | artificial | aa | QVQLVQSGAEVKKPGESVKVSCKASGYTFTNYGMNWVK QAPGQCLEWMGWINTYTGEPTYADKFQGRVTMTTDTS TSTAYMEIRNLGGDDTAVYYCARWSWSDGYYVYFDYW GQGTSVTVSS |
| 28 | CD33 VH E11 | Artificial | aa | QVQLVQSGAEVKKPGESVKVSCKASGYTFTNYGMNWVK QAPGQGLEWMGWINTYTGEPTYADKFQGRVTMTTDTS TSTAYMEIRNLGGDDTAVYYCARWSWSDGYYVYFDYW GQGTSVTVSS |
| 29 | CD33 HCDR1 E11 | artificial | aa | NYGMN |
| 30 | CD33 HCDR2 E11 | artificial | aa | WINTYTGEPTYADKFQG |
| 31 | CD33 HCDR3 E11 | artificial | aa | WSWSDGYYVYFDY |
| 32 | CD33 CC VL E11 | artificial | aa | DIVMTQSPDSLTVSLGERTTINCKSSQSVLDSSTNKNSLA WYQQKPGQPPKLLLSWASTRESGIPDRFSGSGSGTDFTL TIDSPQPEDSATYYCQQSAHFPITFGCGTRLEIK |
| 33 | CD33 VL E11 | artificial | aa | DIVMTQSPDSLTVSLGERTTINCKSSQSVLDSSTNKNSLA WYQQKPGQPPKLLLSWASTRESGIPDRFSGSGSGTDFTL TIDSPQPEDSATYYCQQSAHFPITFGCGTRLEIK |
| 34 | CD33 LCDR1 E11 | artificial | aa | KSSQSVLDSSTNKNSLA |
| 35 | CD33 LCDR2 E11 | artificial | aa | WASTRES |
| 36 | CD33 LCDR3 E11 | artificial | aa | QQSAHFPIT |
| 37 | CD33 HL CC E11 | artificial | aa | QVQLVQSGAEVKKPGESVKVSCKASGYTFTNYGMNWVK QAPGQCLEWMGWINTYTGEPTYADKFQGRVTMTTDTS TSTAYMEIRNLGGDDTAVYYCARWSWSDGYYVYFDYW GQGTSVTVSSGGGGSGGGGSGGGGSDIVMTQSPDSLTV SLGERTTINCKSSQSVLDSSTNKNSLAWYQQKPGQPPKLL LSWASTRESGIPDRFSGSGSGTDFTLTIDSPQPEDSATYYC QQSAHFPITFGCGTRLEIK |
| 38 | CD33 HL E11 | artificial | aa | QVQLVQSGAEVKKPGESVKVSCKASGYTFTNYGMNWVK QAPGQGLEWMGWINTYTGEPTYADKFQGRVTMTTDTS TSTAYMEIRNLGGDDTAVYYCARWSWSDGYYVYFDYW GQGTSVTVSSGGGGSGGGGSGGGGSDIVMTQSPDSLTV SLGERTTINCKSSQSVLDSSTNKNSLAWYQQKPGQPPKLL LSWASTRESGIPDRFSGSGSGTDFTLTIDSPQPEDSATYYC QQSAHFPITFGCGTRLEIK |
| 39 | CD33 CC E11 HL x I2C HL Bispecific molecule | artificial | aa | QVQLVQSGAEVKKPGESVKVSCKASGYTFTNYGMNWVK QAPGQCLEWMGWINTYTGEPTYADKFQGRVTMTTDTS TSTAYMEIRNLGGDDTAVYYCARWSWSDGYYVYFDYW GQGTSVTVSSGGGGSGGGGSGGGGSDIVMTQSPDSLTV SLGERTTINCKSSQSVLDSSTNKNSLAWYQQKPGQPPKLL LSWASTRESGIPDRFSGSGSGTDFTLTIDSPQPEDSATYYC QQSAHFPITFGCGTRLEIKSGGGGSEVQLVESGGGLVQP GGSLKLSCAASGFTFNKYAMNWVRQAPGKGLEWVARIR SKYNNYATYYADSVKDRFTISRDDSKNTAYLQMNNLKTE DTAVYYCVRHGNFGNSYISYWAYWGQGTLVTVSSGGGG SGGGGSGGGGSQTVVTQEPSLTVSPGGTVTLTCGSSTGA VTSGNYPNWVQQKPGQAPRGLIGGTKFLAPGTPARFSG SLLGGKAALTLSGVQPEDEAEYYCVLWYSNRWVFGGGTK LTVL |
| 40 | CD33 E11 HL x I2C HL | artificial | aa | MGWSCIILFLVATATGVHSQVQLVQSGAEVKKPGESVKV SCKASGYTFTNYGMNWVKQAPGQGLEWMGWINTYTG EPTYADKFQGRVTMTTDTSTSTAYMEIRNLGGDDTAVYY |

TABLE 5-continued

Sequence table

| | | | | |
|---|---|---|---|---|
| | | | | CARWSWSDGYYVYFDYWGQGTSVTVSSGGGGSGGGG<br>SGGGGSDIVMTQSPDSLTVSLGERTTINCKSSQSVLDSST<br>NKNSLAWYQQKPGQPPKLLLSWASTRESGIPDRFSGSGS<br>GTDFTLTIDSPQPEDSATYYCQQSAHFPITFGQGTRLEIKS<br>GGGGSEVQLVESGGGLVQPGGSLKLSCAASGFTFNKYA<br>MNWVRQAPGKGLEWVARIRSKYNNYATYYADSVKDRFT<br>ISRDDSKNTAYLQMNNLKTEDTAVYYCVRHGNFGNSYIS<br>YWAYWGQGTLVTVSSGGGGSGGGGSGGGGSQTVVTQ<br>EPSLTVSPGGTVTLTCGSSTGAVTSGNYPNWVQQKPGQ<br>APRGLIGGTKFLAPGTPARFSGSLLGGKAALTLSGVQPED<br>EAEYYCVLWYSNRWVFGGGTKLTVLHHHHHH |
| 41 | CD33 CC x<br>I2C-scFc<br>Bispecific HLE<br>molecule | artificial | aa | QVQLVQSGAEVKKPGESVKVSCKASGYTFTNYGMNWVK<br>QAPGQCLEWMGWINTYTGEPTYADKFQGRVTMTTDTS<br>TSTAYMEIRNLGGDDTAVYYCARWSWSDGYYVYFDYW<br>GQGTSVTVSSGGGGSGGGGSGGGGSDIVMTQSPDSLTV<br>SLGERTTINCKSSQSVLDSSTNKNSLAWYQQKPGQPPKLL<br>LSWASTRESGIPDRFSGSGSGTDFTLTIDSPQPEDSATYYC<br>QQSAHFPITFGCGTRLEIKSGGGGSEVQLVESGGGLVQP<br>GGSLKLSCAASGFTFNKYAMNWVRQAPGKGLEWVARIR<br>SKYNNYATYYADSVKDRFTISRDDSKNTAYLQMNNLKTE<br>DTAVYYCVRHGNFGNSYISYWAYWGQGTLVTVSSGGGG<br>SGGGGSGGGGSQTVVTQEPSLTVSPGGTVTLTCGSSTGA<br>VTSGNYPNWVQQKPGQAPRGLIGGTKFLAPGTPARFSG<br>SLLGGKAALTLSGVQPEDEAEYYCVLWYSNRWVFGGGTK<br>LTVLGGGGDKTHTCPPCPAPELLGGPSVFLFPPKPKDTLM<br>ISRTPEVTCVVVDVSHEDPEVKFNWYVDGVEVHNAKTKP<br>CEEQYGSTYRCVSVLTVLHQDWLNGKEYKCKVSNKALPA<br>PIEKTISKAKGQPREPQVYTLPPSREEMTKNQVSLTCLVKG<br>FYPSDIAVEWESNGQPENNYKTTPPVLDSDGSFFLYSKLT<br>VDKSRWQQGNVFSCSVMHEALHNHYTQKSLSLSPGKGG<br>GGSGGGGSGGGGSGGGGSGGGGSGGGGSDKTHTCPP<br>CPAPELLGGPSVFLFPPKPKDTLMISRTPEVTCVVVDVSHE<br>DPEVKFNWYVDGVEVHNAKTKPCEEQYGSTYRCVSVLTV<br>LHQDWLNGKEYKCKVSNKALPAPIEKTISKAKGQPREPQ<br>VYTLPPSREEMTKNQVSLTCLVKGFYPSDIAVEWESNGQ<br>PENNYKTTPPVLDSDGSFFLYSKLTVDKSRWQQGNVFSC<br>SVMHEALHNHYTQKSLSLSPGK |
| 42 | EGFRvIIIxCD3-<br>scFc VH<br>CDR1 | artificial | aa | NYGMH |
| 43 | EGFRvIIIxCD3-<br>scFc VH<br>CDR2 | artificial | aa | VIWYDGSDKYYADSVRG |
| 44 | EGFRvIIIxCD3-<br>scFc VH<br>CDR3 | artificial | aa | DGYDILTGNPRDFDY |
| 45 | EGFRvIIIxCD3-<br>scFc VL CDR1 | artificial | aa | RSSQSLVHSDGNTYLS |
| 46 | EGFRvIIIxCD3-<br>scFc VL CDR2 | artificial | aa | RISRRFS |
| 47 | EGFRvIIIxCD3-<br>scFc VL CDR3 | artificial | aa | MQSTHVPRT |
| 48 | EGFRvIII_CCx<br>CD3-scFc VH | artificial | aa | QVQLVESGGGVVQSGRSLRLSCAASGFTFRNYGMHWVR<br>QAPGKCLEWVAVIWYDGSDKYYADSVRGRFTISRDNSKN<br>TLYLQMNSLRAEDTAVYYCARDGYDILTGNPRDFDYWG<br>QGTLVTVSS |
| 49 | EGFRvIII_CCx<br>CD3-scFc VL | artificial | aa | DTVMTQTPLSSHVTLGQPASISCRSSQSLVHSDGNTYLS<br>WLQQRPGQPPRLLIYRISRRFSGVPDRFSGSGAGTDFTLEI<br>SRVEAEDVGVYYCMQSTHVPRTFGCGTKVEIK |
| 50 | EGFRvIII_CCx<br>CD3-scFc scFv | artificial | aa | QVQLVESGGGVVQSGRSLRLSCAASGFTFRNYGMHWVR<br>QAPGKCLEWVAVIWYDGSDKYYADSVRGRFTISRDNSKN<br>TLYLQMNSLRAEDTAVYYCARDGYDILTGNPRDFDYWG<br>QGTLVTVSSGGGGSGGGGSGGGGSDTVMTQTPLSSHVT<br>LGQPASISCRSSQSLVHSDGNTYLSWLQQRPGQPPRLLIY<br>RISRRFSGVPDRFSGSGAGTDFTLEISRVEAEDVGVYYCM<br>QSTHVPRTFGCGTKVEIK |

TABLE 5-continued

Sequence table

| 51 | EGFRvIII_CCx CD3-scFc Bispecific molecule | artificial | aa | QVQLVESGGGVVQSGRSLRLSCAASGFTFRNYGMHWVR QAPGKCLEWVAVIWYDGSDKYYADSVRGRFTISRDNSKN TLYLQMNSLRAEDTAVYYCARDGYDILTGNPRDFDYWG QGTLVTVSSGGGGSGGGGSGGGGSDTVMTQTPLSSHVT LGQPASISCRSSQSLVHDGNTYLSWLQQRPGQPPRLLIY RISRRFSGVPDRFSGSGAGTDFTLEISRVEAEDVGVYYCM QSTHVPRTFGCGTKVEIKSGGGGSEVQLVESGGGLVQPG GSLKLSCAASGFTFNKYAMNWVRQAPGKGLEWVARIRS KYNNYATYYADSVKDRFTISRDDSKNTAYLQMNNLKTED TAVYYCVRHGNFGNSYISYWAYWGQGTLVTVSSGGGGS GGGGSGGGGSQTVVTQEPSLTVSPGGTVTLTCGSSTGAV TSGNYPNWVQQKPGQAPRGLIGGTKFLAPGTPARFSGSL LGGKAALTLSGVQPEDEAEYYCVLWYSNRWVFGGGTKLT VL |
| --- | --- | --- | --- | --- |
| 52 | EGFRvIII_CCx CD3-scFc Bispecific HLE molecule | artificial | aa | QVQLVESGGGVVQSGRSLRLSCAASGFTFRNYGMHWVR QAPGKCLEWVAVIWYDGSDKYYADSVRGRFTISRDNSKN TLYLQMNSLRAEDTAVYYCARDGYDILTGNPRDFDYWG QGTLVTVSSGGGGSGGGGSGGGGSDTVMTQTPLSSHVT LGQPASISCRSSQSLVHDGNTYLSWLQQRPGQPPRLLIY RISRRFSGVPDRFSGSGAGTDFTLEISRVEAEDVGVYYCM QSTHVPRTFGCGTKVEIKSGGGGSEVQLVESGGGLVQPG GSLKLSCAASGFTFNKYAMNWVRQAPGKGLEWVARIRS KYNNYATYYADSVKDRFTISRDDSKNTAYLQMNNLKTED TAVYYCVRHGNFGNSYISYWAYWGQGTLVTVSSGGGGS GGGGSGGGGSQTVVTQEPSLTVSPGGTVTLTCGSSTGAV TSGNYPNWVQQKPGQAPRGLIGGTKFLAPGTPARFSGSL LGGKAALTLSGVQPEDEAEYYCVLWYSNRWVFGGGTKLT VLGGGGDKTHTCPPCPAPELLGGPSVFLFPPKPKDTLMIS RTPEVTCVVVDVSHEDPEVKFNWYVDGVEVHNAKTKPC EEQYGSTYRCVSVLTVLHQDWLNGKEYKCKVSNKALPAPI EKTISKAKGQPREPQVYTLPPSREEMTKNQVSLTCLVKGF YPSDIAVEWESNGQPENNYKTTPPVLDSDGSFFLYSKLTV DKSRWQQGNVFSCSVMHEALHNHYTQKSLSLSPGKGG GGSGGGGSGGGGSGGGGSGGGGSGGGGSDKTHTCPP CPAPELLGGPSVFLFPPKPKDTLMISRTPEVTCVVVDVSHE DPEVKFNWYVDGVEVHNAKTKPCEEQYGSTYRCVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 53 | MSLN_5 VH CDR1 | artificial | aa | DYYMT |
| 54 | MSLN_5 VH CDR2 | artificial | aa | YISSSGSTIYYADSVKG |
| 55 | MSLN_5 VH CDR3 | artificial | aa | DRNSHFDY |
| 56 | MSLN_5 VL CDR1 | artificial | aa | RASQGINTWLA |
| 57 | MSLN_5 VL CDR2 | artificial | aa | GASGLQS |
| 58 | MSLN_5 VL CDR3 | artificial | aa | QQAKSFPRT |
| 59 | MSLN_5 VH | artificial | aa | QVQLVESGGGLVKPGGSLRLSCAASGFTFSDYYMTWIRQ APGKGLEWLSYISSSGSTIYYADSVKGRFTISRDNAKNSLFL QMNSLRAEDTAVYYCARDRNSHFDYWGQGTLVTVSS |
| 60 | MSLN_5 VL | artificial | aa | DIQMTQSPSSVSASVGDRVTITCRASQGINTWLAWYQQ KPGKAPKLLIYGASGLQSGVPSRFSGSGSGTDFTLTISSLQP EDFATYYCQQAKSFPRTFGQGTKVEIK |
| 61 | MSLN_5 scFv | artificial | aa | QVQLVESGGGLVKPGGSLRLSCAASGFTFSDYYMTWIRQ APGKGLEWLSYISSSGSTIYYADSVKGRFTISRDNAKNSLFL QMNSLRAEDTAVYYCARDRNSHFDYWGQGTLVTVSSG GGGSGGGGSGGGGSDIQMTQSPSSVSASVGDRVTITCR ASQGINTWLAWYQQKPGKAPKLLIYGASGLQSGVPSRFS GSGSGTDFTLTISSLQPEDFATYYCQQAKSFPRTFGQGTK VEIK |

TABLE 5-continued

Sequence table

| 62 | MSLN_5xI2C0 bispecific molecule | artificial | aa | QVQLVESGGGLVKPGGSLRLSCAASGFTFSDYYMTWIRQ APGKGLEWLSYISSSGSTIYYADSVKGRFTISRDNAKNSLFL QMNSLRAEDTAVYYCARDRNSHFDYWGQGTLVTVSSG GGGSGGGGSGGGGSDIQMTQSPSSVSASVGDRVTITCR ASQGINTWLAWYQQKPGKAPKLLIYGASGLQSGVPSRFS GSGSGTDFTLTISSLQPEDFATYYCQQAKSFPRTFGQGTK VEIKSGGGGSEVQLVESGGGLVQPGGSLKLSCAASGFTFN KYAMNWVRQAPGKGLEWVARIRSKYNNYATYYADSVK DRFTISRDDSKNTAYLQMNNLKTEDTAVYYCVRHGNFGN SYISYWAYWGQGTLVTVSSGGGGSGGGGSGGGGSQTV VTQEPSLTVSPGGTVTLTCGSSTGAVTSGNYPNWVQQKP GQAPRGLIGGTKFLAPGTPARFSGSLLGGKAALTLSGVQP EDEAEYYCVLWYSNRWVFGGGTKLTVL |
| 63 | MSLN_5xCD3-scFc Bispecific HLE molecule | artificial | aa | QVQLVESGGGLVKPGGSLRLSCAASGFTFSDYYMTWIRQ APGKGLEWLSYISSSGSTIYYADSVKGRFTISRDNAKNSLFL QMNSLRAEDTAVYYCARDRNSHFDYWGQGTLVTVSSG GGGSGGGGSGGGGSDIQMTQSPSSVSASVGDRVTITCR ASQGINTWLAWYQQKPGKAPKLLIYGASGLQSGVPSRFS GSGSGTDFTLTISSLQPEDFATYYCQQAKSFPRTFGQGTK VEIKSGGGGSEVQLVESGGGLVQPGGSLKLSCAASGFTFN KYAMNWVRQAPGKGLEWVARIRSKYNNYATYYADSVK DRFTISRDDSKNTAYLQMNNLKTEDTAVYYCVRHGNFGN SYISYWAYWGQGTLVTVSSGGGGSGGGGSGGGGSQTV VTQEPSLTVSPGGTVTLTCGSSTGAVTSGNYPNWVQQKP GQAPRGLIGGTKFLAPGTPARFSGSLLGGKAALTLSGVQP EDEAEYYCVLWYSNRWVFGGGTKLTVLGGGGDKTHTCP PCPAPELLGGPSVFLFPPKPKDTLMISRTPEVTCVVVDVSH EDPEVKFNWYVDGVEVHNAKTKPCEEQYGSTYRCVSVLT VLHQDWLNGKEYKCKVSNKALPAPIEKTISKAKGQPREP QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSLSPGKGGGGSGGGGSGGGGS GGGGSGGGGSGGGGSDKTHTCPPCPAPELLGGPSVFLFP PKPKDTLMISRTPEVTCVVVDVSHEDPEVKFNWYVDGVE VHNAKTKPCEEQYGSTYRCVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSL SLSPGK |
| 64 | MSLN_5_CCx CD3-scFc Bispecific HLE molecule | artificial | aa | QVQLVESGGGLVKPGGSLRLSCAASGFTFSDHYMSWIRQ APGKCLEWFSYISSSGGIIYYADSVKGRFTISRDNAKNSLYL QMNSLRAEDTAVYYCARDVGSHFDYWGQGTLVTVSSG GGGSGGGGSGGGGSDIQMTQSPSSVSASVGDRVTITCR ASQDISRWLAWYQQKPGKAPKLLISAASRLQSGVPSRFS GSGSGTDFTLTISSLQPEDFAIYYCQQAKSFPRTFGCGTKV EIKSGGGGSEVQLVESGGGLVQPGGSLKLSCAASGFTFNK YAMNWVRQAPGKGLEWVARIRSKYNNYATYYADSVKD RFTISRDDSKNTAYLQMNNLKTEDTAVYYCVRHGNFGNS YISYWAYWGQGTLVTVSSGGGGSGGGGSGGGGSQTVV TQEPSLTVSPGGTVTLTCGSSTGAVTSGNYPNWVQQKP GQAPRGLIGGTKFLAPGTPARFSGSLLGGKAALTLSGVQP EDEAEYYCVLWYSNRWVFGGGTKLTVLGGGGDKTHTCP PCPAPELLGGPSVFLFPPKPKDTLMISRTPEVTCVVVDVSH EDPEVKFNWYVDGVEVHNAKTKPCEEQYGSTYRCVSVLT VLHQDWLNGKEYKCKVSNKALPAPIEKTISKAKGQPREP QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSLSPGKGGGGSGGGGSGGGGS GGGGSGGGGSGGGGSDKTHTCPPCPAPELLGGPSVFLFP PKPKDTLMISRTPEVTCVVVDVSHEDPEVKFNWYVDGVE VHNAKTKPCEEQYGSTYRCVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSL SLSPGK |
| 65 | CDR-H1 CDH19 65254.007 | artificial | aa | SYGMH |
| 66 | CDR-H2 CDH19 65254.007 | artificial | aa | FIWYEGSNKYYAESVKD |

TABLE 5-continued

Sequence table

| 67 | CDR-H3 CDH19 65254.007 | artificial | aa | RAGIIGTIGYYYGMDV |
|---|---|---|---|---|
| 68 | CDR-L1 CDH19 65254.007 | artificial | aa | SGDRLGEKYTS |
| 69 | CDR-L2 CDH19 65254.007 | artificial | aa | QDTKRPS |
| 70 | CDR-L3 CDH19 65254.007 | artificial | aa | QAWESSTVV |
| 71 | VH CDH19 65254.007 | artificial | aa | QVQLVESGGGVVQPGGSLRLSCAASGFTFSSYGMHWVR QAPGKGLEWVAFIWYEGSNKYYAESVKDRFTISRDNSKN TLYLQMNSLRAEDTAVYYCARRAGIIGTIGYYYGMDVWG QGTTVTVSS |
| 72 | VL CDH19 65254.007 | artificial | aa | SYELTQPPSVSVSPGQTASITCSGDRLGEKYTSWYQQRPG QSPLLVIYQDTKRPSGIPERFSGSNSGNTATLTISGTQAMD EADYYCQAWESSTVVFGGGTKLTVLS |
| 73 | VH-VL CDH19 65254.007 | artificial | aa | QVQLVESGGGVVQPGGSLRLSCAASGFTFSSYGMHWVR QAPGKGLEWVAFIWYEGSNKYYAESVKDRFTISRDNSKN TLYLQMNSLRAEDTAVYYCARRAGIIGTIGYYYGMDVWG QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGGGTKLTVLS |
| 74 | CDH19 65254.007 x I2C | artificial | aa | QVQLVESGGGVVQPGGSLRLSCAASGFTFSSYGMHWVR QAPGKGLEWVAFIWYEGSNKYYAESVKDRFTISRDNSKN TLYLQMNSLRAEDTAVYYCARRAGIIGTIGYYYGMDVWG QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGGGTKLTVLSGGGGSEVQLVESGGGLVQPGGSLKL SCAASGFTFNKYAMNWVRQAPGKGLEWVARIRSKYNNY ATYYADSVKDRFTISRDDSKNTAYLQMNNLKTEDTAVYYC VRHGNFGNSYISYWAYWGQGTLVTVSSGGGGSGGGGS GGGGSQTVVTQEPSLTVSPGGTVTLTCGSSTGAVTSGNY PNWVQQKPGQAPRGLIGGTKFLAPGTPARFSGSLLGGKA ALTLSGVQPEDEAEYYCVLWYSNRWVFGGGTKLTVLHH HHHH |
| 75 | CDH19 65254.007 x I2C-scFc Bispecific HLE molecule | artificial | aa | QVQLVESGGGVVQPGGSLRLSCAASGFTFSSYGMHWVR QAPGKGLEWVAFIWYEGSNKYYAESVKDRFTISRDNSKN TLYLQMNSLRAEDTAVYYCARRAGIIGTIGYYYGMDVWG QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGGGTKLTVLSGGGGSEVQLVESGGGLVQPGGSLKL SCAASGFTFNKYAMNWVRQAPGKGLEWVARIRSKYNNY ATYYADSVKDRFTISRDDSKNTAYLQMNNLKTEDTAVYYC VRHGNFGNSYISYWAYWGQGTLVTVSSGGGGSGGGGS GGGGSQTVVTQEPSLTVSPGGTVTLTCGSSTGAVTSGNY PNWVQQKPGQAPRGLIGGTKFLAPGTPARFSGSLLGGKA ALTLSGVQPEDEAEYYCVLWYSNRWVFGGGTKLTVLGG GGDKTHTCPPCPAPELLGGPSVFLFPPKPKDTLMISRTPEV TCVVVDVSHEDPEVKFNWYVDGVEVHNAKTKPCEEQYG STYRCVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGKGGGGSGGG GSGGGGSGGGGSGGGGSDKTHTCPPCPAPELLG GPSVFLFPPKPKDTLMISRTPEVTCVVVDVSHEDPEVKFN WYVDGVEVHNAKTKPCEEQYGSTYRCVSVLTVLHQDWL NGKEYKCKVSNKALPAPIEKTISKAKGQPREPQVYTLPPSR EEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 76 | CDH19 65254.007 x I2C- | artificial | aa | QVQLVESGGGVVQPGGSLRLSCAASGFTFSSYGMHWVR QAPGKGLEWVAFIWYEGSNKYYAESVKDRFTISRDNSKN TLYLQMNSLRAEDTAVYYCARRAGIIGTIGYYYGMDVWG |

TABLE 5-continued

Sequence table

| | | | | |
|---|---|---|---|---|
| | scFc_delGK Bispecific HLE molecule | | | QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGGGTKLTVLSGGGGSEVQLVESGGGLVQPGGSLKL SCAASGFTFNKYAMNWVRQAPGKGLEWVARIRSKYNNY ATYYADSVKDRFTISRDDSKNTAYLQMNNLKTEDTAVYYC VRHGNFGNSYISYWAYWGQGTLVTVSSGGGGSGGGGS GGGGSQTVVTQEPSLTVSPGGTVTLTCGSSTGAVTSGNY PNWVQQKPGQAPRGLIGGTKFLAPGTPARFSGSLLGGKA ALTLSGVQPEDEAEYYCVLWYSNRWVFGGGTKLTVLGG GGDKTHTCPPCPAPELLGGPSVFLFPPKPKDTLMISRTPEV TCVVVDVSHEDPEVKFNWYVDGVEVHNAKTKPCEEQYG STYRCVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGGGGSGGGGS GGGGSGGGGSGGGGSGGGGSDKTHTCPPCPAPELLGG PSVFLFPPKPKDTLMISRTPEVTCVVVDVSHEDPEVKFNW YVDGVEVHNAKTKPCEEQYGSTYRCVSVLTVLHQDWLN GKEYKCKVSNKALPAPIEKTISKAKGQPREPQVYTLPPSRE EMTKNQVSLTCLVKGFYPSDIAVEWESNGQPENNYKTTP PVLDSDGSFFLYSKLTVDKSRWQQGNVFSCSVMHEALH NHYTQKSLSLSPGK |
| 77 | CDH19 65254.007_CC x I2C-scFc VH | artificial | aa | QVQLVESGGGVVQPGGSLRLSCAASGFTFSSYGMHWVR QAPGKCLEWVAFIWYEGSNKYYAESVKDRFTISRDNSKN TLYLQMNSLRAEDTAVYYCARRAGIIGTIGYYYGMDVWG QGTTVTVSS |
| 78 | CDH19 65254.007_CC x I2C-scFc VL | artificial | aa | SYELTQPPSVSVSPGQTASITCSGDRLGEKYTSWYQQRPG QSPLLVIYQDTKRPSGIPERFSGSNSGNTATLTISGTQAMD EADYYCQAWESSTVVFGCGTKLTVL |
| 79 | CDH19 65254.007_CC x I2C-scFc scFv | artificial | aa | QVQLVESGGGVVQPGGSLRLSCAASGFTFSSYGMHWVR QAPGKCLEWVAFIWYEGSNKYYAESVKDRFTISRDNSKN TLYLQMNSLRAEDTAVYYCARRAGIIGTIGYYYGMDVWG QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGCGTKLTVL |
| 80 | CDH19 65254.007_CC x I2C-scFc Bispecific molecule | artificial | aa | QVQLVESGGGVVQPGGSLRLSCAASGFTFSSYGMHWVR QAPGKCLEWVAFIWYEGSNKYYAESVKDRFTISRDNSKN TLYLQMNSLRAEDTAVYYCARRAGIIGTIGYYYGMDVWG QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGCGTKLTVLSGGGGSEVQLVESGGGLVQPGGSLKL SCAASGFTFNKYAMNWVRQAPGKGLEWVARIRSKYNNY ATYYADSVKDRFTISRDDSKNTAYLQMNNLKTEDTAVYYC VRHGNFGNSYISYWAYWGQGTLVTVSSGGGGSGGGGS GGGGSQTVVTQEPSLTVSPGGTVTLTCGSSTGAVTSGNY PNWVQQKPGQAPRGLIGGTKFLAPGTPARFSGSLLGGKA ALTLSGVQPEDEAEYYCVLWYSNRWVFGGGTKLTVL |
| 81 | CDH19 65254.007_CC x I2C-scFc Bispecific HLE molecule | artificial | aa | QVQLVESGGGVVQPGGSLRLSCAASGFTFSSYGMHWVR QAPGKCLEWVAFIWYEGSNKYYAESVKDRFTISRDNSKN TLYLQMNSLRAEDTAVYYCARRAGIIGTIGYYYGMDVWG QGTTVTVSSGGGGSGGGGSGGGGSSYELTQPPSVSVSP GQTASITCSGDRLGEKYTSWYQQRPGQSPLLVIYQDTKRP SGIPERFSGSNSGNTATLTISGTQAMDEADYYCQAWESS TVVFGCGTKLTVLSGGGGSEVQLVESGGGLVQPGGSLKL SCAASGFTFNKYAMNWVRQAPGKGLEWVARIRSKYNNY ATYYADSVKDRFTISRDDSKNTAYLQMNNLKTEDTAVYYC VRHGNFGNSYISYWAYWGQGTLVTVSSGGGGSGGGGS GGGGSQTVVTQEPSLTVSPGGTVTLTCGSSTGAVTSGNY PNWVQQKPGQAPRGLIGGTKFLAPGTPARFSGSLLGGKA ALTLSGVQPEDEAEYYCVLWYSNRWVFGGGTKLTVLGG GGDKTHTCPPCPAPELLGGPSVFLFPPKPKDTLMISRTPEV TCVVVDVSHEDPEVKFNWYVDGVEVHNAKTKPCEEQYG STYRCVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGKGGGGSGGG GSGGGGSGGGGSGGGGSDKTHTCPPCPAPELLG GPSVFLFPPKPKDTLMISRTPEVTCVVVDVSHEDPEVKFN WYVDGVEVHNAKTKPCEEQYGSTYRCVSVLTVLHQDWL |

TABLE 5-continued

Sequence table

| | | | | |
|---|---|---|---|---|
| | | | | NGKEYKCKVSNKALPAPIEKTISKAKGQPREPQVYTLPPSR<br>EEMTKNQVSLTCLVKGFYPSDIAVEWESNGQPENNYKTT<br>PPVLDSDGSFFLYSKLTVDKSRWQQGNVFSCSVMHEALH<br>NHYTQKSLSLSPGK |
| 82 | CDH19<br>65254.007_CC<br>x I2C-<br>scFc_delGK<br>Bispecific HLE<br>molecule | artificial | aa | QVQLVESGGGVVQPGGSLRLSCAASGFTFSSYGMHWVR<br>QAPGKCLEWVAFIWYEGSNKYYAESVKDRFTISRDNSKN<br>TLYLQMNSLRAEDTAVYYCARRAGIIGTIGYYYGMDVWG<br>QGTTVTVSSGGGGSGGGGSGGGGSSYELTQPPSVSVSP<br>GQTASITCSGDRLGEKYTSWYQQRPGQSPLLVIYQDTKRP<br>SGIPERFSGSNSGNTATLTISGTQAMDEADYYCQAWESS<br>TVVFGCGTKLTVLSGGGGSEVQLVESGGGLVQPGGSLKL<br>SCAASGFTFNKYAMNWVRQAPGKGLEWVARIRSKYNNY<br>ATYYADSVKDRFTISRDDSKNTAYLQMNNLKTEDTAVYYC<br>VRHGNFGNSYISYWAYWGQGTLVTVSSGGGGSGGGGS<br>GGGGSQTVVTQEPSLTVSPGGTVTLTCGSSTGAVTSGNY<br>PNWVQQKPGQAPRGLIGGTKFLAPGTPARFSGSLLGGKA<br>ALTLSGVQPEDEAEYYCVLWYSNRWVFGGGTKLTVLGG<br>GGDKTHTCPPCPAPELLGGPSVFLFPPKPKDTLMISRTPEV<br>TCVVVDVSHEDPEVKFNWYVDGVEVHNAKTKPCEEQYG<br>STYRCVSVLTVLHQDWLNGKEYKCKVSNKALPAPIEKTISK<br>AKGQPREPQVYTLPPSREEMTKNQVSLTCLVKGFYPSDIA<br>VEWESNGQPENNYKTTPPVLDSDGSFFLYSKLTVDKSRW<br>QQGNVFSCSVMHEALHNHYTQKSLSLSPGGGGSGGGGS<br>GGGGSGGGGSGGGGSGGGGSDKTHTCPPCPAPELLGG<br>PSVFLFPPKPKDTLMISRTPEVTCVVVDVSHEDPEVKFNW<br>YVDGVEVHNAKTKPCEEQYGSTYRCVSVLTVLHQDWLN<br>GKEYKCKVSNKALPAPIEKTISKAKGQPREPQVYTLPPSRE<br>EMTKNQVSLTCLVKGFYPSDIAVEWESNGQPENNYKTTP<br>PVLDSDGSFFLYSKLTVDKSRWQQGNVFSCSVMHEALH<br>NHYTQKSLSLSPGK |
| 83 | FLT3_7<br>A8xCD3-scFc<br>VH CDR1 | artificial | aa | NARMGVS |
| 84 | FLT3_7<br>A8xCD3-scFc<br>VH CDR2 | artificial | aa | HIFSNDEKSYSTSLKN |
| 85 | FLT3_7<br>A8xCD3-scFc<br>VH CDR3 | artificial | aa | IVGYGSGWYGFFDY |
| 86 | FLT3_7<br>A8xCD3-scFc<br>VL CDR1 | artificial | aa | RASQGIRNDLG |
| 87 | FLT3_7<br>A8xCD3-scFc<br>VL CDR2 | artificial | aa | AASTLQS |
| 88 | FLT3_7<br>A8xCD3-scFc<br>VL CDR3 | artificial | aa | LQHNSYPLT |
| 89 | FLT3_7<br>A8xCD3-scFc<br>VH | artificial | aa | QVTLKESGPTLVKPTETLTLTCTLSGFSLNNARMGVSWIR<br>QPPGKCLEWLAHIFSNDEKSYSTSLKNRLTISKDSSKTQVV<br>LTMTNVDPVDTATYYCARIVGYGSGWYGFFDYWGQGTL<br>VTVSS |
| 90 | FLT3_A8-<br>scFc VL | artificial | aa | DIQMTQSPSSLSASVGDRVTITCRASQGIRNDLGWYQQK<br>PGKAPKRLIYAASTLQSGVPSRFSGSGSGTEFTLTISSLQPE<br>DFATYYCLQHNSYPLTFGCGTKVEIK |
| 91 | FLT3_7<br>A8xCD3-scFv | artificial | aa | QVTLKESGPTLVKPTETLTLTCTLSGFSLNNARMGVSWIR<br>QPPGKCLEWLAHIFSNDEKSYSTSLKNRLTISKDSSKTQVV<br>LTMTNVDPVDTATYYCARIVGYGSGWYGFFDYWGQGTL<br>VTVSSGGGGSGGGGSGGGGSDIQMTQSPSSLSASVGDR<br>VTITCRASQGIRNDLGWYQQKPGKAPKRLIYAASTLQSGV<br>PSRFSGSGSGTEFTLTISSLQPEDFATYYCLQHNSYPLTFGC<br>GTKVEIK |
| 92 | FLT3_7<br>A8xCD3<br>Bispecific<br>molecule | artificial | aa | QVTLKESGPTLVKPTETLTLTCTLSGFSLNNARMGVSWIR<br>QPPGKCLEWLAHIFSNDEKSYSTSLKNRLTISKDSSKTQVV<br>LTMTNVDPVDTATYYCARIVGYGSGWYGFFDYWGQGTL<br>VTVSSGGGGSGGGGSGGGGSDIQMTQSPSSLSASVGDR<br>VTITCRASQGIRNDLGWYQQKPGKAPKRLIYAASTLQSGV |

TABLE 5-continued

Sequence table

|  |  |  |  |  |
|---|---|---|---|---|
|  |  |  |  | PSRFSGSGSGTEFTLTISSLQPEDFATYYCLQHNSYPLTFGC GTKVEIKSGGGGSEVQLVESGGGLVQPGGSLKLSCAASGF TFNKYAMNWVRQAPGKGLEWVARIRSKYNNYATYYADS VKDRFTISRDDSKNTAYLQMNNLKTEDTAVYYCVRHGNF GNSYISYWAYWGQGTLVTVSSGGGGSGGGGSGGGGSQ TVVTQEPSLTVSPGGTVTLTCGSSTGAVTSGNYPNWVQQ KPGQAPRGLIGGTKFLAPGTPARFSGSLLGGKAALTLSGV QPEDEAEYYCVLWYSNRWVFGGGTKLTVL |
| 93 | FLT3_7 A8xCD3-scFc Bispecific HLE molecule | artificial | aa | QVTLKESGPTLVKPTETLTLTCTLSGFSLNNARMGVSWIR QPPGKCLEWLAHIFSNDEKSYSTSLKNRLTISKDSSKTQVV LTMTNVDPVDTATYYCARIVGYGSGWYGFFDYWGQGTL VTVSSGGGGSGGGGSGGGGSDIQMTQSPSSLSASVGDR VTITCRASQGIRNDLGWYQQKPGKAPKRLIYAASTLQSGV PSRFSGSGSGTEFTLTISSLQPEDFATYYCLQHNSYPLTFGC GTKVEIKSGGGGSEVQLVESGGGLVQPGGSLKLSCAASGF TFNKYAMNWVRQAPGKGLEWVARIRSKYNNYATYYADS VKDRFTISRDDSKNTAYLQMNNLKTEDTAVYYCVRHGNF GNSYISYWAYWGQGTLVTVSSGGGGSGGGGSGGGGSQ TVVTQEPSLTVSPGGTVTLTCGSSTGAVTSGNYPNWVQQ KPGQAPRGLIGGTKFLAPGTPARFSGSLLGGKAALTLSGV QPEDEAEYYCVLWYSNRWVFGGGTKLTVLGGGGDKTHT CPPCPAPELLGGPSVFLFPPKPKDTLMISRTPEVTCVVVDV SHEDPEVKFNWYVDGVEVHNAKTKPCEEQYGSTYRCVS VLTVLHQDWLNGKEYKCKVSNKALPAPIEKTISKAKGQPR EPQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGKGGGGSGGGGSGGGG SGGGGSGGGGSGGGGSDKTHTCPPCPAPELLGGPSVFLF PPKPKDTLMISRTPEVTCVVVDVSHEDPEVKFNWYVDGV EVHNAKTKPCEEQYGSTYRCVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDS DGSFFLYSKLTVDKSRWQQGNVFSCSVMHEALHNHYTQ KSLSLSPGK |
| 94 | VH CDR1 DLL3_1_CC_ delGK | artificial | aa | SYYWS |
| 95 | VH CDR2 DLL3_1_CC_ delGK | artificial | aa | YVYYSGTTNYNPSLKS |
| 96 | VH CDR3 DLL3_1_CC_ delGK | artificial | aa | IAVTGFYFDY |
| 97 | VL CDR1 DLL3_1_CC_ delGK | artificial | aa | RASQRVNNNYLA |
| 98 | VL CDR2 DLL3_1_CC_ delGK | artificial | aa | GASSRAT |
| 99 | VL CDR3 DLL3_1_CC_ delGK | artificial | aa | QQYDRSPLT |
| 100 | VH DLL3_1_CC_ delGK | artificial | aa | QVQLQESGPGLVKPSETLSLTCTVSGGSISSYYWSWIRQP PGKCLEWIGYVYYSGTTNYNPSLKSRVTISVDTSKNQFSLK LSSVTAADTAVYYCASIAVTGFYFDYWGQGTLVTVSS |
| 101 | VL DLL3_1_CC_ delGK | artificial | aa | EIVLTQSPGTLSLSPGERVTLSCRASQRVNNNYLAWYQQR PGQAPRLLIYGASSRATGIPDRFSGSGSGTDFTLTISRLEPE DFAVYYCQQYDRSPLTFGCGTKLEIK |
| 102 | DLL3_1_CC_ delGK | artificial | aa | QVQLQESGPGLVKPSETLSLTCTVSGGSISSYYWSWIRQP PGKCLEWIGYVYYSGTTNYNPSLKSRVTISVDTSKNQFSLK LSSVTAADTAVYYCASIAVTGFYFDYWGQGTLVTVSSGG GGSGGGGSGGGGSEIVLTQSPGTLSLSPGERVTLSCRASQ RVNNNYLAWYQQRPGQAPRLLIYGASSRATGIPDRFSGS GSGTDFTLTISRLEPEDFAVYYCQQYDRSPLTFGCGTKLEIK |

TABLE 5-continued

Sequence table

| | | | | |
|---|---|---|---|---|
| 103 | DLL3_1_CCxCD3_ delGK Bispecific molecule | artificial | aa | QVQLQESGPGLVKPSETLSLTCTVSGGSISSYYWSWIRQP PGKCLEWIGYVYYSGTTNYNPSLKSRVTISVDTSKNQFSLK LSSVTAADTAVYYCASIAVTGFYFDYWGQGTLVTVSSGG GGSGGGGSGGGGSEIVLTQSPGTLSLSPGERVTLSCRASQ RVNNNYLAWYQQRPGQAPRLLIYGASSRATGIPDRFSGS GSGTDFTLTISRLEPEDFAVYYCQQYDRSPLTFGCGTKLEIK SGGGGSEVQLVESGGGLVQPGGSLKLSCAASGFTFNKYA MNWVRQAPGKGLEWVARIRSKYNNYATYYADSVKDRFT ISRDDSKNTAYLQMNNLKTEDTAVYYCVRHGNFGNSYIS YWAYWGQGTLVTVSSGGGGSGGGGSGGGGSQTVVTQ EPSLTVSPGGTVTLTCGSSTGAVTSGNYPNWVQQKPGQ APRGLIGGTKFLAPGTPARFSGSLLGGKAALTLSGVQPED EAEYYCVLWYSNRWVFGGGTKLTVL |
| 104 | DLL3_1_CCxCD3-scFc_delGK Bispecific HLE molecule | artificial | aa | QVQLQESGPGLVKPSETLSLTCTVSGGSISSYYWSWIRQP PGKCLEWIGYVYYSGTTNYNPSLKSRVTISVDTSKNQFSLK LSSVTAADTAVYYCASIAVTGFYFDYWGQGTLVTVSSGG GGSGGGGSGGGGSEIVLTQSPGTLSLSPGERVTLSCRASQ RVNNNYLAWYQQRPGQAPRLLIYGASSRATGIPDRFSGS GSGTDFTLTISRLEPEDFAVYYCQQYDRSPLTFGCGTKLEIK SGGGGSEVQLVESGGGLVQPGGSLKLSCAASGFTFNKYA MNWVRQAPGKGLEWVARIRSKYNNYATYYADSVKDRFT ISRDDSKNTAYLQMNNLKTEDTAVYYCVRHGNFGNSYIS YWAYWGQGTLVTVSSGGGGSGGGGSGGGGSQTVVTQ EPSLTVSPGGTVTLTCGSSTGAVTSGNYPNWVQQKPGQ APRGLIGGTKFLAPGTPARFSGSLLGGKAALTLSGVQPED EAEYYCVLWYSNRWVFGGGTKLTVLGGGGDKTHTCPPC PAPELLGGPSVFLFPPKPKDTLMISRTPEVTCVVVDVSHED PEVKFNWYVDGVEVHNAKTKPCEEQYGSTYRCVSVLTVL HQDWLNGKEYKCKVSNKALPAPIEKTISKAKGQPREPQV YTLPPSREEMTKNQVSLTCLVKGFYPSDIAVEWESNGQPE NNYKTTPPVLDSDGSFFLYSKLTVDKSRWQQGNVFSCSV MHEALHNHYTQKSLSLSPGGGGSGGGGSGGGGSGGGG SGGGGSGGGGSDKTHTCPPCPAPELLGGPSVFLFPPKPK DTLMISRTPEVTCVVVDVSHEDPEVKFNWYVDGVEVHN AKTKPCEEQYGSTYRCVSVLTVLHQDWLNGKEYKCKVSN KALPAPIEKTISKAKGQPREPQVYTLPPSREEMTKNQVSLT CLVKGFYPSDIAVEWESNGQPENNYKTTPPVLDSDGSFFL YSKLTVDKSRWQQGNVFSCSVMHEALHNHYTQKSLSLSP GK |
| 105 | VH CDR1 CD19 97-G1RE-C2 | artificial | aa | SYGMH |
| 106 | VH CDR2 CD19 97-G1RE-C2 | artificial | aa | VISYEGSNKYYAESVKG |
| 107 | VH CDR3 CD19 97-G1RE-C2 | artificial | aa | DRGTIFGNYGLEV |
| 108 | VH CD19 97-G1RE-C2 CC | artificial | aa | QVQLVESGGGVVQPGRSLRLSCAASGFTFSSYGMHWVR QAPGKCLEWVAVISYEGSNKYYAESVKGRFTISRDNSKNT LYLQMNSLRDEDTAVYYCARDRGTIFGNYGLEVWGQGT TVTVSS |
| 109 | VL CDR1 CD19 97-G1RE-C2 | artificial | aa | RSSQSLLHKNAFNYLD |
| 110 | VL CDR2 CD19 97-G1RE-C2 | artificial | aa | LGSNRAS |
| 111 | VL CDR3 CD19 97-G1RE-C2 | artificial | aa | MQALQTPFT |
| 112 | VL CD19 97-G1RE-C2 CC | artificial | aa | DIVMTQSPLSLPVISGEPASISCRSSQSLLHKNAFNYLDWY LQKPGQSPQLLIYLGSNRASGVPDRFSGSGSGTDFTLKISR VEAEDVGVYYCMQALQTPFTFGCGTKVDIK |
| 113 | CD19 97-G1RE-C2 CC x I2C0 | artificial | aa | MDMRVPAQLLGLLLLWLRGARCDIVMTQSPLSLPVISGE PASISCRSSQSLLHKNAFNYLDWYLQKPGQSPQLLIYLGSN RASGVPDRFSGSGSGTDFTLKISRVEAEDVGVYYCMQAL |

TABLE 5-continued

| | | Sequence table | | |
|---|---|---|---|---|
| | | | | QTPFTFGCGTKVDIKGGGGSGGGGSGGGGSQVQLVESG<br>GGVVQPGRSLRLSCAASGFTFSSYGMHWVRQAPGKCLE<br>WVAVISYEGSNKYYAESVKGRFTISRDNSKNTLYLQMNSL<br>RDEDTAVYYCARDRGTIFGNYGLEVWGQGTTVTVSSGG<br>GGSEVQLVESGGGLVQPGGSLKLSCAASGFTFNKYAMN<br>WVRQAPGKGLEWVARIRSKYNNYATYYADSVKDRFTISR<br>DDSKNTAYLQMNNLKTEDTAVYYCVRHGNFGNSYISYW<br>AYWGQGTLVTVSSGGGGSGGGGSGGGGSQTVVTQEPS<br>LTVSPGGTVTLTCGSSTGAVTSGNYPNWVQQKPGQAPR<br>GLIGGTKFLAPGTPARFSGSLLGGKAALTLSGVQPEDEAEY<br>YCVLWYSNRWVFGGGTKLTVL |
| 114 | CD19 97-<br>G1RE-C2 CC x<br>I2C0-scFc | artificial | aa | MDMRVPAQLLGLLLLWLRGARCDIVMTQSPLSLPVISGE<br>PASISCRSSQSLLHKNAFNYLDWYLQKPGQSPQLLIYLGSN<br>RASGVPDRFSGSGSGTDFTLKISRVEAEDVGVYYCMQAL<br>QTPFTFGCGTKVDIKGGGGSGGGGSGGGGSQVQLVESG<br>GGVVQPGRSLRLSCAASGFTFSSYGMHWVRQAPGKCLE<br>WVAVISYEGSNKYYAESVKGRFTISRDNSKNTLYLQMNSL<br>RDEDTAVYYCARDRGTIFGNYGLEVWGQGTTVTVSSGG<br>GGSEVQLVESGGGLVQPGGSLKLSCAASGFTFNKYAMN<br>WVRQAPGKGLEWVARIRSKYNNYATYYADSVKDRFTISR<br>DDSKNTAYLQMNNLKTEDTAVYYCVRHGNFGNSYISYW<br>AYWGQGTLVTVSSGGGGSGGGGSGGGGSQTVVTQEPS<br>LTVSPGGTVTLTCGSSTGAVTSGNYPNWVQQKPGQAPR<br>GLIGGTKFLAPGTPARFSGSLLGGKAALTLSGVQPEDEAEY<br>YCVLWYSNRWVFGGGTKLTVLGGGGDKTHTCPPCPAPE<br>LLGGPSVFLFPPKPKDTLMISRTPEVTCVVVDVSHEDPEVK<br>FNWYVDGVEVHNAKTKPCEEQYGSTYRCVSVLTVLHQD<br>WLNGKEYKCKVSNKALPAPIEKTISKAKGQPREPQVYTLP<br>PSREEMTKNQVSLTCLVKGFYPSDIAVEWESNGQPENNY<br>KTTPPVLDSDGSFFLYSKLTVDKSRWQQGNVFSCSVMHE<br>ALHNHYTQKSLSLSPGKGGGGSGGGGSGGGGSGGGGS<br>GGGGSGGGGSDKTHTCPPCPAPELLGGPSVFLFPPKPKD<br>TLMISRTPEVTCVVVDVSHEDPEVKFNWYVDGVEVHNA<br>KTKPCEEQYGSTYRCVSVLTVLHQDWLNGKEYKCKVSNK<br>ALPAPIEKTISKAKGQPREPQVYTLPPSREEMTKNQVSLTC<br>LVKGFYPSDIAVEWESNGQPENNYKTTPPVLDSDGSFFLY<br>SKLTVDKSRWQQGNVFSCSVMHEALHNHYTQKSLSLSP<br>GK |
| 115 | VH CDR1<br>CDH3 G8A 6-<br>B12 | artificial | aa | SYPIN |
| 116 | VH CDR2<br>CDH3 G8A 6-<br>B12 | artificial | aa | VIWTGGGTNYASSVKG |
| 117 | VH CDR3<br>CDH3 G8A 6-<br>B12 | artificial | aa | SRGVYDFDGRGAMDY |
| 118 | VL CDR1<br>CDH3 G8A 6-<br>B12 | artificial | aa | KSSQSLLYSSNQKNYFA |
| 119 | VL CDR2<br>CDH3 G8A 6-<br>B12 | artificial | aa | WASTRES |
| 120 | VL CDR3<br>CDH3 G8A 6-<br>B12 | artificial | aa | QQYYSYPYT |
| 121 | VH CDH3 G8A<br>6-612 | artificial | aa | EVQLLESGGGLVQPGGSLRLSCAASGFSFSSYPINWVRQA<br>PGKGLEWVGVIWTGGGTNYASSVKGRFTISRDNSKNTVY<br>LQMNSLRAEDTAVYYCAKSRGVYDFDGRGAMDYWGQ<br>GTLVTVSS |
| 122 | VL CDH3 G8A<br>6-612 | artificial | aa | DIVMTQSPDSLAVSLGERATINCKSSQSLLYSSNQKNYFA<br>WYQQKPGQPPKLLIYWASTRESGVPDRFSGSGSGTDFTL<br>TISSLQAEDVAVYYCQQYYSYPYTFGQGTKLEIK |
| 123 | CDH3 G8A 6-<br>B12 scFv | artificial | aa | EVQLLESGGGLVQPGGSLRLSCAASGFSFSSYPINWVRQA<br>PGKGLEWVGVIWTGGGTNYASSVKGRFTISRDNSKNTVY<br>LQMNSLRAEDTAVYYCAKSRGVYDFDGRGAMDYWGQ<br>GTLVTVSSGGGGSGGGGSGGGGSDIVMTQSPDSLAVSL<br>GERATINCKSSQSLLYSSNQKNYFAWYQQKPGQPPKLLIY |

TABLE 5-continued

Sequence table

| | | | | |
|---|---|---|---|---|
| | | | | WASTRESGVPDRFSGSGSGTDFTLTISSLQAEDVAVYYCQ QYYSYPYTFGQGTKLEIK |
| 124 | CDH3 G8A 6-B12 x I2C0 bispecific molecule | artificial | aa | EVQLLESGGGLVQPGGSLRLSCAASGFSFSSYPINWVRQA PGKGLEWVGVIWTGGGTNYASSVKGRFTISRDNSKNTVY LQMNSLRAEDTAVYYCAKSRGVYDFDGRGAMDYWGQ GTLVTVSSGGGGSGGGGSGGGGSDIVMTQSPDSLAVSL GERATINCKSSQSLLYSSNQKNYFAWYQQKPGQPPKLLIY WASTRESGVPDRFSGSGSGTDFTLTISSLQAEDVAVYYCQ QYYSYPYTFGQGTKLEIKSGGGGSEVQLVESGGGLVQPG GSLKLSCAASGFTFNKYAMNWVRQAPGKGLEWVARIRS KYNNYATYYADSVKDRFTISRDDSKNTAYLQMNNLKTED TAVYYCVRHGNFGNSYISYWAYWGQGTLVTVSSGGGGS GGGGSGGGGSQTVVTQEPSLTVSPGGTVTLTCGSSTGAV TSGNYPNWVQQKPGQAPRGLIGGTKFLAPGTPARFSGSL LGGKAALTLSGVQPEDEAEYYCVLWYSNRWVFGGGTKLT VL |
| 125 | CDH3 G8A 6-B12 x I2C0 bispecific molecule HLE | artificial | aa | EVQLLESGGGLVQPGGSLRLSCAASGFSFSSYPINWVRQA PGKGLEWVGVIWTGGGTNYASSVKGRFTISRDNSKNTVY LQMNSLRAEDTAVYYCAKSRGVYDFDGRGAMDYWGQ GTLVTVSSGGGGSGGGGSGGGGSDIVMTQSPDSLAVSL GERATINCKSSQSLLYSSNQKNYFAWYQQKPGQPPKLLIY WASTRESGVPDRFSGSGSGTDFTLTISSLQAEDVAVYYCQ QYYSYPYTFGQGTKLEIKSGGGGSEVQLVESGGGLVQPG GSLKLSCAASGFTFNKYAMNWVRQAPGKGLEWVARIRS KYNNYATYYADSVKDRFTISRDDSKNTAYLQMNNLKTED TAVYYCVRHGNFGNSYISYWAYWGQGTLVTVSSGGGGS GGGGSGGGGSQTVVTQEPSLTVSPGGTVTLTCGSSTGAV TSGNYPNWVQQKPGQAPRGLIGGTKFLAPGTPARFSGSL LGGKAALTLSGVQPEDEAEYYCVLWYSNRWVFGGGTKLT VLGGGGDKTHTCPPCPAPELLGGPSVFLFPPKPKDTLMIS RTPEVTCVVVDVSHEDPEVKFNWYVDGVEVHNAKTKPC EEQYGSTYRCVSVLTVLHQDWLNGKEYKCKVSNKALPAPI EKTISKAKGQPREPQVYTLPPSREEMTKNQVSLTCLVKGF YPSDIAVEWESNGQPENNYKTTPPVLDSDGSFFLYSKLTV DKSRWQQGNVFSCSVMHEALHNHYTQKSLSLSPGKGG GGSGGGGSGGGGSGGGGSGGGGSGGGGSDKTHTCPP CPAPELLGGPSVFLFPPKPKDTLMISRTPEVTCVVVDVSHE DPEVKFNWYVDGVEVHNAKTKPCEEQYGSTYRCVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |
| 126 | BCMA A7 27-C4-G7 CDR1 VH | artificial | aa | NHIIH |
| 127 | BCMA A7 27-C4-G7 CDR2 VH | artificial | aa | YINPYPGYHAYNEKFQG |
| 128 | BCMA A7 27-C4-G7 CDR3 VH | artificial | aa | DGYYRDTDVLDY |
| 129 | BCMA A7 27-C4-G7 CDR1 VL | artificial | aa | QASQDISNYLN |
| 130 | BCMA A7 27-C4-G7 CDR2 VL | artificial | aa | YTSRLHT |
| 131 | BCMA A7 27-C4-G7 CDR3 VL | artificial | aa | QQGNTLPWT |
| 132 | BCMA A7 27-C4-G7 CC (44/100) VH | artificial | aa | QVQLVQSGAEVKKPGASVKVSCKASGYTFTNHIIHWVRQ APGQCLEWMGYINPYPGYHAYNEKFQGRATMTSDTSTS TVYMELSSLRSEDTAVYYCARDGYYRDTDVLDYWGQGTL VTVSS |
| 133 | BCMA A7 27-C4-G7 CC (44/100) VL | artificial | aa | DIQMTQSPSSLSASVGDRVTITCQASQDISNYLNWYQQK PGKAPKLLIYYTSRLHTGVPSRFSGSGSGTDFTFTISSLEPE DIATYYCQQGNTLPWTFGCGTKLEIK |

TABLE 5-continued

Sequence table

| | | | | |
|---|---|---|---|---|
| 134 | BCMA A7 27-C4-G7 CC (44/100) scFv | artificial | aa | QVQLVQSGAEVKKPGASVKVSCKASGYTFTNHIIHWVRQ APGQCLEWMGYINPYPGYHAYNEKFQGRATMTSDTSTS TVYMELSSLRSEDTAVYYCARDGYYRDTDVLDYWGQGTL VTVSSGGGGSGGGGSGGGGSDIQMTQSPSSLSASVGDR VTITCQASQDISNYLNWYQQKPGKAPKLLIYYTSRLHTGV PSRFSGSGSGTDFTFTISSLEPEDIATYYCQQGNTLPWTFG CGTKLEIK |
| 135 | BCMA A7 27-C4-G7 CC (44/100) x I2C0 bispecific molecule | artificial | aa | QVQLVQSGAEVKKPGASVKVSCKASGYTFTNHIIHWVRQ APGQCLEWMGYINPYPGYHAYNEKFQGRATMTSDTSTS TVYMELSSLRSEDTAVYYCARDGYYRDTDVLDYWGQGTL VTVSSGGGGSGGGGSGGGGSDIQMTQSPSSLSASVGDR VTITCQASQDISNYLNWYQQKPGKAPKLLIYYTSRLHTGV PSRFSGSGSGTDFTFTISSLEPEDIATYYCQQGNTLPWTFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWV QQKPGQAPRGLIGGTKFLAPGTPARFSGSLLGGKAALTLSG VQPEDEAEYYCVLWYSNRWVFGGGTKLTVL |
| 136 | BCMA A7 27-C4-G7 CC (44/100) x I2C0-scFc bispecific molecule HLE | artificial | aa | QVQLVQSGAEVKKPGASVKVSCKASGYTFTNHIIHWVRQ APGQCLEWMGYINPYPGYHAYNEKFQGRATMTSDTSTS TVYMELSSLRSEDTAVYYCARDGYYRDTDVLDYWGQGTL VTVSSGGGGSGGGGSGGGGSDIQMTQSPSSLSASVGDR VTITCQASQDISNYLNWYQQKPGKAPKLLIYYTSRLHTGV PSRFSGSGSGTDFTFTISSLEPEDIATYYCQQGNTLPWTFG CGTKVEIKSGGGGSEVQLVESGGGLVQPGGSLKLSCAAS GFTFNKYAMNWVRQAPGKGLEWVARIRSKYNNYATYY ADSVKDRFTISRDDSKNTAYLQMNNLKTEDTAVYYCVRH GNFGNSYISYWAYWGQGTLVTVSSGGGGSGGGGSGGG GSQTVVTQEPSLTVSPGGTVTLTCGSSTGAVTSGNYPNW VQQKPGQAPRGLIGGTKFLAPGTPARFSGSLLGGKAALTL SGVQPEDEAEYYCVLWYSNRWVFGGGTKLTVLGGGGDK THTCPPCPAPELLGGPSVFLFPPKPKDTLMISRTPEVTCVV VDVSHEDPEVKFNWYVDGVEVHNAKTKPCEEQYGSTYR CVSVLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRWQ QGNVFSCSVMHEALHNHYTQKSLSLSPGKGGGGSGGGG SGGGGSGGGGSGGGGSGGGGSDKTHTCPPCPAPELLGG PSVFLFPPKPKDTLMISRTPEVTCVVVDVSHEDPEVKFNW YVDGVEVHNAKTKPCEEQYGSTYRCVSVLTVLHQDWLN GKEYKCKVSNKALPAPIEKTISKAKGQPREPQVYTLPPSRE EMTKNQVSLTCLVKGFYPSDIAVEWESNGQPENNYKTTP PVLDSDGSFFLYSKLTVDKSRWQQGNVFSCSVMHEALH NHYTQKSLSLSPGK |
| 137 | PM 76-B10.17 CC VH CDR1 | artificial | aa | DYYMY |
| 138 | PM 76-B10.17 CC VH CDR2 | artificial | aa | IISDAGYYTYYSDIIKG |
| 139 | PM 76-1310.17 CC VH CDR3 | artificial | aa | GFPLLRHGAMDY |
| 140 | PM 76-1310.17 CC VL CDR1 | artificial | aa | KASQNVDANVA |
| 141 | PM 76-1310.17 CC VL CDR2 | artificial | aa | SASYVYW |
| 142 | PM 76-1310.17 CC VL CDR3 | artificial | aa | QQYDQQLIT |
| 143 | PM 76-1310.17 CC VH | artificial | aa | QVQLVESGGGLVKPGESLRLSCAASGFTFSDYYMYWVRQ APGKCLEWVAIISDAGYYTYYSDIIKGRFTISRDNAKNSLYL QMNSLKAEDTAVYYCARGFPLLRHGAMDYWGQGTLVT VSS |

TABLE 5-continued

Sequence table

| | | | | |
|---|---|---|---|---|
| 144 | PM 76-1310.17 CC VL | artificial | aa | DIQMTQSPSSLSASVGDRVTITCKASQNVDANVAWYQQ KPGQAPKSLIYSASYVYWDVPSRFSGSASGTDFTLTISSVQ SEDFATYYCQQYDQQLITFGCGTKLEIK |
| 145 | PM 76-1310.17 CC scFv | artificial | aa | QVQLVESGGGLVKPGESLRLSCAASGFTFSDYYMYWVRQ APGKCLEWVAIISDAGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDANVAWYQQKPGQAPKSLIYSASYVYWDV PSRFSGSASGTDFTLTISSVQSEDFATYYCQQYDQQLITFG CGTKLEIK |
| 146 | PM 76-1310.17 CC x I2C0 bispecific molecule | artificial | aa | QVQLVESGGGLVKPGESLRLSCAASGFTFSDYYMYWVRQ APGKCLEWVAIISDAGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDANVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVL |
| 147 | PM 76-1310.17 CC x I2C0-scFc bispecific HLE molecule | artificial | aa | QVQLVESGGGLVKPGESLRLSCAASGFTFSDYYMYWVRQ APGKCLEWVAIISDAGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDANVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVLGGGGDKTH TCPPCPAPELLGGPSVFLFPPKPKDTLMISRTPEVTCVVVD VSHEDPEVKFNWYVDGVEVHNAKTKPCEEQYGSTYRCV SVLTVLHQDWLNGKEYKCKVSNKALPAPIEKTISKAKGQP REPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGKGGGGSGGGGSGG GGSGGGGSGGGGSGGGGSDKTHTCPPCPAPELLGGPSV FLFPPKPKDTLMISRTPEVTCVVVDVSHEDPEVKFNWYV DGVEVHNAKTKPCEEQYGSTYRCVSVLTVLHQDWLNGK EYKCKVSNKALPAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHY TQKSLSLSPGK |
| 148 | PM 76-B10.17 CC x I2C0-scFc_delGK bispecific HLE molecule | artificial | aa | QVQLVESGGGLVKPGESLRLSCAASGFTFSDYYMYWVRQ APGKCLEWVAIISDAGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDANVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVLGGGGDKTH TCPPCPAPELLGGPSVFLFPPKPKDTLMISRTPEVTCVVVD VSHEDPEVKFNWYVDGVEVHNAKTKPCEEQYGSTYRCV SVLTVLHQDWLNGKEYKCKVSNKALPAPIEKTISKAKGQP REPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGGGGSGGGGSGGGG SGGGGSGGGGSGGGGSDKTHTCPPCPAPELLGGPSVFLF PPKPKDTLMISRTPEVTCVVVDVSHEDPEVKFNWYVDGV |

TABLE 5-continued

Sequence table

| | | | | |
|---|---|---|---|---|
| | | | | EVHNAKTKPCEEQYGSTYRCVSVLTVLHQDWLNGKEYKC<br>KVSNKALPAPIEKTISKAKGQPREPQVYTLPPSREEMTKN<br>QVSLTCLVKGFYPSDIAVEWESNGQPENNYKTTPPVLDS<br>DGSFFLYSKLTVDKSRWQQGNVFSCSVMHEALHNHYTQ<br>KSLSLSPGK |
| 149 | PM 76-<br>B10.17 CC x<br>I2C0 CC<br>(103/43)-scFc<br>bispecific<br>molecule | artificial | aa | QVQLVESGGGLVKPGESLRLSCAASGFTFSDYYMYWVRQ<br>APGKCLEWVAIISDAGYYTYYSDIIKGRFTISRDNAKNSLYL<br>QMNSLKAEDTAVYYCARGFPLLRHGAMDYWGQGTLVT<br>VSSGGGGSGGGGSGGGGSDIQMTQSPSSLSASVGDRVT<br>ITCKASQNVDANVAWYQQKPGQAPKSLIYSASYVYWDV<br>PSRFSGSASGTDFTLTISSVQSEDFATYYCQQYDQQLITFG<br>CGTKLEIKSGGGGSEVQLVESGGGLVQPGGSLKLSCAASG<br>FTFNKYAMNWVRQAPGKGLEWVARIRSKYNNYATYYAD<br>SVKDRFTISRDDSKNTAYLQMNNLKTEDTAVYYCVRHGN<br>FGNSYISYWAYCGQGTLVTVSSGGGGSGGGGSGGGGSQ<br>TVVTQEPSLTVSPGGTVTLTCGSSTGAVTSGNYPNWVQQ<br>KPGQCPRGLIGGTKFLAPGTPARFSGSLLGGKAALTLSGV<br>QPEDEAEYYCVLWYSNRWVFGGGTKLTVL |
| 150 | PM 76-<br>1310.17 CC x<br>I2C0 CC<br>(103/43)-scFc<br>bispecific<br>HLE molecule | artificial | aa | QVQLVESGGGLVKPGESLRLSCAASGFTFSDYYMYWVRQ<br>APGKCLEWVAIISDAGYYTYYSDIIKGRFTISRDNAKNSLYL<br>QMNSLKAEDTAVYYCARGFPLLRHGAMDYWGQGTLVT<br>VSSGGGGSGGGGSGGGGSDIQMTQSPSSLSASVGDRVT<br>ITCKASQNVDANVAWYQQKPGQAPKSLIYSASYVYWDV<br>PSRFSGSASGTDFTLTISSVQSEDFATYYCQQYDQQLITFG<br>CGTKLEIKSGGGGSEVQLVESGGGLVQPGGSLKLSCAASG<br>FTFNKYAMNWVRQAPGKGLEWVARIRSKYNNYATYYAD<br>SVKDRFTISRDDSKNTAYLQMNNLKTEDTAVYYCVRHGN<br>FGNSYISYWAYCGQGTLVTVSSGGGGSGGGGSGGGGSQ<br>TVVTQEPSLTVSPGGTVTLTCGSSTGAVTSGNYPNWVQQ<br>KPGQCPRGLIGGTKFLAPGTPARFSGSLLGGKAALTLSGV<br>QPEDEAEYYCVLWYSNRWVFGGGTKLTVLGGGGDKTHT<br>CPPCPAPELLGGPSVFLFPPKPKDTLMISRTPEVTCVVVDV<br>SHEDPEVKFNWYVDGVEVHNAKTKPCEEQYGSTYRCVS<br>VLTVLHQDWLNGKEYKCKVSNKALPAPIEKTISKAKGQPR<br>EPQVYTLPPSREEMTKNQVSLTCLVKGFYPSDIAVEWESN<br>GQPENNYKTTPPVLDSDGSFFLYSKLTVDKSRWQQGNVF<br>SCSVMHEALHNHYTQKSLSLSPGKGGGGSGGGGSGGGG<br>SGGGGSGGGGSGGGGSDKTHTCPPCPAPELLGGPSVFLF<br>PPKPKDTLMISRTPEVTCVVVDVSHEDPEVKFNWYVDGV<br>EVHNAKTKPCEEQYGSTYRCVSVLTVLHQDWLNGKEYKC<br>KVSNKALPAPIEKTISKAKGQPREPQVYTLPPSREEMTKN<br>QVSLTCLVKGFYPSDIAVEWESNGQPENNYKTTPPVLDS<br>DGSFFLYSKLTVDKSRWQQGNVFSCSVMHEALHNHYTQ<br>KSLSLSPGK |
| 151 | PM 76-<br>1310.17 CC x<br>I2C0 CC<br>(103/43)-<br>scFc_delGK<br>bispecific<br>HLE molecule | artificial | aa | QVQLVESGGGLVKPGESLRLSCAASGFTFSDYYMYWVRQ<br>APGKCLEWVAIISDAGYYTYYSDIIKGRFTISRDNAKNSLYL<br>QMNSLKAEDTAVYYCARGFPLLRHGAMDYWGQGTLVT<br>VSSGGGGSGGGGSGGGGSDIQMTQSPSSLSASVGDRVT<br>ITCKASQNVDANVAWYQQKPGQAPKSLIYSASYVYWDV<br>PSRFSGSASGTDFTLTISSVQSEDFATYYCQQYDQQLITFG<br>CGTKLEIKSGGGGSEVQLVESGGGLVQPGGSLKLSCAASG<br>FTFNKYAMNWVRQAPGKGLEWVARIRSKYNNYATYYAD<br>SVKDRFTISRDDSKNTAYLQMNNLKTEDTAVYYCVRHGN<br>FGNSYISYWAYCGQGTLVTVSSGGGGSGGGGSGGGGSQ<br>TVVTQEPSLTVSPGGTVTLTCGSSTGAVTSGNYPNWVQQ<br>KPGQCPRGLIGGTKFLAPGTPARFSGSLLGGKAALTLSGV<br>QPEDEAEYYCVLWYSNRWVFGGGTKLTVLGGGGDKTHT<br>CPPCPAPELLGGPSVFLFPPKPKDTLMISRTPEVTCVVVDV<br>SHEDPEVKFNWYVDGVEVHNAKTKPCEEQYGSTYRCVS<br>VLTVLHQDWLNGKEYKCKVSNKALPAPIEKTISKAKGQPR<br>EPQVYTLPPSREEMTKNQVSLTCLVKGFYPSDIAVEWESN<br>GQPENNYKTTPPVLDSDGSFFLYSKLTVDKSRWQQGNVF<br>SCSVMHEALHNHYTQKSLSLSPGGGGSGGGGSGGGGSG<br>GGGSGGGGSGGGGSDKTHTCPPCPAPELLGGPSVFLFPP<br>KPKDTLMISRTPEVTCVVVDVSHEDPEVKFNWYVDGVEV<br>HNAKTKPCEEQYGSTYRCVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLS<br>LSPGK |
| 152 | PM 76-<br>B10.11 CC VH<br>CDR1 | artificial | aa | DYYMY |

TABLE 5-continued

Sequence table

| 153 | PM 76-B10.11 CC VH CDR2 | artificial | aa | IISDGGYYTYYSDIIKG |
| --- | --- | --- | --- | --- |
| 154 | PM 76-B10.11 CC VH CDR3 | artificial | aa | GFPLLRHGAMDY |
| 155 | PM 76-B10.11 CC VL CDR1 | artificial | aa | KASQNVDTNVA |
| 156 | PM 76-B10.11 CC VL CDR2 | artificial | aa | SASYVYW |
| 157 | PM 76-B10.11 CC VL CDR3 | artificial | aa | QQYDQQLIT |
| 158 | PM 76-B10.11 CC VH | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSS |
| 159 | PM 76-B10.11 CC VL | artificial | aa | DIQMTQSPSSLSASVGDRVTITCKASQNVDTNVAWYQQ KPGQAPKSLIYSASYVYWDVPSRFSGSASGTDFTLTISSVQ SEDFATYYCQQYDQQLITFGGGTKLEIK |
| 160 | PM 76-B10.11 CC scFv | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIK |
| 161 | PM 76-B10.11 CC x I2C0 bispecific molecule | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VVQPEDEAEYYCVLWYSNRWVFGGGTKLTVL |
| 162 | PM 76-1310.11 CC x I2C0-scFc bispecific HLE molecule | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVLGGGGDKTH TCPPCPAPELLGGPSVFLFPPKPKDTLMISRTPEVTCVVVD VSHEDPEVKFNWYVDGVEVHNAKTKPCEEQYGSTYRCV SVLTVLHQDWLNGKEYKCKVSNKALPAPIEKTISKAKGQP REPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGKGGGGSGGGGSGG GGSGGGGSGGGGSGGGGSDKTHTCPPCPAPELLGGPSV FLFPPKPKDTLMISRTPEVTCVVVDVSHEDPEVKFNWYV DGVEVHNAKTKPCEEQYGSTYRCVSVLTVLHQDWLNGK EYKCKVSNKALPAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHY TQKSLSLSPGK |

TABLE 5-continued

Sequence table

| 163 | PM 76-1310.11 CC x I2C0-scFc_delGK bispecific HLE molecule | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVLGGGGDKTH TCPPCPAPELLGGPSVFLFPPKPKDTLMISRTPEVTCVVVD VSHEDPEVKFNWYVDGVEVHNAKTKPCEEQYGSTYRCV SVLTVLHQDWLNGKEYKCKVSNKALPAPIEKTISKAKGQP REPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGGGGSGGGGSGGGG SGGGGSGGGGSGGGGSDKTHTCPPCPAPELLGGPSVFLF PPKPKDTLMISRTPEVTCVVVDVSHEDPEVKFNWYVDGV EVHNAKTKPCEEQYGSTYRCVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDS DGSFFLYSKLTVDKSRWQQGNVFSCSVMHEALHNHYTQ KSLSLSPGK |
| 164 | PM 76-610.11 CC x I2C0 CC (103/43)-scFc bispecific molecule | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYCGQGTLVTVSSGGGGSGGGGSGGGGSQ TVVTQEPSLTVSPGGTVTLTCGSSTGAVTSGNYPNWVQQ KPGQCPRGLIGGTKFLAPGTPARFSGSLLGGKAALTLSGV QPEDEAEYYCVLWYSNRWVFGGGTKLTVL |
| 165 | PM 76-610.11 CC x I2C0 CC (103/43)-scFc bispecific HLE molecule | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYCGQGTLVTVSSGGGGSGGGGSGGGGSQ TVVTQEPSLTVSPGGTVTLTCGSSTGAVTSGNYPNWVQQ KPGQCPRGLIGGTKFLAPGTPARFSGSLLGGKAALTLSGV QPEDEAEYYCVLWYSNRWVFGGGTKLTVLGGGGDKTHT CPPCPAPELLGGPSVFLFPPKPKDTLMISRTPEVTCVVVDV SHEDPEVKFNWYVDGVEVHNAKTKPCEEQYGSTYRCVS VLTVLHQDWLNGKEYKCKVSNKALPAPIEKTISKAKGQPR EPQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGKGGGGSGGGGSGGGG SGGGGSGGGGSGGGGSDKTHTCPPCPAPELLGGPSVFLF PPKPKDTLMISRTPEVTCVVVDVSHEDPEVKFNWYVDGV EVHNAKTKPCEEQYGSTYRCVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDS DGSFFLYSKLTVDKSRWQQGNVFSCSVMHEALHNHYTQ KSLSLSPGK |
| 166 | PM 76-B10.11 CC x I2C0 CC (103/43)-scFc_deIGK bispecific HLE molecule | artificial | aa | QVQLVESGGGLVKPGESLRLSCAASGFTFSDYYMYWVRQ APGKGLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG GGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYCGQGTLVTVSSGGGGSGGGGSGGGGSQ |

TABLE 5-continued

Sequence table

| | | | | |
|---|---|---|---|---|
| | | | | TVVTQEPSLTVSPGGTVTLTCGSSTGAVTSGNYPNWVQQ<br>KPGQCPRGLIGGTKFLAPGTPARFSGSLLGGKAALTLSGV<br>QPEDEAEYYCVLWYSNRWVFGGGTKLTVLGGGGDKTHT<br>CPPCPAPELLGGPSVFLFPPKPKDTLMISRTPEVTCVVVDV<br>SHEDPEVKFNWYVDGVEVHNAKTKPCEEQYGSTYRCVS<br>VLTVLHQDWLNGKEYKCKVSNKALPAPIEKTISKAKGQPR<br>EPQVYTLPPSREEMTKNQVSLTCLVKGFYPSDIAVEWESN<br>GQPENNYKTTPPVLDSDGSFFLYSKLTVDKSRWQQGNVF<br>SCSVMHEALHNHYTQKSLSLSPGGGSGGGGSGGGGSG<br>GGGSGGGGSGGGGSDKTHTCPPCPAPELLGGPSVFLFPP<br>KPKDTLMISRTPEVTCVVVDVSHEDPEVKFNWYVDGVEV<br>HNAKTKPCEEQYGSTYRCVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLS<br>LSPGK |
| 167 | PM 76-<br>B10.11 CC x<br>I2C0-scFc VH<br>CDR1 | artificial | aa | DYYMY |
| 168 | PM 76-<br>B10.11 CC x<br>I2C0-scFc VH<br>CDR2 | artificial | aa | IISDGGYYTYYSDIIKG |
| 169 | PM 76-<br>B10.11 CC x<br>I2C0-scFc VH<br>CDR3 | artificial | aa | GFPLLRHGAMDY |
| 170 | PM 76-<br>B10.11 CC x<br>I2C0-scFc VL<br>CDR1 | artificial | aa | KASQNVDTNVA |
| 171 | PM 76-<br>B10.11 CC x<br>I2C0-scFc VL<br>CDR2 | artificial | aa | SASYVYW |
| 172 | PM 76-<br>B10.11 CC x<br>I2C0-scFc VL<br>CDR3 | artificial | aa | QQYDQQLIT |
| 173 | PM 76-<br>1310.11 CC x<br>I2C0-scFc VH | artificial | aa | QVQLVESGGGLVKPGESLRLSCAASGFTFSDYYMYWVRQ<br>APGKCLEWVAIISDGGYYTYYSDIIKGRFTISRDNAKNSLYL<br>QMNSLKAEDTAVYYCARGFPLLRHGAMDYWGQGTLVT<br>VSS |
| 174 | PM 76-<br>1310.11 CC x<br>I2C0-scFc VL | artificial | aa | DIQMTQSPSSLSASVGDRVTITCKASQNVDTNVAWYQQ<br>KPGQAPKSLIYSASYVYWDVPSRFSGSASGTDFTLTISSVQ<br>SEDFATYYCQQYDQQLITFGCGTKLEIK |
| 175 | PM 76-<br>1310.11 CC x<br>I2C0-scFc<br>scFv | artificial | aa | QVQLVESGGGLVKPGESLRLSCAASGFTFSDYYMYWVRQ<br>APGKCLEWVAIISDGGYYTYYSDIIKGRFTISRDNAKNSLYL<br>QMNSLKAEDTAVYYCARGFPLLRHGAMDYWGQGTLVT<br>VSSGGGGSGGGGSGGGGSDIQMTQSPSSLSASVGDRVT<br>ITCKASQNVDTNVAWYQQKPGQAPKSLIYSASYVYWDV<br>PSRFSGSASGTDFTLTISSVQSEDFATYYCQQYDQQLITFG<br>CGTKLEIK |
| 176 | PM 76-<br>1310.11 CC x<br>I2C0-scFc<br>bispecific<br>molecule | artificial | aa | QVQLVESGGGLVKPGESLRLSCAASGFTFSDYYMYWVRQ<br>APGKCLEWVAIISDGGYYTYYSDIIKGRFTISRDNAKNSLYL<br>QMNSLKAEDTAVYYCARGFPLLRHGAMDYWGQGTLVT<br>VSSGGGGSGGGGSGGGGSDIQMTQSPSSLSASVGDRVT<br>ITCKASQNVDTNVAWYQQKPGQAPKSLIYSASYVYWDV<br>PSRFSGSASGTDFTLTISSVQSEDFATYYCQQYDQQLITFG<br>CGTKLEIKSGGGGSEVQLVESGGGLVQPGGSLKLSCAASG<br>FTFNKYAMNWVRQAPGKGLEWVARIRSKYNNYATYYAD<br>SVKDRFTISRDDSKNTAYLQMNNLKTEDTAVYYCVRHGN<br>FGNSYISYWAYWGQGTLVTSSGGGGSGGGGSGGGGS<br>QTVVTQEPSLTVSPGGTVTLTCGSSTGAVTSGNYPNWVQ<br>QKPGQAPRGLIGGTKFLAPGTPARFSGSLLGGKAALTLSG<br>VQPEDEAEYYCVLWYSNRWVFGGGTKLTVL |

TABLE 5-continued

Sequence table

| | | | | |
|---|---|---|---|---|
| 177 | PM 76-1310.11 CC x I2C0-scFc bispecific HLE molecule | artificial | aa | QVQLVESGGGLVKPGESLRLSCAASGFTFSDYYMYWVRQ APGKCLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVLGGGGDKTH TCPPCPAPELLGGPSVFLFPPKPKDTLMISRTPEVTCVVVD VSHEDPEVKFNWYVDGVEVHNAKTKPCEEQYGSTYRCV SVLTVLHQDWLNGKEYKCKVSNKALPAPIEKTISKAKGQP REPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGKGGGGSGGGGSGG GGSGGGGSGGGGSGGGGSDKTHTCPPCPAPELLGGPSV FLFPPKPKDTLMISRTPEVTCVVVDVSHEDPEVKFNWYV DGVEVHNAKTKPCEEQYGSTYRCVSVLTVLHQDWLNGK EYKCKVSNKALPAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHY TQKSLSLSPGK |
| 178 | PM 76-B10.11 CC x I2C0-scFc_delGK bispecific HLE molecule | artificial | aa | QVQLVESGGGLVKPGESLRLSCAASGFTFSDYYMYWVRQ APGKCLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYWGQGTLVTVSSGGGGSGGGGSGGGGS QTVVTQEPSLTVSPGGTVTLTCGSSTGAVTSGNYPNWVQ QKPGQAPRGLIGGTKFLAPGTPARFSGSLLGGKAALTLSG VQPEDEAEYYCVLWYSNRWVFGGGTKLTVLGGGGDKTH TCPPCPAPELLGGPSVFLFPPKPKDTLMISRTPEVTCVVVD VSHEDPEVKFNWYVDGVEVHNAKTKPCEEQYGSTYRCV SVLTVLHQDWLNGKEYKCKVSNKALPAPIEKTISKAKGQP REPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGGGGSGGGGSGGGG SGGGGSGGGGSGGGGSDKTHTCPPCPAPELLGGPSVFLF PPKPKDTLMISRTPEVTCVVVDVSHEDPEVKFNWYVDGV EVHNAKTKPCEEQYGSTYRCVSVLTVLHQDWLNGKEYKC KVSNKALPAPIEKTISKAKGQPREPQVYTLPPSREEMTKN QVSLTCLVKGFYPSDIAVEWESNGQPENNYKTTPPVLDS DGSFFLYSKLTVDKSRWQQGNVFSCSVMHEALHNHYTQ KSLSLSPGK |
| 179 | PM 76-B10.11 CC x I2C0 CC (103/43)-scFc bispecific molecule | artificial | aa | QVQLVESGGGLVKPGESLRLSCAASGFTFSDYYMYWVRQ APGKCLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYCGQGTLVTVSSGGGGSGGGGSGGGGSQ TVVTQEPSLTVSPGGTVTLTCGSSTGAVTSGNYPNWVQQ KPGQCPRGLIGGTKFLAPGTPARFSGSLLGGKAALTLSGV QPEDEAEYYCVLWYSNRWVFGGGTKLTVL |
| 180 | PM 76-B10.11 CC x I2C0 CC (103/43)-scFc bispecific HLE molecule | artificial | aa | QVQLVESGGGLVKPGESLRLSCAASGFTFSDYYMYWVRQ APGKCLEWVAIISDGGYYTYYSDIIKGRFTISRDNAKNSLYL QMNSLKAEDTAVYYCARGFPLLRHGAMDYWGQGTLVT VSSGGGGSGGGGSGGGGSDIQMTQSPSSLSASVGDRVT ITCKASQNVDTNVAWYQQKPGQAPKSLIYSASYVYWDV PSRFSGSASGTDFTLTISSVQSEDFATYYCQQYDQQLITFG CGTKLEIKSGGGGSEVQLVESGGGLVQPGGSLKLSCAASG FTFNKYAMNWVRQAPGKGLEWVARIRSKYNNYATYYAD SVKDRFTISRDDSKNTAYLQMNNLKTEDTAVYYCVRHGN FGNSYISYWAYCGQGTLVTVSSGGGGSGGGGSGGGGSQ |

TABLE 5-continued

Sequence table

| | | | | |
|---|---|---|---|---|
| | | | | TVVTQEPSLTVSPGGTVTLTCGSSTGAVTSGNYPNWVQQ<br>KPGQCPRGLIGGTKFLAPGTPARFSGSLLGGKAALTLSGV<br>QPEDEAEYYCVLWYSNRWVFGGGTKLTVLGGGGDKTHT<br>CPPCPAPELLGGPSVFLFPPKPKDTLMISRTPEVTCVVVDV<br>SHEDPEVKFNWYVDGVEVHNAKTKPCEEQYGSTYRCVS<br>VLTVLHQDWLNGKEYKCKVSNKALPAPIEKTISKAKGQPR<br>EPQVYTLPPSREEMTKNQVSLTCLVKGFYPSDIAVEWESN<br>GQPENNYKTTPPVLDSDGSFFLYSKLTVDKSRWQQGNVF<br>SCSVMHEALHNHYTQKSLSLSPGKGGGGSGGGGSGGGG<br>SGGGGSGGGGSGGGGSDKTHTCPPCPAPELLGGPSVFLF<br>PPKPKDTLMISRTPEVTCVVVDVSHEDPEVKFNWYVDGV<br>EVHNAKTKPCEEQYGSTYRCVSVLTVLHQDWLNGKEYKC<br>KVSNKALPAPIEKTISKAKGQPREPQVYTLPPSREEMTKN<br>QVSLTCLVKGFYPSDIAVEWESNGQPENNYKTTPPVLDS<br>DGSFFLYSKLTVDKSRWQQGNVFSCSVMHEALHNHYTQ<br>KSLSLSPGK |
| 181 | PM 76-<br>B10.11 CC x<br>I2C0 CC<br>(103/43)-<br>scFc_delGK<br>bispecific<br>HLE molecule | artificial | aa | QVQLVESGGGLVKPGESLRLSCAASGFTFSDYYMYWVRQ<br>APGKCLEWVAIISDGYYTYYSDIIKGRFTISRDNAKNSLYL<br>QMNSLKAEDTAVYYCARGFPLLRHGAMDYWGQGTLVT<br>VSSGGGGSGGGGSGGGGSDIQMTQSPSSLSASVGDRVT<br>ITCKASQNVDTNVAWYQQKPGQAPKSLIYSASYVYWDV<br>PSRFSGSASGTDFTLTISSVQSEDFATYYCQQYDQQLITFG<br>CGTKLEIKSGGGGSEVQLVESGGGLVQPGGSLKLSCAASG<br>FTFNKYAMNWVRQAPGKGLEWVARIRSKYNNYATYYAD<br>SVKDRFTISRDDSKNTAYLQMNNLKTEDTAVYYCVRHGN<br>FGNSYISYWAYCGQGTLVTVSSGGGGSGGGGSGGGGSQ<br>TVVTQEPSLTVSPGGTVTLTCGSSTGAVTSGNYPNWVQQ<br>KPGQCPRGLIGGTKFLAPGTPARFSGSLLGGKAALTLSGV<br>QPEDEAEYYCVLWYSNRWVFGGGTKLTVLGGGGDKTHT<br>CPPCPAPELLGGPSVFLFPPKPKDTLMISRTPEVTCVVVDV<br>SHEDPEVKFNWYVDGVEVHNAKTKPCEEQYGSTYRCVS<br>VLTVLHQDWLNGKEYKCKVSNKALPAPIEKTISKAKGQPR<br>EPQVYTLPPSREEMTKNQVSLTCLVKGFYPSDIAVEWESN<br>GQPENNYKTTPPVLDSDGSFFLYSKLTVDKSRWQQGNVF<br>SCSVMHEALHNHYTQKSLSLSPGGGGSGGGGSGGGGSG<br>GGGSGGGGSGGGGSDKTHTCPPCPAPELLGGPSVFLFPP<br>KPKDTLMISRTPEVTCVVVDVSHEDPEVKFNWYVDGVEV<br>HNAKTKPCEEQYGSTYRCVSVLTVLHQDWLNGKEYKCKV<br>SNKALPAPIEKTISKAKGQPREPQVYTLPPSREEMTKNQV<br>SLTCLVKGFYPSDIAVEWESNGQPENNYKTTPPVLDSDGS<br>FFLYSKLTVDKSRWQQGNVFSCSVMHEALHNHYTQKSLS<br>LSPGK |

The invention claimed is:

1. A method for reducing or preventing the formation of high molecular weight protein aggregates of a bispecific antibody construct in a pharmaceutical composition, the method comprising providing a pharmaceutical composition comprising
   i) a bispecific antibody construct, wherein the construct binds to a target cell surface antigen via a first binding domain and to the T cell surface antigen CD3 via a second binding domain, wherein the bispecific antibody construct is present in a concentration in the range from 0.5 µg/ml to 20 mg/ml;
   ii) benzyl alcohol in a concentration in the range from 0.11 to 0.9% (w/v), and
   iii) a buffer comprising a salt selected from the group consisting of phosphate, acetate, citrate, succinate and tartrate, or wherein the buffer comprises histidine, glycine, TRIS glycine, Tris, or mixtures thereof, wherein the benzyl alcohol serves to physically and microbiologically stabilize the pharmaceutical composition during storage and administration, wherein the bispecific antibody construct shows reduction or prevention of the formation of protein aggregates (high molecular weight (HMW) species), and wherein the percentile HMW concentration is below 5%, and wherein the composition is stored until use as a solution in a frozen state or as a lyophilisate and is then administered, after dilution or reconstitution, without requiring additional benzyl alcohol for dilution or reconstitution.

2. The method of claim 1, wherein the bispecific antibody construct is present at a concentration in a range selected from the group consisting of:
   (a) 0.5 to 200 µg/ml at a pH of 6.5 to 7.5,
   (b) 0.5 to 1000 µg/ml at a pH of 4.0 to 6.0,
   (c) 0.5 µg to 2 mg in the presence of a CD3 binding domain stabilizing agent, and
   (d) 0.5 µg to 20 mg, at a pH of 4.0 to 7.5,
   wherein the bispecific antibody comprises a third binding domain which comprises two polypeptide monomers, each comprising a hinge, a CH2 and a CH3 domain, wherein said two polypeptide monomers are fused to each other via a peptide linker, and wherein said third binding domain comprises in an amino to carboxyl order:
   hinge-CH2-CH3-linker-hinge-CH2-CH3.

3. The method of claim 1, wherein the bispecific antibody construct is a bispecific single chain antibody construct.

4. The method of claim 1, wherein the buffer is selected from the group consisting of: potassium phosphate, acetic acid/sodium acetate, citric acid/sodium citrate, succinic acid/sodium succinate, tartaric acid/sodium tartrate, and histidine/histidine HCl or mixtures thereof.

5. The method of claim 1, wherein the buffer is present at a concentration in a range from 0.1 to 150 mM.

6. The method of claim 1, wherein the buffer comprises citrate.

7. The method of claim 6, wherein the citrate is present at a concentration in a range from 0.25 to 50 mM.

8. The method of claim 1, wherein the pH of the composition is in a range from 4.0 to 8.0.

9. The method of claim 1, wherein the composition further comprises one or more excipients selected from the group consisting of: sucrose, trehalose, mannitol, sorbitol, arginine, lysine, polysorbate 20, polysorbate 80, poloxamer 188, and pluronic, and combinations thereof.

10. The method of claim 9, wherein the composition further comprises polysorbate and/or lysine HCL, or wherein the composition does not further comprise polysorbate and/or lysine HCL if the concentration of the bispecific antibody construct is at least 10 µg/ml.

11. The method of claim 1, wherein the first binding domain of the bispecific antibody construct binds to at least one target cell surface antigen selected from the group consisting of: CD19, CD33, EGFRvIII, MSLN, CDH19, FLT3, DLL3, CDH3, BCMA and PSMA.

12. The method of claim 1, wherein the first binding domain comprises a VH region and a VL region comprising CDR-H1, CDR-H2, CDR-H3, CDR-L1, CDR-L2, and CDR-L3 selected from the group consisting of:
   (a) CDR-H1 as set forth in SEQ ID NO: 1, CDR-H2 as set forth in SEQ ID NO: 2, CDR-H3 as set forth in SEQ ID NO: 3, CDR-L1 as set forth in SEQ ID NO: 4, CDR-L2 as set forth in SEQ ID NO: 5 and CDR-L3 as set forth in SEQ ID NO: 6;
   (b) CDR-H1 as set forth in SEQ ID NO: 29, CDR-H2 as set forth in SEQ ID NO: 30, CDR-H3 as set forth in SEQ ID NO: 31, CDR-L1 as set forth in SEQ ID NO: 34, CDR-L2 as set forth in SEQ ID NO: 35 and CDR-L3 as set forth in SEQ ID NO: 36;
   (c) CDR-H1 as set forth in SEQ ID NO: 42, CDR-H2 as set forth in SEQ ID NO: 43, CDR-H3 as set forth set forth in SEQ ID NO: 44, CDR-L1 as set forth in SEQ ID NO: 45, CDR-L2 as set forth in SEQ ID NO: 46 and CDR-L3 as set forth in SEQ ID NO: 47;
   (d) CDR-H1 as set forth in SEQ ID NO: 53, CDR-H2 as set forth in SEQ ID NO: 54, CDR-H3 as set forth in SEQ ID NO: 55, CDR-L1 as set forth in SEQ ID NO: 56, CDR-L2 as set forth in SEQ ID NO: 57 and CDR-L3 as set forth in SEQ ID NO: 58;
   (e) CDR-H1 as set forth in SEQ ID NO: 65, CDR-H2 as set forth in SEQ ID NO: 66, CDR-H3 as set forth in SEQ ID NO: 67, CDR-L1 as set forth in SEQ ID NO: 68, CDR-L2 as set forth in SEQ ID NO: 69 and CDR-L3 as set forth in SEQ ID NO: 70;
   (f) CDR-H1 as set forth in SEQ ID NO: 83, CDR-H2 as set forth in SEQ ID NO: 84, CDR-H3 as set forth in SEQ ID NO: 85, CDR-L1 as set forth in SEQ ID NO: 86, CDR-L2 as set forth in SEQ ID NO: 87 and CDR-L3 as set forth in SEQ ID NO: 88;
   (g) CDR-H1 as set forth in SEQ ID NO: 94, CDR-H2 as set forth in SEQ ID NO: 95, CDR-H3 as set forth in SEQ ID NO: 96, CDR-L1 as set forth in SEQ ID NO: 97, CDR-L2 as set forth in SEQ ID NO: 98 and CDR-L3 as set forth in SEQ ID NO: 99;
   (h) CDR-H1 as set forth in SEQ ID NO: 105, CDR-H2 as set forth in SEQ ID NO: 106, CDR-H3 as set forth in SEQ ID NO: 107, CDR-L1 as set forth in SEQ ID NO: 109, CDR-L2 as set forth in SEQ ID NO: 110 and CDR-L3 as set forth in SEQ ID NO: 111;
   (i) CDR-H1 as set forth in SEQ ID NO: 115, CDR-H2 as set forth in SEQ ID NO: 116, CDR-H3 as set forth in SEQ ID NO: 117, CDR-L1 as set forth in SEQ ID NO: 118, CDR-L2 as set forth in SEQ ID NO: 119 and CDR-L3 as set forth in SEQ ID NO: 120;
   (j) CDR-H1 as set forth in SEQ ID NO: 126, CDR-H2 as set forth in SEQ ID NO: 127, CDR-H3 as set forth in SEQ ID NO: 128, CDR-L1 as set forth in SEQ ID NO: 129, CDR-L2 as set forth in SEQ ID NO: 130 and CDR-L3 as set forth in SEQ ID NO: 131;
   (k) CDR-H1 as set forth in SEQ ID NO: 137, CDR-H2 as set forth in SEQ ID NO: 138, CDR-H3 as set forth in SEQ ID NO: 139, CDR-L1 as set forth in SEQ ID NO: 140, CDR-L2 as set forth in SEQ ID NO: 141 and CDR-L3 as set forth in SEQ ID NO: 142;
   (l) CDR-H1 as set forth in SEQ ID NO: 152, CDR-H2 as set forth in SEQ ID NO: 153, CDR-H3 as set forth in SEQ ID NO: 154, CDR-L1 as set forth in SEQ ID NO: 155, CDR-L2 as set forth in SEQ ID NO: 156 and CDR-L3 as set forth in SEQ ID NO: 157; and
   (m) CDR-H1 as set forth in SEQ ID NO: 167, CDR-H2 as set forth in SEQ ID NO: 168, CDR-H3 as set forth in SEQ ID NO: 169, CDR-L1 as set forth in SEQ ID NO: 170, CDR-L2 as set forth in SEQ ID NO: 171 and CDR-L3 as set forth in SEQ ID NO: 172.

13. The method of claim 1, wherein the composition is liquid.

14. The method of claim 1, wherein the multimers are dimers.

15. The method of claim 13, wherein the composition comprises less than 5% of multimers of the bispecific antibody construct for a time period of at least 4 days at room temperature.

16. The method of claim 1, wherein the composition is suitable for storage at −50° C., −40° C., −30° C., or −20° C.

17. The method of claim 16,
   wherein the composition comprises the bispecific antibody comprising a third binding domain which comprises two polypeptide monomers, each comprising a hinge, a CH2 and a CH3 domain,
   wherein said two polypeptide monomers are fused to each other via a peptide linker, and
   wherein said third binding domain comprises in an amino to carboxyl order:
   hinge-CH2-CH3-linker-hinge-CH2-CH3.

18. The method of claim 1, wherein the composition is provided as a lyophilisate for storage.

* * * * *